United States Patent
Torisu et al.

(10) Patent No.: US 7,153,852 B2
(45) Date of Patent: *Dec. 26, 2006

(54) INDOLE COMPOUNDS, PROCESS FOR PRODUCING THE SAME AND DRUGS CONTAINING THE SAME AS THE ACTIVE INGREDIENT

(75) Inventors: Kazuhiko Torisu, Mishima-gun (JP); Tomoyuki Hasegawa, Sakai-gun (JP); Kaoru Kobayashi, Mishima-gun (JP); Fumio Nambu, Mishima-gun (JP)

(73) Assignee: Ono Pharmaceutical Co., Ltd., Osaka (JP)

( * ) Notice: Subject to any disclaimer, the term of this patent is extended or adjusted under 35 U.S.C. 154(b) by 55 days.

This patent is subject to a terminal disclaimer.

(21) Appl. No.: 10/488,834

(22) PCT Filed: Sep. 6, 2002

(86) PCT No.: PCT/JP02/09077

§ 371 (c)(1),
(2), (4) Date: Mar. 8, 2004

(87) PCT Pub. No.: WO03/022813

PCT Pub. Date: Mar. 20, 2003

(65) Prior Publication Data

US 2005/0004096 A1    Jan. 6, 2005

(30) Foreign Application Priority Data

Sep. 7, 2001    (JP)    ............... 2001-271281

(51) Int. Cl.
A61K 31/538    (2006.01)
A61K 31/404    (2006.01)
C07D 265/36    (2006.01)
C07D 209/08    (2006.01)

(52) U.S. Cl. .................. 514/230.5; 514/414; 514/415; 544/105; 548/454; 548/455

(58) Field of Classification Search ................ 544/105; 548/455, 454; 514/230.5, 414, 415

See application file for complete search history.

(56) References Cited

U.S. PATENT DOCUMENTS

| | | | | |
|---|---|---|---|---|
| 5,234,942 | A * | 8/1993 | Bernstein et al. | ........... 514/415 |
| 5,290,788 | A * | 3/1994 | Stevens et al. | ............. 514/314 |
| 5,811,439 | A * | 9/1998 | Ogawa et al. | ............... 514/369 |
| 6,743,793 | B1 * | 6/2004 | Torisu et al. | ............... 514/249 |
| 2004/0180885 | A1 * | 9/2004 | Torisu et al. | ........... 514/227.8 |
| 2005/0004097 | A1 * | 1/2005 | Torisu et al. | .......... 514/210.21 |

FOREIGN PATENT DOCUMENTS

| | | |
|---|---|---|
| EP | 780389 A1 | 6/1977 |
| EP | 458342 A1 | 11/1991 |
| EP | 509400 A1 * | 10/1992 |
| EP | 1 262 475 A1 | 12/2002 |
| WO | WO 01/66520 A1 | 9/2001 |
| WO | WO 200166520 A1 * | 9/2001 |
| WO | WO 2004037788 A1 * | 5/2004 |

OTHER PUBLICATIONS

Torisu, K., et al., "Discovery of a new class of potent, selective, and orally active prostaglandin D2 receptor antagonists," Bioorganic & Medicinal Chemistry, vol. 12(20), pp. 5361-5378 (Oct. 2004) esp. p. 5362, Figure 1, compounds 1, 2, 4, 5a-i, 9a-i.*

Torisu, K., et al., "Discovery of orally active prostaglandin D2 receptor anagonists," Bioorganic & Medicinal Chemistry Letters, vol. 14(19), pp. 4891-4895 (Oct. 2004), especially at p. 4893, Table 2, compounds 2d, 3g-i.*

Torisu, K., et al., "Development of prostaglandin D2 receptor antagonist," Bioorganic & Medicinal Chemistry, vol. 12(17), pp. 4685-4700 (Sep. 2004); esp. at p. 4690, compounds 3g-3k.*

MacKay, Ian and Rosen, Fred, "Autoimmune Diseases," N. Engl. J. Med., vol. 345(5), pp. 340-350 (Aug., 2001), especially at p. 345, Figure 2, lines 1, 2.*

(Continued)

*Primary Examiner*—Kamal A. Saeed
*Assistant Examiner*—Michael Barker
(74) *Attorney, Agent, or Firm*—Sughrue Mion, PLLC

(57) ABSTRACT

Indole derivatives represented by formula (I)

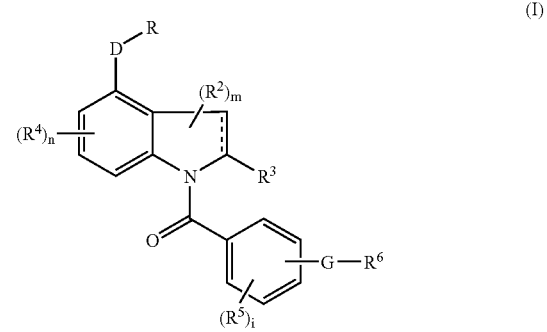

wherein all symbols represent the same as that in specification), production methods thereof, and DP receptor antagonist comprising them as active ingredients.

Since the compounds of formula (I) binds and antagonizes to DP receptor, they are useful for the prevention and/or treatment against allergic diseases, diseases accompanied with itching, secondary diseases generated by behaviors caused by itching, inflammation, chronic obstructive pulmonary disease, ischemic reperfusion disorder, cerebrovascular disorder, pleuritis complicated by rheumatoid arthritis, ulcerative colitis.

23 Claims, No Drawings

OTHER PUBLICATIONS

O'Dell, James, "Therapeutic Strategies for Rheumatoid Arthritis," N. Engl. J. Med., vol. 350, pp. 2591-2602 (Jun. 2004)(strategies for treating Rheumatoid Arthritis with TNF-$\alpha$ inhibitors).*

Prokunina and Riquelme, M., "The genetic basis of systemic lupus erythematosus—knowledge of today and thought for tomorrow," Human Molecular Genetics, vol. 13(Rev. Issue 1), pp. R143-R148 (2004), esp. at p. R144 (PD-1 Pathway), p. R145 (IFN Pathway).*

Rahman, A., "Autoantibodies, lupus and science of sabotage," Rheumatology, vol. 43(11), pp. 1326-1336 (2004), especially at p. 1326, col. 2, lines 9-15.*

* cited by examiner

INDOLE COMPOUNDS, PROCESS FOR PRODUCING THE SAME AND DRUGS CONTAINING THE SAME AS THE ACTIVE INGREDIENT

TECHNICAL FIELD

The present invention relates to indole derivatives.
More specifically, the present invention relates to indole derivatives represented by formula (I):

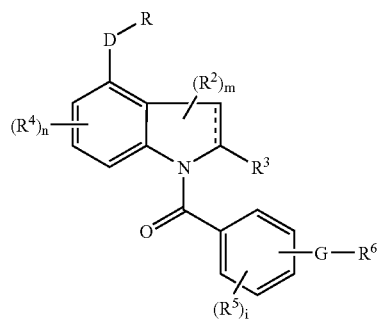

wherein all symbols have the same meanings as described below), the non-toxic salts,
(2) productin methods, and
(3) medicines comprising them as an active ingredient.

BACKGROUND ART

Prostaglandin $D_2$ (hereinafter referred to as "$PGD_2$") are known as a metabolite in the arachidonic acid cascade, and are thought to be one of chemical transmitters that take part in allergic disease, for example, allergic rhinitis, bronchial asthma, and conjunctivitis allergic. It has been known that $PGD_2$ is produced from mast cells and free $PGD_2$ shows bronchoconstriction, permeability accentuation, vasodilation or shrinkage, mucus secretion promotion, and platelet aggregation inhibitory effect. It has been reported that $PGD_2$ induces airway contraction and rhinostenosis symptom in vivo and the increase in $PGD_2$ concentration has been recognized in the pathologic topical of systemic mast cytosis (mastocytosis) patients, nasal allergy patients, bronchial asthma patients, atopic dermatitis patients, and urticaria patients, etc(*New Eng. J. Med.*, 303, 1400–1404 (1980), Am. Rev. Respir. Dis., 128, 597–602 (1983), J. Allergy Clin. Immunol., 88, 33–42 (1991), Arch Otolaryngol Head Neck Surg, 113, 179–83 (1987), J. Allergy Clin. Immunol., 82, 869–77 (1988), J. Immunol., 146, 671–6 (1991), J. Allergy Clin. Immunol., 83, 905–12 (1989), N. Engl. J. Med., 315, 800–4 (1986), Am. Rev. Respir. Dis., 142, 126–32 (1990), J. Allergy Clin. Immunol., 87, 540–8 (1991), J. Allergy Clin. Immunol., 78, 458–61 (1986)). Also, PGD is considered to relate to neuro activities, especially, sleep, hormone secretion, and pain. Furthermore, there are reports suggesting participations in platelet aggregation, glycogen metabolism, ocular tension adjustment and the like.

$PGD_2$ shows its effects by binding to DP receptor which is one of receptor thereof. A DP receptor antagonist binds and is antagonistic to its receptor so that it can inhibit the function. Accordingly, it is considered to be useful for the prevention and/or treatment of diseases, for example, allergic diseases (allergic rhinitis, allergic conjunctivitis, atopic dermatitis, bronchial asthma, food allergy, etc.), systemic mastocytosis, disorders due to systemic mastocyte activation, anaphylactic shock, bronchoconstriction, urticaria, eczema, psoriasis, allergic bronchopulmonary aspergillosis, paranasal sinusitis, migraine, nasal polyp, hypersensitive angitis, eosinophilia, contact dermatitis, diseases accompanied with itching (such as atopic dermatitis, urticaria, allergic conjunctivitis, allergic rhinitis, contact dermatitis, etc.), secondary diseases (such as cataracta, retinodialysis, inflammation, infection, dysgryphia, etc.) generated by behaviors caused by itching (scratching behaviors, beating, etc.), inflammation, chronic obstructive pulmonary disease, ischemic reperfusion disorder, cerebrovascular disorder, brain damage, hepatopathy, graft rejection, autoimmune disease, rheumatoid arthritis, pleuritis complicated by rheumatoid arthritis, osteoarthritis, crohn's disease, ulcerative colitis, pain and the like. Moreover, it is considered to relate to sleeping and platelet aggregation and to be useful for these diseases.

It is known that $PGD_2$ binds with chemoattractant receptor-homologous molecule expressed on Th2 cells (CRTH2 besides DP receptor, and has the migration action on Th 2 cell, eosinophil, and basophil(J. Exp. Med., 193, 255–261 (2001), Blood, 98, 1942–1948 (2001)). Since $PGD_2$ is a ligand to both of DP and CRTH2 receptors in Th2 cells, eosinophils, and basophils in vivo, DP receptor antagonists are expected to bind with CRTH2 receptor, and to antagonize the biological activity.

So, it is considered to be useful for the prevention and/or treatment of diseases, allergic diseases, for example, allergic rhinitis, allergic conjunctivitis, atopic dermatitis, bronchial asthma, food allergy, etc., systemic mastocytosis, disorders due to systemic mastocyte activation, anaphylactic shock, bronchoconstriction, urticaria, eczema, allergic bronchopulmonary aspergillosis, paranasal sinusitis, migraine, nasal polyp, hypersensitive angitis, eosinophilia, contact dermatitis, diseases accompanied with itching such as atopic dermatitis, urticaria, allergic conjunctivitis, allergic rhinitis, contact dermatitis, etc.; secondary diseases such as cataracta, retinodialysis, inflammation, infection, dysgryphia, etc. generated by behaviors caused by itching (scratching behaviors, beating, etc.), inflammation, chronic obstructive pulmonary disease, ischemic reperfusion disorder, cerebrovascular disorder, pleuritis complicated by rheumatoid arthritis, ulcerative colitis and the like.

Some $PGD_2$ receptor antagonists are known conventionally, and BW-A868C represented by the following formula (A) is considered to be the most selective:

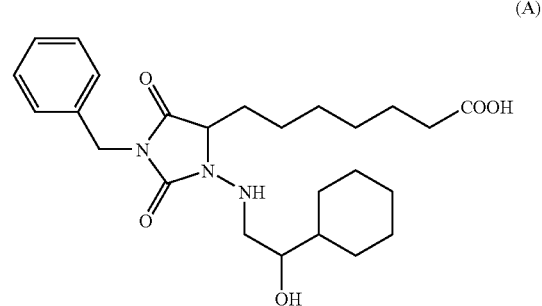

Recently, $PGD_2$ receptor antagonists comprising thromboxane derivatives have been published in WO 98/25915, WO 98/25919, WO 97/00853, WO 98/15502 and the like.

DISCLOSURE OF THE INVENTION

As prostaglandin receptors, a lot of receptor including the subtype exist and the pharmacological action is respectively different. Then, if a new compound that weakly binds to other prostaglandin receptors and specifically binds to $PGD_2$ receptor, especially DP receptor can be found, there is a possibility to become a medicine having a little side effect because of disappear of other actions, and discovery of such a medicine is necessary.

The present inventors intensively studied to find a compound which specifically binds to $PGD_2$ receptor, especially DP receptor and show an antagonistic activity and found that the object could be attained by indole derivatives represented by formula (I), and thus the present invention has been completed.

That is, the present invention relates to indole derivatives represented by formula (I):

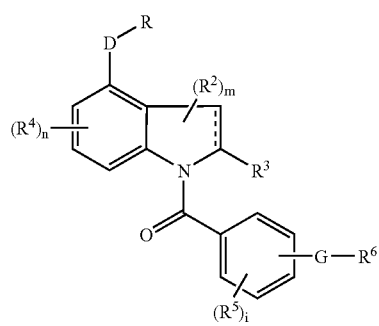

(I)

wherein R represents —$COR^1$, —$CH_2OR^0$, or —$COOR^{20}$, $R^0$ represents a hydrogen atom or C2–6 acyl group, $R^1$ represents a hydroxyl group, C1–6 alkoxy group, —$NR^8R^9$ wherein $R^8$ and $R^9$ represent a hydrogen atom, C1–6 alkyl group, —$SO_2R^{13}$ ($R^{13}$ represents C1–6 alkyl group, C3–15 saturated or unsaturated carbocyclic ring, or 4 to 15-membered heterocycle containing 1 to 5 of nitrogen atom(s) sulfur atom(s), and/or oxygen atom(s).), $R^{20}$ represents allyl or benzyl group.), $R^2$ represents a hydrogen atom, C1–6 alkyl, C1–6 alkoxy, C2–6 alkoxyalkyl, a halogen atom, amino, trihalomethyl, cyano, hydroxyl, benzyl, or 4-methoxybenzyl group, $R^3$ represents a hydrogen atom, C1–6 alkyl, C1–6 alkoxy, a halogen atom, trihalomethyl, cyano, or hydroxyl group, $R^4$ and $R^5$ represent a hydrogen atom, C1–6 alkyl, C1–6 alkoxy, C2–6 alkoxyalkyl group, a halogen atom, nitro, amino, trihalomethyl, trihalomethoxy, cyano or hydroxyl group, respectively, D represents a single bond, C1–6 alkylene, C2–6 alkenylene, or C1–6 oxyalkylene group, -G-$R^6$ represents 1) G represents C1–6 alkylene that maybe replaced by 1 or 2 of oxygen atom(s) and/or sulfur atom(s), C2–6 alkenylene that may be replaced by 1 or 2 of oxygen atom(s) and/or sulfur atom(s)(these alkylene and alkenylene group may be substituted by hydroxyl or C1–4 alkoxy group.), —C(O)NH—, —NHC(O)—, —$SO_2NH$—, —$NHSO_2$—, or diazo group, $R^6$ represents C3–15 saturated or unsaturated carbocyclic ring, or 4 to 15-membered heterocycle containing 1 to 5 of nitrogen atom(s) sulfur atom(s), and/or oxygen atom(s) (these rings may be substituted by 1 to 5 group(s) selected from C1–6 alkyl, C1–10 alkoxy, C2–6 alkoxyalkyl, a halogen atom, hydroxyl, trihalomethyl, nitro, amino, phenyl, phenoxy, oxo, C2–6 acyl, C1–6 alkane sulphonyl, and cyano group.), or 2) together with G and $R^6$,
   (i) C1–15 alkyl group that may be replaced by 1 to 5 of oxygen atom(s) and/or sulfur atom(s),
   (ii) C2–15 alkenyl group that may be replaced by 1 to 5 of oxygen atom(s) and/or sulfur atom(s)(these alkyl, alkenyl, and alkynyl groups may be substituted by 1 to 12 of groups selected from C1–6 alkoxy, a halogen atom, hydroxyl, cyano, oxo groups, and —$NR^{11}R^{12}$ group wherein $R^{11}$ and $R^{12}$ represent a hydrogen atom, C1–6 alkyl, C2–6 alkenyl, phenyl, benzoyl, naphthyl, phenyl group substituted with C1–6 alkyl group, or C1–6 alkyl group substituted by phenyl or cyano group, respectively), n represents 1 to 3,
m represents 1 to 3,
i represents 1 to 4,

- - - - - represents a single bond or a double bond.), or non-toxic salts thereof, (2) the production methods, and (3) the medicines comprising them as an active ingredient.

As the C1–6 alkyl group in this specification, methyl, ethyl, propyl, butyl, pentyl, hexyl group, and isomers thereof are included As the C1–5 alkyl group in this specification, methyl, ethyl, propyl, butyl, pentyl, and these isomers are included.

As the C1–6 alkoxy group in this specification, methoxy, ethoxy, propyloxy, butyloxy, pentyloxy, hexyloxy, and these isomers are included.

As the C1–10 alkoxy group in this specification, methoxy, ethoxy, propyloxy, butyloxy, pentyloxy, hexyloxy, heptyloxy, octyloxy, nonyloxy, decyloxy, and these isomers are included.

As the C1–4 alkoxy group in this specification, methoxy, ethoxy, propyloxy, butyloxy, and these isomers are included.

As the C1–15 alkyl group in this specification, methyl, ethyl, propyl, butyl, pentyl, hexyl, heptyl, octyl, nonyl, decyl, undecyl, dodecyl, tridecyl, tetradecyl, pentadecyl, and these isomers are included.

In this specification, the C1–15 alkyl group that may be replaced by 1 to 5 of oxygen atom(s) and/or sulfur atom(s) represents the one which 1 to 5 of arbitrary carbon atom(s) of the above alkyl was/were replaced by oxygen atoms and/or sulfur atoms.

As the C2–15 alkenyl group in this specification, ethenyl, propenyl, butenyl, pentenyl, hexenyl, heptenyl, octenyl, nonenyl, decenyl, undecenyl, dodecenyl, tridecenyl, tetradecenyl, pentadecenyl, and these isomers are included.

In this specification, the C2–15 alkenyl group that may be replaced by 1 to 5 of oxygen atom(s) and/or sulfur atom(s) represents the one which 1 to 5 of arbitrary saturated carbon atom(s) of the above alkenyl group was/were replaced by oxygen atoms and/or sulfur atoms.

As the C2–15 alkynyl group in this specification, ethynyl, propynyl, butynyl, pentinyl, hexynyl, heptynyl, octynyl, nonynyl, decynyl, undecynyl, dodecynyl, tridecynyl, tetradecynyl, pentadecynyl, and these isomers are included.

In this specification, the C2–15 alkynyl group that may be replaced by 1 to 5 of oxygen atom(s) and/or sulfur atom(s)

represents the one which 1 to 5 of arbitrary saturated carbon atom(s) of the above alkynyl group was/were replaced by oxygen atoms and/or sulfur atoms.

As the C2–6 alkoxyalkyl group in this specification, methoxymethyl, methoxyethyl, methoxypropyl, methoxybutyl, methoxy pentyl, ethoxymethyl, ethoxyethyl, ethoxypropyl, ethoxybutyl, propyl oxymethyl, propyloxyethyl, propyloxypropyl, butyloxymethyl, butyloxyethyl, pentyloxymethyl, and these isomers are included.

As the C1–6 alkylene group in this specification, methylene, ethylene, trimethylene, tetramethylene, pentamethylene, hexamethylene, and these isomers are included.

As the C1–4 alkylene group in this specification, methylene, ethylene, trimethylene, tetramethylene, and these isomers are included.

As the C2–6 alkenylene group in this specification, ethenylene, propenylene, butenylene, pentenylene, hexenylene, and these isomers are included.

As the C2–4 alkenylene group in this specification, ethenylene, propenylene, butenylene and these isomers are included.

As the C1–6 oxyalkylene group in this specification, oxymethylene, oxyethylene, oxytrimethylene, oxytetramethylene, oxy pentamethylene, oxyhexamethylene, and these isomers are included.

In this specification, as the C1–6 alkylene group that may be replaced by 1 to 2 of oxygen atom(s) and/or sulfur atom(s), the groups, which arbitrary carbon atoms of the above C1–6 alkylene group was replaced by oxygen atoms and/or sulfur atoms, are included.

In this specification, as the C2–6 alkenylene group that may be replaced by 1 or 2 of oxygen atom(s) and/or sulfur atom(s), the groups, which arbitrary saturated carbon atoms of the above C2–6 alkenylene group was replaced by oxygen atoms and/or the sulfur atoms, are included.

As the C2–6 alkenyl group in this specification, ethenyl, propenyl, butenyl, pentenyl, hexenyl, and these isomers are included.

The halogen atom in this specification represents fluorine, chlorine, bromide, or iodine.

The trihalomethyl group in this specification represents trifluoromethyl, trichloromethyl, tribromomethyl, or triiodomethyl.

The trihalomethoxy group in this specification represents trifluoromethoxy, trichloromethoxy, tribromomethoxy, or triiodomethoxy.

As the C2–6 acyl group in this specification, ethanoyl, propanoyl, butanoyl, pentanoyl, hexanoyl, and these isomers are included.

As the C1–6 alkanesulphonyl group in this specification, methanesulfonyl, ethanesulfonyl, propanesulfonyl, butanesulfonyl, pentanesulfonyl, hexanesulfonyl, and these isomers are included.

As the carbocyclic ring having 3 to 15 of carbons in this specification, monocyclic, dicyclic, or tricycle unsaturated or saturated carbocyclic ring having 3 to 15 of carbons is included.

As the monocyclic, dicyclic, or tricycle unsaturated or saturated carbocyclic ring having 3 to 15 of carbons, cyclopropane, cyclobutane, cyclopentane, cyclohexane, cycloheptane, cyclooctane, cyclopentene, cyclohexane, cyclopentadiene, cyclohexadiene, benzene, pentalene, indene, naphthalene, azulene, perhydropentalene, perhydroindene, dihydronaphthalene, tetrahydronaphthalene, perhydronaphthalene, perhydroazulene, heptalene, biphenylene, fluorene, phenanthrene, anthracene, dihydroanthracene, tetrahydroanthracene, perhydroanthracene, fluorene, dihydro fluorene, tetrahydro fluorene, perhydrofluorene, norbornane, norpinane, norbornane, norbornene, norpinane, and nolpinen ring, etc. are included.

The 4 to 15-membered heterocycle that contains 1 to 5 of nitrogen, sulfur, and oxygen atom(s) in this specification may be saturated or unsaturated, and for example, the groups represented by the following formulas are included.

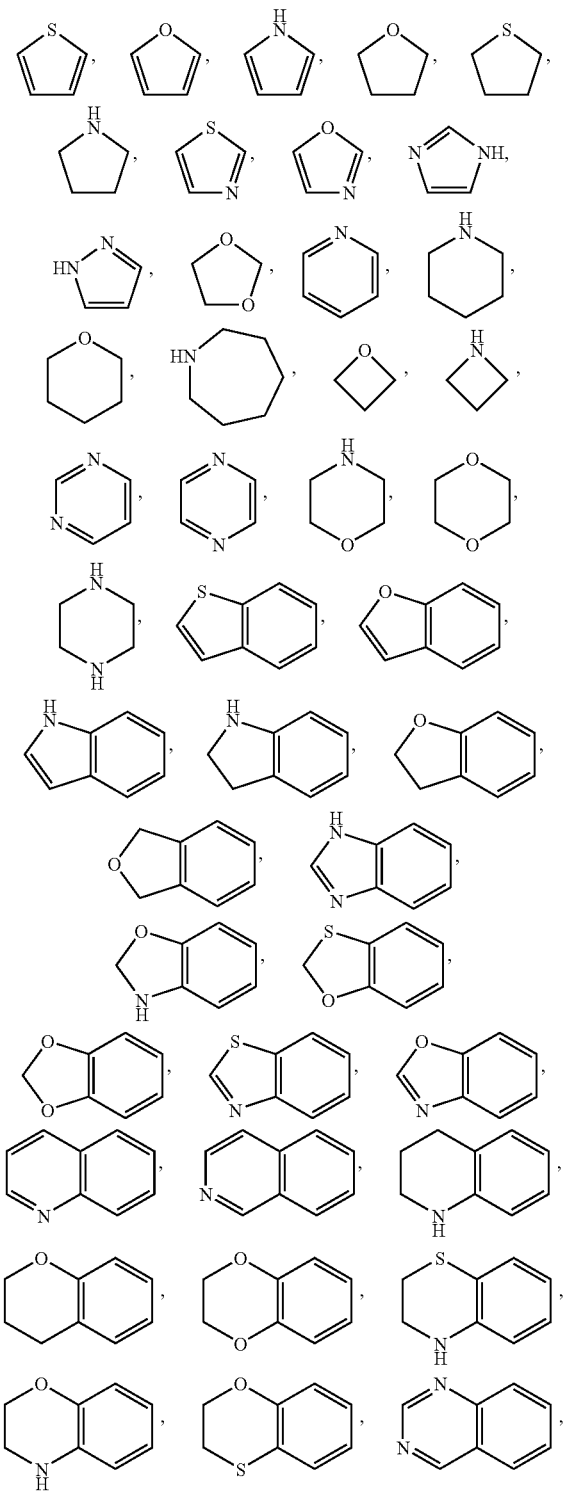

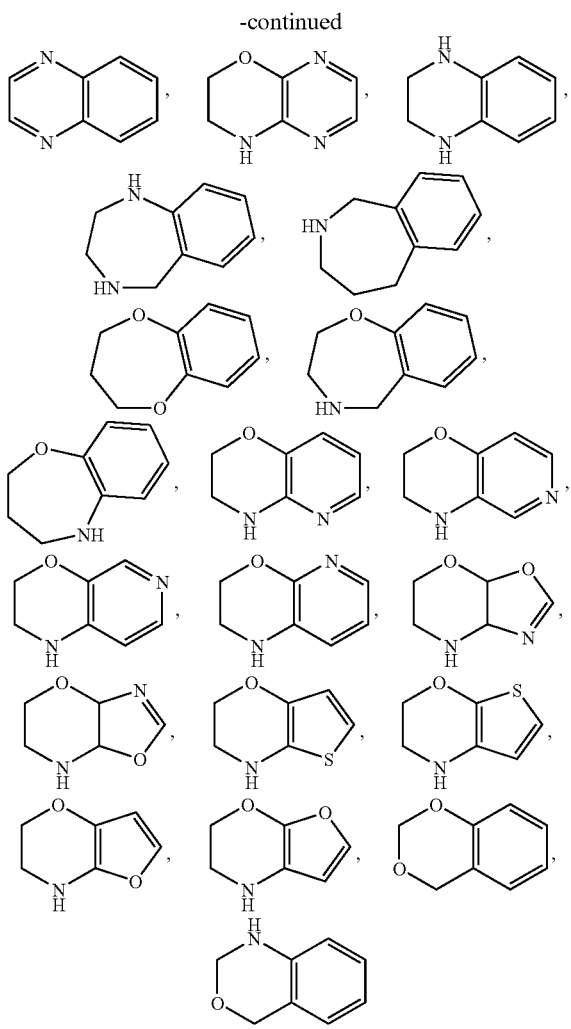

As R in formula (I), —COR¹ or —CH₂OR⁰ group is suitable, and —COR¹ is more suitable.

As $R^0$ in formula (I), a hydrogen atom or C2–6 acyl group is suitable, and a hydrogen atom is more suitable.

As $R^1$ in formula (I), hydroxyl or C1–6 alkoxy group is suitable, and hydroxyl or C1–4 alkoxy group is more suitable.

As $R^2$ in formula (I), a hydrogen atom, C1–6 alkyl, or C1–6 alkoxyalkyl group is suitable, and a hydrogen atom, C1–2 alkyl, or C1–2 alkoxyalkyl group is more suitable.

As $R^3$ in formula (I), a hydrogen atom or C1–6 alkyl group is suitable.

As $R^4$ in formula (I), a hydrogen atom or C1–6 alkyl group is suitable, and a hydrogen atom or C1–2 alkyl group is more suitable.

As $R^5$ in formula (I), a hydrogen atom or C1–6 alkyl group is suitable, and a hydrogen atom or C1–2 alkyl group is more suitable.

As D in formula (I), a single bond or C1–6 alkylene group is suitable, and a single bond or C1–2 alkylene group is more suitable.

As G in formula (I), C1–6 alkylene group that may be replaced by 1 or 2 of oxygen atom(s) is suitable, and C1–2 alkylene group that may be replaced by an oxygen atom is more suitable.

As $R^6$ in formula (I), C5–10 carbocyclic ring wherein substituents are arbitrarily included, or monocyclic or 5 to 10-membered bicyclic heterocycles containing 1 to 3 of nitrogen atom(s), oxygen atom(s), and/or sulfur atom(s) are suitable, 9 to 10-membered bicyclic heterocycles containing 1 to 3 of nitrogen atom(s), oxygen atom(s), and/or sulfur atom(s), which arbitrarily contain substituents, are more suitable, and the heterocycles represented by the following, which arbitrarily contain substituents, are further suitable.

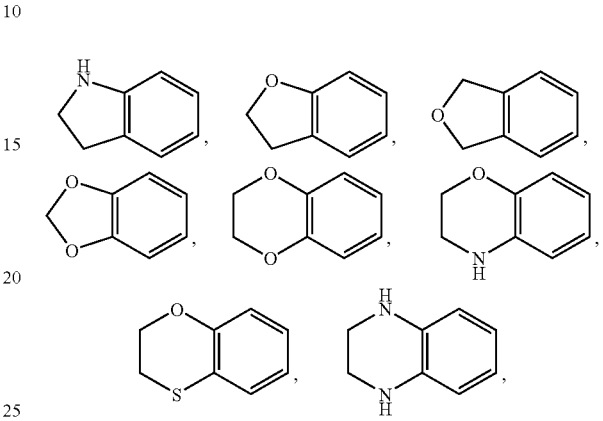

Unless otherwise specified, all isomers are included in the present invention. For example, alkyl, alkoxy and alkylene group includes straight or branched ones. In addition, isomers on double bond, ring, fused ring (E-, Z-, cis-, trans-isomer), isomers generated from asymmetric carbon atom(s) (R—, S—, α-, β-isomer, enantiomer, diastereomer), optically active isomers (D-, L-, d-, l-isomer), polar compounds generated by chromatographic separation (more polar compound, less polar compound), equilibrium compounds, rotamer, mixtures thereof at voluntary ratios and racemic mixtures are also included in the present invention.

According to the present invention, unless otherwise indicated and as is apparent for those skilled in the art, symbol ⋰⋰⋰ indicates that it is bound to the opposite side of the sheet (namely α-configuration), symbol ▰ indicates that it is bound to the front side of the sheet (namely β-configuration), and symbol ╱ indicates that it is a mixture of α-configuration and β-configuration.

In the compounds represented by formula (I), as suitable compounds, a compound represented by formula (I-A-1);

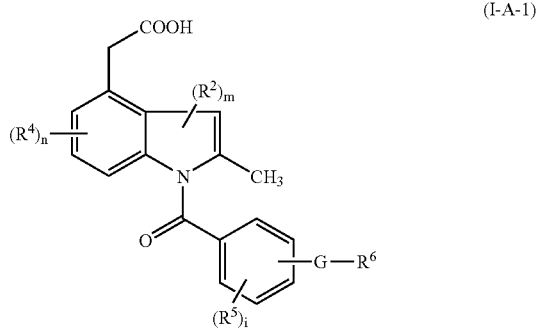

wherein all symbols represent the same meanings as the described above., a compound represented by formula (I-A-2);

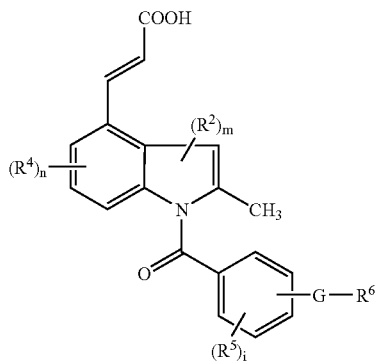
(I-A-2)

wherein all symbols represent the same meanings as the described above., a compound represented by formula (I-A-3);

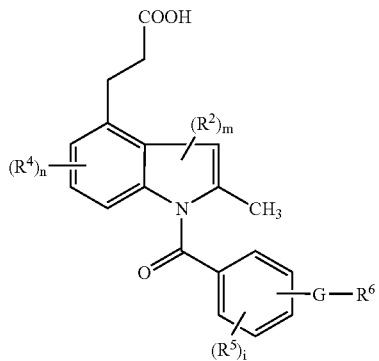
(I-A-3)

wherein all symbols represent the same meanings as the described above, a compound represented by formula (I-A-4);

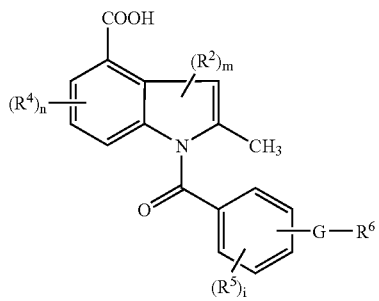
(I-A-4)

wherein all symbols represent the same meanings as the described above., a compound represented by formula (I-A-5);

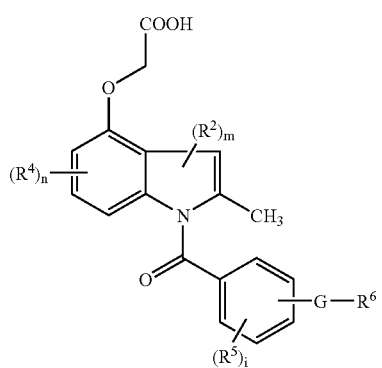
(I-A-5)

wherein all symbols represent the same meanings as the described above., a compound represented by formula (I-A-6);

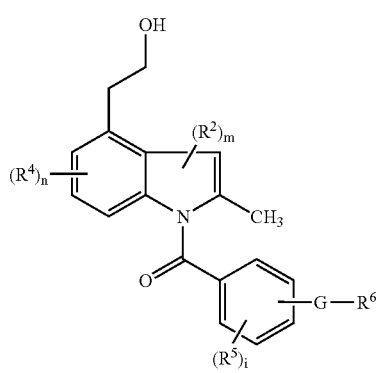
(I-A-6)

wherein all symbols represent the same meanings as the described above., a compound represented by formula (I-A-7);

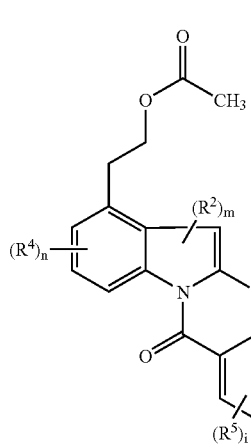
(I-A-7)

wherein all symbols represent the same meanings as the described above., a compound represented by formula (I-B-1);

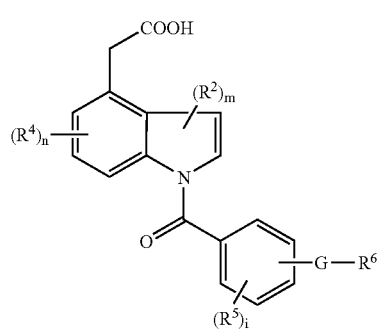

wherein all symbols represent the same meanings as the described above., a compound represented by formula (I-B-2);

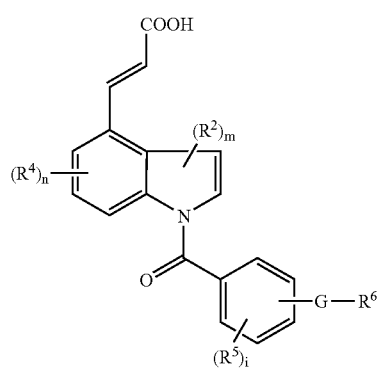

wherein all symbols represent the same meanings as the described above., a compound represented by formula (I-B-3);

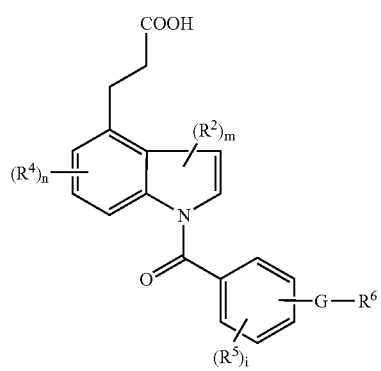

wherein all symbols represent the same meanings as the described above., a compound represented by formula (I-B-4);

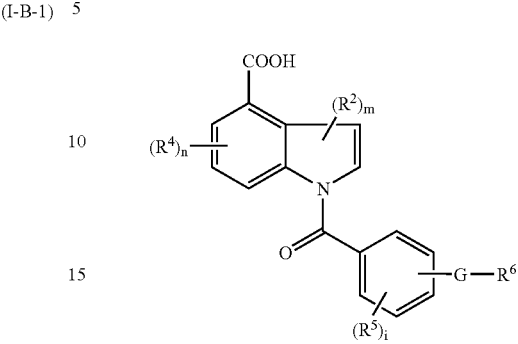

wherein all symbols represent the same meanings as described above, a compound represented by formula (I-B-5);

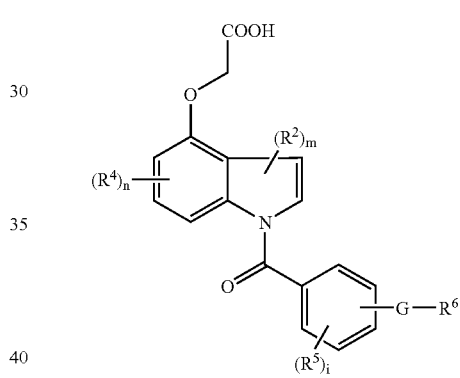

wherein all symbols represent the same meanings as the described above., a compound represented by formula (I-B-6);

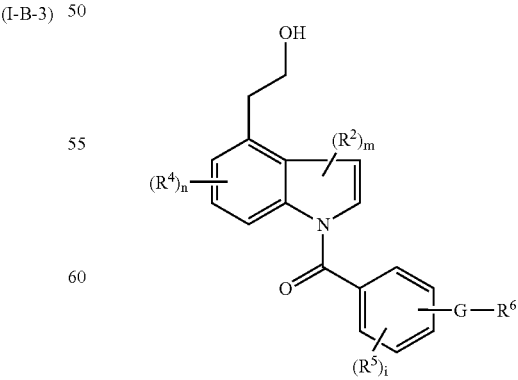

wherein all symbols represent the same meanings as the described above., a compound represented by formula (I-B-7);

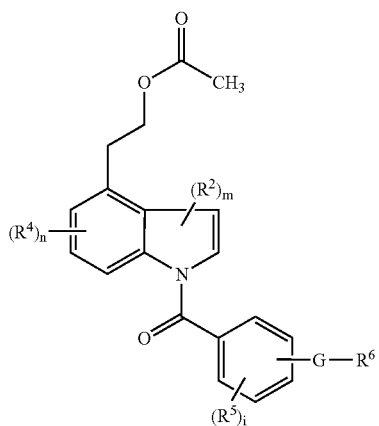

wherein all symbols represent the same meanings as the described above., a compound represented by formula (I-B-8);

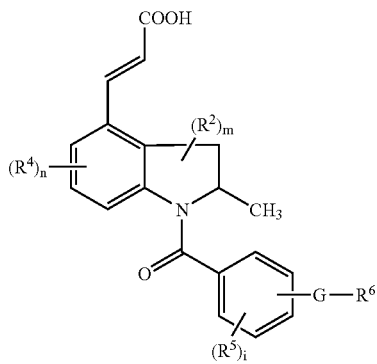

wherein all symbols represent the same meanings as the described above., a compound represented by formula (I-C-1);

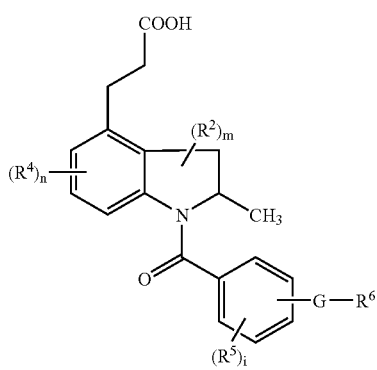

wherein all symbols represent the same meanings as the described above., a compound represented by formula (I-C-2);

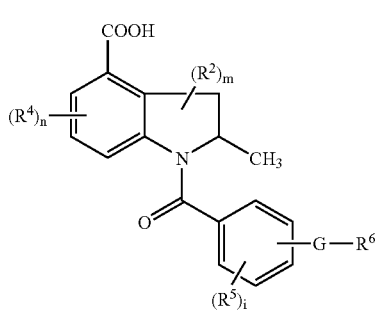

wherein all symbols represent the same meanings as the described above., a compound represented by formula (I-C-3);

(I-C-3)

wherein all symbols represent the same meanings as the described above., a compound represented by formula (I-C-4);

(I-C-4)

wherein all symbols represent the same meanings as the described above., a compound represented by formula (I-C-5);

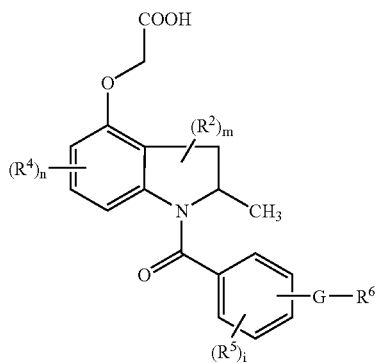
(I-C-5)

wherein all symbols represent the same meanings as the described above., a compound represented by formula (I-C-6);

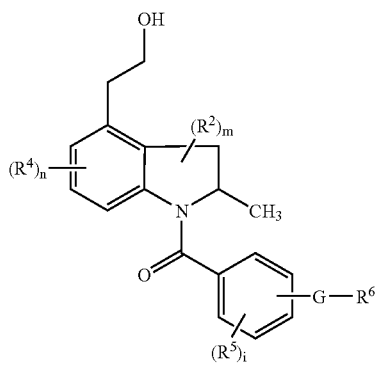
(I-C-6)

wherein all symbols represent the same meanings as the described above., a compound represented by formula (I-C-7);

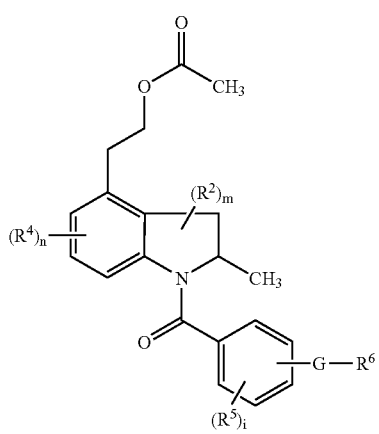
(I-C-7)

wherein all symbols represent the same meanings as the described above., a compound represented by formula (I-C-8);

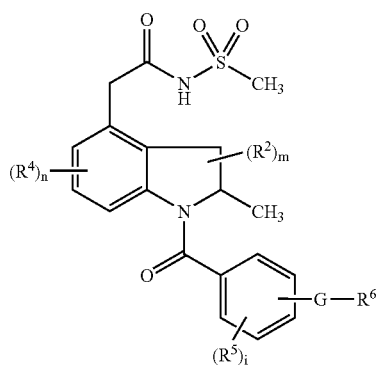
(I-C-8)

wherein all symbols represent the same meanings as the described above., a compound represented by formula (I-D-1);

(I-D-1)

wherein all symbols represent the same meanings as the described above., a compound represented by formula (I-D-2);

(I-D-2)

wherein all symbols represent the same meanings as the described above., a compound represented by formula (I-D-3);

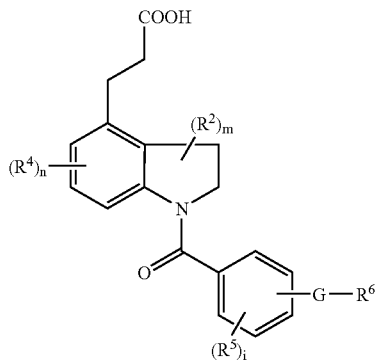

wherein all symbols represent the same meanings as the described above.,
a compound represented by formula (I-D-4);

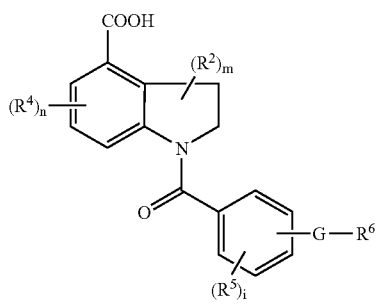

wherein all symbols represent the same meanings as the described above.,
a compound represented by formula (I-D-5);

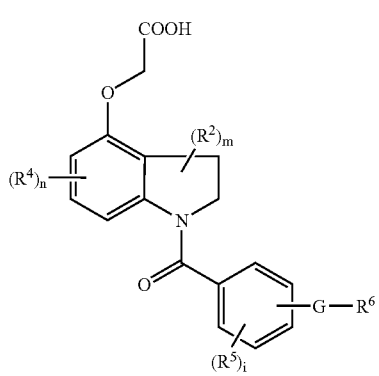

wherein all symbols represent the same meanings as the described above., a compound represented by formula (I-D-6);

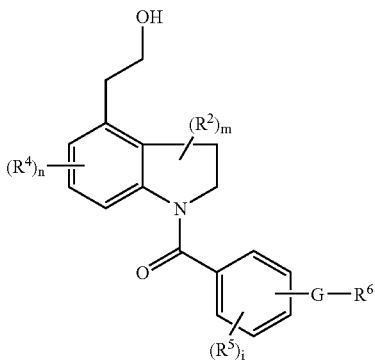

wherein all symbols represent the same meanings as the described above.,
a compound represented by formula (I-D-7);

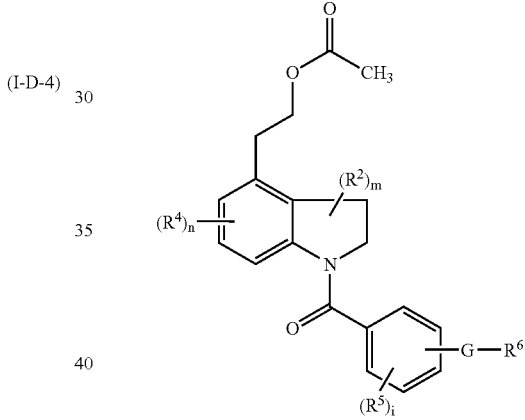

wherein all symbols represent the same meanings as the described above., or
a compound represented by formula (I-D-8);

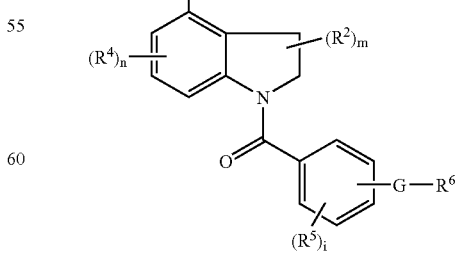

wherein all symbols represent the same meanings as the described above is included.

In concrete compounds of the present invention, the compounds represented in the following table 1 to 54, the compounds of examples, and non-toxic salts thereof are included.

TABLE 1

TABLE 1-continued
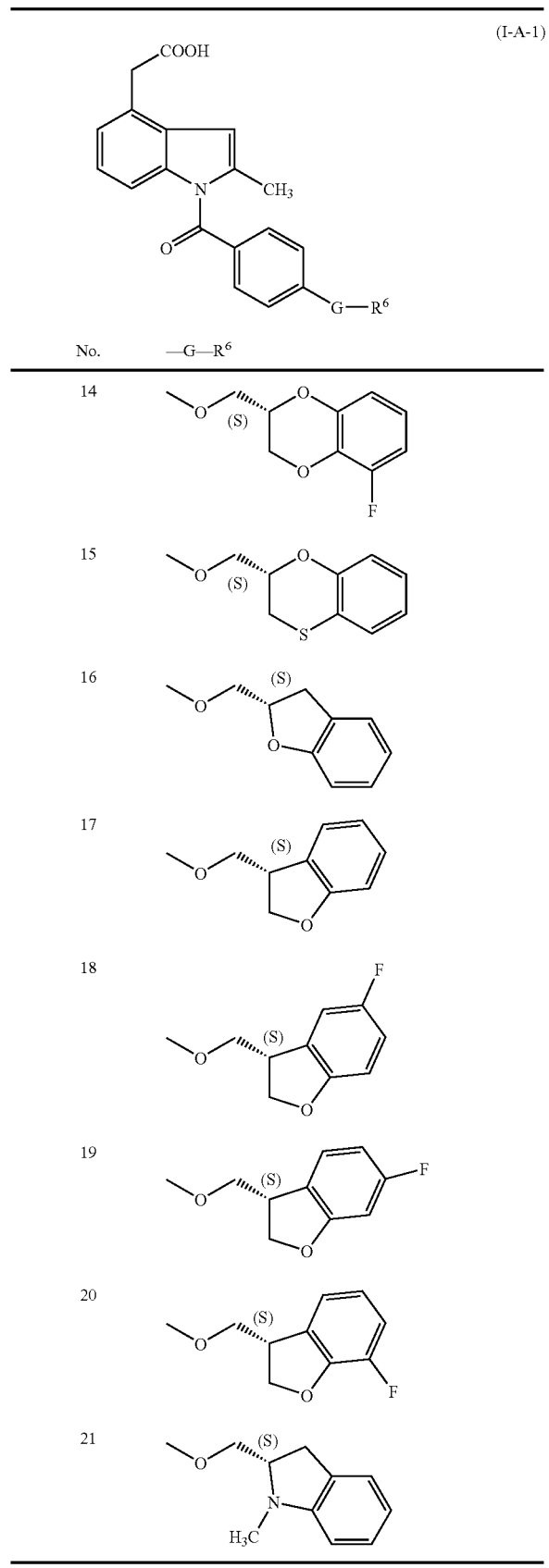
TABLE 2
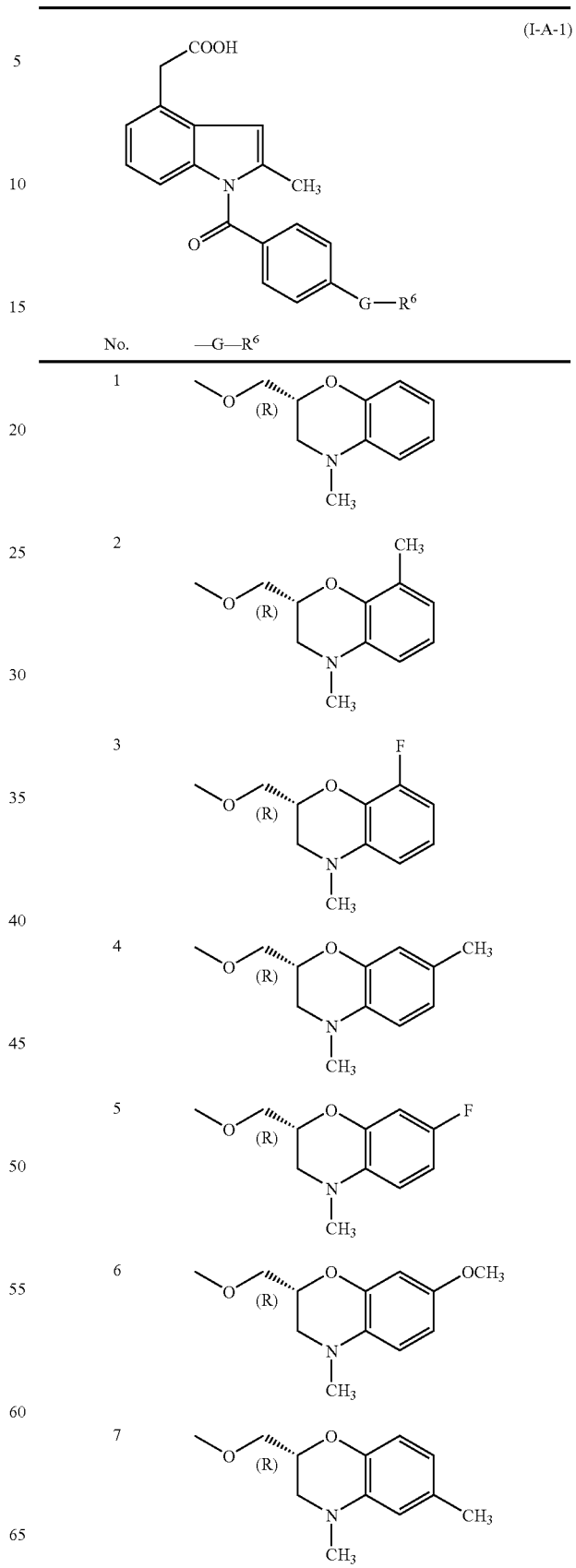

TABLE 2-continued
(I-A-1)
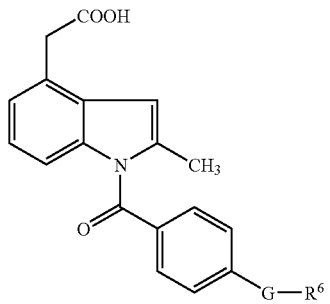
| No. | —G—R⁶ |
|---|---|
| 8 | 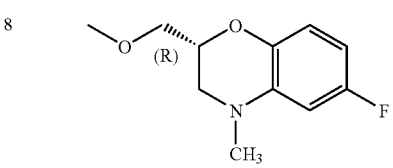 |
| 9 | 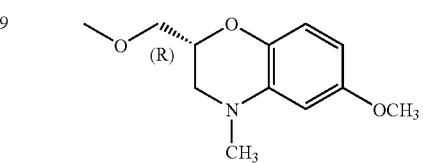 |
| 10 | 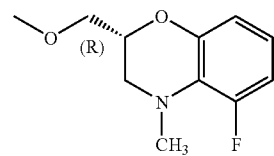 |
| 11 | 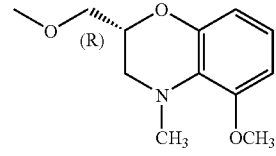 |
| 12 | 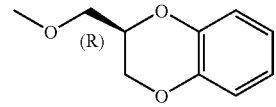 |
| 13 | 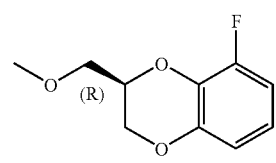 |
| 14 | 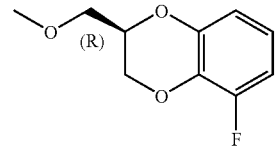 |
TABLE 2-continued
(I-A-1)
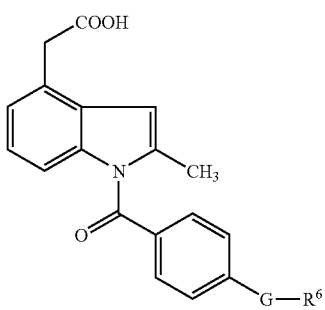
| No. | —G—R⁶ |
|---|---|
| 15 | 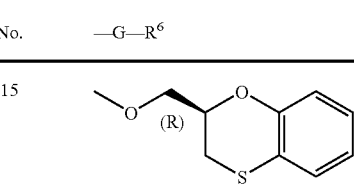 |
| 16 | 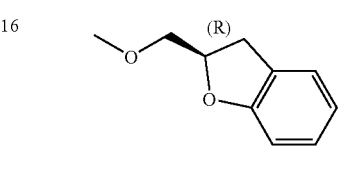 |
| 17 | 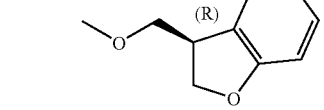 |
| 18 | 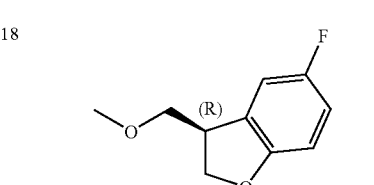 |
| 19 | 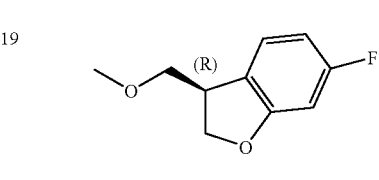 |
| 20 | 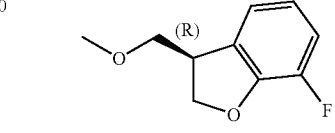 |
| 21 | 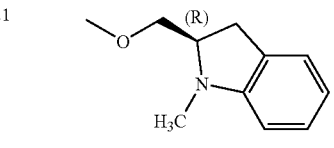 |

TABLE 3

(I-A-2)

| No. | —G—R⁶ |
|---|---|
| 1 | 4-methyl-(2S)-methoxymethyl-3,4-dihydro-2H-1,4-benzoxazine |
| 2 | 4,8-dimethyl-(2S)-methoxymethyl-3,4-dihydro-2H-1,4-benzoxazine |
| 3 | 8-fluoro-4-methyl-(2S)-methoxymethyl-3,4-dihydro-2H-1,4-benzoxazine |
| 4 | 4,7-dimethyl-(2S)-methoxymethyl-3,4-dihydro-2H-1,4-benzoxazine |
| 5 | 7-fluoro-4-methyl-(2S)-methoxymethyl-3,4-dihydro-2H-1,4-benzoxazine |
| 6 | 7-methoxy-4-methyl-(2S)-methoxymethyl-3,4-dihydro-2H-1,4-benzoxazine |
| 7 | 4,6-dimethyl-(2S)-methoxymethyl-3,4-dihydro-2H-1,4-benzoxazine |
| 8 | 6-fluoro-4-methyl-(2S)-methoxymethyl-3,4-dihydro-2H-1,4-benzoxazine |
| 9 | 6-methoxy-4-methyl-(2S)-methoxymethyl-3,4-dihydro-2H-1,4-benzoxazine |
| 10 | 5-fluoro-4-methyl-(2S)-methoxymethyl-3,4-dihydro-2H-1,4-benzoxazine |
| 11 | 5-methoxy-4-methyl-(2S)-methoxymethyl-3,4-dihydro-2H-1,4-benzoxazine |
| 12 | (2S)-methoxymethyl-2,3-dihydro-1,4-benzodioxine |
| 13 | 5-fluoro-(2S)-methoxymethyl-2,3-dihydro-1,4-benzodioxine |

TABLE 3-continued
TABLE 4
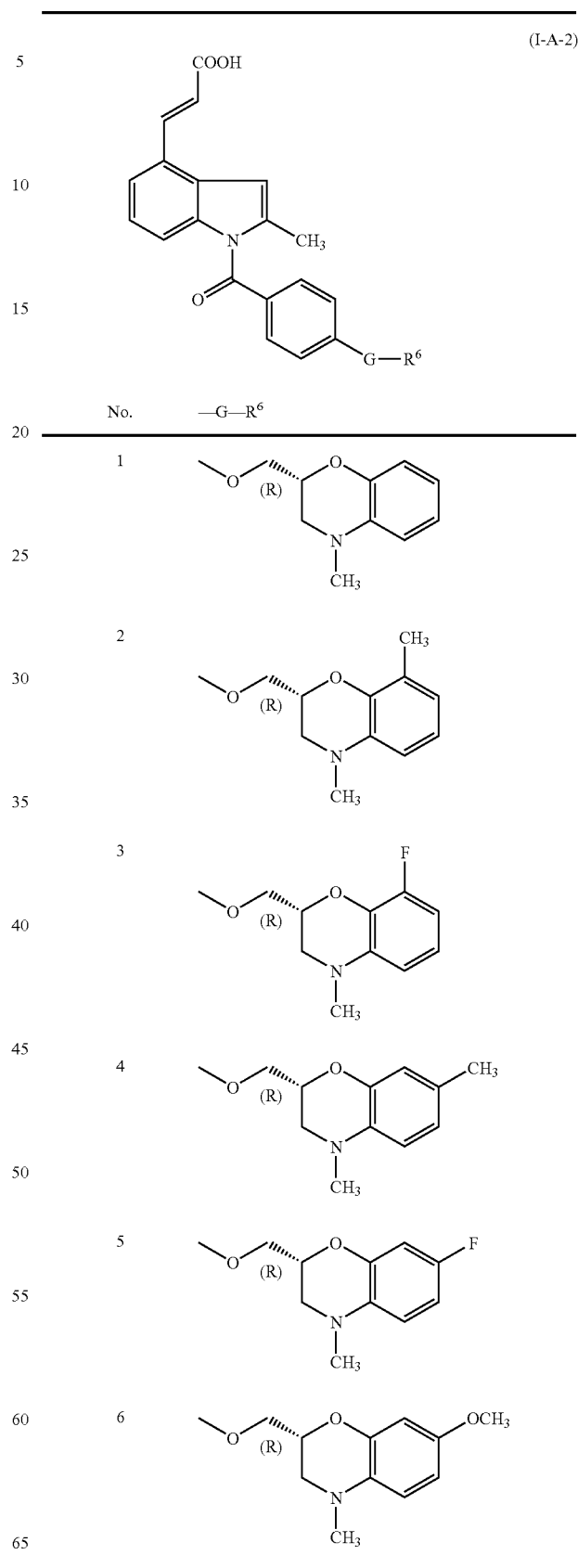

TABLE 4-continued
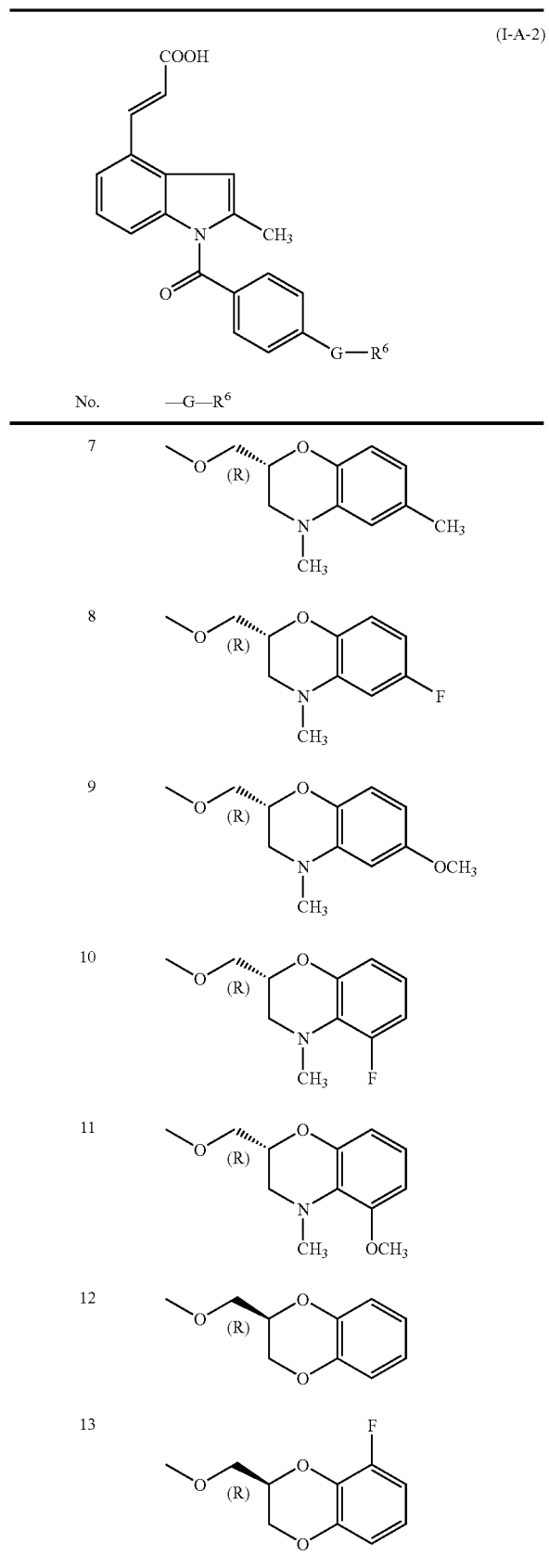
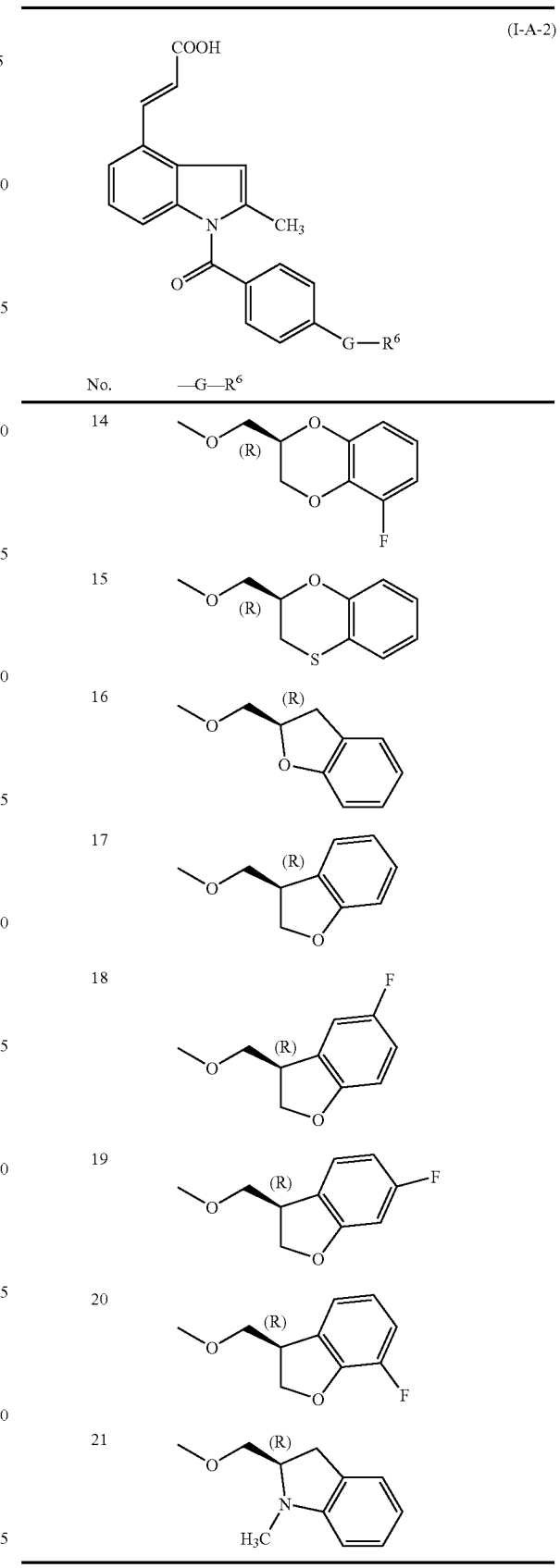

TABLE 5

(I-A-3) structure: indole core with 2-methyl, N-acylated with 4-(G-R⁶)benzoyl, and 4-position bearing -CH₂CH₂COOH.

| No. | —G—R⁶ |
|---|---|
| 1 | (S)-2-(methoxymethyl)-4-methyl-3,4-dihydro-2H-1,4-benzoxazine |
| 2 | (S)-2-(methoxymethyl)-4,8-dimethyl-3,4-dihydro-2H-1,4-benzoxazine |
| 3 | (S)-8-fluoro-2-(methoxymethyl)-4-methyl-3,4-dihydro-2H-1,4-benzoxazine |
| 4 | (S)-2-(methoxymethyl)-4,7-dimethyl-3,4-dihydro-2H-1,4-benzoxazine |
| 5 | (S)-7-fluoro-2-(methoxymethyl)-4-methyl-3,4-dihydro-2H-1,4-benzoxazine |
| 6 | (S)-2-(methoxymethyl)-7-methoxy-4-methyl-3,4-dihydro-2H-1,4-benzoxazine |
| 7 | (S)-2-(methoxymethyl)-4,6-dimethyl-3,4-dihydro-2H-1,4-benzoxazine |
| 8 | (S)-6-fluoro-2-(methoxymethyl)-4-methyl-3,4-dihydro-2H-1,4-benzoxazine |
| 9 | (S)-2-(methoxymethyl)-6-methoxy-4-methyl-3,4-dihydro-2H-1,4-benzoxazine |
| 10 | (S)-5-fluoro-2-(methoxymethyl)-4-methyl-3,4-dihydro-2H-1,4-benzoxazine |
| 11 | (S)-2-(methoxymethyl)-5-methoxy-4-methyl-3,4-dihydro-2H-1,4-benzoxazine |
| 12 | (S)-2-(methoxymethyl)-2,3-dihydro-1,4-benzodioxine |
| 13 | (S)-5-fluoro-2-(methoxymethyl)-2,3-dihydro-1,4-benzodioxine |

TABLE 5-continued
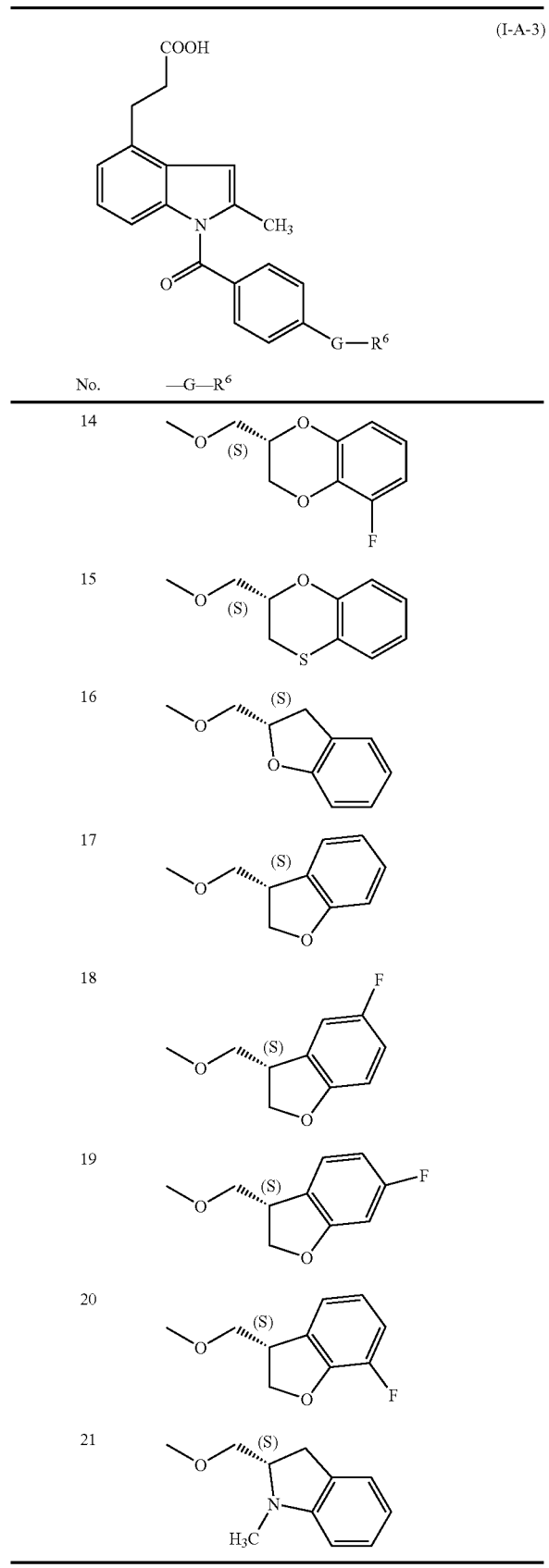
TABLE 6
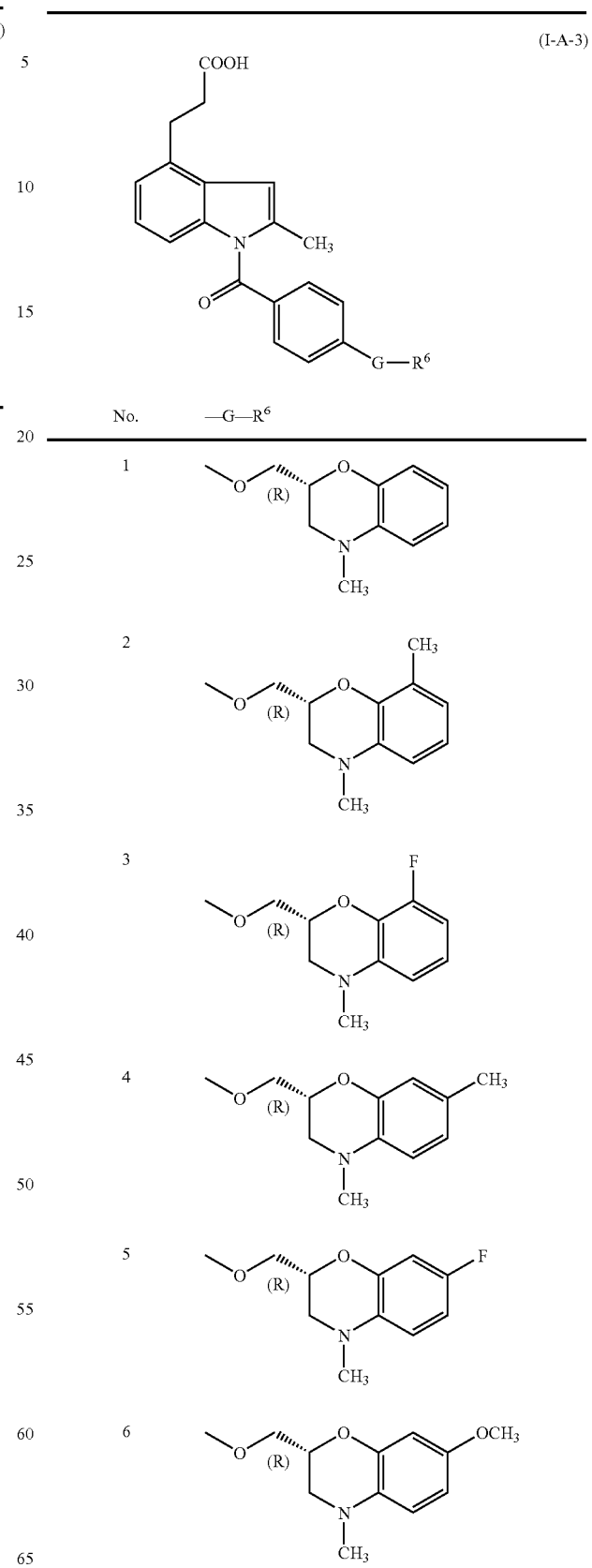

TABLE 6-continued
(I-A-3)
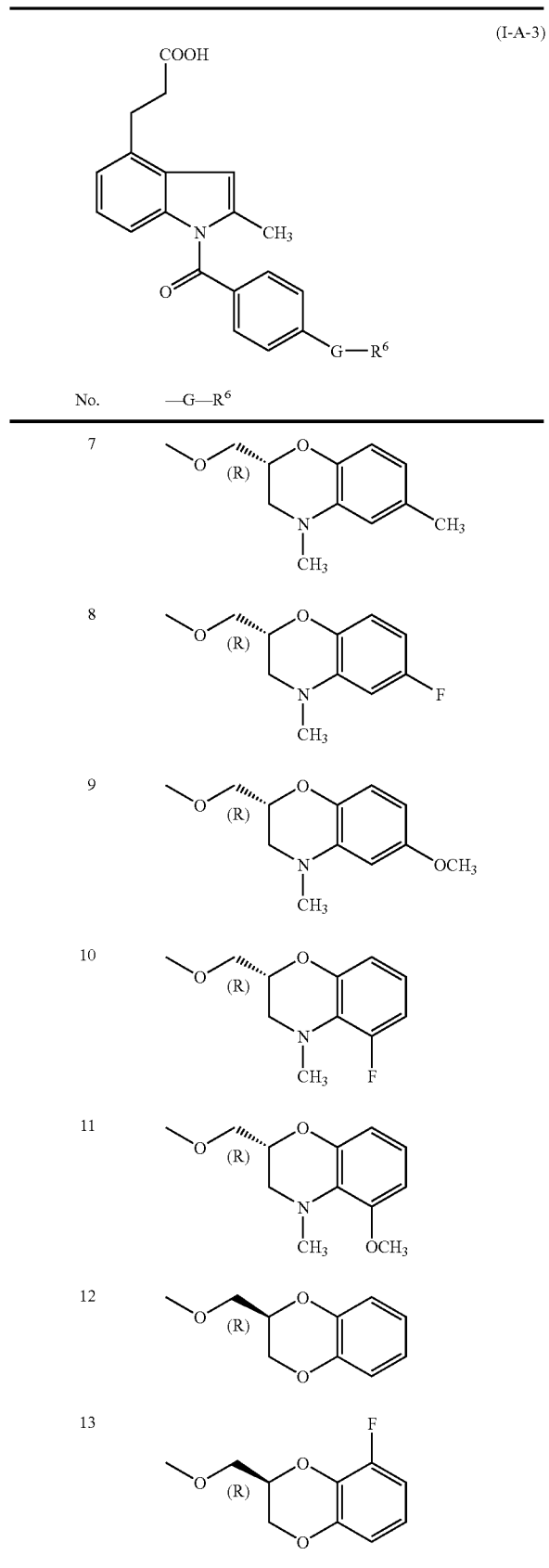
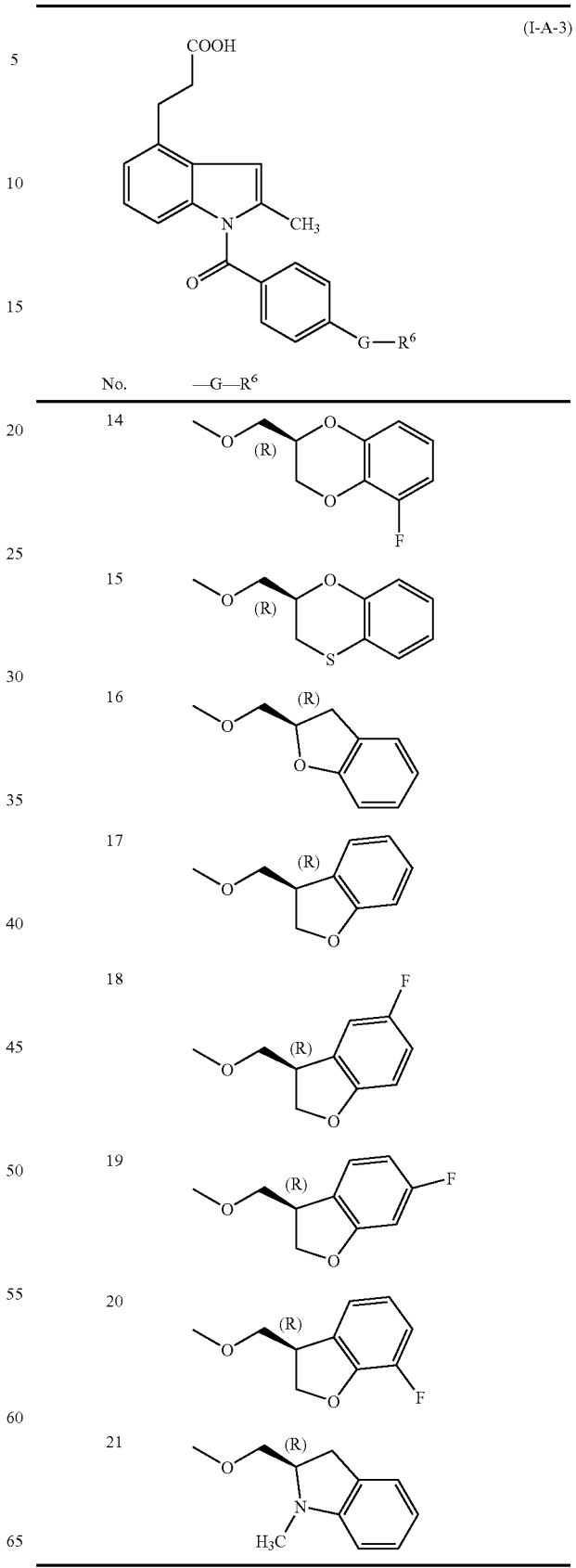

TABLE 7
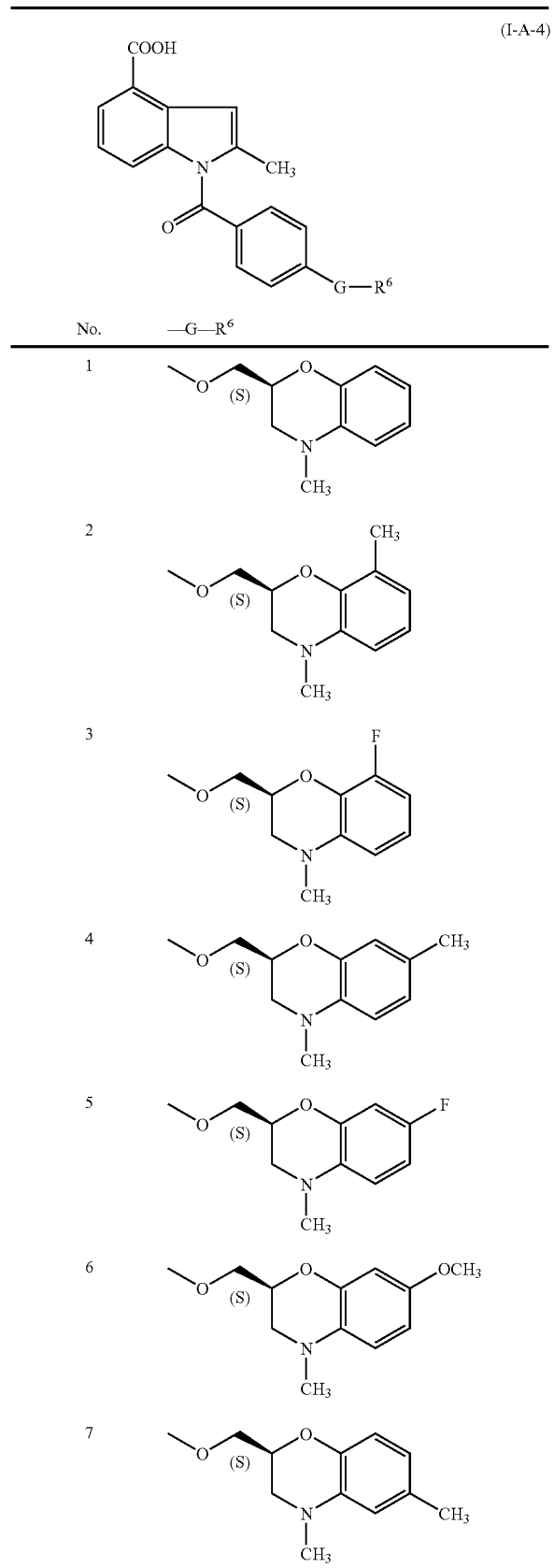
TABLE 7-continued
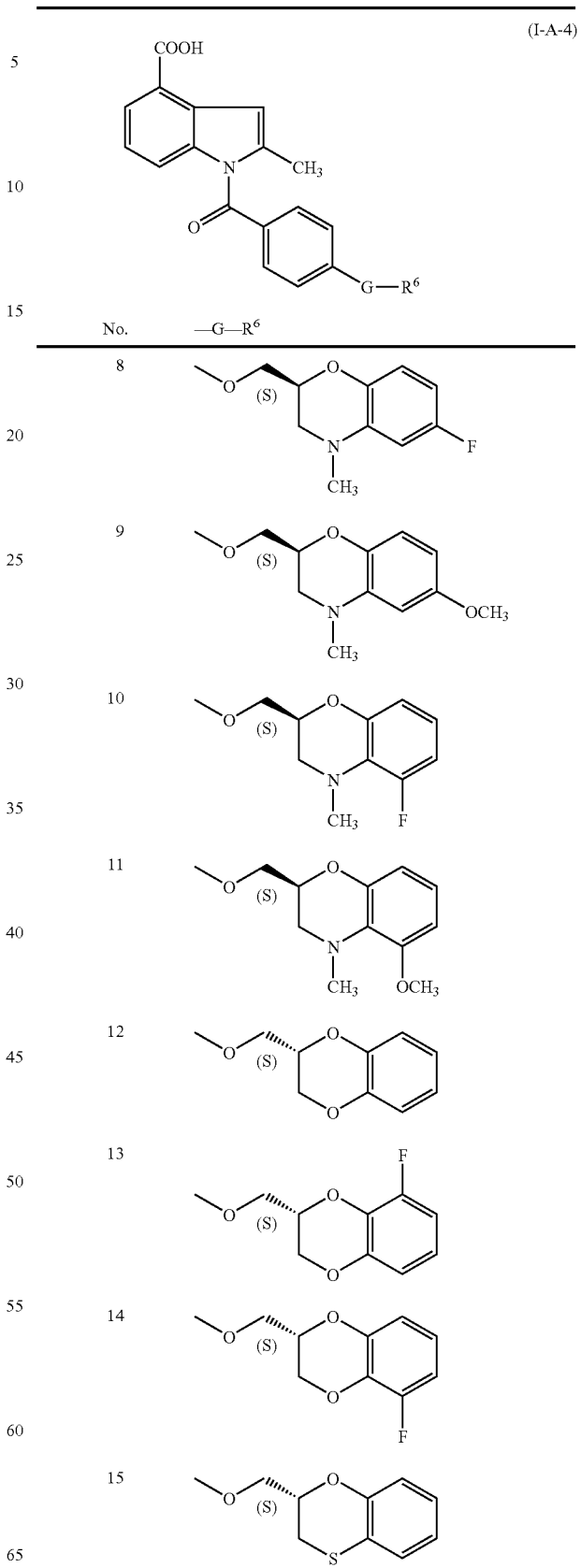

TABLE 7-continued (I-A-4)

| No. | —G—R⁶ |
|---|---|
| 16 | (S)-2-(methoxymethyl)-2,3-dihydrobenzofuran |
| 17 | (S)-3-(methoxymethyl)-2,3-dihydrobenzofuran |
| 18 | (S)-3-(methoxymethyl)-5-fluoro-2,3-dihydrobenzofuran |
| 19 | (S)-3-(methoxymethyl)-6-fluoro-2,3-dihydrobenzofuran |
| 20 | (S)-3-(methoxymethyl)-7-fluoro-2,3-dihydrobenzofuran |
| 21 | (S)-2-(methoxymethyl)-1-methyl-2,3-dihydroindoline |

TABLE 8

(I-A-4)

| No. | —G—R⁶ |
|---|---|
| 1 | (R)-2-(methoxymethyl)-4-methyl-3,4-dihydro-2H-1,4-benzoxazine |
| 2 | (R)-2-(methoxymethyl)-4,8-dimethyl-3,4-dihydro-2H-1,4-benzoxazine |
| 3 | (R)-2-(methoxymethyl)-8-fluoro-4-methyl-3,4-dihydro-2H-1,4-benzoxazine |
| 4 | (R)-2-(methoxymethyl)-4,7-dimethyl-3,4-dihydro-2H-1,4-benzoxazine |
| 5 | (R)-2-(methoxymethyl)-7-fluoro-4-methyl-3,4-dihydro-2H-1,4-benzoxazine |
| 6 | (R)-2-(methoxymethyl)-7-methoxy-4-methyl-3,4-dihydro-2H-1,4-benzoxazine |
| 7 | (R)-2-(methoxymethyl)-4,6-dimethyl-3,4-dihydro-2H-1,4-benzoxazine |

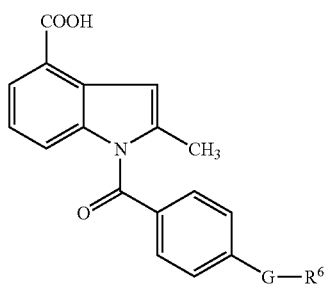

TABLE 9
(I-A-5)
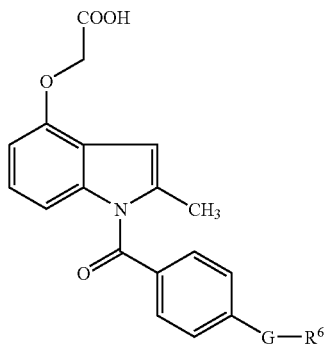
| No. | —G—R⁶ |
|---|---|
| 1 | 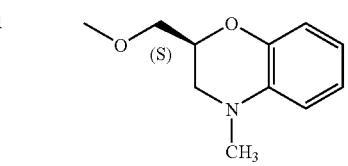 |
| 2 | 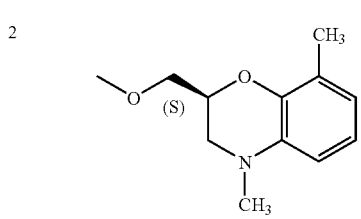 |
| 3 | 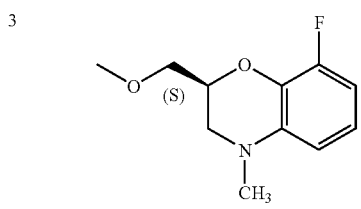 |
| 4 | 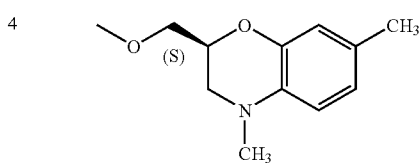 |
| 5 | 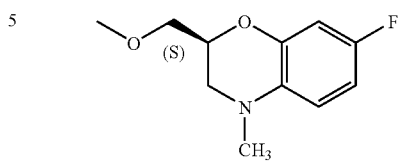 |
| 6 | 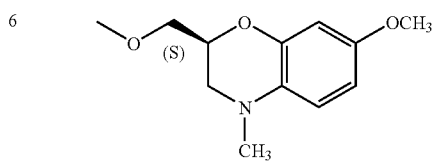 |
TABLE 9-continued
(I-A-5)
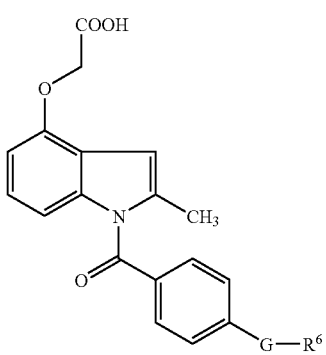
| No. | —G—R⁶ |
|---|---|
| 7 | 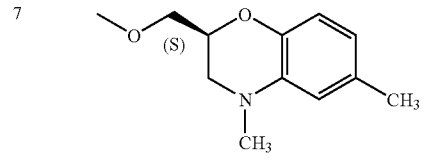 |
| 8 | 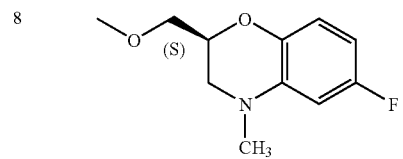 |
| 9 | 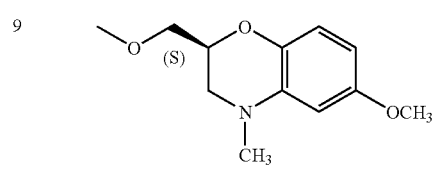 |
| 10 | 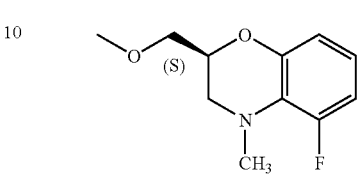 |
| 11 | 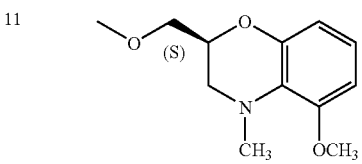 |
| 12 | |
| 13 | |

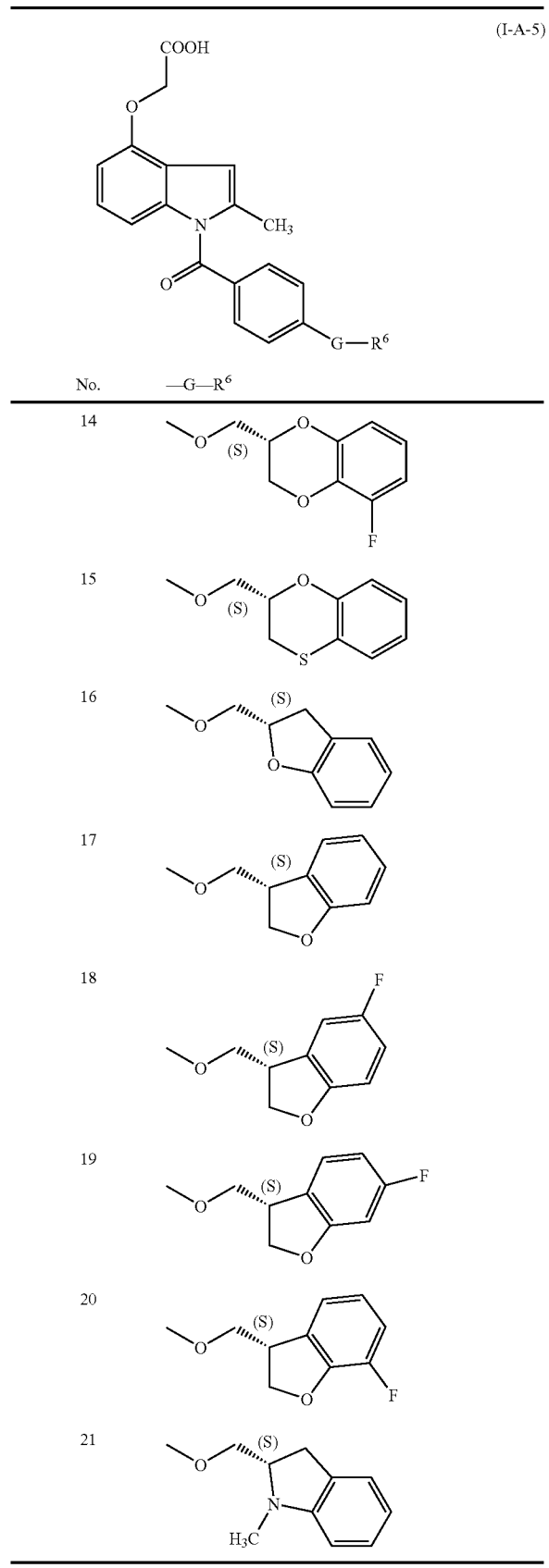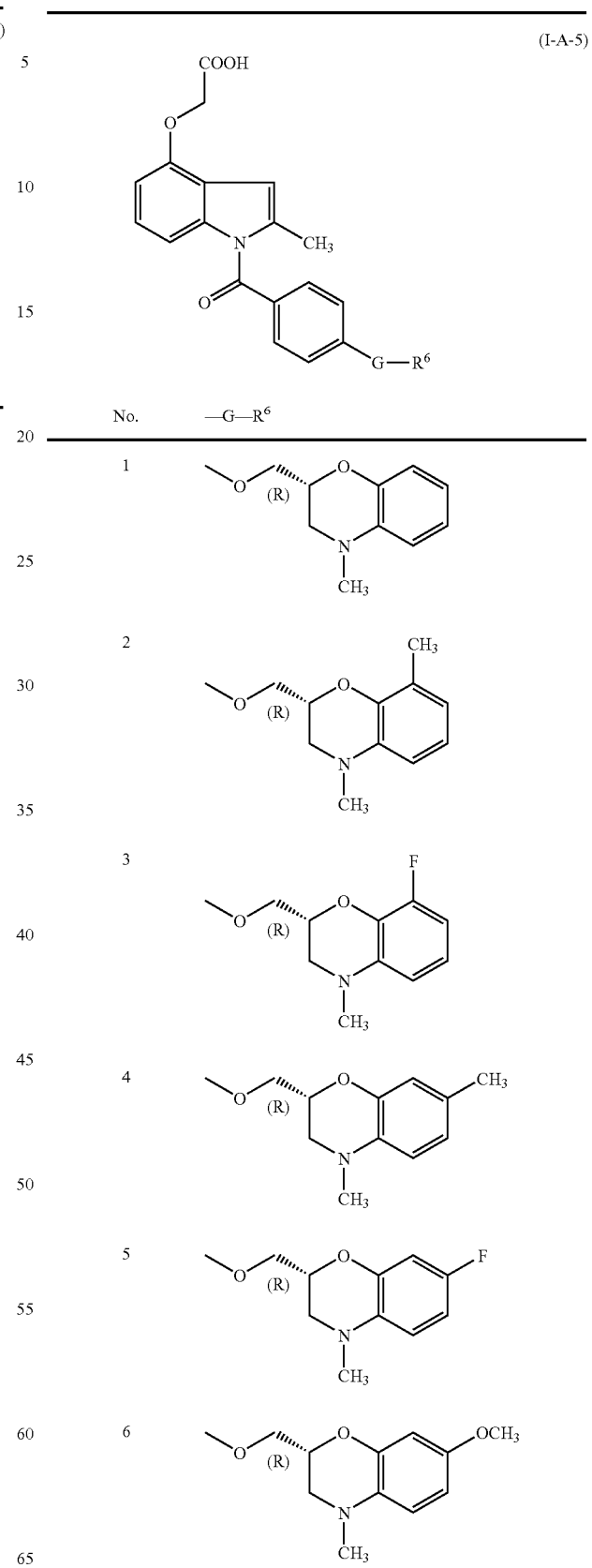

TABLE 10-continued (I-A-5)

| No. | —G—R⁶ |
|---|---|
| 7 | 4-methyl-6-methyl-benzoxazine with (R)-CH₂OCH₃ |
| 8 | 4-methyl-6-fluoro-benzoxazine with (R)-CH₂OCH₃ |
| 9 | 4-methyl-6-methoxy-benzoxazine with (R)-CH₂OCH₃ |
| 10 | 4-methyl-5-fluoro-benzoxazine with (R)-CH₂OCH₃ |
| 11 | 4-methyl-5-methoxy-benzoxazine with (R)-CH₂OCH₃ |
| 12 | benzodioxine with (R)-CH₂OCH₃ |
| 13 | 5-fluoro-benzodioxine with (R)-CH₂OCH₃ |
| 14 | 8-fluoro-benzodioxine with (R)-CH₂OCH₃ |
| 15 | benzoxathiine with (R)-CH₂OCH₃ |
| 16 | benzofuran with (R)-CH₂OCH₃ |
| 17 | benzofuran with (R)-CH₂OCH₃ (3-position) |
| 18 | 5-fluoro-benzofuran with (R)-CH₂OCH₃ |
| 19 | 6-fluoro-benzofuran with (R)-CH₂OCH₃ |
| 20 | 7-fluoro-benzofuran with (R)-CH₂OCH₃ |
| 21 | N-methyl-indoline with (R)-CH₂OCH₃ |

TABLE 11
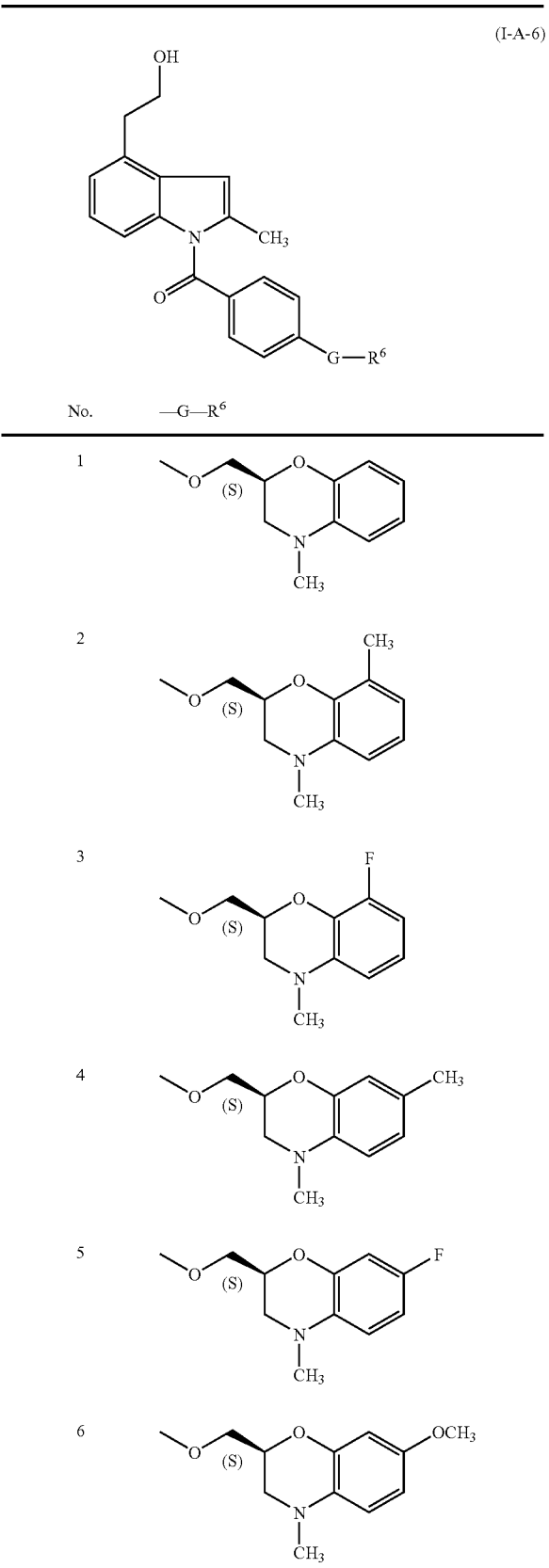
TABLE 11-continued
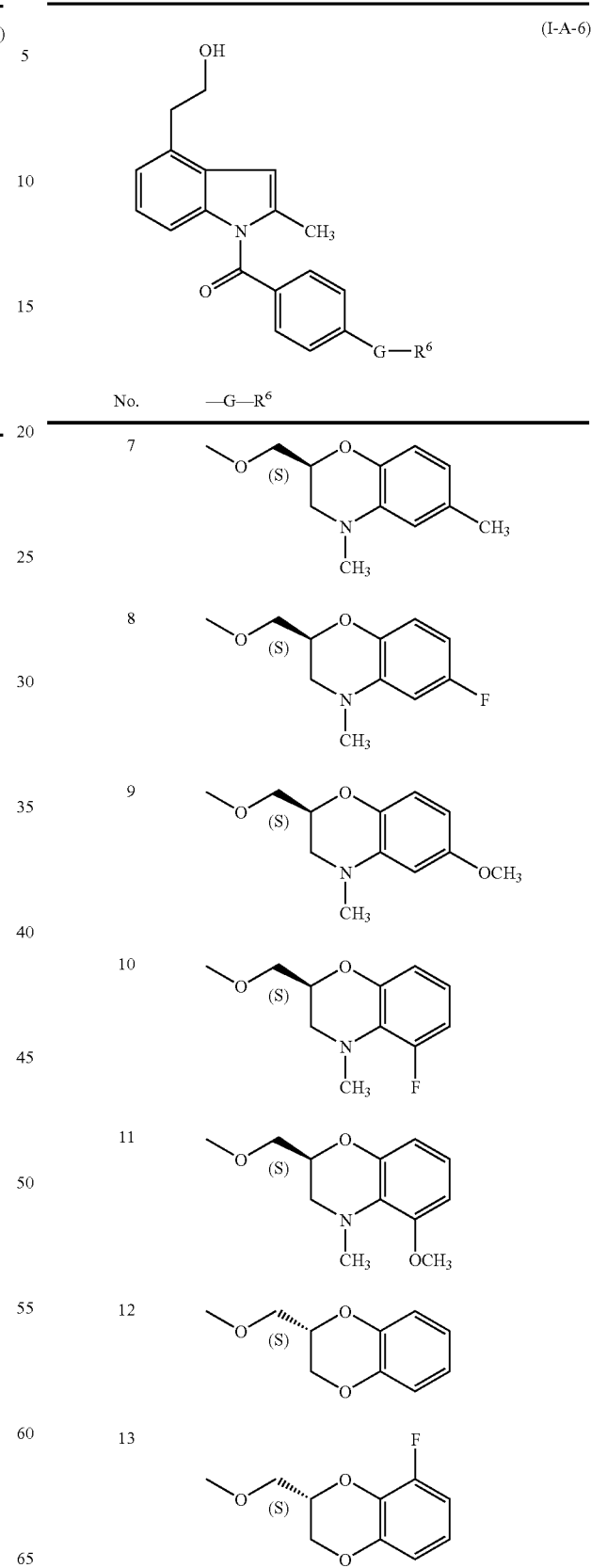

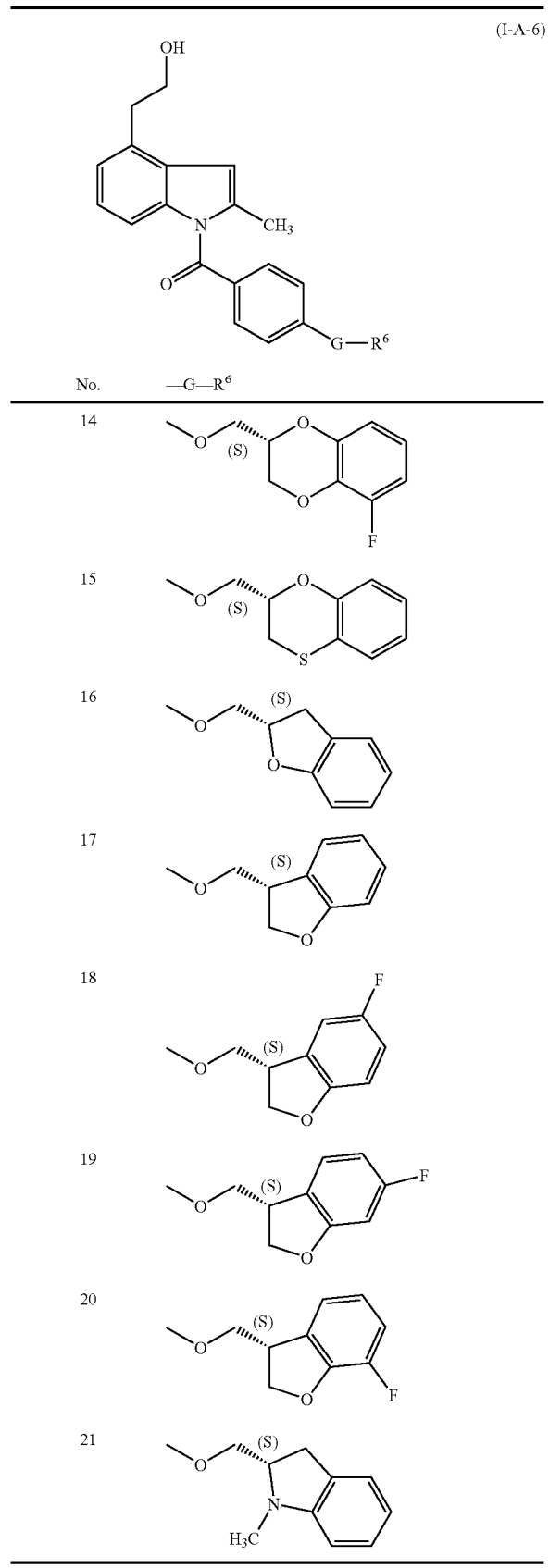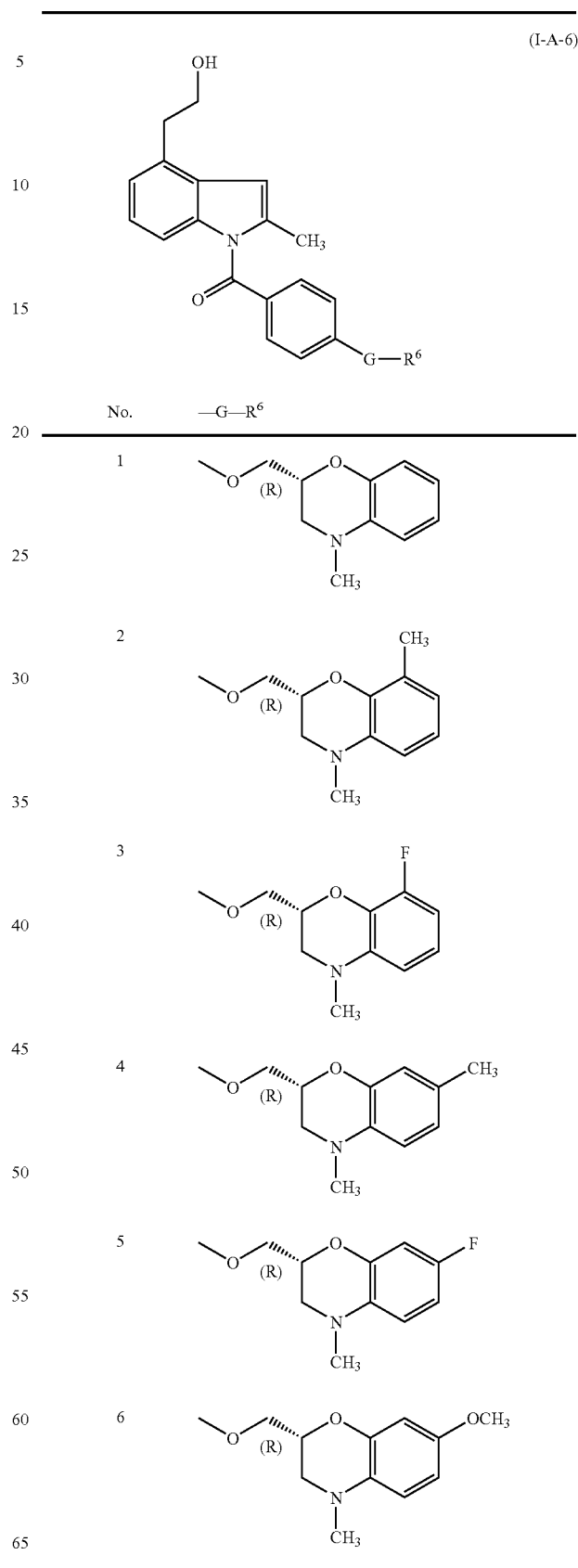

TABLE 12-continued
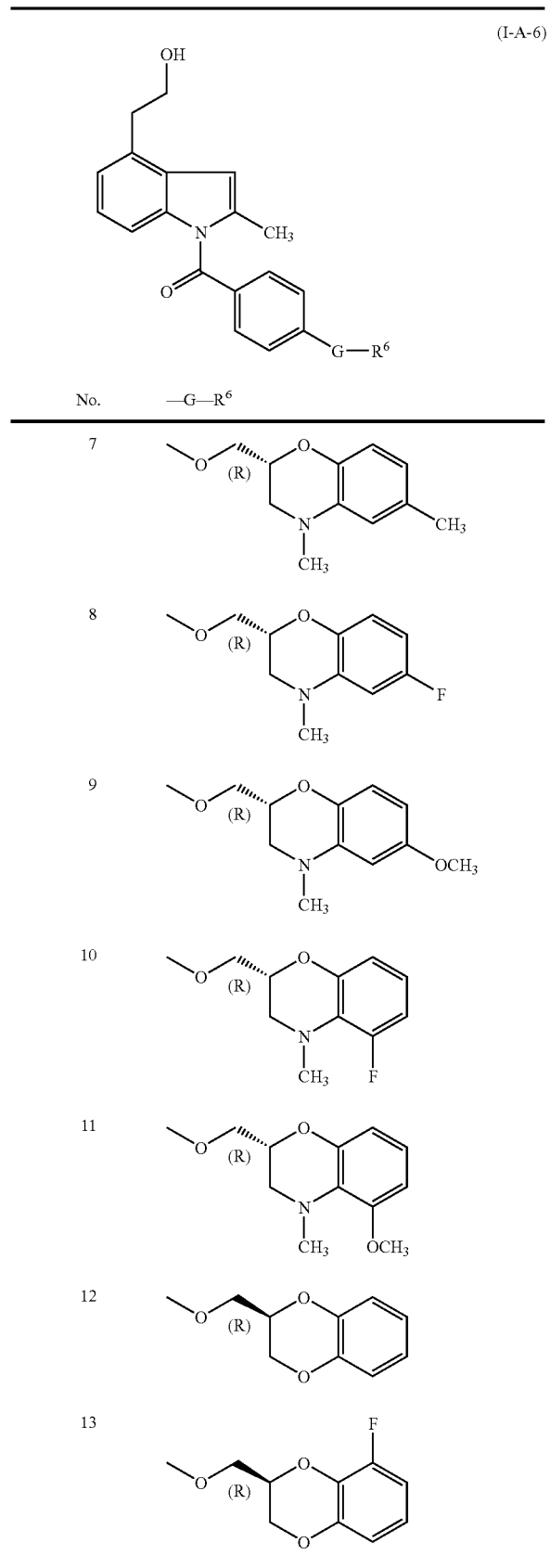
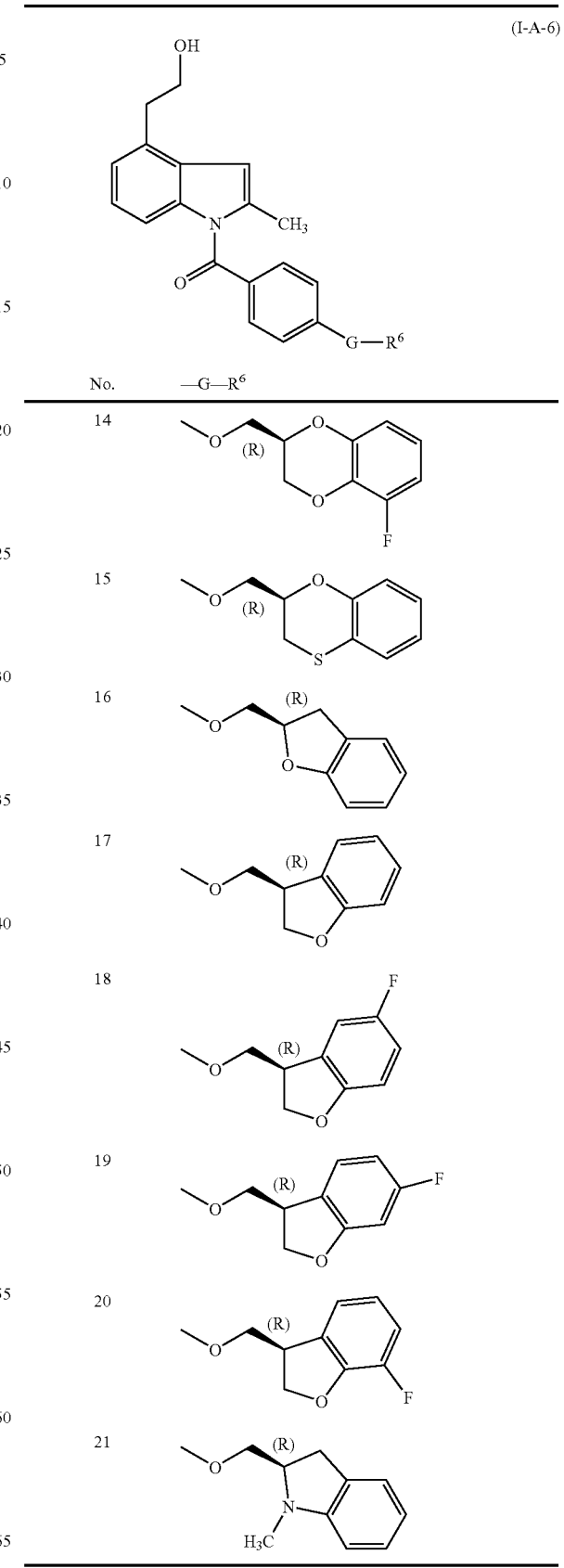

TABLE 13

(I-A-7)

[Structure: 2-(2-methyl-1-{4-(G-R6)benzoyl}-1H-indol-4-yl)ethyl acetate]

| No. | —G—R⁶ |
|---|---|
| 1 | (S)-4-methyl-2-(methoxymethyl)-3,4-dihydro-2H-1,4-benzoxazine |
| 2 | (S)-4,8-dimethyl-2-(methoxymethyl)-3,4-dihydro-2H-1,4-benzoxazine |
| 3 | (S)-8-fluoro-4-methyl-2-(methoxymethyl)-3,4-dihydro-2H-1,4-benzoxazine |
| 4 | (S)-4,7-dimethyl-2-(methoxymethyl)-3,4-dihydro-2H-1,4-benzoxazine |
| 5 | (S)-7-fluoro-4-methyl-2-(methoxymethyl)-3,4-dihydro-2H-1,4-benzoxazine |
| 6 | (S)-7-methoxy-4-methyl-2-(methoxymethyl)-3,4-dihydro-2H-1,4-benzoxazine |

TABLE 13-continued (I-A-7)

[Structure: 2-(2-methyl-1-{4-(G-R6)benzoyl}-1H-indol-4-yl)ethyl acetate]

| No. | —G—R⁶ |
|---|---|
| 7 | (S)-4,6-dimethyl-2-(methoxymethyl)-3,4-dihydro-2H-1,4-benzoxazine |
| 8 | (S)-6-fluoro-4-methyl-2-(methoxymethyl)-3,4-dihydro-2H-1,4-benzoxazine |
| 9 | (S)-6-methoxy-4-methyl-2-(methoxymethyl)-3,4-dihydro-2H-1,4-benzoxazine |
| 10 | (S)-5-fluoro-4-methyl-2-(methoxymethyl)-3,4-dihydro-2H-1,4-benzoxazine |
| 11 | (S)-5-methoxy-4-methyl-2-(methoxymethyl)-3,4-dihydro-2H-1,4-benzoxazine |
| 12 | (S)-2-(methoxymethyl)-2,3-dihydro-1,4-benzodioxine |
| 13 | (S)-5-fluoro-2-(methoxymethyl)-2,3-dihydro-1,4-benzodioxine |

TABLE 13-continued
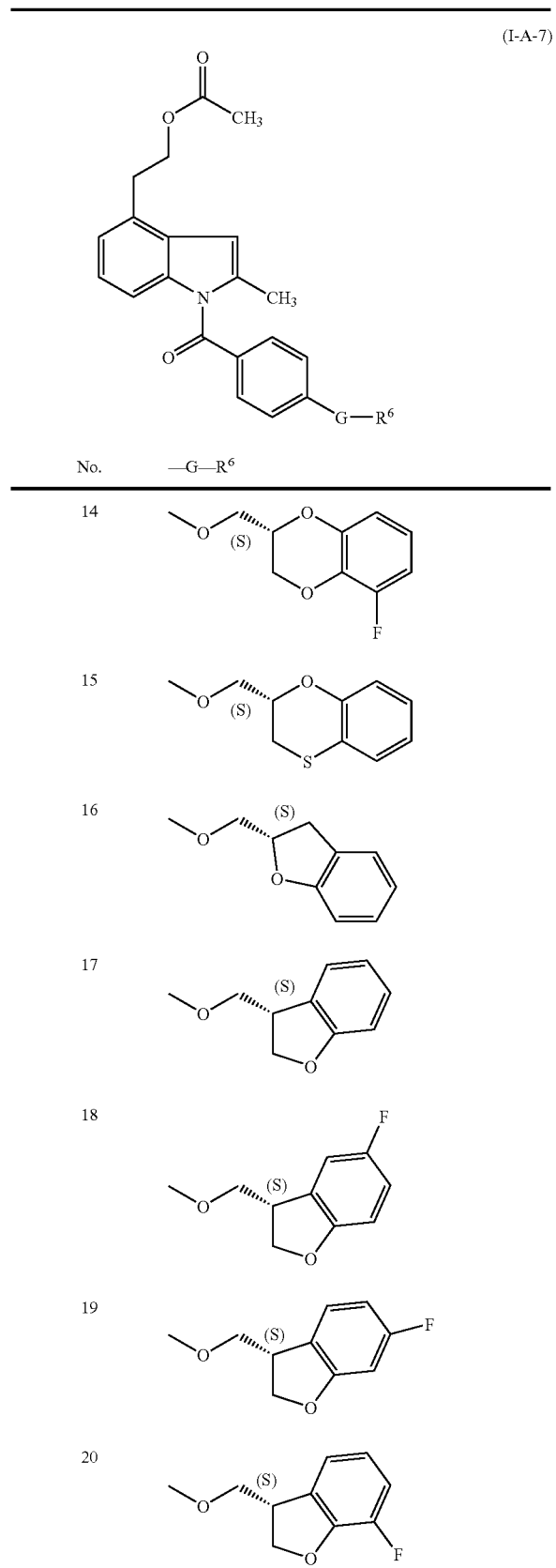
TABLE 13-continued
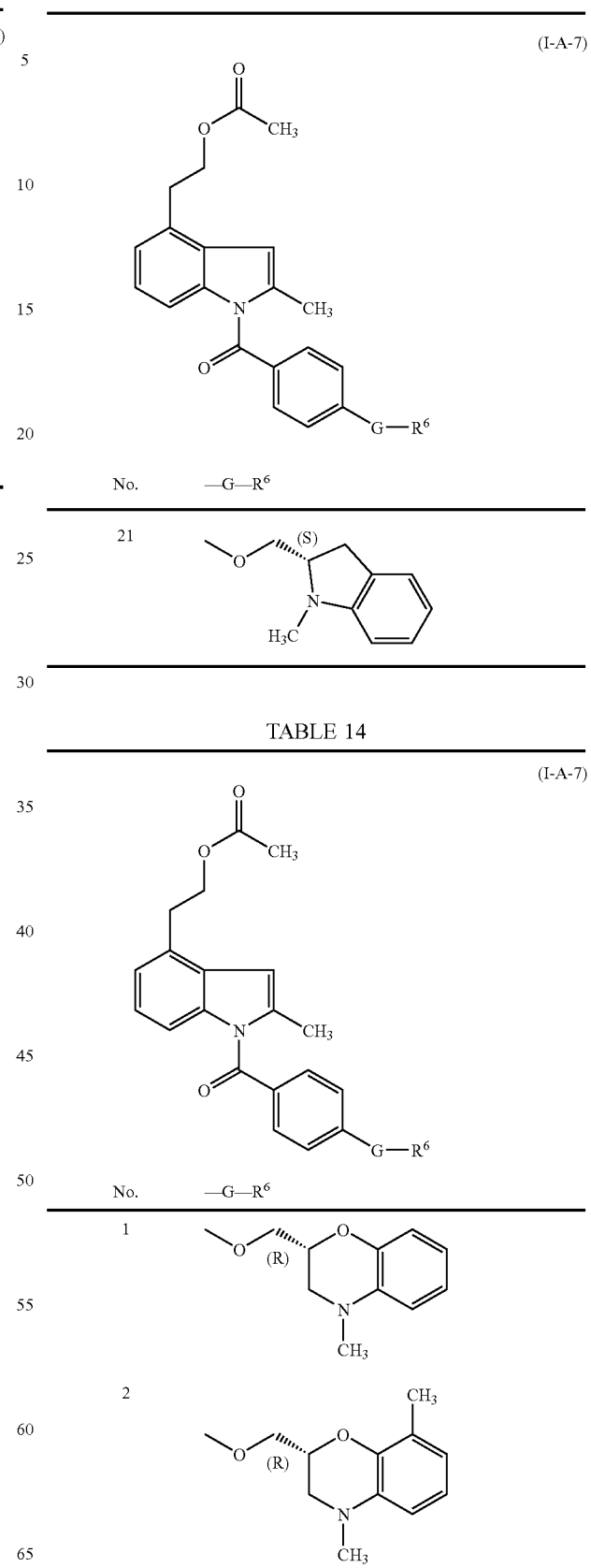
TABLE 14

TABLE 14-continued (I-A-7)

| No. | —G—R⁶ |
|---|---|
| 3 | (R)-2-methoxymethyl-8-fluoro-4-methyl-3,4-dihydro-2H-benzo[1,4]oxazine |
| 4 | (R)-2-methoxymethyl-7-methyl-4-methyl-3,4-dihydro-2H-benzo[1,4]oxazine |
| 5 | (R)-2-methoxymethyl-7-fluoro-4-methyl-3,4-dihydro-2H-benzo[1,4]oxazine |
| 6 | (R)-2-methoxymethyl-7-methoxy-4-methyl-3,4-dihydro-2H-benzo[1,4]oxazine |
| 7 | (R)-2-methoxymethyl-6-methyl-4-methyl-3,4-dihydro-2H-benzo[1,4]oxazine |
| 8 | (R)-2-methoxymethyl-6-fluoro-4-methyl-3,4-dihydro-2H-benzo[1,4]oxazine |
| 9 | (R)-2-methoxymethyl-6-methoxy-4-methyl-3,4-dihydro-2H-benzo[1,4]oxazine |
| 10 | (R)-2-methoxymethyl-5-fluoro-4-methyl-3,4-dihydro-2H-benzo[1,4]oxazine |
| 11 | (R)-2-methoxymethyl-5-methoxy-4-methyl-3,4-dihydro-2H-benzo[1,4]oxazine |
| 12 | (R)-2-methoxymethyl-2,3-dihydro-benzo[1,4]dioxine |
| 13 | (R)-2-methoxymethyl-5-fluoro-2,3-dihydro-benzo[1,4]dioxine |
| 14 | (R)-2-methoxymethyl-8-fluoro-2,3-dihydro-benzo[1,4]dioxine |
| 15 | (R)-2-methoxymethyl-2,3-dihydro-benzo[1,4]oxathiine |

TABLE 14-continued (I-A-7)

| No. | —G—R⁶ |
|---|---|
| 16 | (R) 2,3-dihydrobenzofuran-2-yl methoxymethyl |
| 17 | (R) 2,3-dihydrobenzofuran-3-yl methoxymethyl |
| 18 | (R) 5-fluoro-2,3-dihydrobenzofuran-3-yl methoxymethyl |
| 19 | (R) 6-fluoro-2,3-dihydrobenzofuran-3-yl methoxymethyl |
| 20 | (R) 7-fluoro-2,3-dihydrobenzofuran-3-yl methoxymethyl |
| 21 | (R) 1-methylindolin-2-yl methoxymethyl |

TABLE 15

(I-A-8)

| No. | —G—R⁶ |
|---|---|
| 1 | (S) 4-methyl-3,4-dihydro-2H-benzo[1,4]oxazin-2-yl methoxymethyl |
| 2 | (S) 4,8-dimethyl-3,4-dihydro-2H-benzo[1,4]oxazin-2-yl methoxymethyl |
| 3 | (S) 8-fluoro-4-methyl-3,4-dihydro-2H-benzo[1,4]oxazin-2-yl methoxymethyl |
| 4 | (S) 4,7-dimethyl-3,4-dihydro-2H-benzo[1,4]oxazin-2-yl methoxymethyl |
| 5 | (S) 7-fluoro-4-methyl-3,4-dihydro-2H-benzo[1,4]oxazin-2-yl methoxymethyl |
| 6 | (S) 7-methoxy-4-methyl-3,4-dihydro-2H-benzo[1,4]oxazin-2-yl methoxymethyl |

TABLE 15-continued

TABLE 16
(I-A-8)
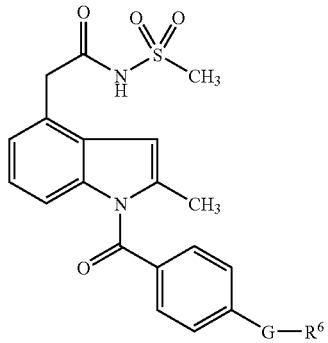
| No. | —G—R⁶ |
|---|---|
| 1 | 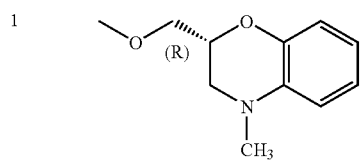 |
| 2 | 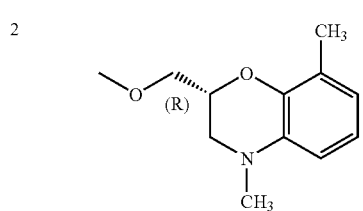 |
| 3 | 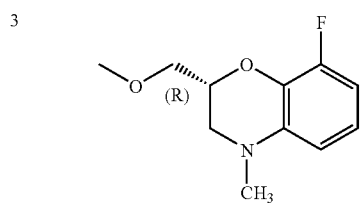 |
| 4 | 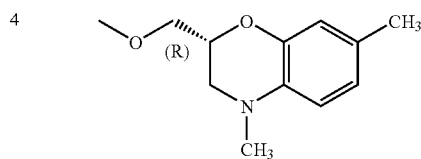 |
| 5 | 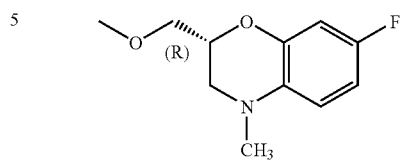 |
| 6 | 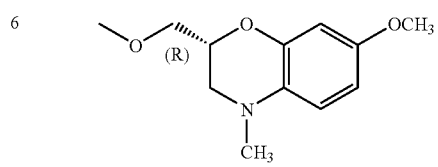 |
TABLE 16-continued
(I-A-8)
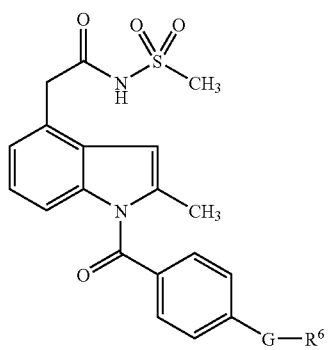
| No. | —G—R⁶ |
|---|---|
| 7 | 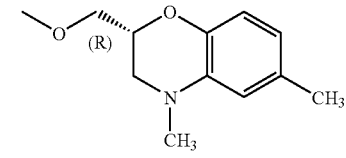 |
| 8 | 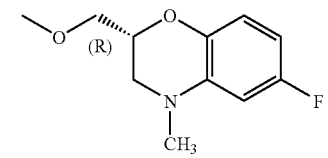 |
| 9 | 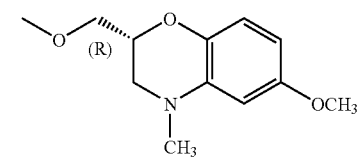 |
| 10 | 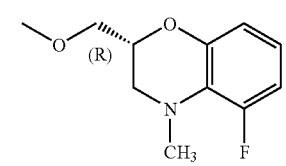 |
| 11 | 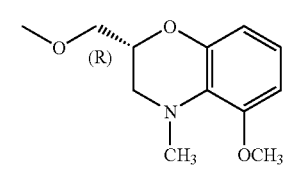 |
| 12 | 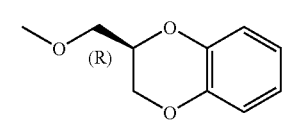 |
| 13 | |

TABLE 16-continued
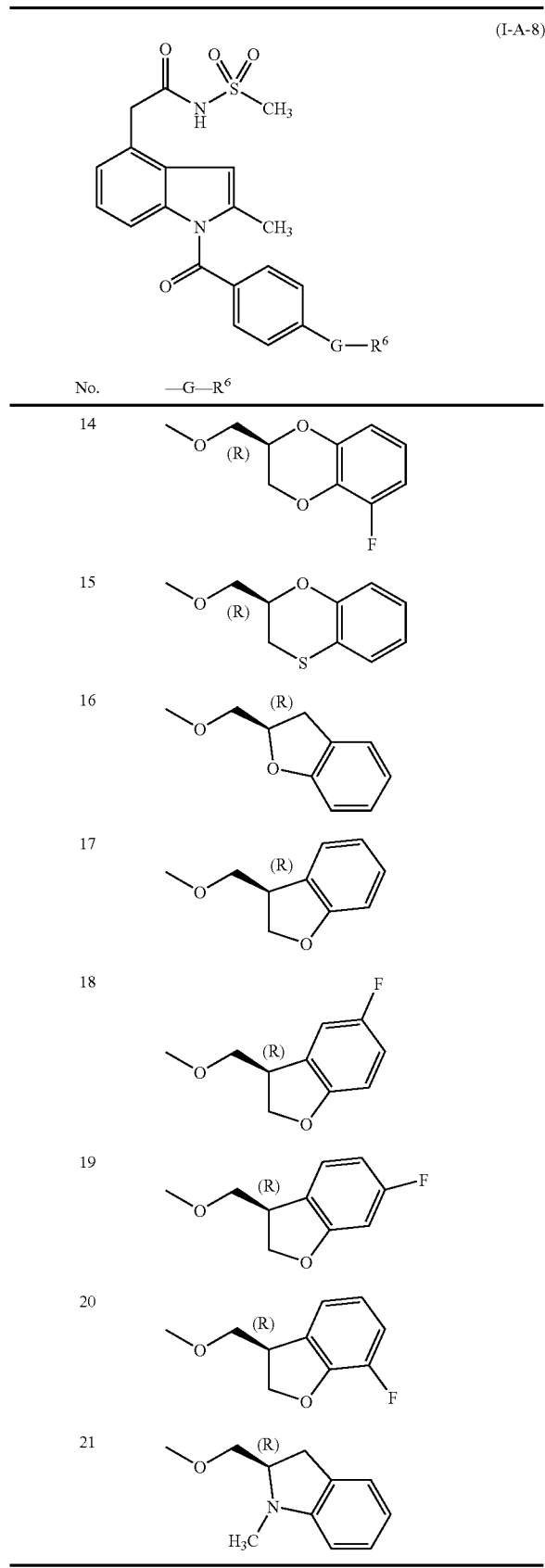
TABLE 17
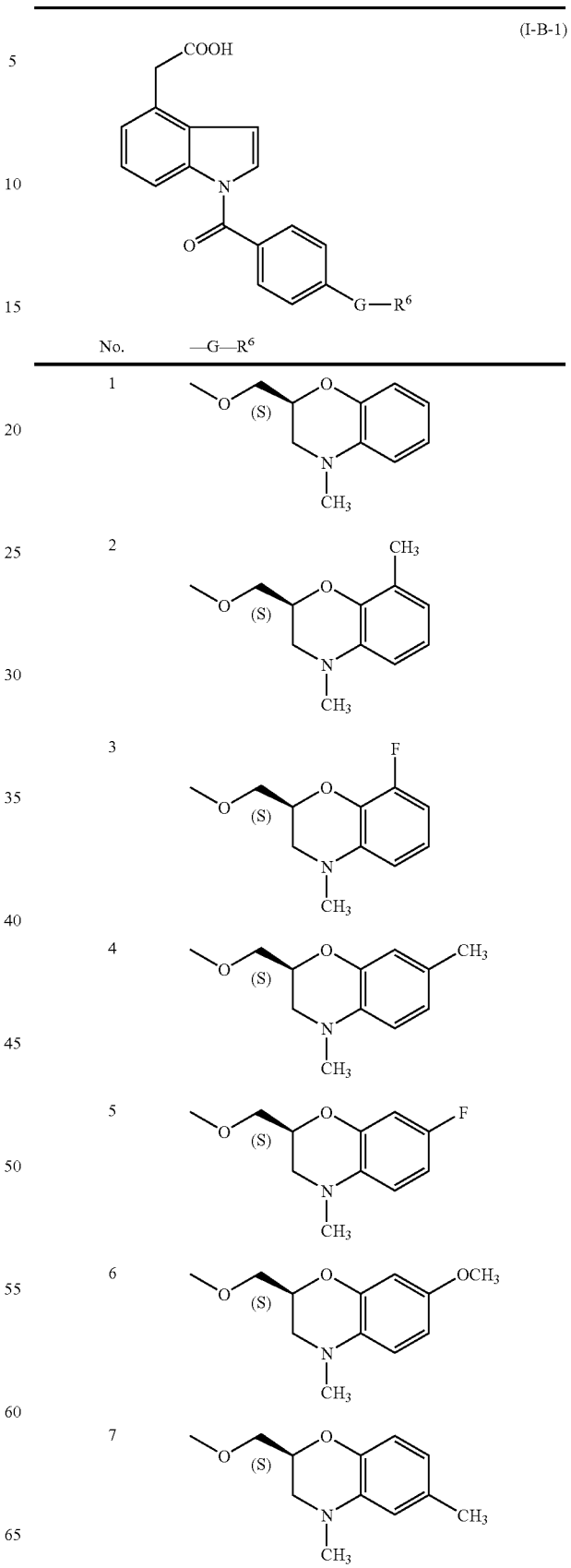

TABLE 17-continued
(I-B-1)
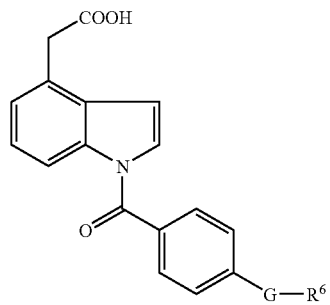
| No. | —G—R⁶ |
|---|---|
| 8 | 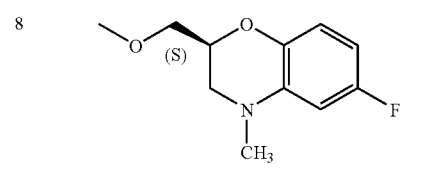 |
| 9 | 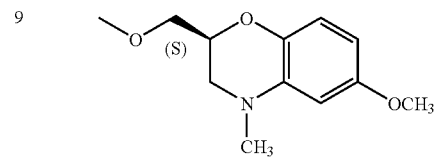 |
| 10 | 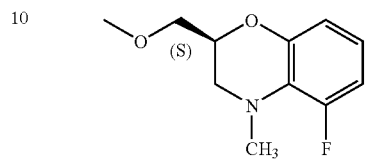 |
| 11 | 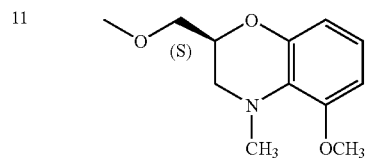 |
| 12 | 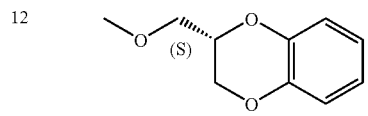 |
| 13 | 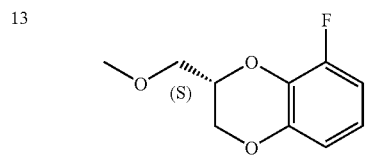 |
| 14 | 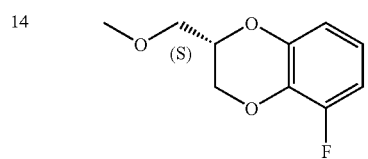 |
TABLE 17-continued
(I-B-1)
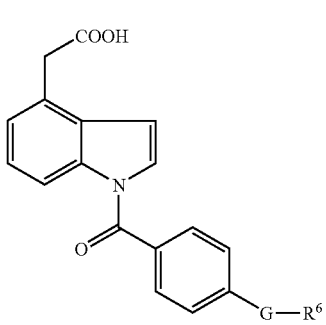
| No. | —G—R⁶ |
|---|---|
| 15 | 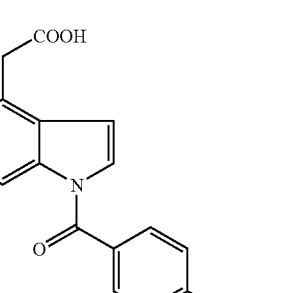 |
| 16 | 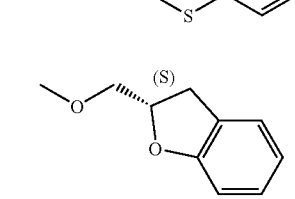 |
| 17 | 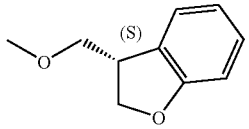 |
| 18 | 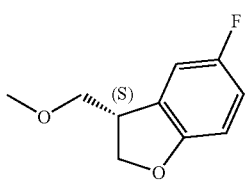 |
| 19 | 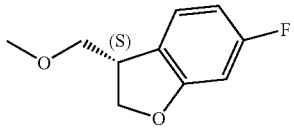 |
| 20 | 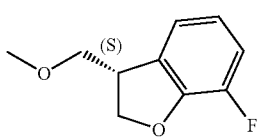 |
| 21 | 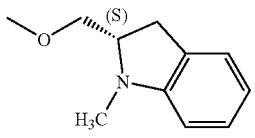 |

TABLE 18

(I-B-1)

| No. | —G—R⁶ |
|---|---|
| 1 | (R)-2-(methoxymethyl)-4-methyl-3,4-dihydro-2H-benzo[b][1,4]oxazine |
| 2 | (R)-2-(methoxymethyl)-4,8-dimethyl-3,4-dihydro-2H-benzo[b][1,4]oxazine |
| 3 | (R)-8-fluoro-2-(methoxymethyl)-4-methyl-3,4-dihydro-2H-benzo[b][1,4]oxazine |
| 4 | (R)-2-(methoxymethyl)-4,7-dimethyl-3,4-dihydro-2H-benzo[b][1,4]oxazine |
| 5 | (R)-7-fluoro-2-(methoxymethyl)-4-methyl-3,4-dihydro-2H-benzo[b][1,4]oxazine |
| 6 | (R)-2-(methoxymethyl)-7-methoxy-4-methyl-3,4-dihydro-2H-benzo[b][1,4]oxazine |
| 7 | (R)-2-(methoxymethyl)-4,6-dimethyl-3,4-dihydro-2H-benzo[b][1,4]oxazine |
| 8 | (R)-6-fluoro-2-(methoxymethyl)-4-methyl-3,4-dihydro-2H-benzo[b][1,4]oxazine |
| 9 | (R)-2-(methoxymethyl)-6-methoxy-4-methyl-3,4-dihydro-2H-benzo[b][1,4]oxazine |
| 10 | (R)-5-fluoro-2-(methoxymethyl)-4-methyl-3,4-dihydro-2H-benzo[b][1,4]oxazine |
| 11 | (R)-2-(methoxymethyl)-5-methoxy-4-methyl-3,4-dihydro-2H-benzo[b][1,4]oxazine |
| 12 | (R)-2-(methoxymethyl)-2,3-dihydro-1,4-benzodioxine |
| 13 | (R)-5-fluoro-2-(methoxymethyl)-2,3-dihydro-1,4-benzodioxine |

TABLE 18-continued
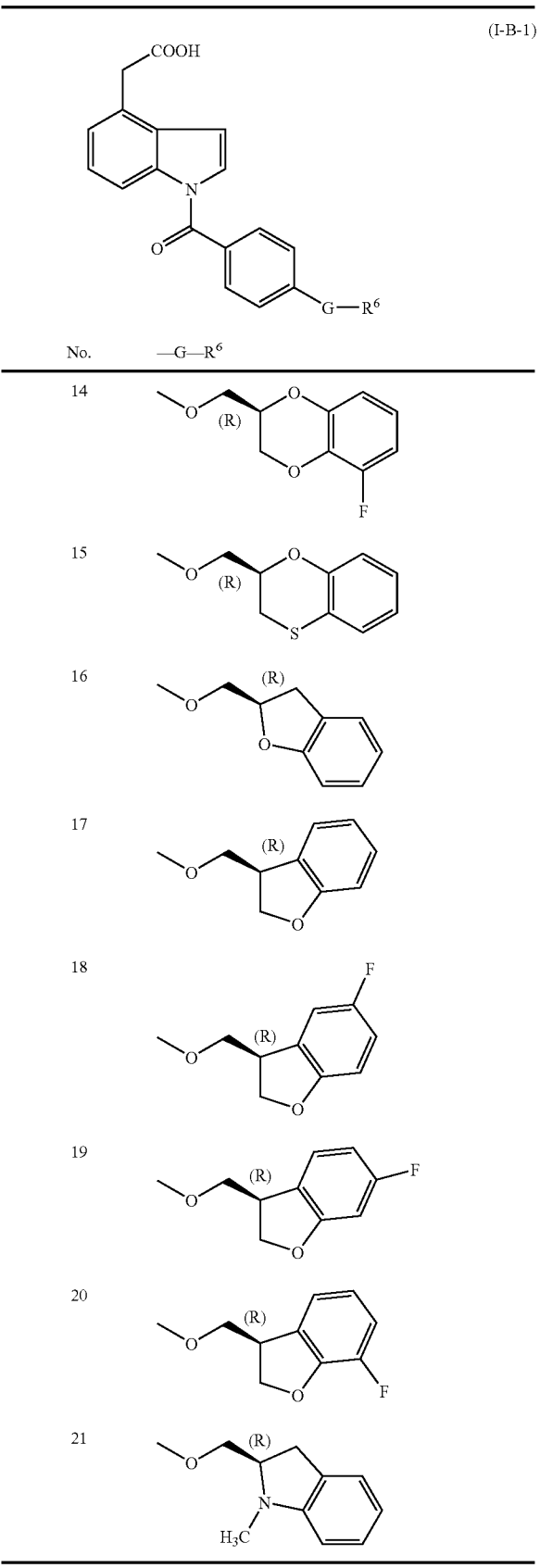
TABLE 19
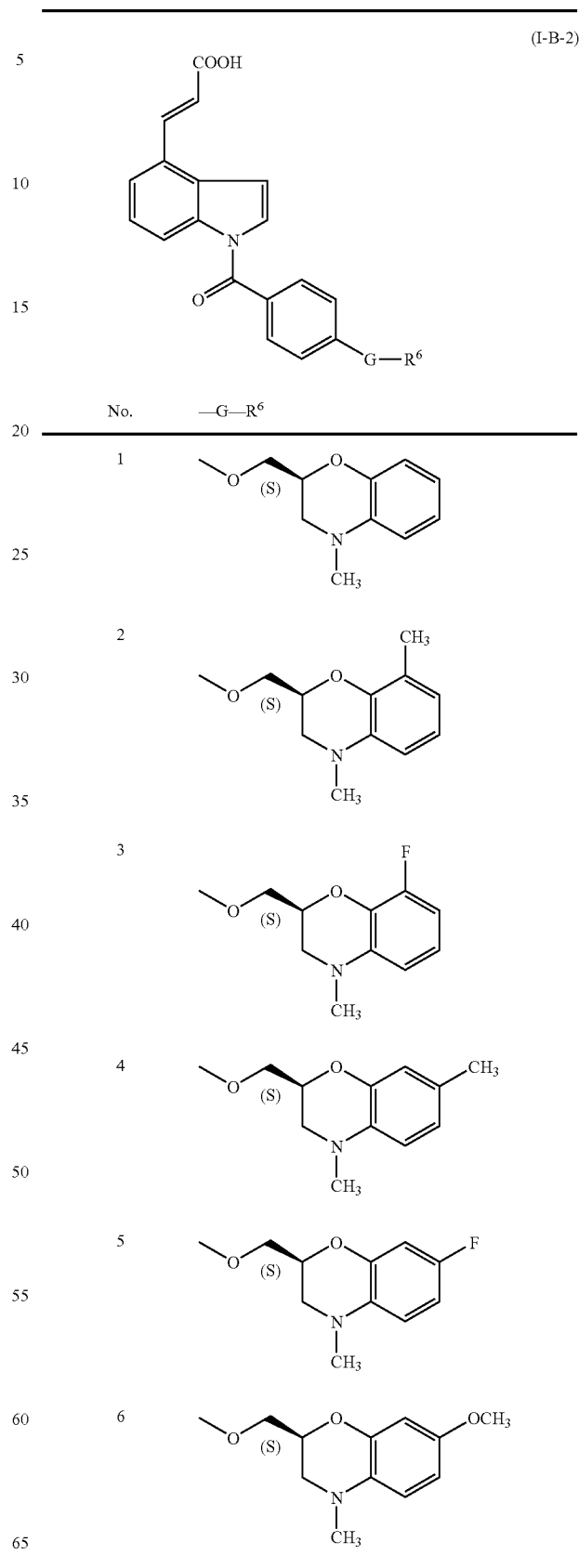

TABLE 19-continued (I-B-2)

| No. | —G—R⁶ |
|---|---|
| 7 | (S)-2-(methoxymethyl)-4,6-dimethyl-3,4-dihydro-2H-benzo[b][1,4]oxazine |
| 8 | (S)-6-fluoro-2-(methoxymethyl)-4-methyl-3,4-dihydro-2H-benzo[b][1,4]oxazine |
| 9 | (S)-2-(methoxymethyl)-6-methoxy-4-methyl-3,4-dihydro-2H-benzo[b][1,4]oxazine |
| 10 | (S)-5-fluoro-2-(methoxymethyl)-4-methyl-3,4-dihydro-2H-benzo[b][1,4]oxazine |
| 11 | (S)-2-(methoxymethyl)-5-methoxy-4-methyl-3,4-dihydro-2H-benzo[b][1,4]oxazine |
| 12 | (S)-2-(methoxymethyl)-2,3-dihydro-1,4-benzodioxine |
| 13 | (S)-5-fluoro-2-(methoxymethyl)-2,3-dihydro-1,4-benzodioxine |
| 14 | (S)-8-fluoro-2-(methoxymethyl)-2,3-dihydro-1,4-benzodioxine |
| 15 | (S)-2-(methoxymethyl)-2,3-dihydro-1,4-benzoxathiine |
| 16 | (S)-2-(methoxymethyl)-2,3-dihydrobenzofuran |
| 17 | (S)-3-(methoxymethyl)-2,3-dihydrobenzofuran |
| 18 | (S)-5-fluoro-3-(methoxymethyl)-2,3-dihydrobenzofuran |
| 19 | (S)-6-fluoro-3-(methoxymethyl)-2,3-dihydrobenzofuran |
| 20 | (S)-7-fluoro-3-(methoxymethyl)-2,3-dihydrobenzofuran |
| 21 | (S)-2-(methoxymethyl)-1-methyl-2,3-dihydroindole |

TABLE 20

(I-B-2) structure: indole with acrylic acid (COOH) at 4-position, N-acylated with 4-(G-R⁶)-benzoyl group.

| No. | —G—R⁶ |
|---|---|
| 1 | (R)-4-methyl-2-(methoxymethyl)-3,4-dihydro-2H-1,4-benzoxazine |
| 2 | (R)-8-methyl-4-methyl-2-(methoxymethyl)-3,4-dihydro-2H-1,4-benzoxazine |
| 3 | (R)-8-fluoro-4-methyl-2-(methoxymethyl)-3,4-dihydro-2H-1,4-benzoxazine |
| 4 | (R)-7-methyl-4-methyl-2-(methoxymethyl)-3,4-dihydro-2H-1,4-benzoxazine |
| 5 | (R)-7-fluoro-4-methyl-2-(methoxymethyl)-3,4-dihydro-2H-1,4-benzoxazine |
| 6 | (R)-7-methoxy-4-methyl-2-(methoxymethyl)-3,4-dihydro-2H-1,4-benzoxazine |
| 7 | (R)-6-methyl-4-methyl-2-(methoxymethyl)-3,4-dihydro-2H-1,4-benzoxazine |
| 8 | (R)-6-fluoro-4-methyl-2-(methoxymethyl)-3,4-dihydro-2H-1,4-benzoxazine |
| 9 | (R)-6-methoxy-4-methyl-2-(methoxymethyl)-3,4-dihydro-2H-1,4-benzoxazine |
| 10 | (R)-5-fluoro-4-methyl-2-(methoxymethyl)-3,4-dihydro-2H-1,4-benzoxazine |
| 11 | (R)-5-methoxy-4-methyl-2-(methoxymethyl)-3,4-dihydro-2H-1,4-benzoxazine |
| 12 | (R)-2-(methoxymethyl)-2,3-dihydro-1,4-benzodioxine |
| 13 | (R)-5-fluoro-2-(methoxymethyl)-2,3-dihydro-1,4-benzodioxine |

TABLE 20-continued (I-B-2)

| No. | —G—R⁶ |
|---|---|
| 14 | (R) 8-fluoro-2,3-dihydro-1,4-benzodioxin-2-ylmethyl methyl ether |
| 15 | (R) 2,3-dihydro-1,4-benzoxathiin-2-ylmethyl methyl ether |
| 16 | (R) 2,3-dihydrobenzofuran-2-ylmethyl methyl ether |
| 17 | (R) 2,3-dihydrobenzofuran-3-ylmethyl methyl ether |
| 18 | (R) 5-fluoro-2,3-dihydrobenzofuran-3-ylmethyl methyl ether |
| 19 | (R) 6-fluoro-2,3-dihydrobenzofuran-3-ylmethyl methyl ether |
| 20 | (R) 7-fluoro-2,3-dihydrobenzofuran-3-ylmethyl methyl ether |
| 21 | (R) 1-methylindolin-2-ylmethyl methyl ether |

TABLE 21

(I-B-3)

| No. | —G—R⁶ |
|---|---|
| 1 | (S) 4-methyl-3,4-dihydro-2H-1,4-benzoxazin-2-ylmethyl methyl ether |
| 2 | (S) 4,8-dimethyl-3,4-dihydro-2H-1,4-benzoxazin-2-ylmethyl methyl ether |
| 3 | (S) 8-fluoro-4-methyl-3,4-dihydro-2H-1,4-benzoxazin-2-ylmethyl methyl ether |
| 4 | (S) 4,7-dimethyl-3,4-dihydro-2H-1,4-benzoxazin-2-ylmethyl methyl ether |
| 5 | (S) 7-fluoro-4-methyl-3,4-dihydro-2H-1,4-benzoxazin-2-ylmethyl methyl ether |
| 6 | (S) 7-methoxy-4-methyl-3,4-dihydro-2H-1,4-benzoxazin-2-ylmethyl methyl ether |

TABLE 21-continued
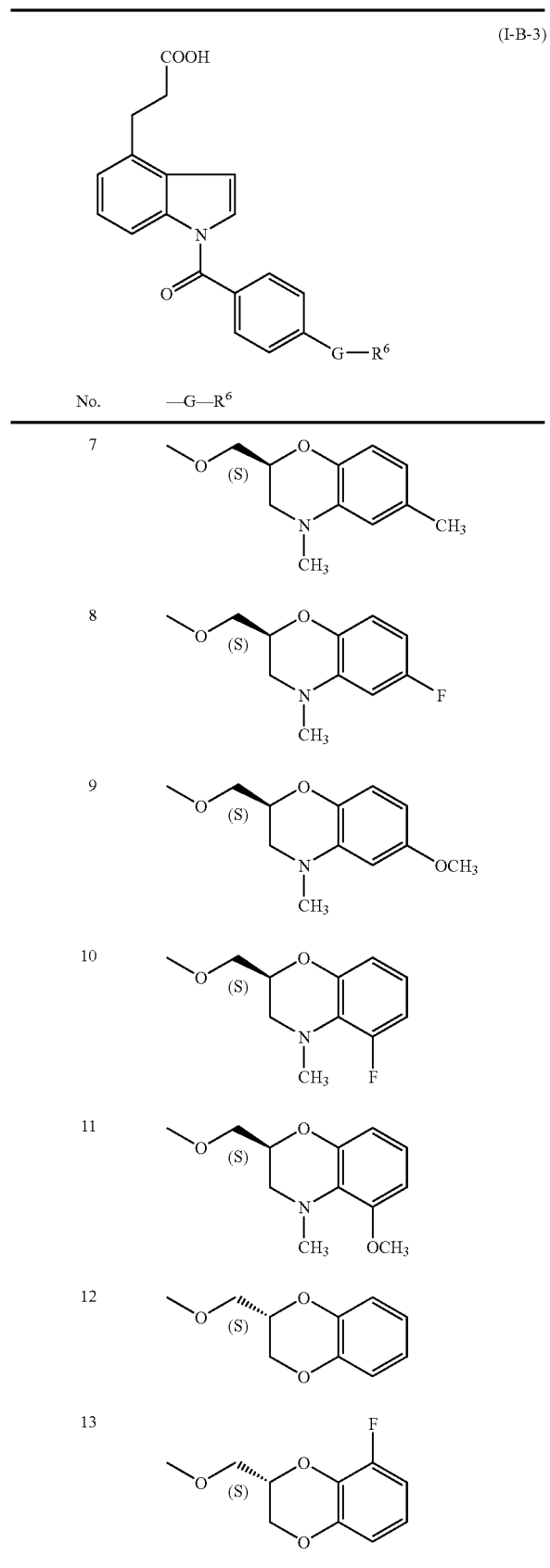
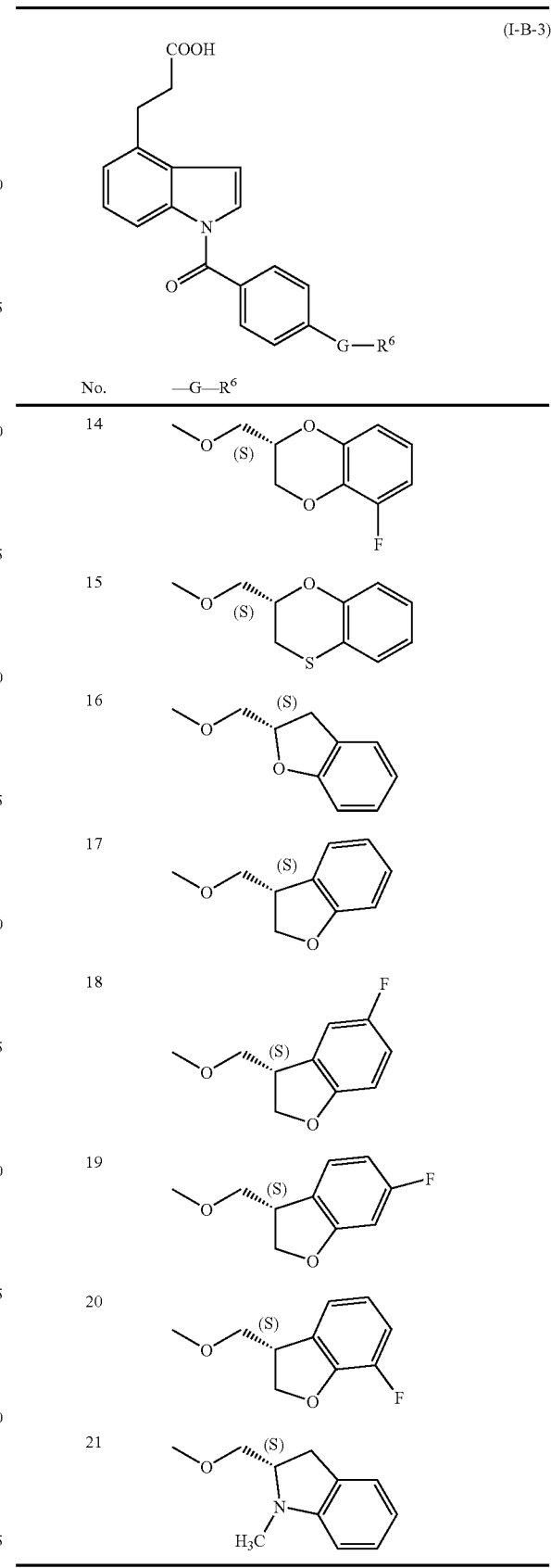

TABLE 22

(I-B-3)

| No. | —G—R⁶ |
|---|---|
| 1 | (R)-4-methyl-2-(methoxymethyl)-3,4-dihydro-2H-1,4-benzoxazine |
| 2 | (R)-4,8-dimethyl-2-(methoxymethyl)-3,4-dihydro-2H-1,4-benzoxazine |
| 3 | (R)-8-fluoro-4-methyl-2-(methoxymethyl)-3,4-dihydro-2H-1,4-benzoxazine |
| 4 | (R)-4,7-dimethyl-2-(methoxymethyl)-3,4-dihydro-2H-1,4-benzoxazine |
| 5 | (R)-7-fluoro-4-methyl-2-(methoxymethyl)-3,4-dihydro-2H-1,4-benzoxazine |
| 6 | (R)-7-methoxy-4-methyl-2-(methoxymethyl)-3,4-dihydro-2H-1,4-benzoxazine |

TABLE 22-continued (I-B-3)

| No. | —G—R⁶ |
|---|---|
| 7 | (R)-4,6-dimethyl-2-(methoxymethyl)-3,4-dihydro-2H-1,4-benzoxazine |
| 8 | (R)-6-fluoro-4-methyl-2-(methoxymethyl)-3,4-dihydro-2H-1,4-benzoxazine |
| 9 | (R)-6-methoxy-4-methyl-2-(methoxymethyl)-3,4-dihydro-2H-1,4-benzoxazine |
| 10 | (R)-5-fluoro-4-methyl-2-(methoxymethyl)-3,4-dihydro-2H-1,4-benzoxazine |
| 11 | (R)-5-methoxy-4-methyl-2-(methoxymethyl)-3,4-dihydro-2H-1,4-benzoxazine |
| 12 | (R)-2-(methoxymethyl)-2,3-dihydro-1,4-benzodioxine |
| 13 | (R)-5-fluoro-2-(methoxymethyl)-2,3-dihydro-1,4-benzodioxine |

TABLE 22-continued (I-B-3)

| No. | —G—R⁶ |
|---|---|
| 14 | 2,3-dihydro-1,4-benzodioxin (R), 8-F, with OCH₂ |
| 15 | 2,3-dihydro-1,4-benzoxathiine (R), with OCH₂ |
| 16 | 2,3-dihydrobenzofuran-2-yl (R), with OCH₂ |
| 17 | 2,3-dihydrobenzofuran-3-yl (R), with OCH₂ |
| 18 | 2,3-dihydrobenzofuran-3-yl (R), 5-F, with OCH₂ |
| 19 | 2,3-dihydrobenzofuran-3-yl (R), 6-F, with OCH₂ |
| 20 | 2,3-dihydrobenzofuran-3-yl (R), 7-F, with OCH₂ |
| 21 | 1-methylindolin-2-yl (R), with OCH₂ |

TABLE 23

(I-B-4)

| No. | —G—R⁶ |
|---|---|
| 1 | 4-methyl-3,4-dihydro-2H-1,4-benzoxazin-2-yl (S), with OCH₂ |
| 2 | 4-methyl-8-CH₃-3,4-dihydro-2H-1,4-benzoxazin-2-yl (S), with OCH₂ |
| 3 | 4-methyl-8-F-3,4-dihydro-2H-1,4-benzoxazin-2-yl (S), with OCH₂ |
| 4 | 4-methyl-7-CH₃-3,4-dihydro-2H-1,4-benzoxazin-2-yl (S), with OCH₂ |
| 5 | 4-methyl-7-F-3,4-dihydro-2H-1,4-benzoxazin-2-yl (S), with OCH₂ |
| 6 | 4-methyl-7-OCH₃-3,4-dihydro-2H-1,4-benzoxazin-2-yl (S), with OCH₂ |
| 7 | 4-methyl-6-CH₃-3,4-dihydro-2H-1,4-benzoxazin-2-yl (S), with OCH₂ |

TABLE 23-continued (I-B-4)

| No. | —G—R⁶ |
|---|---|
| 8 | 4-methyl-6-fluoro-(S)-2-(methoxymethyl)-3,4-dihydro-2H-benzo[1,4]oxazine |
| 9 | 4-methyl-6-methoxy-(S)-2-(methoxymethyl)-3,4-dihydro-2H-benzo[1,4]oxazine |
| 10 | 4-methyl-5-fluoro-(S)-2-(methoxymethyl)-3,4-dihydro-2H-benzo[1,4]oxazine |
| 11 | 4-methyl-5-methoxy-(S)-2-(methoxymethyl)-3,4-dihydro-2H-benzo[1,4]oxazine |
| 12 | (S)-2-(methoxymethyl)-2,3-dihydro-1,4-benzodioxine |
| 13 | 5-fluoro-(S)-2-(methoxymethyl)-2,3-dihydro-1,4-benzodioxine |
| 14 | 8-fluoro-(S)-2-(methoxymethyl)-2,3-dihydro-1,4-benzodioxine |
| 15 | (S)-2-(methoxymethyl)-2,3-dihydro-1,4-benzoxathiine |

TABLE 23-continued (I-B-4)

| No. | —G—R⁶ |
|---|---|
| 16 | (S)-2-(methoxymethyl)-2,3-dihydrobenzofuran |
| 17 | (S)-3-(methoxymethyl)-2,3-dihydrobenzofuran |
| 18 | 5-fluoro-(S)-3-(methoxymethyl)-2,3-dihydrobenzofuran |
| 19 | 6-fluoro-(S)-3-(methoxymethyl)-2,3-dihydrobenzofuran |
| 20 | 7-fluoro-(S)-3-(methoxymethyl)-2,3-dihydrobenzofuran |
| 21 | 1-methyl-(S)-2-(methoxymethyl)-2,3-dihydro-1H-indole |

TABLE 24
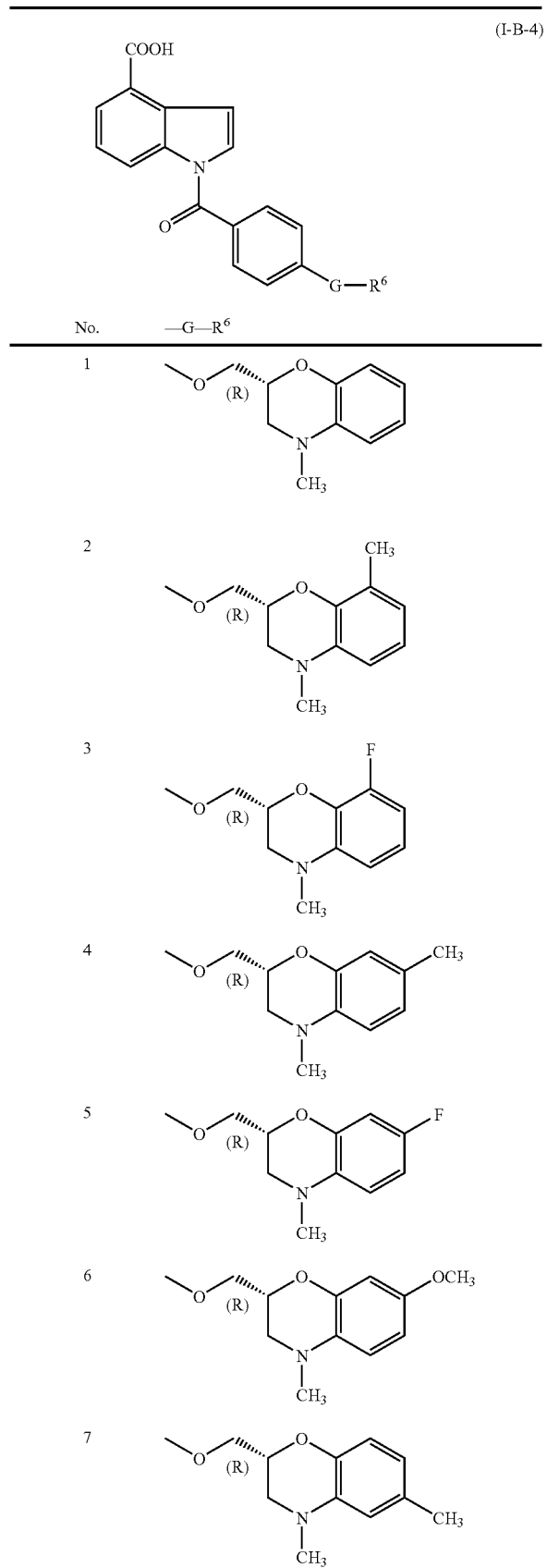
TABLE 24-continued
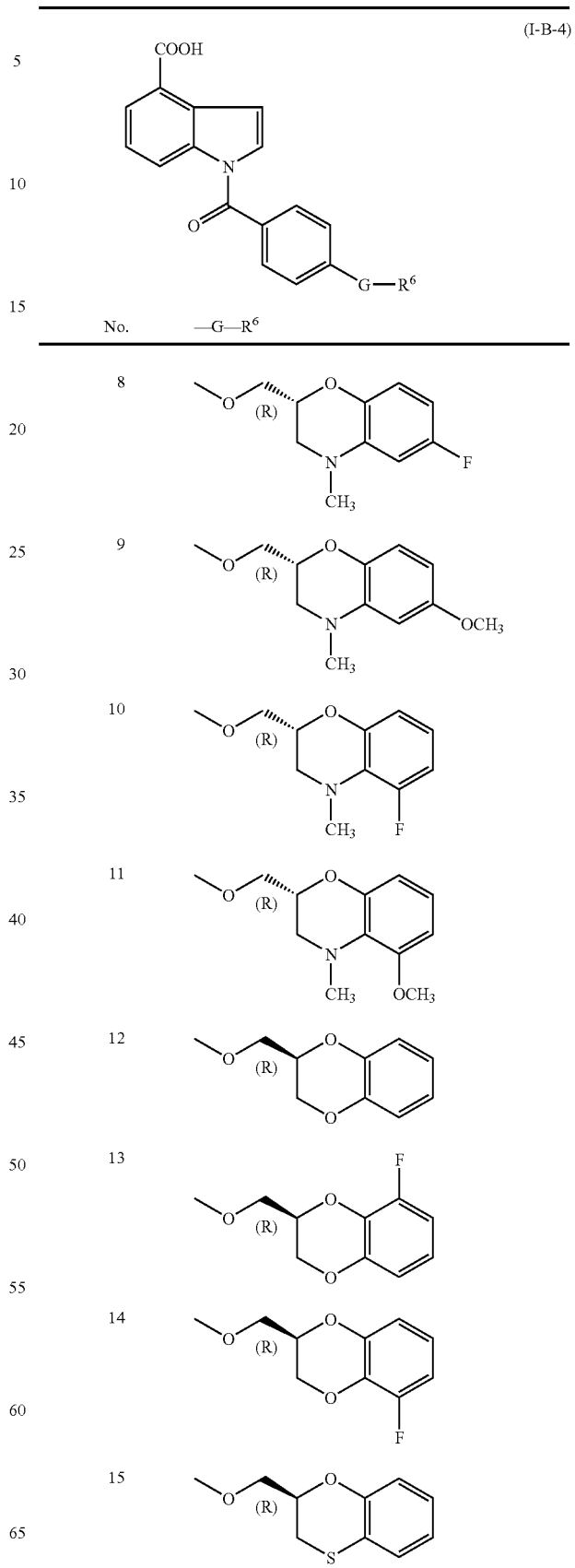

TABLE 24-continued
(I-B-4)
| No. | —G—R⁶ |
|---|---|
| 16 | 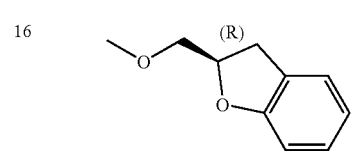 |
| 17 | 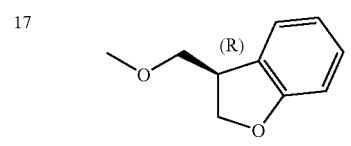 |
| 18 | 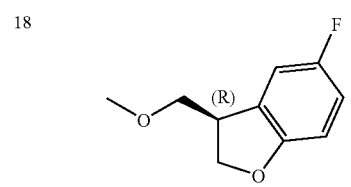 |
| 19 | 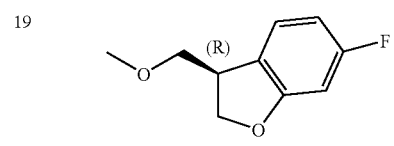 |
| 20 | 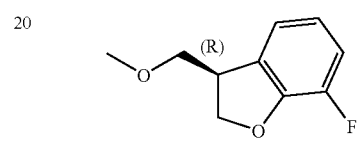 |
| 21 | 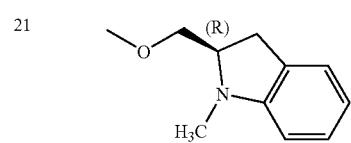 |
TABLE 25
(I-B-5)
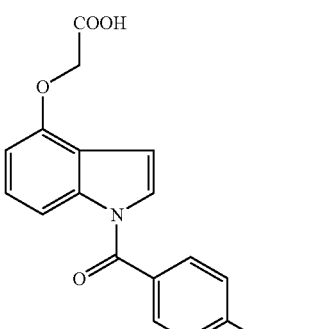
| No. | —G—R⁶ |
|---|---|
| 1 | 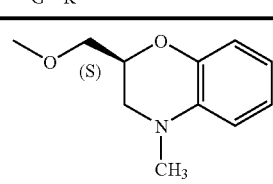 |
| 2 | 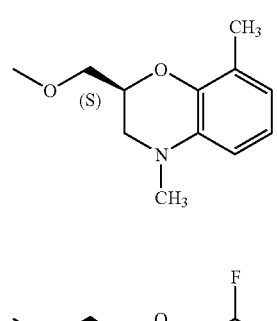 |
| 3 | 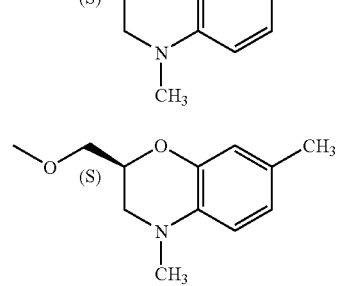 |
| 4 | |
| 5 | 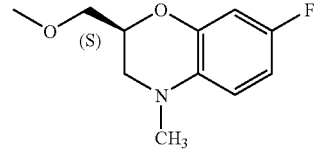 |
| 6 | 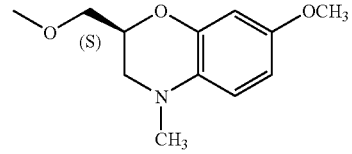 |

TABLE 25-continued
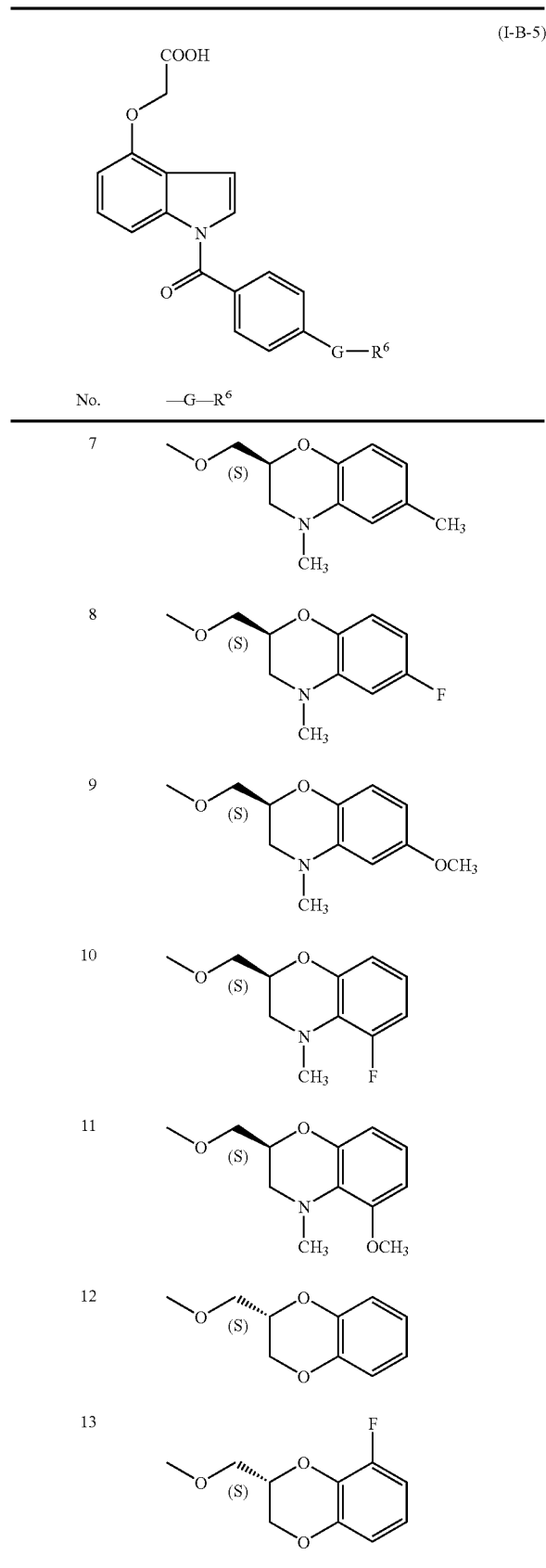
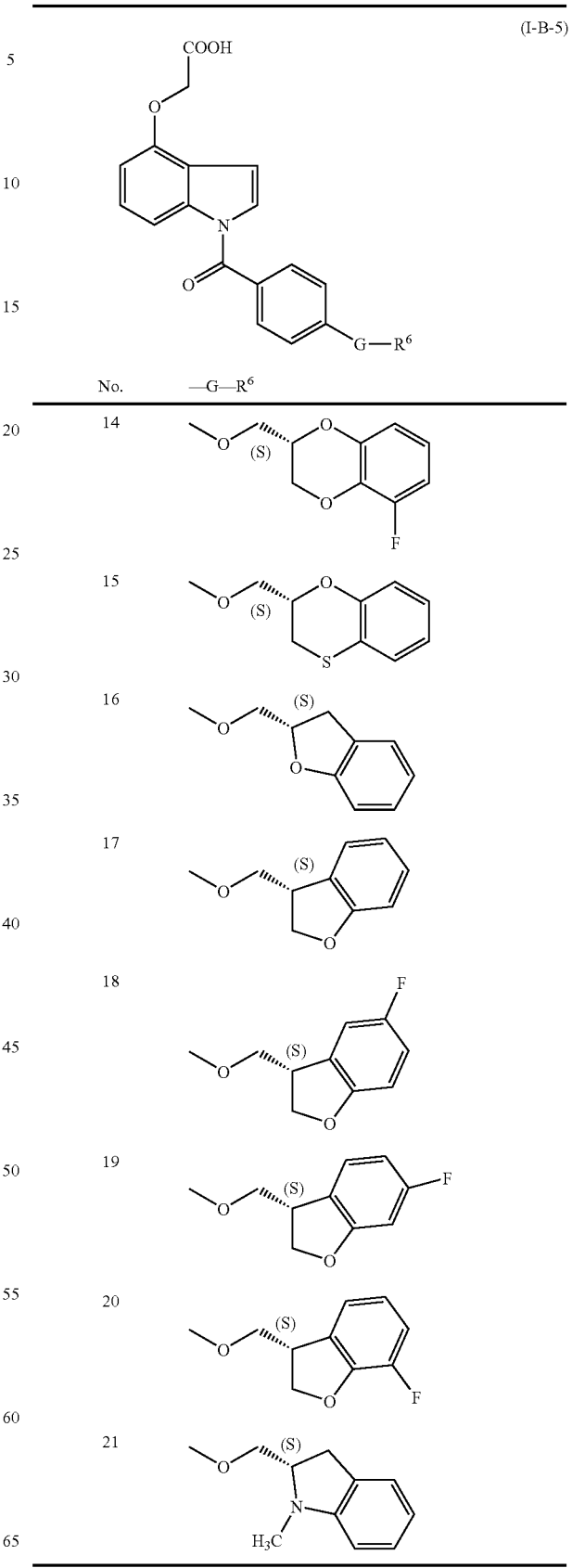

TABLE 26
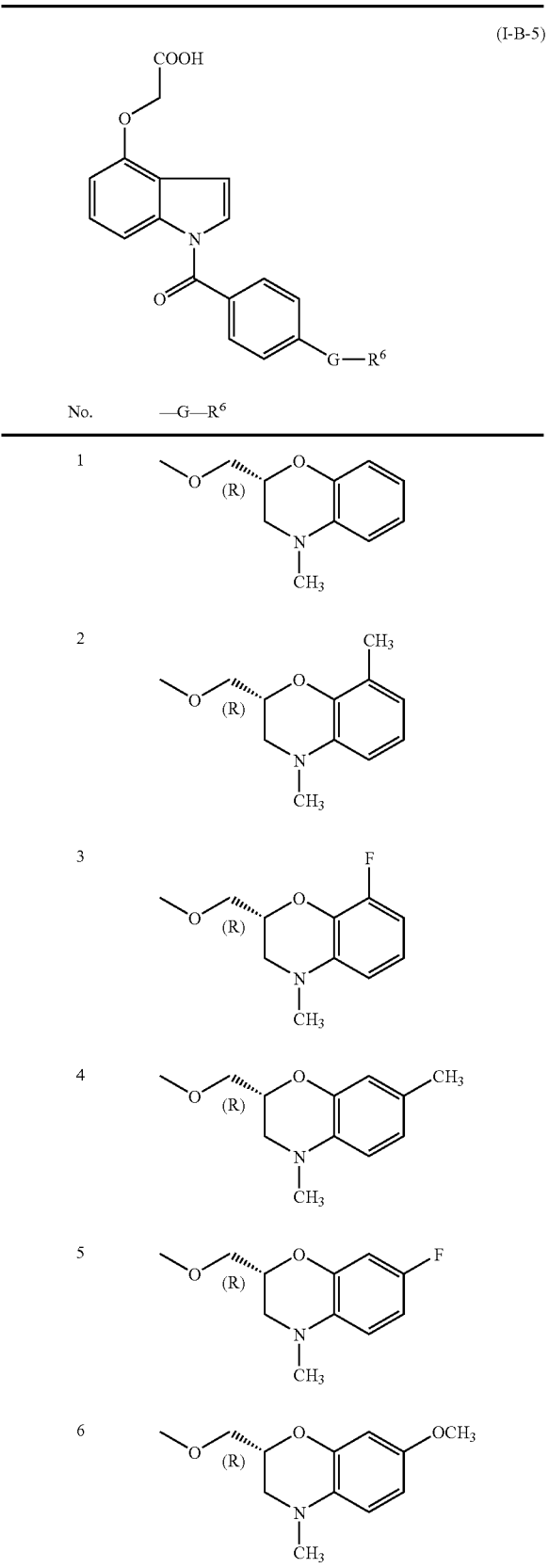
TABLE 26-continued
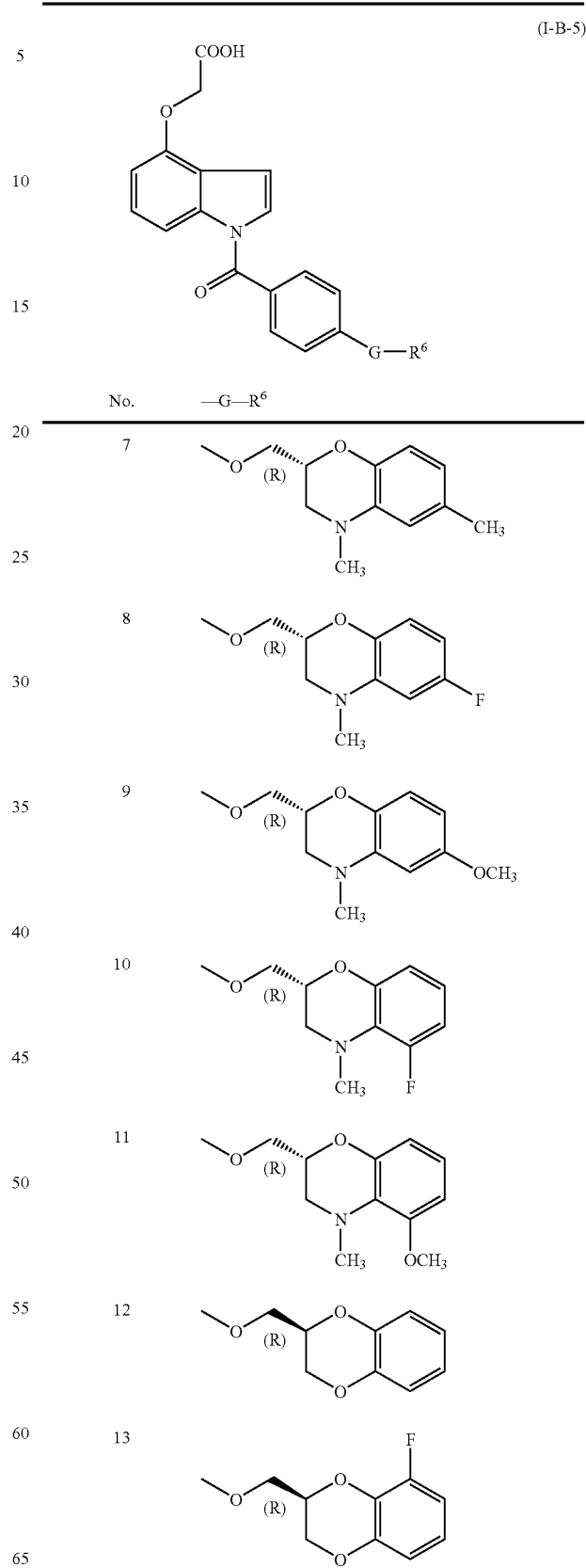

TABLE 26-continued (I-B-5)

| No. | —G—R⁶ |
|---|---|
| 14 | (R)-8-fluoro-2-(methoxymethyl)-2,3-dihydro-1,4-benzodioxine |
| 15 | (R)-2-(methoxymethyl)-2,3-dihydro-1,4-benzoxathiine |
| 16 | (R)-2-(methoxymethyl)-2,3-dihydrobenzofuran |
| 17 | (R)-3-(methoxymethyl)-2,3-dihydrobenzofuran |
| 18 | (R)-5-fluoro-3-(methoxymethyl)-2,3-dihydrobenzofuran |
| 19 | (R)-6-fluoro-3-(methoxymethyl)-2,3-dihydrobenzofuran |
| 20 | (R)-7-fluoro-3-(methoxymethyl)-2,3-dihydrobenzofuran |
| 21 | (R)-2-(methoxymethyl)-1-methyl-2,3-dihydro-1H-indole |

TABLE 27

(I-B-6)

| No. | —G—R⁶ |
|---|---|
| 1 | (S)-2-(methoxymethyl)-4-methyl-3,4-dihydro-2H-1,4-benzoxazine |
| 2 | (S)-2-(methoxymethyl)-4,8-dimethyl-3,4-dihydro-2H-1,4-benzoxazine |
| 3 | (S)-8-fluoro-2-(methoxymethyl)-4-methyl-3,4-dihydro-2H-1,4-benzoxazine |
| 4 | (S)-2-(methoxymethyl)-4,7-dimethyl-3,4-dihydro-2H-1,4-benzoxazine |
| 5 | (S)-7-fluoro-2-(methoxymethyl)-4-methyl-3,4-dihydro-2H-1,4-benzoxazine |
| 6 | (S)-2-(methoxymethyl)-7-methoxy-4-methyl-3,4-dihydro-2H-1,4-benzoxazine |

TABLE 27-continued (I-B-6)

| No. | —G—R⁶ |
|-----|-------|
| 7 | (S)-4-methyl-6-methyl-2-(methoxymethyl)-3,4-dihydro-2H-1,4-benzoxazine |
| 8 | (S)-4-methyl-6-fluoro-2-(methoxymethyl)-3,4-dihydro-2H-1,4-benzoxazine |
| 9 | (S)-4-methyl-6-methoxy-2-(methoxymethyl)-3,4-dihydro-2H-1,4-benzoxazine |
| 10 | (S)-4-methyl-5-fluoro-2-(methoxymethyl)-3,4-dihydro-2H-1,4-benzoxazine |
| 11 | (S)-4-methyl-5-methoxy-2-(methoxymethyl)-3,4-dihydro-2H-1,4-benzoxazine |
| 12 | (S)-2-(methoxymethyl)-2,3-dihydro-1,4-benzodioxine |
| 13 | (S)-5-fluoro-2-(methoxymethyl)-2,3-dihydro-1,4-benzodioxine |
| 14 | (S)-8-fluoro-2-(methoxymethyl)-2,3-dihydro-1,4-benzodioxine |
| 15 | (S)-2-(methoxymethyl)-2,3-dihydro-1,4-benzoxathiine |
| 16 | (S)-2-(methoxymethyl)-2,3-dihydrobenzofuran |
| 17 | (S)-3-(methoxymethyl)-2,3-dihydrobenzofuran |
| 18 | (S)-5-fluoro-3-(methoxymethyl)-2,3-dihydrobenzofuran |
| 19 | (S)-6-fluoro-3-(methoxymethyl)-2,3-dihydrobenzofuran |
| 20 | (S)-7-fluoro-3-(methoxymethyl)-2,3-dihydrobenzofuran |
| 21 | (S)-1-methyl-2-(methoxymethyl)-2,3-dihydroindole |

[Note: The table contains chemical structures for each —G—R⁶ substituent paired with the common core structure (I-B-6) shown above, which consists of an indole bearing a 2-hydroxyethyl group at the 4-position and an N-acyl group formed from a 4-substituted benzoyl moiety.]

TABLE 28
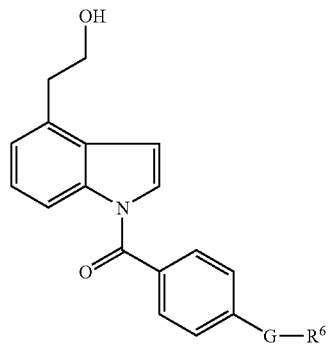
(I-B-6)
| No. | —G—R⁶ |
|---|---|
| 1 | 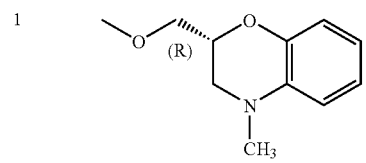 |
| 2 | 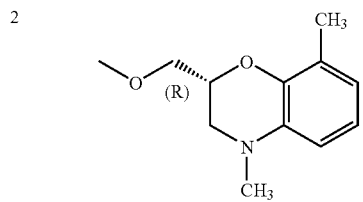 |
| 3 | 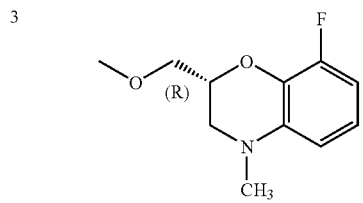 |
| 4 | 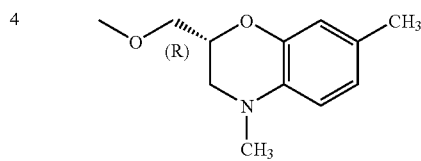 |
| 5 | 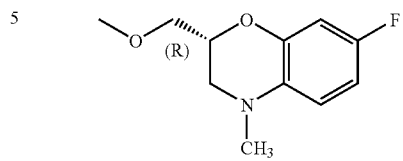 |
| 6 | 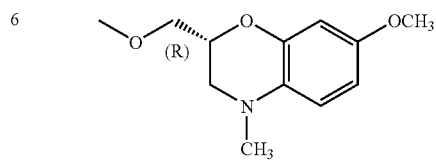 |
TABLE 28-continued
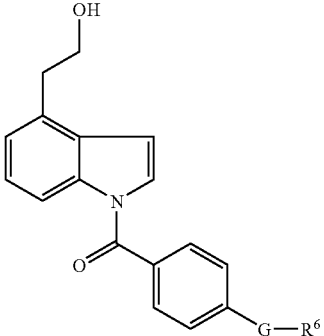
(I-B-6)
| No. | —G—R⁶ |
|---|---|
| 7 | 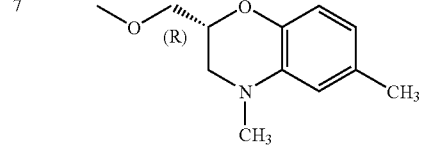 |
| 8 | 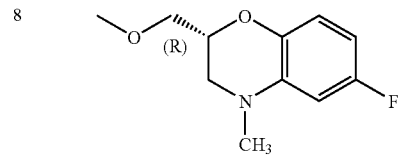 |
| 9 | 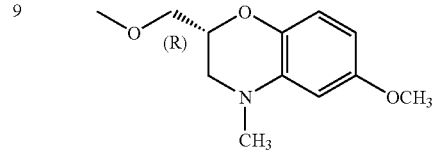 |
| 10 | 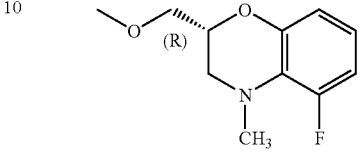 |
| 11 | 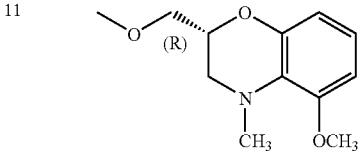 |
| 12 | 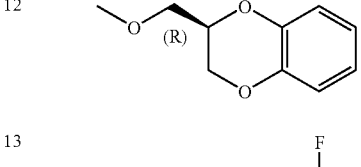 |
| 13 | 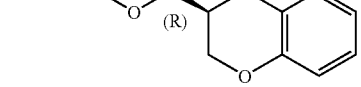 |

TABLE 28-continued (I-B-6)

| No. | —G—R⁶ |
|---|---|
| 14 | (R)-2-(methoxymethyl)-5-fluoro-2,3-dihydro-1,4-benzodioxine |
| 15 | (R)-2-(methoxymethyl)-2,3-dihydro-1,4-benzoxathiine |
| 16 | (R)-2-(methoxymethyl)-2,3-dihydrobenzofuran |
| 17 | (R)-3-(methoxymethyl)-2,3-dihydrobenzofuran |
| 18 | (R)-3-(methoxymethyl)-5-fluoro-2,3-dihydrobenzofuran |
| 19 | (R)-3-(methoxymethyl)-6-fluoro-2,3-dihydrobenzofuran |
| 20 | (R)-3-(methoxymethyl)-7-fluoro-2,3-dihydrobenzofuran |
| 21 | (R)-2-(methoxymethyl)-1-methyl-2,3-dihydroindoline |

TABLE 29

(I-B-7)

| No. | —G—R⁶ |
|---|---|
| 1 | (S)-2-(methoxymethyl)-4-methyl-3,4-dihydro-2H-1,4-benzoxazine |
| 2 | (S)-2-(methoxymethyl)-4,8-dimethyl-3,4-dihydro-2H-1,4-benzoxazine |
| 3 | (S)-2-(methoxymethyl)-8-fluoro-4-methyl-3,4-dihydro-2H-1,4-benzoxazine |
| 4 | (S)-2-(methoxymethyl)-4,7-dimethyl-3,4-dihydro-2H-1,4-benzoxazine |
| 5 | (S)-2-(methoxymethyl)-7-fluoro-4-methyl-3,4-dihydro-2H-1,4-benzoxazine |
| 6 | (S)-2-(methoxymethyl)-7-methoxy-4-methyl-3,4-dihydro-2H-1,4-benzoxazine |

TABLE 29-continued (I-B-7)

| No. | —G—R⁶ |
|---|---|
| 7 | (S)-2-(methoxymethyl)-4-methyl-6-methyl-3,4-dihydro-2H-benzo[b][1,4]oxazine |
| 8 | (S)-2-(methoxymethyl)-4-methyl-6-fluoro-3,4-dihydro-2H-benzo[b][1,4]oxazine |
| 9 | (S)-2-(methoxymethyl)-4-methyl-6-methoxy-3,4-dihydro-2H-benzo[b][1,4]oxazine |
| 10 | (S)-2-(methoxymethyl)-4-methyl-5-fluoro-3,4-dihydro-2H-benzo[b][1,4]oxazine |
| 11 | (S)-2-(methoxymethyl)-4-methyl-5-methoxy-3,4-dihydro-2H-benzo[b][1,4]oxazine |
| 12 | (S)-2-(methoxymethyl)-2,3-dihydro-1,4-benzodioxine |
| 13 | (S)-2-(methoxymethyl)-5-fluoro-2,3-dihydro-1,4-benzodioxine |
| 14 | (S)-2-(methoxymethyl)-8-fluoro-2,3-dihydro-1,4-benzodioxine |
| 15 | (S)-2-(methoxymethyl)-2,3-dihydro-1,4-benzoxathiine |
| 16 | (S)-2-(methoxymethyl)-2,3-dihydrobenzofuran |
| 17 | (S)-3-(methoxymethyl)-2,3-dihydrobenzofuran |
| 18 | (S)-3-(methoxymethyl)-5-fluoro-2,3-dihydrobenzofuran |
| 19 | (S)-3-(methoxymethyl)-6-fluoro-2,3-dihydrobenzofuran |
| 20 | (S)-3-(methoxymethyl)-7-fluoro-2,3-dihydrobenzofuran |

TABLE 29-continued (I-B-7)

| No. | —G—R⁶ |
|---|---|
| 21 | methoxymethyl-(S)-1-methyl-2,3-dihydroindole |

TABLE 30

(I-B-7)

| No. | —G—R⁶ |
|---|---|
| 1 | (R)-2-(methoxymethyl)-4-methyl-3,4-dihydro-2H-1,4-benzoxazine |
| 2 | (R)-2-(methoxymethyl)-4,8-dimethyl-3,4-dihydro-2H-1,4-benzoxazine |

TABLE 30-continued (I-B-7)

| No. | —G—R⁶ |
|---|---|
| 3 | (R)-8-fluoro-2-(methoxymethyl)-4-methyl-3,4-dihydro-2H-1,4-benzoxazine |
| 4 | (R)-2-(methoxymethyl)-4,7-dimethyl-3,4-dihydro-2H-1,4-benzoxazine |
| 5 | (R)-7-fluoro-2-(methoxymethyl)-4-methyl-3,4-dihydro-2H-1,4-benzoxazine |
| 6 | (R)-2-(methoxymethyl)-7-methoxy-4-methyl-3,4-dihydro-2H-1,4-benzoxazine |
| 7 | (R)-2-(methoxymethyl)-4,6-dimethyl-3,4-dihydro-2H-1,4-benzoxazine |
| 8 | (R)-6-fluoro-2-(methoxymethyl)-4-methyl-3,4-dihydro-2H-1,4-benzoxazine |

TABLE 30-continued (I-B-7)

| No. | —G—R⁶ |
|---|---|
| 9 | (R)-2-(methoxymethyl)-4-methyl-7-methoxy-3,4-dihydro-2H-benzo[1,4]oxazine |
| 10 | (R)-2-(methoxymethyl)-4-methyl-5-fluoro-3,4-dihydro-2H-benzo[1,4]oxazine |
| 11 | (R)-2-(methoxymethyl)-4-methyl-5-methoxy-3,4-dihydro-2H-benzo[1,4]oxazine |
| 12 | (R)-2-(methoxymethyl)-2,3-dihydro-1,4-benzodioxine |
| 13 | (R)-2-(methoxymethyl)-5-fluoro-2,3-dihydro-1,4-benzodioxine |
| 14 | (R)-2-(methoxymethyl)-8-fluoro-2,3-dihydro-1,4-benzodioxine |
| 15 | (R)-2-(methoxymethyl)-2,3-dihydro-1,4-benzoxathiine |
| 16 | (R)-2-(methoxymethyl)-2,3-dihydrobenzofuran |
| 17 | (R)-3-(methoxymethyl)-2,3-dihydrobenzofuran |
| 18 | (R)-3-(methoxymethyl)-5-fluoro-2,3-dihydrobenzofuran |
| 19 | (R)-3-(methoxymethyl)-6-fluoro-2,3-dihydrobenzofuran |
| 20 | (R)-3-(methoxymethyl)-7-fluoro-2,3-dihydrobenzofuran |
| 21 | (R)-2-(methoxymethyl)-1-methyl-2,3-dihydro-1H-indole |

TABLE 31

(I-B-8)

| No. | —G—R⁶ |
|---|---|
| 1 | (S)-2-(methoxymethyl)-4-methyl-3,4-dihydro-2H-benzo[b][1,4]oxazine |
| 2 | (S)-2-(methoxymethyl)-4,8-dimethyl-3,4-dihydro-2H-benzo[b][1,4]oxazine |
| 3 | (S)-8-fluoro-2-(methoxymethyl)-4-methyl-3,4-dihydro-2H-benzo[b][1,4]oxazine |
| 4 | (S)-2-(methoxymethyl)-4,7-dimethyl-3,4-dihydro-2H-benzo[b][1,4]oxazine |
| 5 | (S)-7-fluoro-2-(methoxymethyl)-4-methyl-3,4-dihydro-2H-benzo[b][1,4]oxazine |
| 6 | (S)-2-(methoxymethyl)-7-methoxy-4-methyl-3,4-dihydro-2H-benzo[b][1,4]oxazine |

TABLE 31-continued (I-B-8)

| No. | —G—R⁶ |
|---|---|
| 7 | (S)-2-(methoxymethyl)-4,6-dimethyl-3,4-dihydro-2H-benzo[b][1,4]oxazine |
| 8 | (S)-6-fluoro-2-(methoxymethyl)-4-methyl-3,4-dihydro-2H-benzo[b][1,4]oxazine |
| 9 | (S)-2-(methoxymethyl)-6-methoxy-4-methyl-3,4-dihydro-2H-benzo[b][1,4]oxazine |
| 10 | (S)-5-fluoro-2-(methoxymethyl)-4-methyl-3,4-dihydro-2H-benzo[b][1,4]oxazine |
| 11 | (S)-2-(methoxymethyl)-5-methoxy-4-methyl-3,4-dihydro-2H-benzo[b][1,4]oxazine |
| 12 | (S)-2-(methoxymethyl)-2,3-dihydro-1,4-benzodioxine |
| 13 | (S)-5-fluoro-2-(methoxymethyl)-2,3-dihydro-1,4-benzodioxine |

TABLE 31-continued
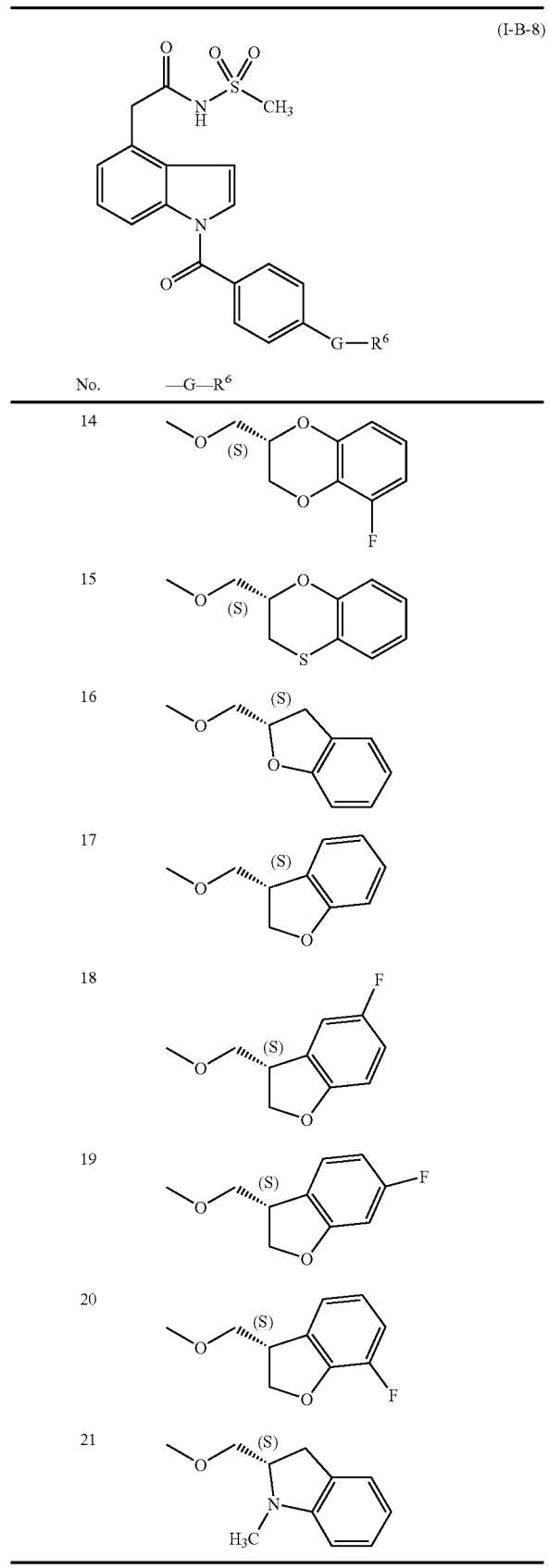
TABLE 32
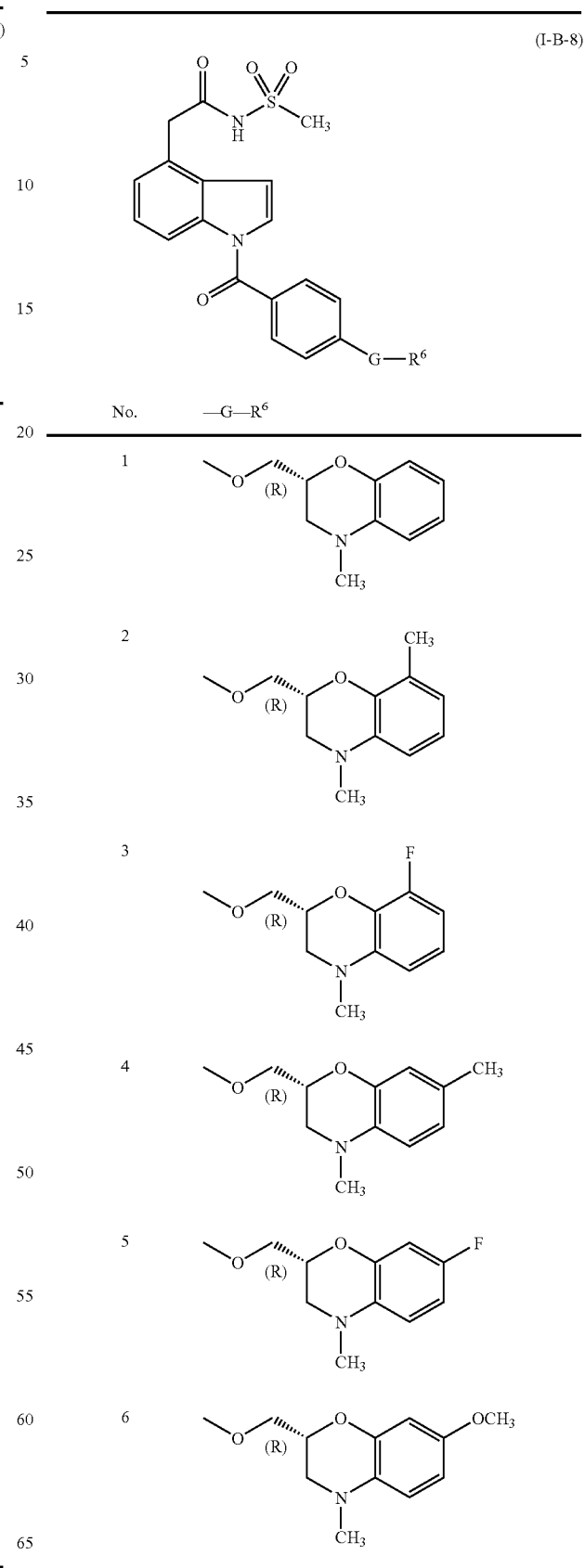

TABLE 32-continued
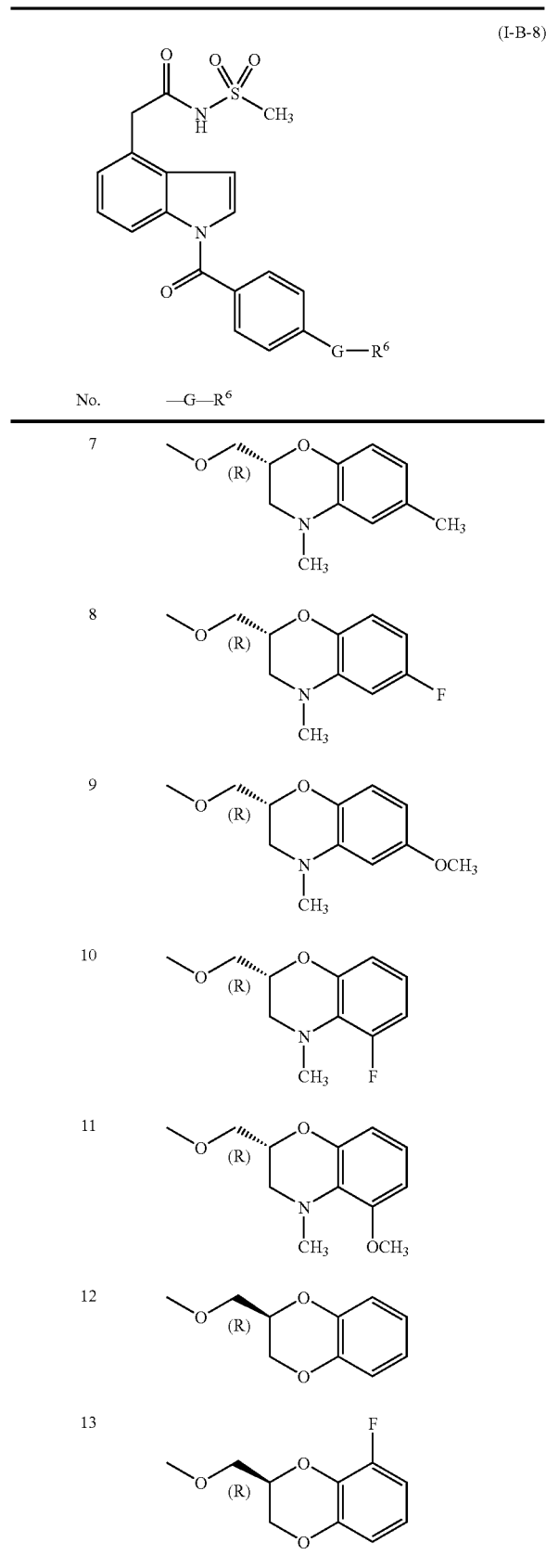
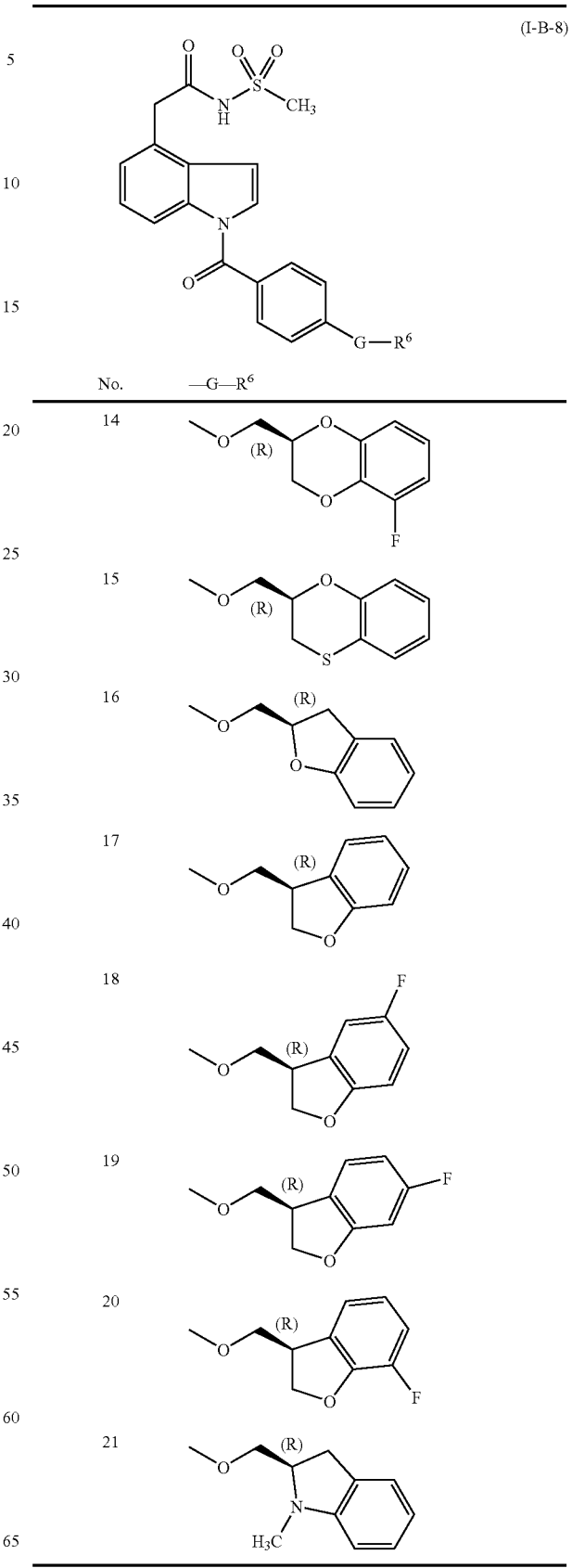

TABLE 33
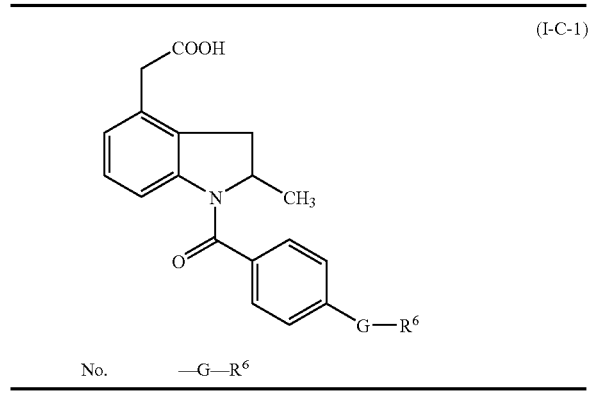
TABLE 33-continued
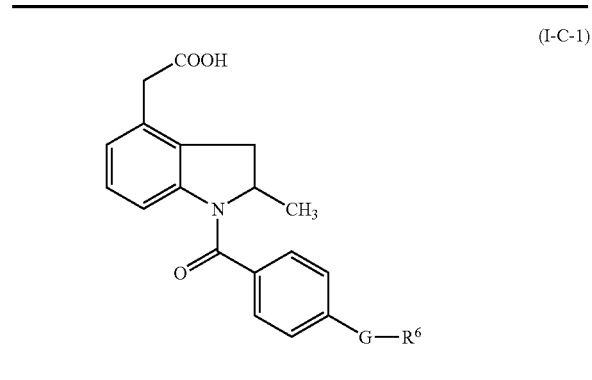

TABLE 33-continued (I-C-1)

| No. | —G—R⁶ |
|---|---|
| 15 | methoxymethyl-(S)-2,3-dihydro-1,4-benzoxathiine |
| 16 | methoxymethyl-(S)-2,3-dihydrobenzofuran (2-position) |
| 17 | methoxymethyl-(S)-2,3-dihydrobenzofuran (3-position) |
| 18 | methoxymethyl-(S)-5-fluoro-2,3-dihydrobenzofuran (3-position) |
| 19 | methoxymethyl-(S)-6-fluoro-2,3-dihydrobenzofuran (3-position) |
| 20 | methoxymethyl-(S)-7-fluoro-2,3-dihydrobenzofuran (3-position) |
| 21 | methoxymethyl-(S)-1-methyl-2,3-dihydroindole |

TABLE 34

(I-C-1)

| No. | —G—R⁶ |
|---|---|
| 1 | methoxymethyl-(R)-4-methyl-3,4-dihydro-2H-1,4-benzoxazine |
| 2 | methoxymethyl-(R)-4,8-dimethyl-3,4-dihydro-2H-1,4-benzoxazine |
| 3 | methoxymethyl-(R)-8-fluoro-4-methyl-3,4-dihydro-2H-1,4-benzoxazine |
| 4 | methoxymethyl-(R)-4,7-dimethyl-3,4-dihydro-2H-1,4-benzoxazine |
| 5 | methoxymethyl-(R)-7-fluoro-4-methyl-3,4-dihydro-2H-1,4-benzoxazine |
| 6 | methoxymethyl-(R)-7-methoxy-4-methyl-3,4-dihydro-2H-1,4-benzoxazine |

TABLE 34-continued
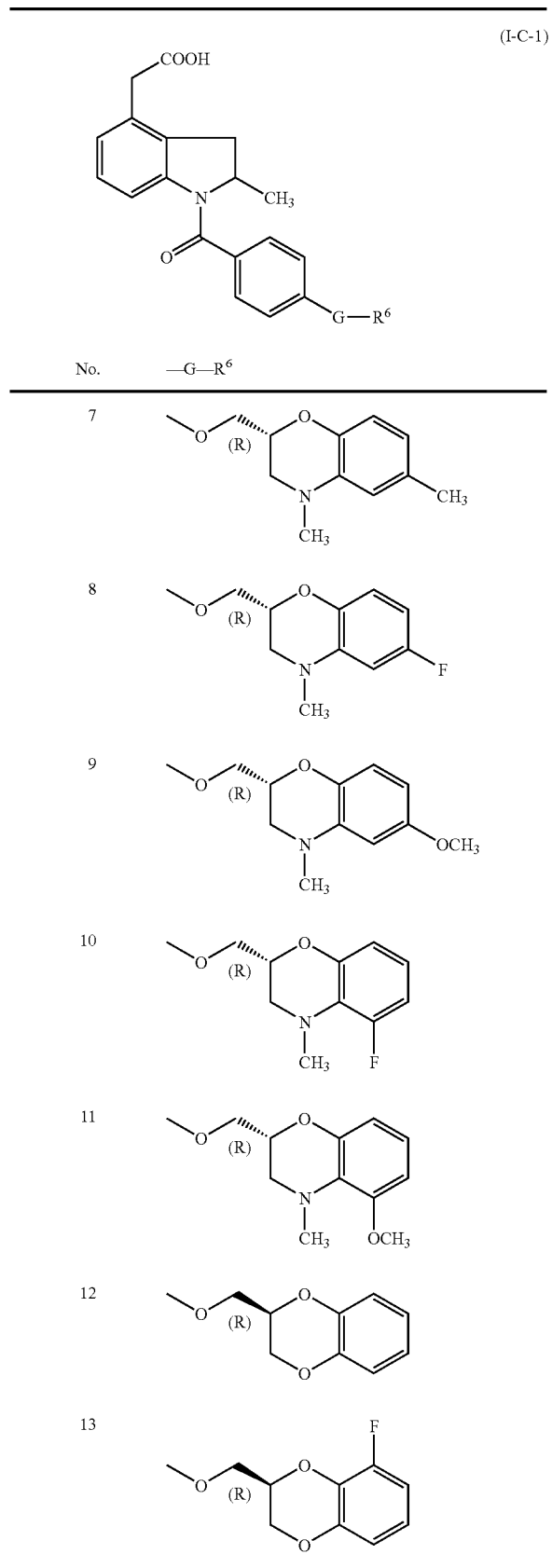
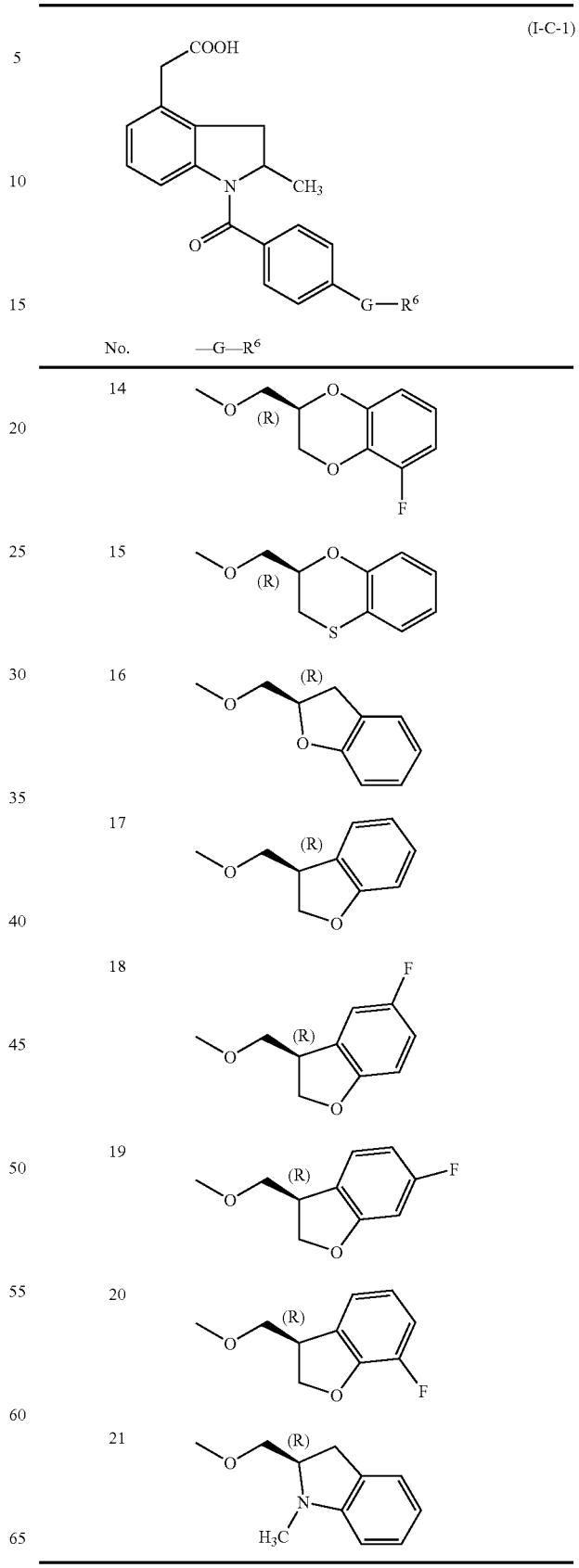

TABLE 35
(I-C-2)
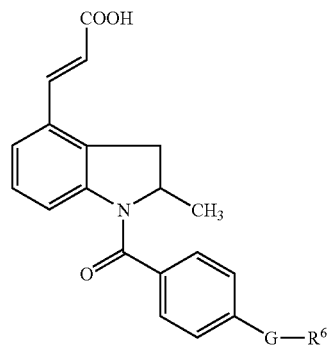
| No. | —G—R⁶ |
|---|---|
| 1 | 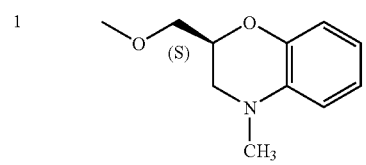 |
| 2 | 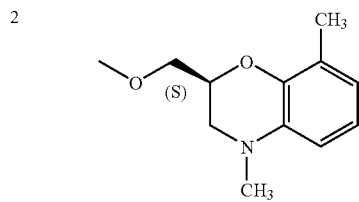 |
| 3 | 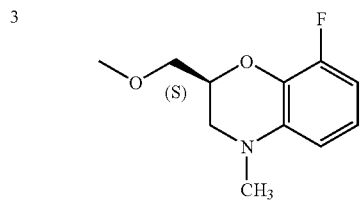 |
| 4 | 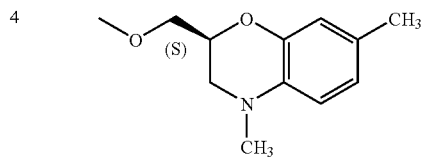 |
| 5 | 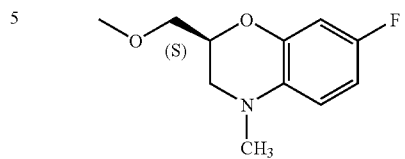 |
| 6 | 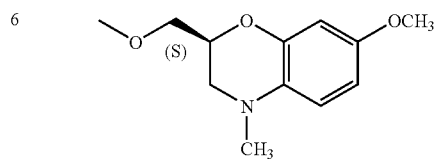 |
TABLE 35-continued
(I-C-2)
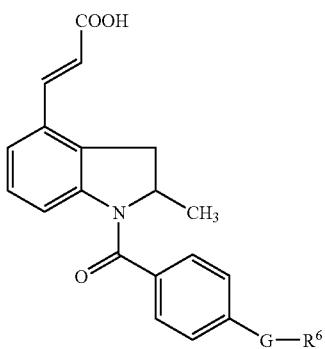
| No. | —G—R⁶ |
|---|---|
| 7 | 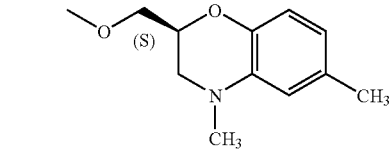 |
| 8 | 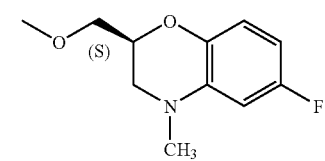 |
| 9 | 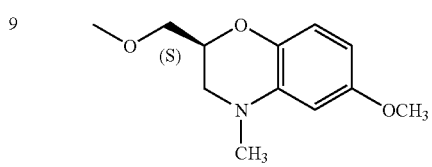 |
| 10 | 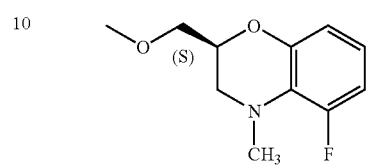 |
| 11 | 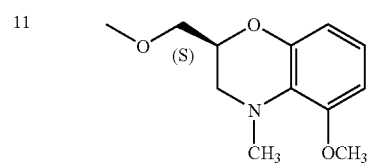 |
| 12 | 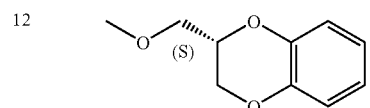 |
| 13 | |

TABLE 35-continued
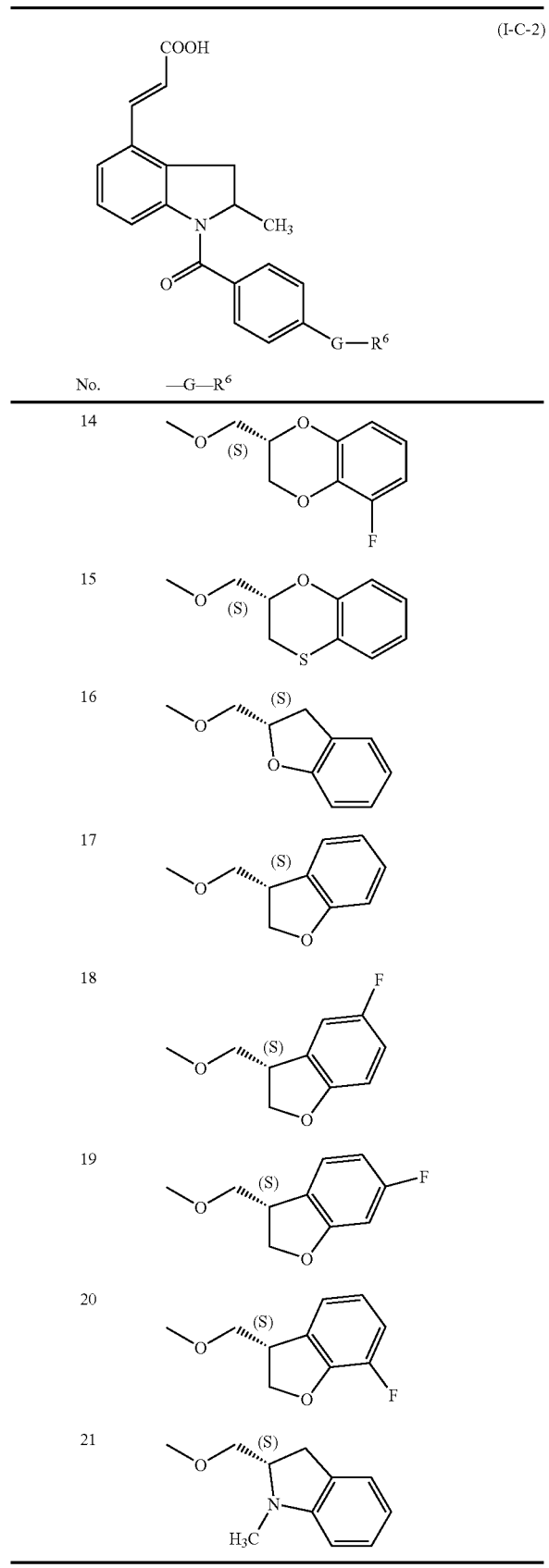
TABLE 36
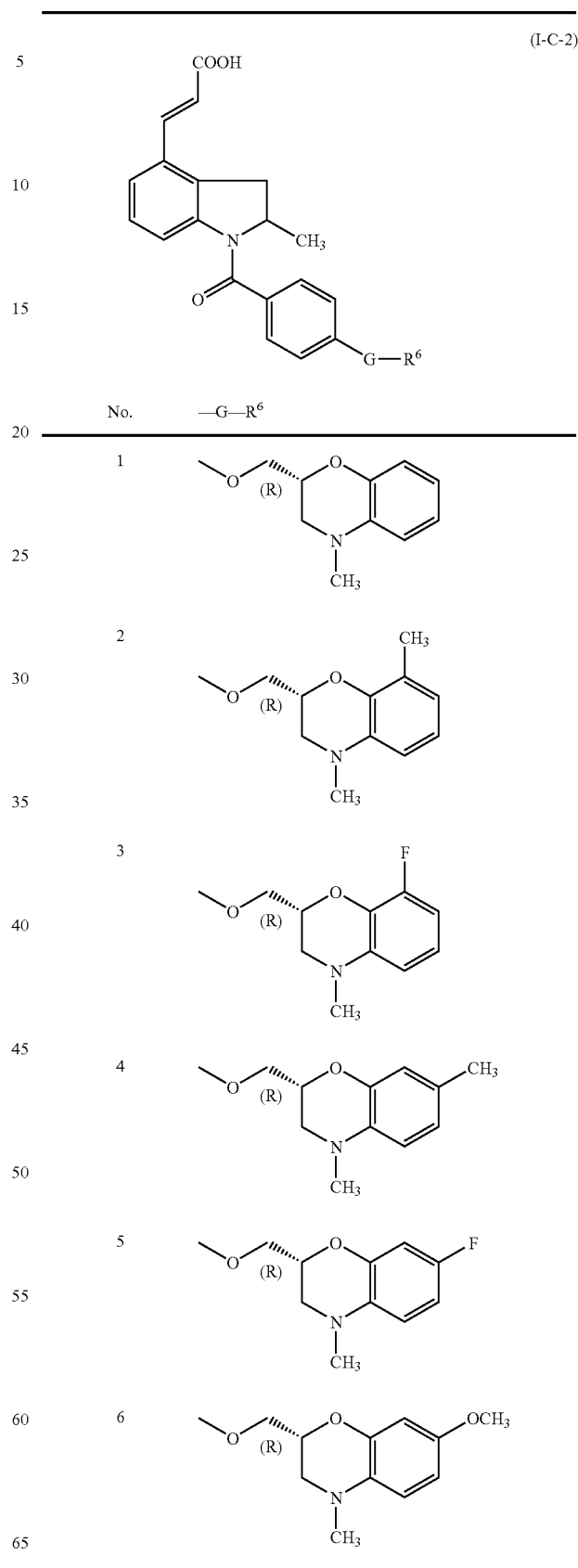

TABLE 36-continued (I-C-2)

| No. | —G—R⁶ |
|---|---|
| 7 | 4-methyl-6-methyl-3,4-dihydro-2H-benzo[1,4]oxazin-2-yl-methoxymethyl (2R) |
| 8 | 4-methyl-6-fluoro-3,4-dihydro-2H-benzo[1,4]oxazin-2-yl-methoxymethyl (2R) |
| 9 | 4-methyl-6-methoxy-3,4-dihydro-2H-benzo[1,4]oxazin-2-yl-methoxymethyl (2R) |
| 10 | 4-methyl-5-fluoro-3,4-dihydro-2H-benzo[1,4]oxazin-2-yl-methoxymethyl (2R) |
| 11 | 4-methyl-5-methoxy-3,4-dihydro-2H-benzo[1,4]oxazin-2-yl-methoxymethyl (2R) |
| 12 | 2,3-dihydro-1,4-benzodioxin-2-yl-methoxymethyl (2R) |
| 13 | 5-fluoro-2,3-dihydro-1,4-benzodioxin-2-yl-methoxymethyl (2R) |
| 14 | 8-fluoro-2,3-dihydro-1,4-benzodioxin-2-yl-methoxymethyl (2R) |
| 15 | 2,3-dihydro-1,4-benzoxathiin-2-yl-methoxymethyl (2R) |
| 16 | 2,3-dihydrobenzofuran-2-yl-methoxymethyl (2R) |
| 17 | 2,3-dihydrobenzofuran-3-yl-methoxymethyl (3R) |
| 18 | 5-fluoro-2,3-dihydrobenzofuran-3-yl-methoxymethyl (3R) |
| 19 | 6-fluoro-2,3-dihydrobenzofuran-3-yl-methoxymethyl (3R) |
| 20 | 7-fluoro-2,3-dihydrobenzofuran-3-yl-methoxymethyl (3R) |
| 21 | 1-methyl-2,3-dihydro-1H-indol-2-yl-methoxymethyl (2R) |

TABLE 37
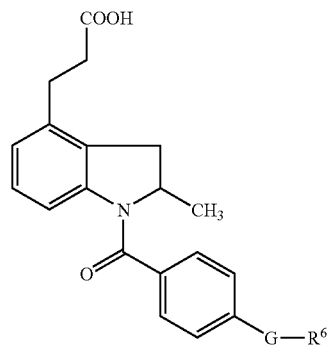
(I-C-3)
| No. | —G—R⁶ |
|---|---|
| 1 | 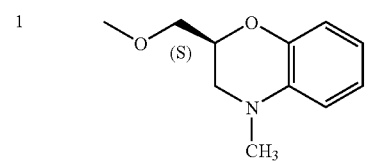 |
| 2 | 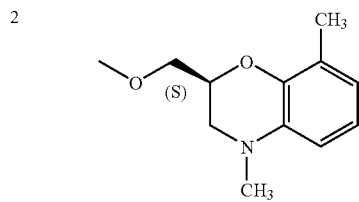 |
| 3 | 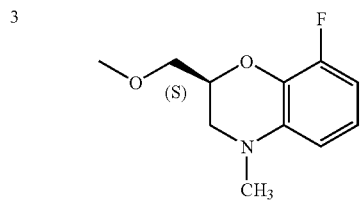 |
| 4 | 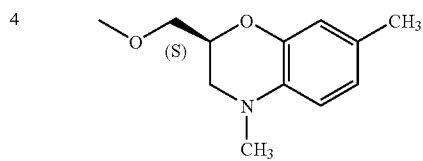 |
| 5 | 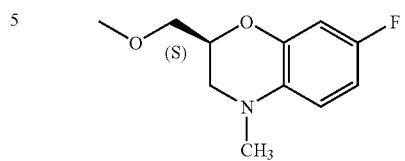 |
| 6 | 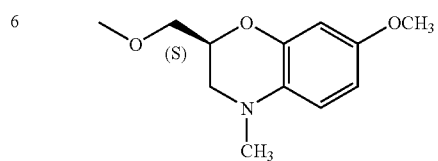 |
TABLE 37-continued
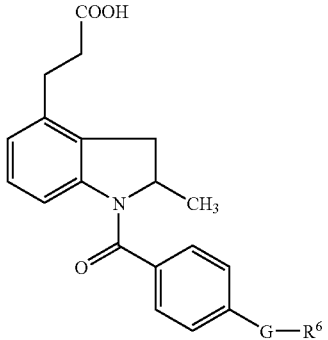
(I-C-3)
| No. | —G—R⁶ |
|---|---|
| 7 | 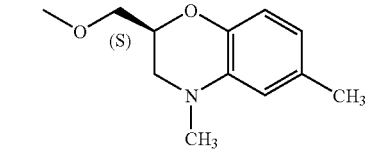 |
| 8 | 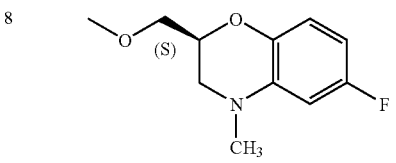 |
| 9 | 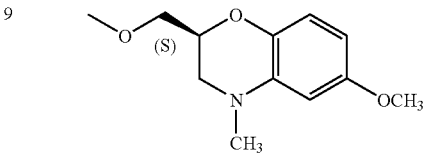 |
| 10 | 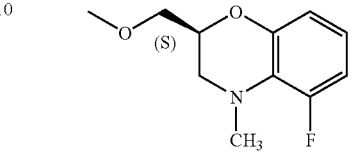 |
| 11 | 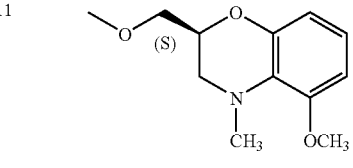 |
| 12 | 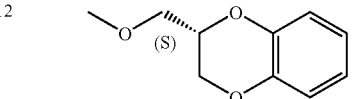 |
| 13 | 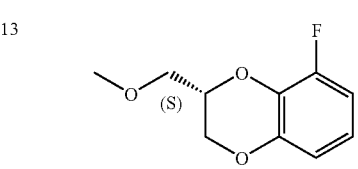 |

TABLE 37-continued
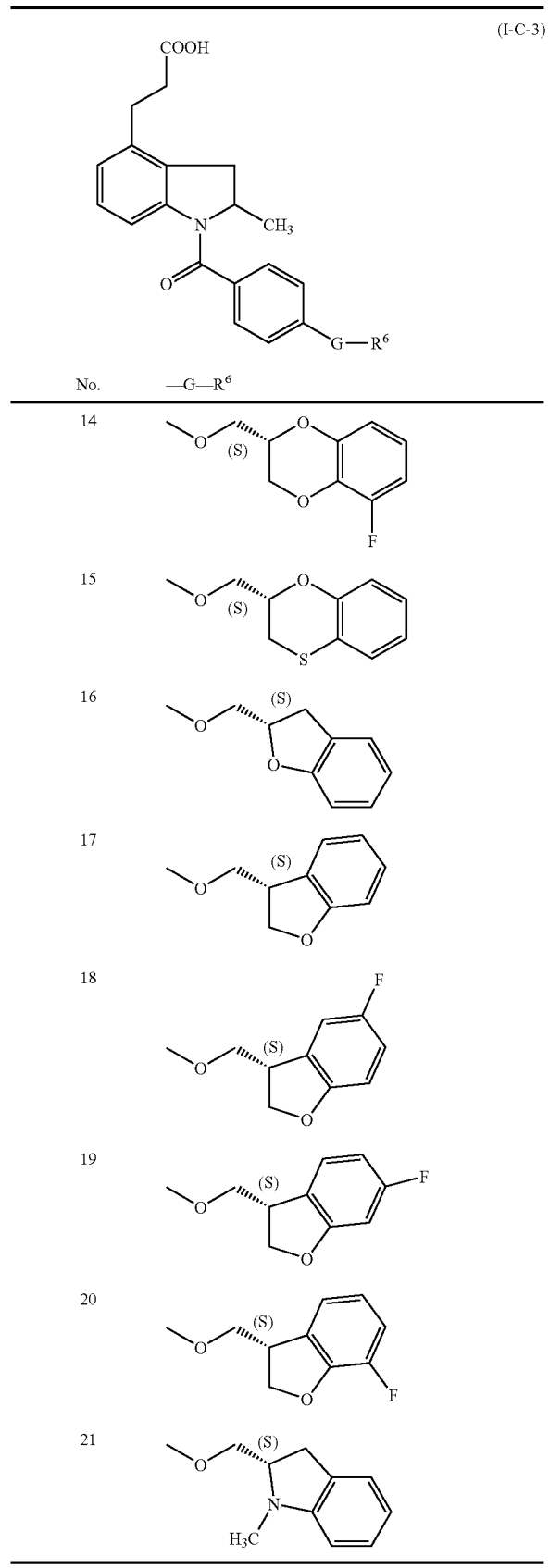
TABLE 38
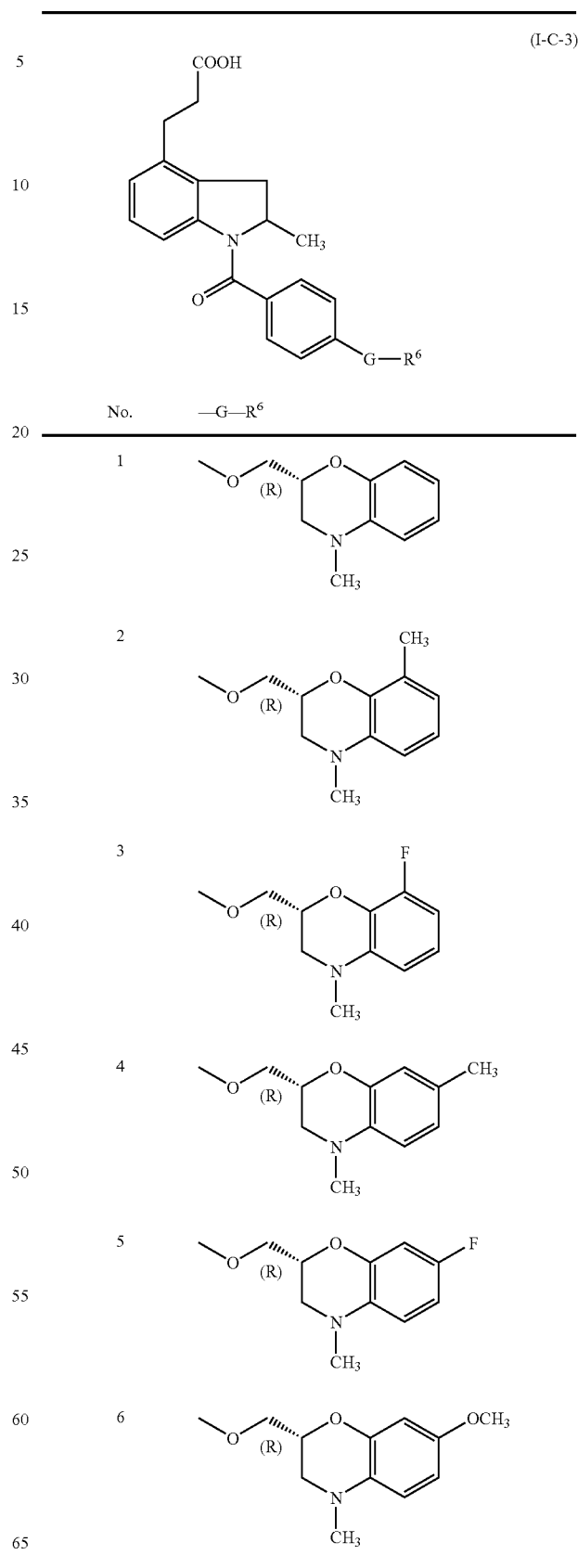

TABLE 38-continued
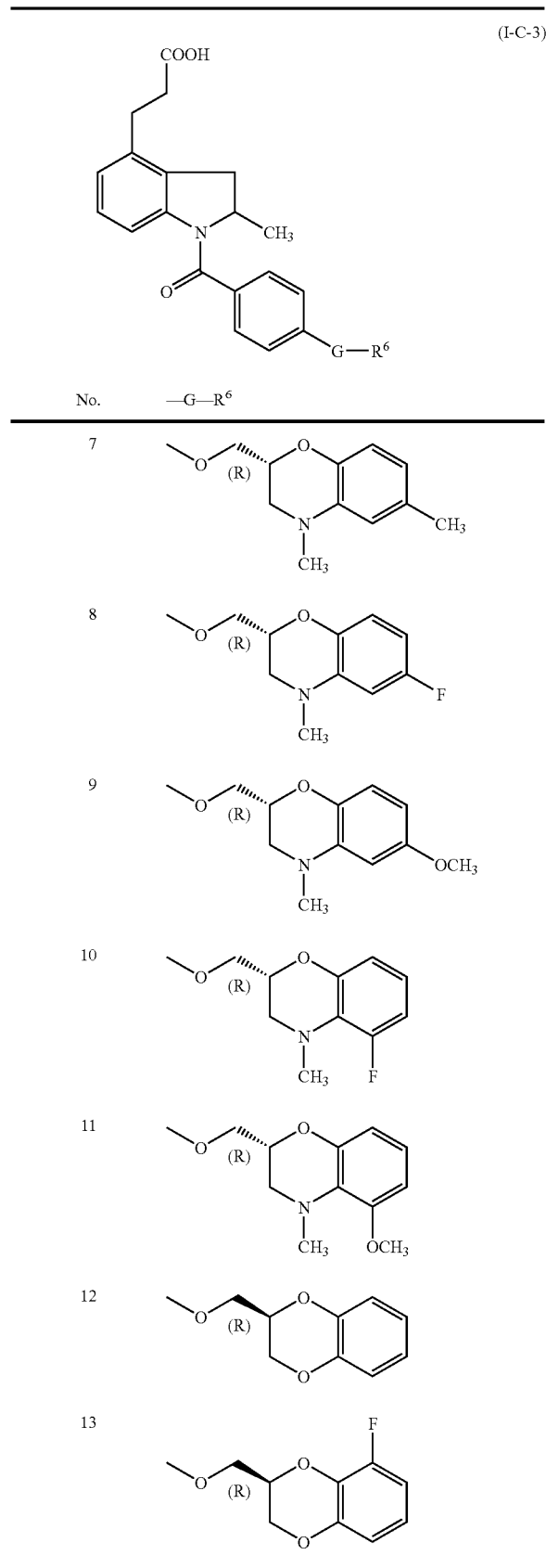
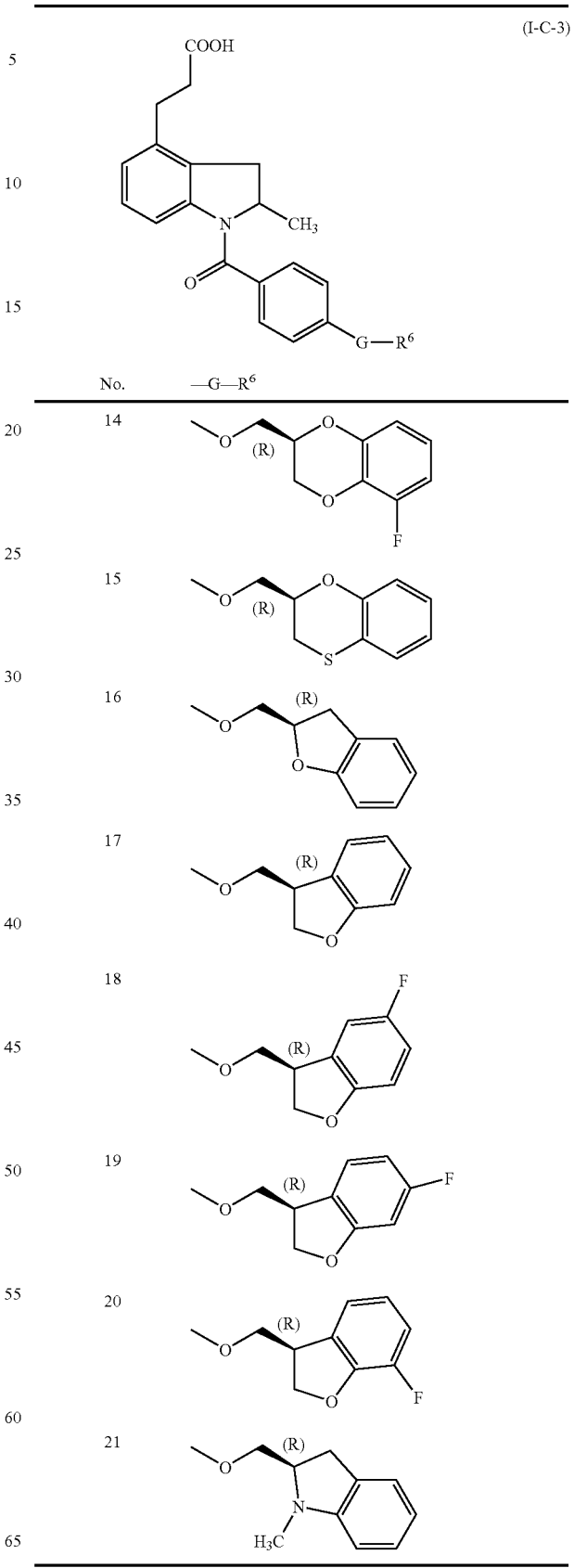

TABLE 39
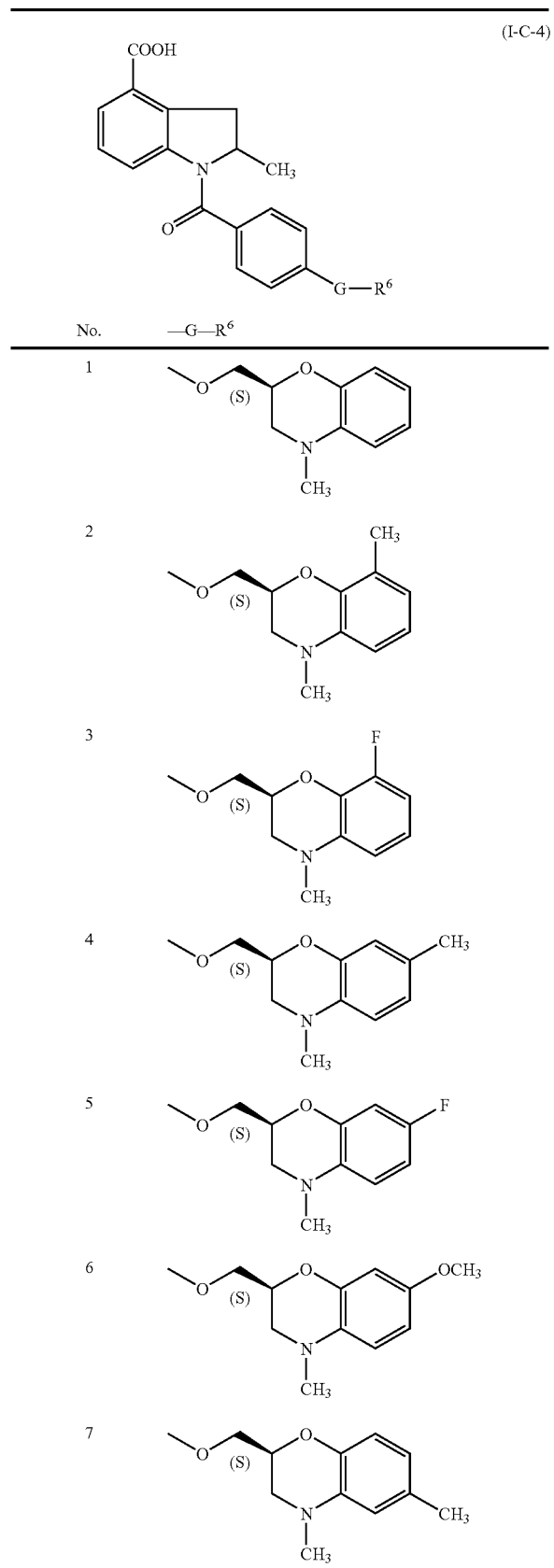
TABLE 39-continued
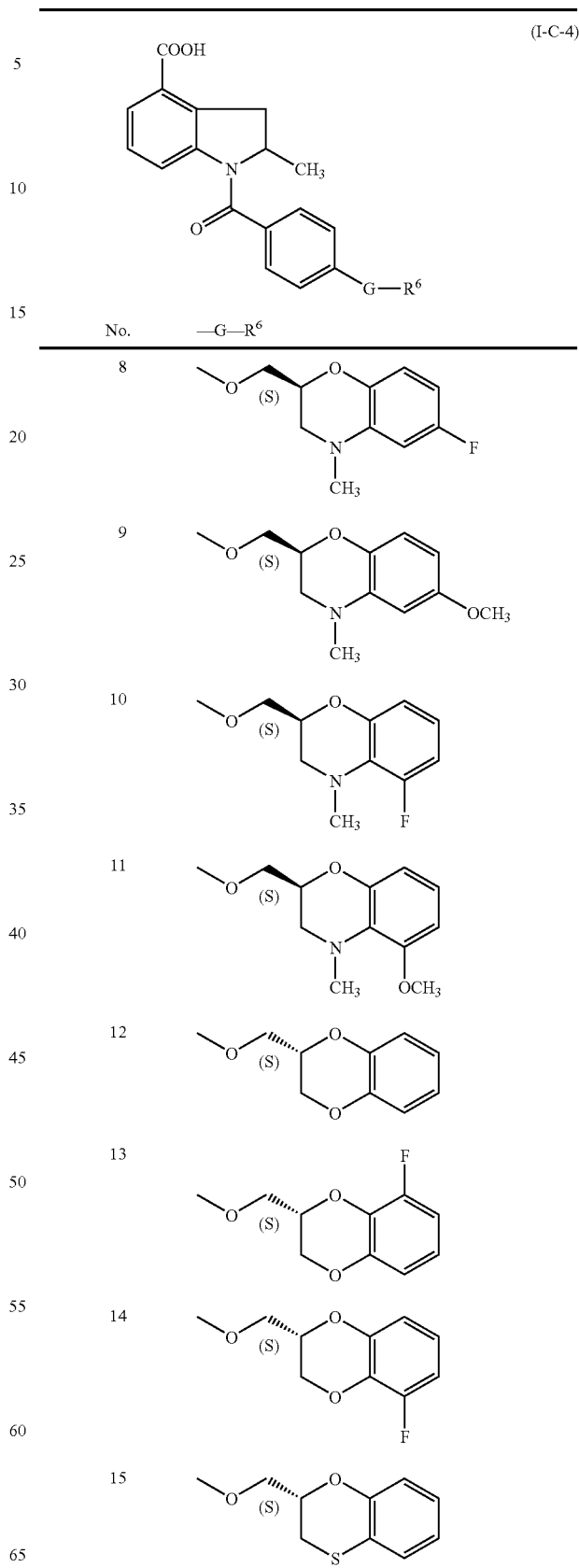

TABLE 39-continued (I-C-4)

| No. | —G—R⁶ |
|---|---|
| 16 | (S)-2-(methoxymethyl)-2,3-dihydrobenzofuran |
| 17 | (S)-3-(methoxymethyl)-2,3-dihydrobenzofuran |
| 18 | (S)-3-(methoxymethyl)-5-fluoro-2,3-dihydrobenzofuran |
| 19 | (S)-3-(methoxymethyl)-6-fluoro-2,3-dihydrobenzofuran |
| 20 | (S)-3-(methoxymethyl)-7-fluoro-2,3-dihydrobenzofuran |
| 21 | (S)-2-(methoxymethyl)-1-methyl-2,3-dihydroindole |

TABLE 40

(I-C-4)

| No. | —G—R⁶ |
|---|---|
| 1 | (R)-2-(methoxymethyl)-4-methyl-3,4-dihydro-2H-1,4-benzoxazine |
| 2 | (R)-2-(methoxymethyl)-4,8-dimethyl-3,4-dihydro-2H-1,4-benzoxazine |
| 3 | (R)-2-(methoxymethyl)-8-fluoro-4-methyl-3,4-dihydro-2H-1,4-benzoxazine |
| 4 | (R)-2-(methoxymethyl)-4,7-dimethyl-3,4-dihydro-2H-1,4-benzoxazine |
| 5 | (R)-2-(methoxymethyl)-7-fluoro-4-methyl-3,4-dihydro-2H-1,4-benzoxazine |
| 6 | (R)-2-(methoxymethyl)-7-methoxy-4-methyl-3,4-dihydro-2H-1,4-benzoxazine |
| 7 | (R)-2-(methoxymethyl)-4,6-dimethyl-3,4-dihydro-2H-1,4-benzoxazine |

TABLE 40-continued
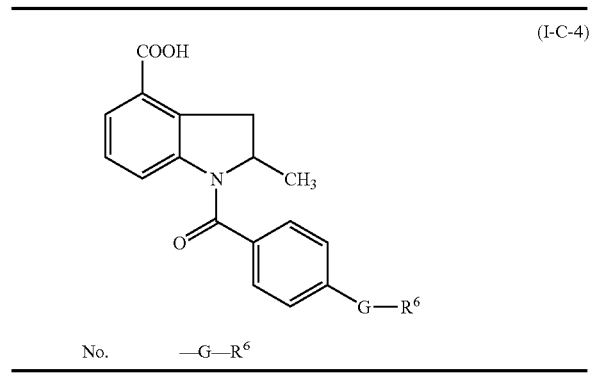
(I-C-4)
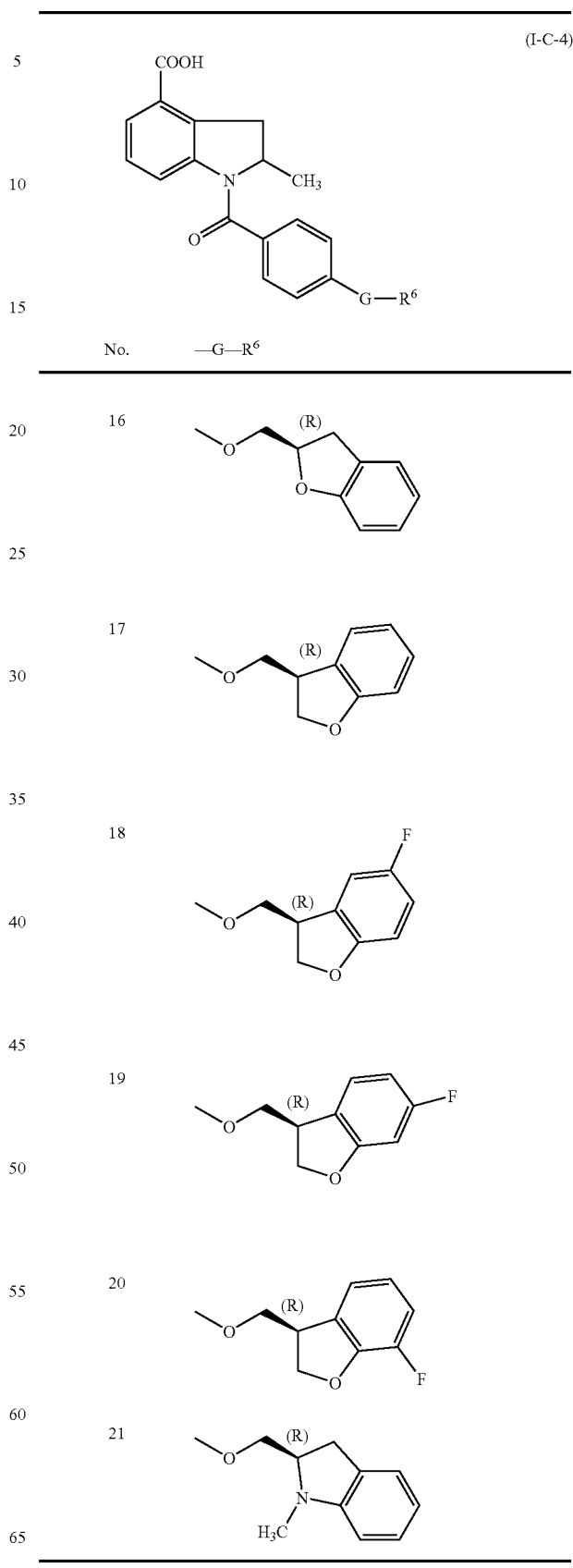

TABLE 41
(I-C-5)
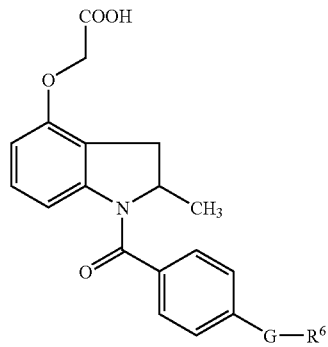
| No. | —G—R⁶ |
|---|---|
| 1 | 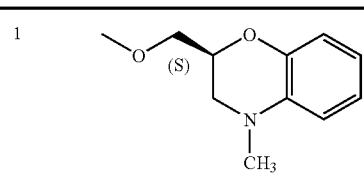 |
| 2 | 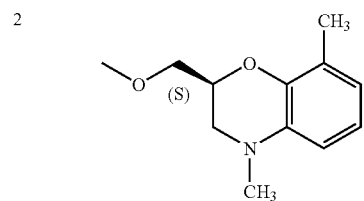 |
| 3 | 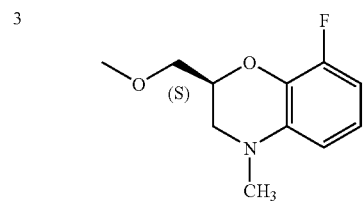 |
| 4 | 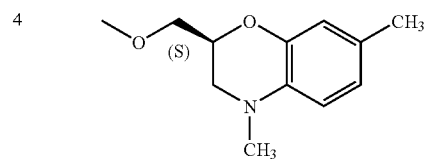 |
| 5 | 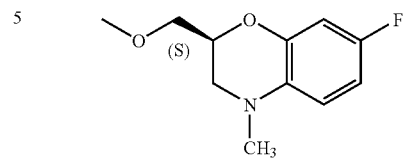 |
| 6 | 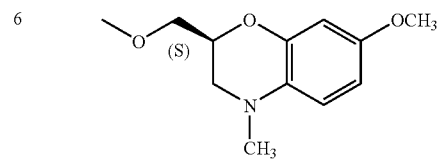 |
TABLE 41-continued
(I-C-5)
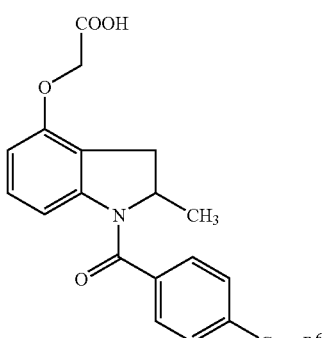
| No. | —G—R⁶ |
|---|---|
| 7 | 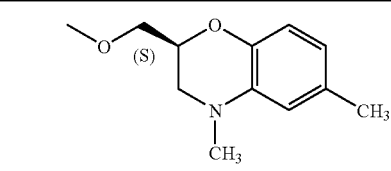 |
| 8 | 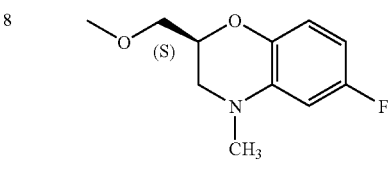 |
| 9 | 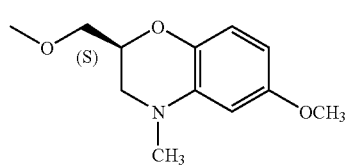 |
| 10 | 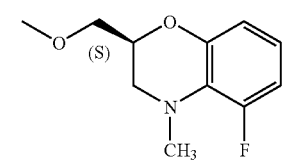 |
| 11 | 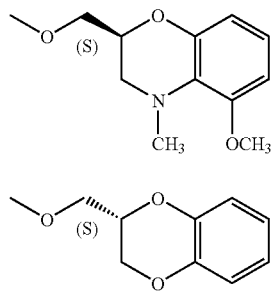 |
| 12 | 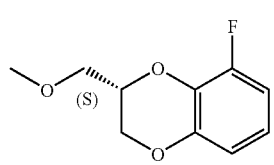 |
| 13 | 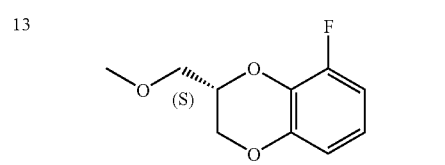 |

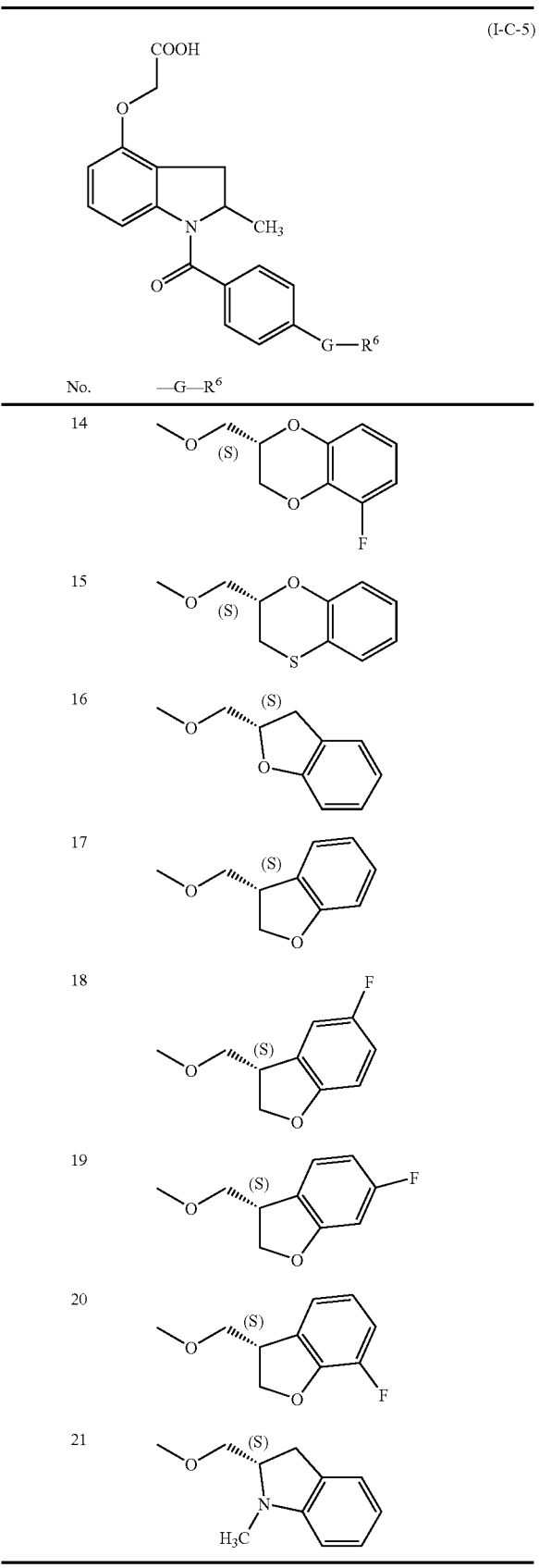
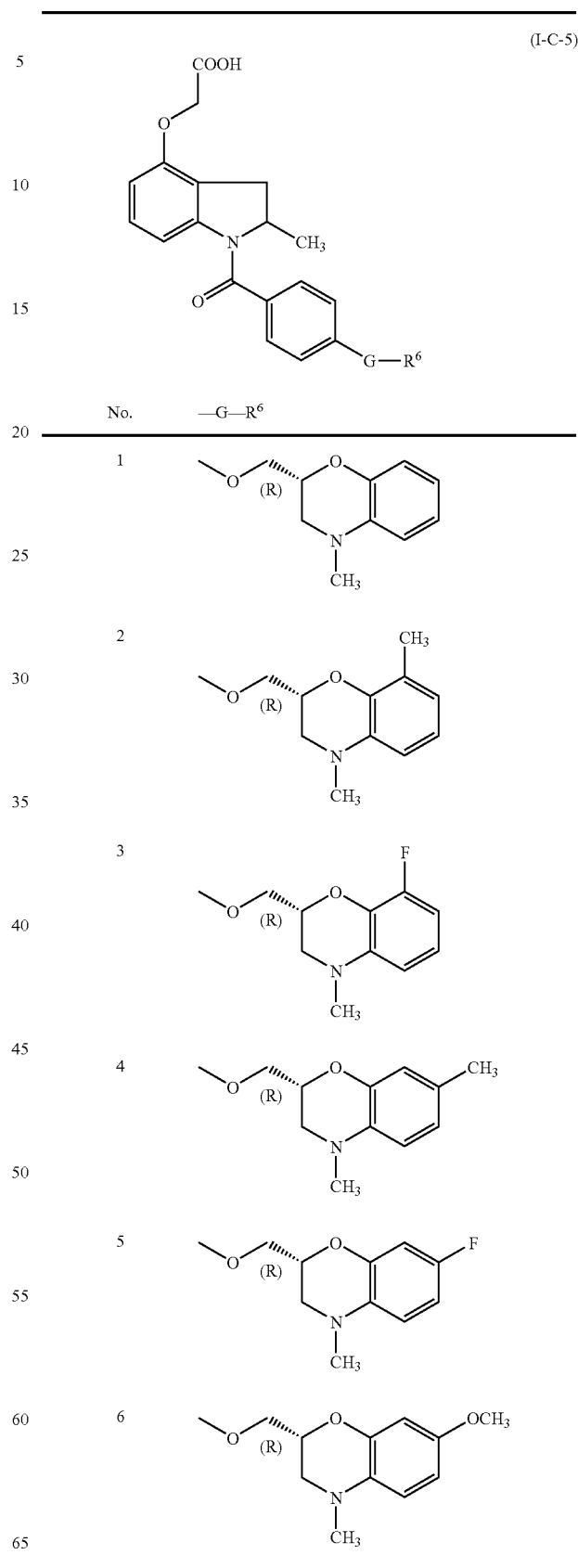

TABLE 42-continued
(I-C-5)
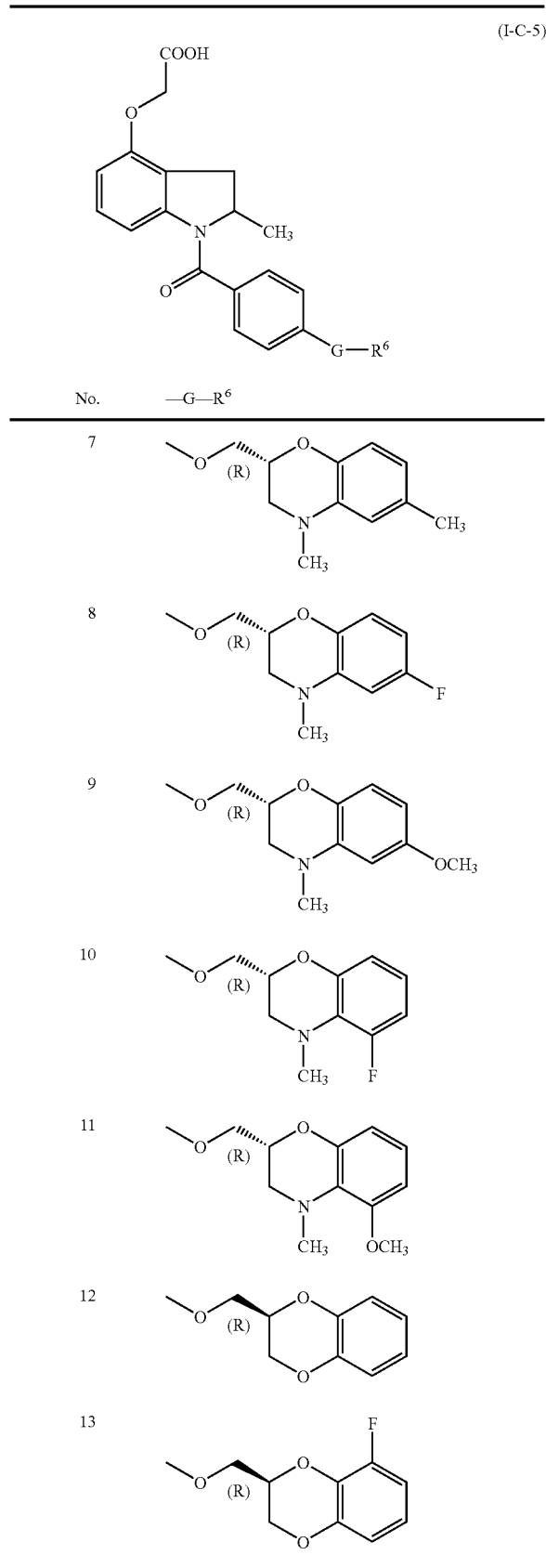
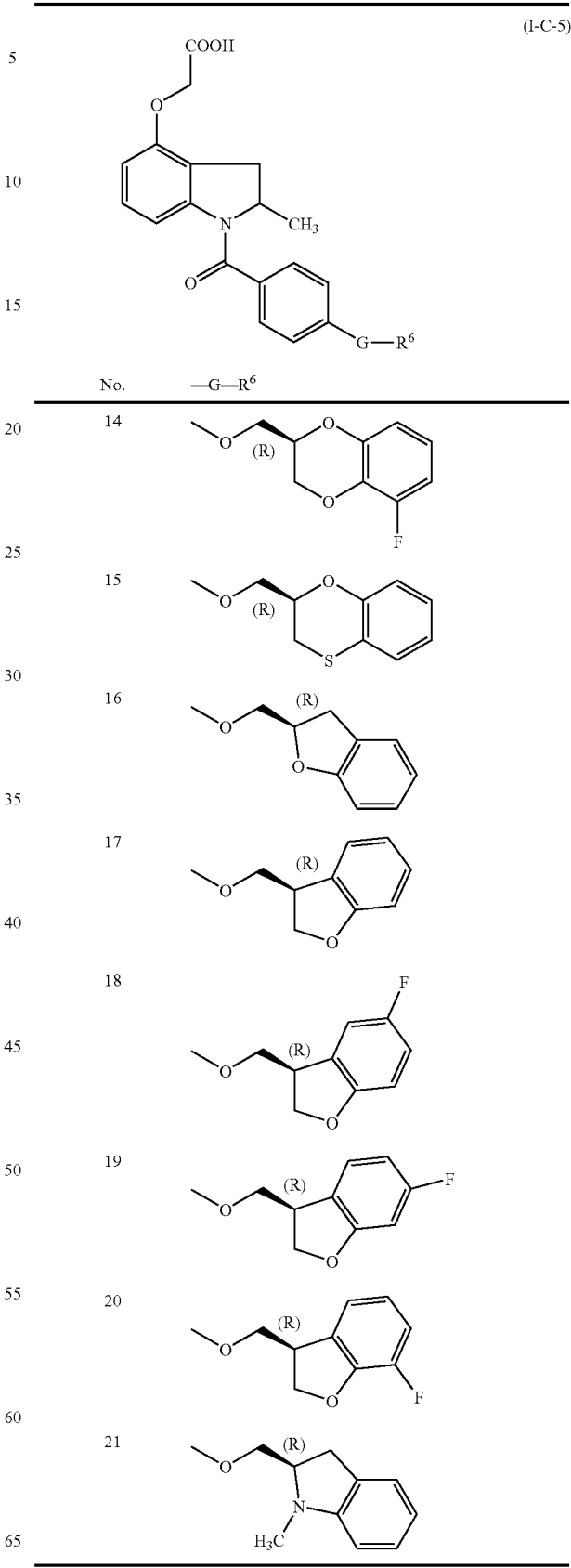

TABLE 43

(I-C-6)

| No. | —G—R⁶ |
|---|---|
| 1 | (S)-2-(methoxymethyl)-4-methyl-3,4-dihydro-2H-benzo[b][1,4]oxazine |
| 2 | (S)-2-(methoxymethyl)-4,8-dimethyl-3,4-dihydro-2H-benzo[b][1,4]oxazine |
| 3 | (S)-8-fluoro-2-(methoxymethyl)-4-methyl-3,4-dihydro-2H-benzo[b][1,4]oxazine |
| 4 | (S)-2-(methoxymethyl)-4,7-dimethyl-3,4-dihydro-2H-benzo[b][1,4]oxazine |
| 5 | (S)-7-fluoro-2-(methoxymethyl)-4-methyl-3,4-dihydro-2H-benzo[b][1,4]oxazine |
| 6 | (S)-2-(methoxymethyl)-7-methoxy-4-methyl-3,4-dihydro-2H-benzo[b][1,4]oxazine |

TABLE 43-continued (I-C-6)

| No. | —G—R⁶ |
|---|---|
| 7 | (S)-2-(methoxymethyl)-4,6-dimethyl-3,4-dihydro-2H-benzo[b][1,4]oxazine |
| 8 | (S)-6-fluoro-2-(methoxymethyl)-4-methyl-3,4-dihydro-2H-benzo[b][1,4]oxazine |
| 9 | (S)-2-(methoxymethyl)-6-methoxy-4-methyl-3,4-dihydro-2H-benzo[b][1,4]oxazine |
| 10 | (S)-5-fluoro-2-(methoxymethyl)-4-methyl-3,4-dihydro-2H-benzo[b][1,4]oxazine |
| 11 | (S)-2-(methoxymethyl)-5-methoxy-4-methyl-3,4-dihydro-2H-benzo[b][1,4]oxazine |
| 12 | (S)-2-(methoxymethyl)-2,3-dihydro-1,4-benzodioxine |
| 13 | (S)-5-fluoro-2-(methoxymethyl)-2,3-dihydro-1,4-benzodioxine |

TABLE 43-continued (I-C-6)

[Structure: indoline with 2-hydroxyethyl at 4-position, N-methyl at 2-position, N-acyl with 4-substituted benzoyl group bearing —G—R⁶]

| No. | —G—R⁶ |
|---|---|
| 14 | (S)-methoxymethyl-benzodioxine with F |
| 15 | (S)-methoxymethyl-benzoxathiine |
| 16 | (S)-methoxymethyl-2,3-dihydrobenzofuran |
| 17 | (S)-methoxymethyl-2,3-dihydrobenzofuran |
| 18 | (S)-methoxymethyl-2,3-dihydrobenzofuran with 5-F |
| 19 | (S)-methoxymethyl-2,3-dihydrobenzofuran with 6-F |
| 20 | (S)-methoxymethyl-2,3-dihydrobenzofuran with 7-F |
| 21 | (S)-methoxymethyl-N-methyl-indoline |

TABLE 44

(I-C-6)

[Structure: indoline with 2-hydroxyethyl at 4-position, N-methyl at 2-position, N-acyl with 4-substituted benzoyl group bearing —G—R⁶]

| No. | —G—R⁶ |
|---|---|
| 1 | (R)-methoxymethyl-4-methyl-3,4-dihydro-2H-benzo[1,4]oxazine |
| 2 | (R)-methoxymethyl-4,8-dimethyl-3,4-dihydro-2H-benzo[1,4]oxazine |
| 3 | (R)-methoxymethyl-8-fluoro-4-methyl-3,4-dihydro-2H-benzo[1,4]oxazine |
| 4 | (R)-methoxymethyl-4,7-dimethyl-3,4-dihydro-2H-benzo[1,4]oxazine |
| 5 | (R)-methoxymethyl-7-fluoro-4-methyl-3,4-dihydro-2H-benzo[1,4]oxazine |
| 6 | (R)-methoxymethyl-7-methoxy-4-methyl-3,4-dihydro-2H-benzo[1,4]oxazine |

TABLE 44-continued (I-C-6)

| No. | —G—R⁶ |
|---|---|
| 7 | 2,3-dihydro-4-methyl-6-methyl-benzo[1,4]oxazine with (R)-CH₂OMe |
| 8 | 2,3-dihydro-4-methyl-6-fluoro-benzo[1,4]oxazine with (R)-CH₂OMe |
| 9 | 2,3-dihydro-4-methyl-6-methoxy-benzo[1,4]oxazine with (R)-CH₂OMe |
| 10 | 2,3-dihydro-4-methyl-5-fluoro-benzo[1,4]oxazine with (R)-CH₂OMe |
| 11 | 2,3-dihydro-4-methyl-5-methoxy-benzo[1,4]oxazine with (R)-CH₂OMe |
| 12 | 2,3-dihydro-benzo[1,4]dioxine with (R)-CH₂OMe |
| 13 | 5-fluoro-2,3-dihydro-benzo[1,4]dioxine with (R)-CH₂OMe |
| 14 | 8-fluoro-2,3-dihydro-benzo[1,4]dioxine with (R)-CH₂OMe |
| 15 | 2,3-dihydro-benzo[1,4]oxathiine with (R)-CH₂OMe |
| 16 | 2,3-dihydrobenzofuran with (R)-CH₂OMe at 2-position |
| 17 | 2,3-dihydrobenzofuran with (R)-CH₂OMe at 3-position |
| 18 | 5-fluoro-2,3-dihydrobenzofuran with (R)-CH₂OMe at 3-position |
| 19 | 6-fluoro-2,3-dihydrobenzofuran with (R)-CH₂OMe at 3-position |
| 20 | 7-fluoro-2,3-dihydrobenzofuran with (R)-CH₂OMe at 3-position |
| 21 | 1-methyl-2,3-dihydro-indole with (R)-CH₂OMe at 2-position |

TABLE 45
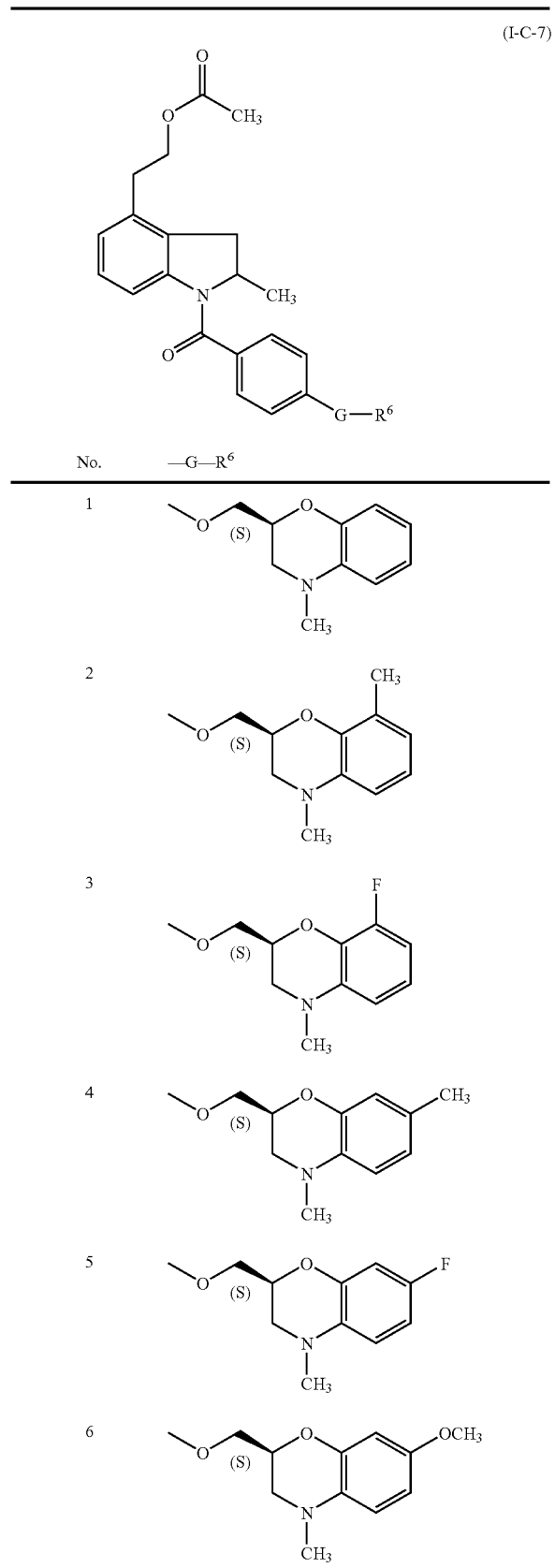
TABLE 45-continued
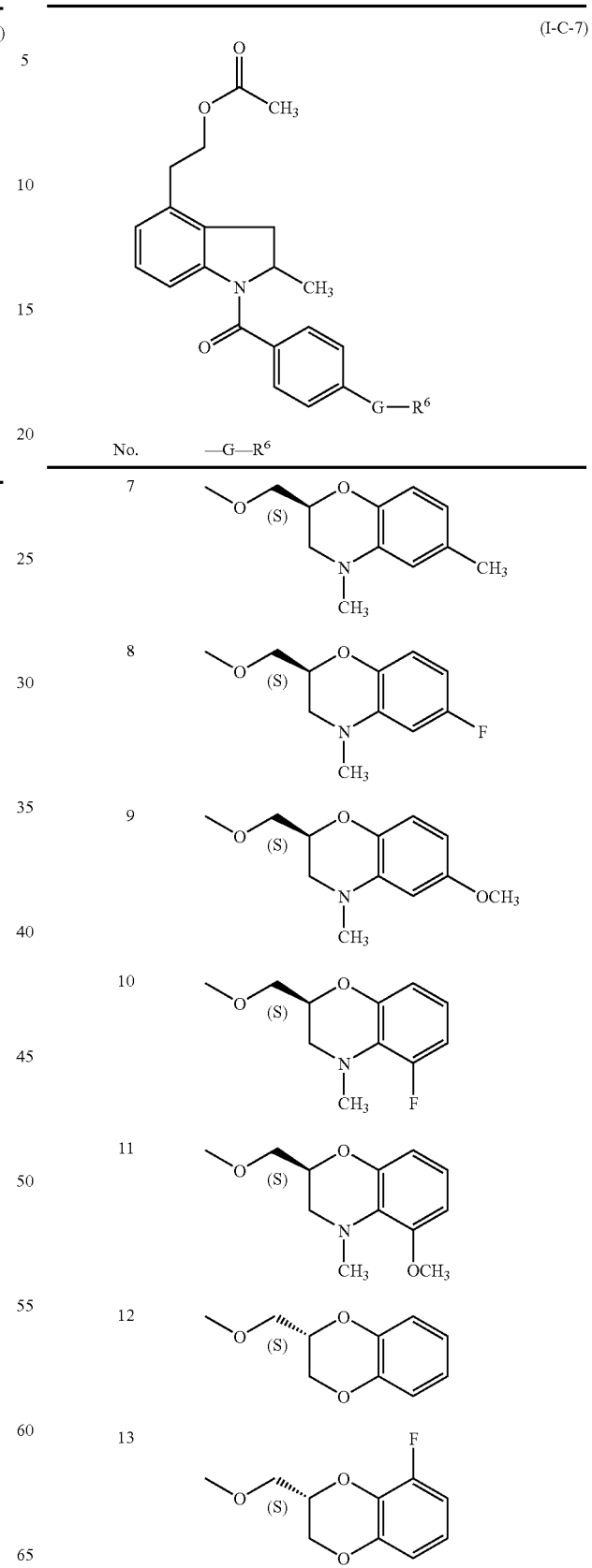

TABLE 45-continued
(I-C-7)
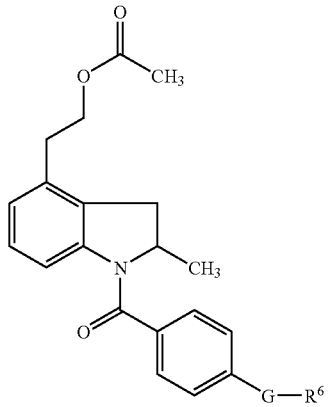
| No. | —G—R⁶ |
|---|---|
| 14 | 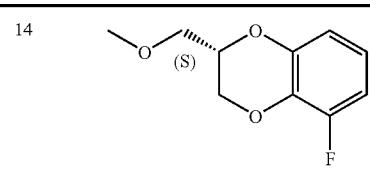 |
| 15 | 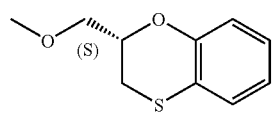 |
| 16 | 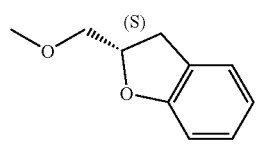 |
| 17 | 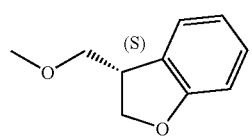 |
| 18 | 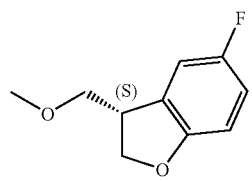 |
| 19 | 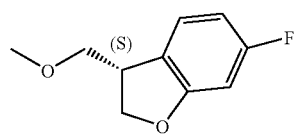 |
| 20 | 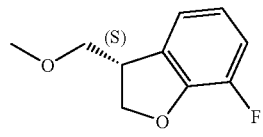 |
TABLE 45-continued
(I-C-7)
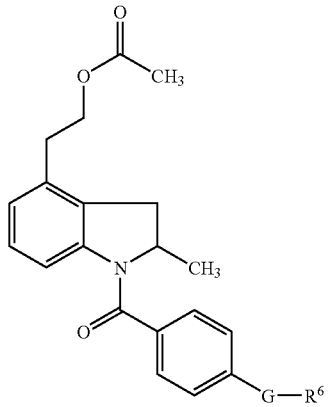
| No. | —G—R⁶ |
|---|---|
| 21 | 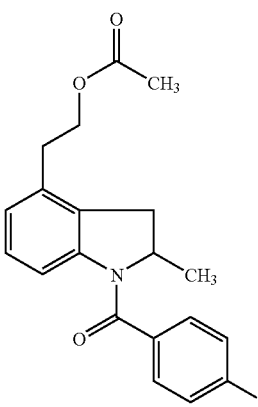 |
TABLE 46
(I-C-7)
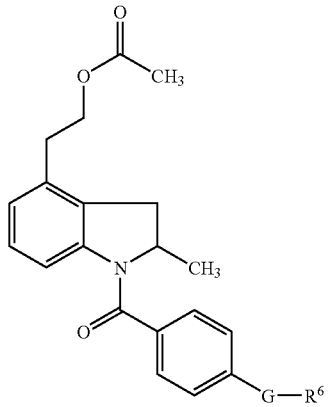
| No. | —G—R⁶ |
|---|---|
| 1 | 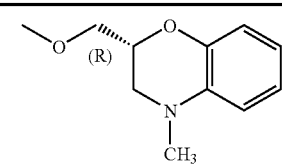 |
| 2 | 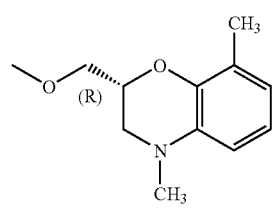 |

TABLE 46-continued
(I-C-7)
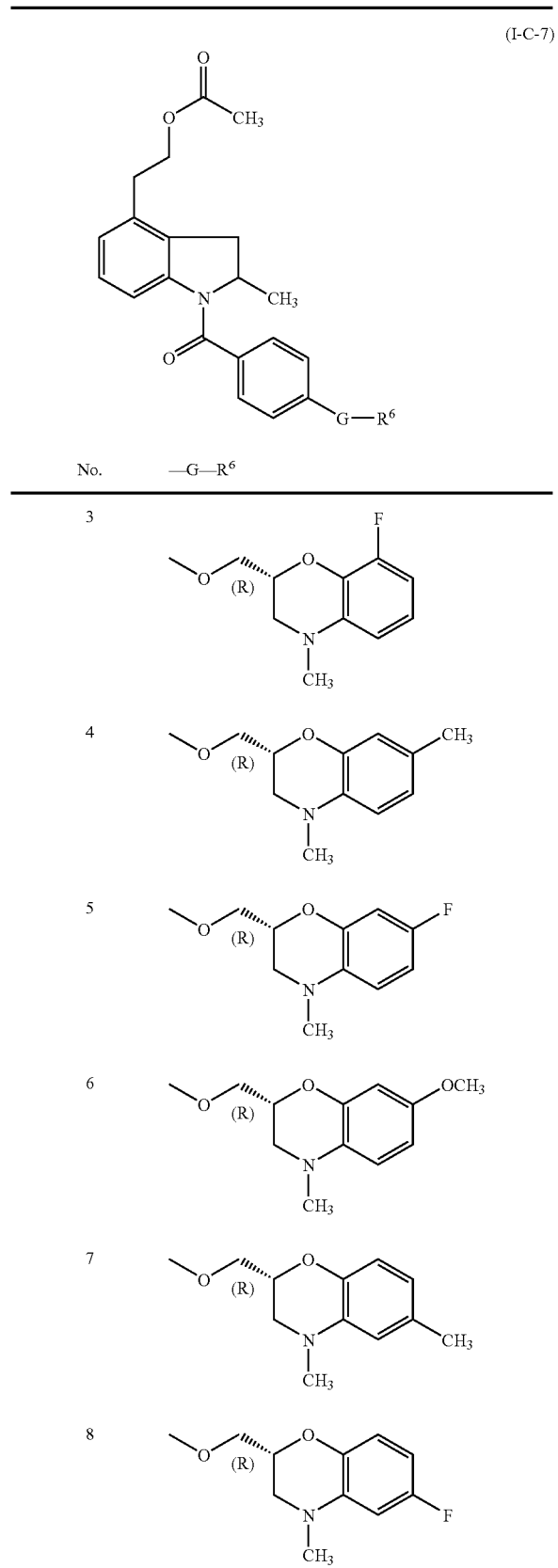
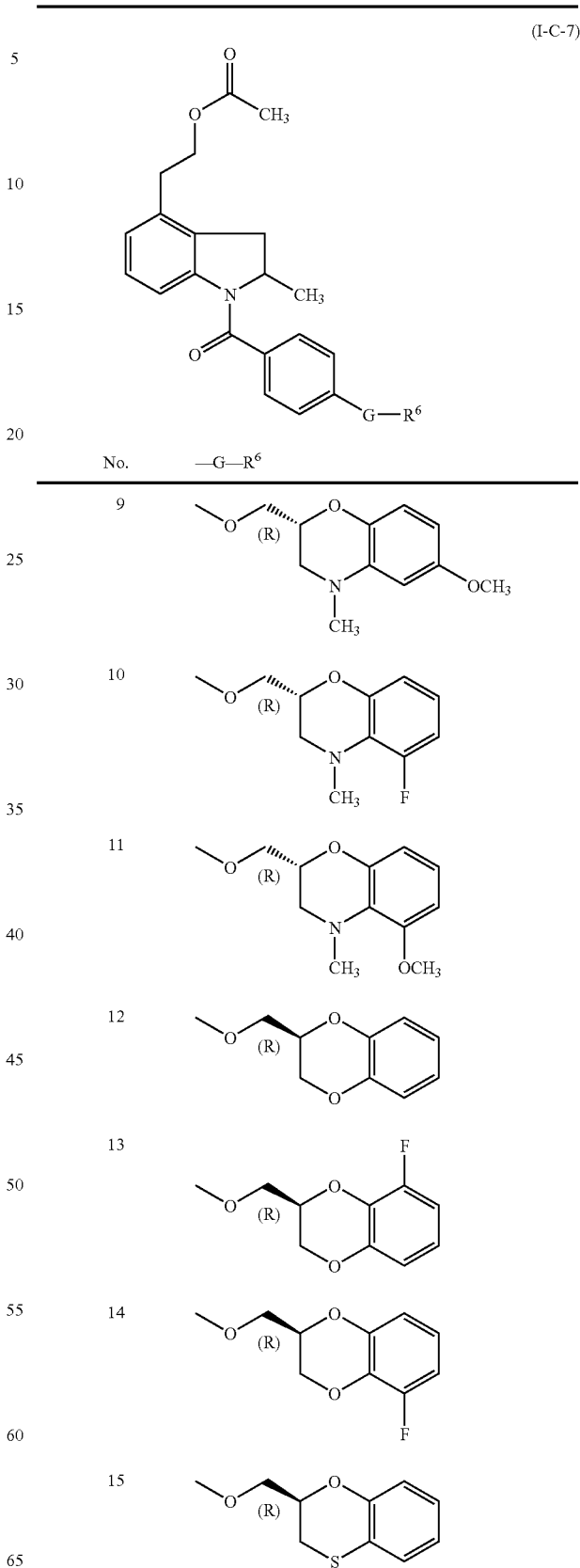

TABLE 46-continued (I-C-7)

| No. | —G—R⁶ |
|---|---|
| 16 | (R)-methoxymethyl-2,3-dihydrobenzofuran |
| 17 | (R)-3-methoxymethyl-2,3-dihydrobenzofuran |
| 18 | (R)-3-methoxymethyl-5-fluoro-2,3-dihydrobenzofuran |
| 19 | (R)-3-methoxymethyl-6-fluoro-2,3-dihydrobenzofuran |
| 20 | (R)-3-methoxymethyl-7-fluoro-2,3-dihydrobenzofuran |
| 21 | (R)-2-methoxymethyl-1-methylindoline |

TABLE 47

(I-C-8)

| No. | —G—R⁶ |
|---|---|
| 1 | (S)-2-methoxymethyl-4-methyl-3,4-dihydro-2H-benzo[1,4]oxazine |
| 2 | (S)-2-methoxymethyl-4,8-dimethyl-3,4-dihydro-2H-benzo[1,4]oxazine |
| 3 | (S)-2-methoxymethyl-8-fluoro-4-methyl-3,4-dihydro-2H-benzo[1,4]oxazine |
| 4 | (S)-2-methoxymethyl-4,7-dimethyl-3,4-dihydro-2H-benzo[1,4]oxazine |
| 5 | (S)-2-methoxymethyl-7-fluoro-4-methyl-3,4-dihydro-2H-benzo[1,4]oxazine |
| 6 | (S)-2-methoxymethyl-7-methoxy-4-methyl-3,4-dihydro-2H-benzo[1,4]oxazine |

TABLE 47-continued
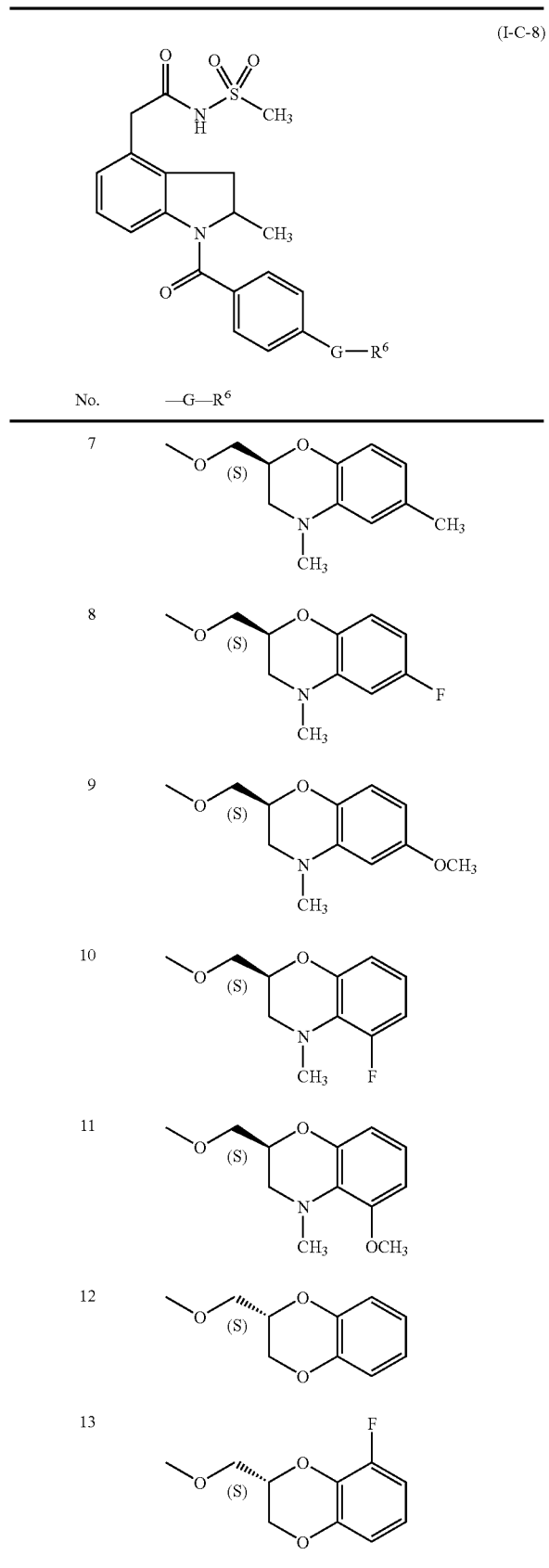
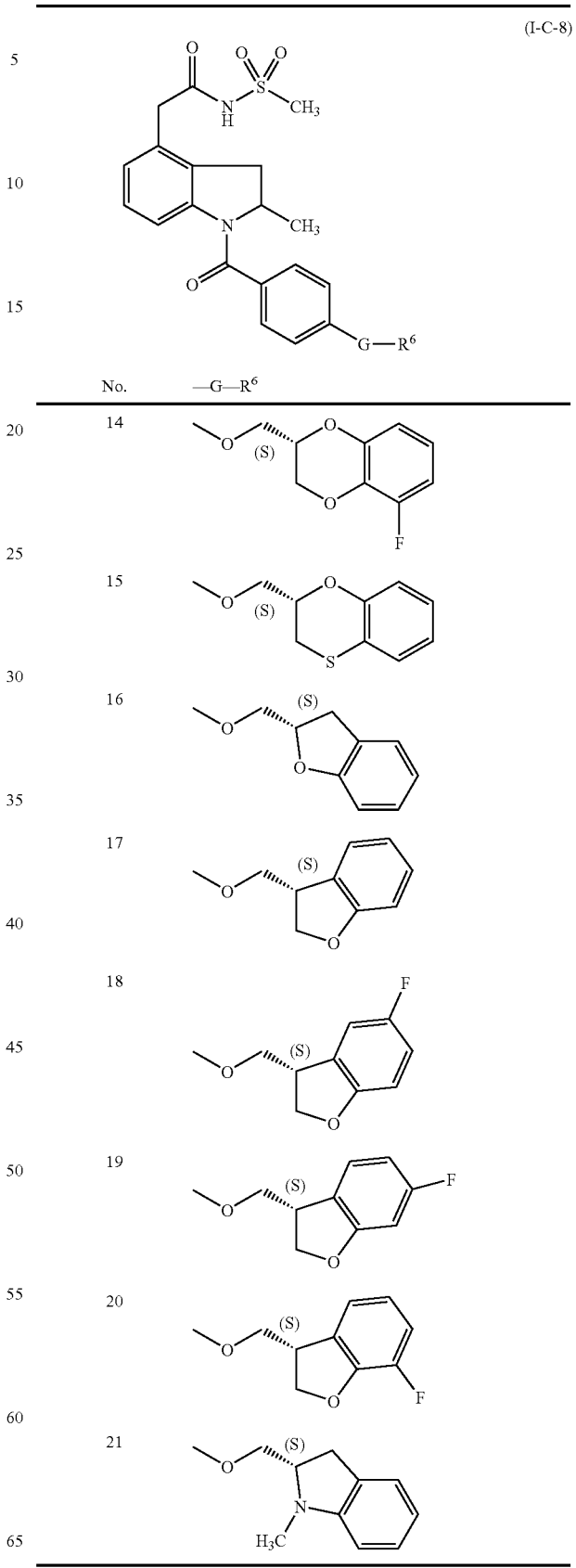

TABLE 48

(I-C-8)

| No. | —G—R⁶ |
|---|---|
| 1 | 2-(R)-methoxymethyl-4-methyl-3,4-dihydro-2H-benzo[1,4]oxazine |
| 2 | 2-(R)-methoxymethyl-4,8-dimethyl-3,4-dihydro-2H-benzo[1,4]oxazine |
| 3 | 2-(R)-methoxymethyl-8-fluoro-4-methyl-3,4-dihydro-2H-benzo[1,4]oxazine |
| 4 | 2-(R)-methoxymethyl-4,7-dimethyl-3,4-dihydro-2H-benzo[1,4]oxazine |
| 5 | 2-(R)-methoxymethyl-7-fluoro-4-methyl-3,4-dihydro-2H-benzo[1,4]oxazine |
| 6 | 2-(R)-methoxymethyl-7-methoxy-4-methyl-3,4-dihydro-2H-benzo[1,4]oxazine |

TABLE 48-continued (I-C-8)

| No. | —G—R⁶ |
|---|---|
| 7 | 2-(R)-methoxymethyl-4,6-dimethyl-3,4-dihydro-2H-benzo[1,4]oxazine |
| 8 | 2-(R)-methoxymethyl-6-fluoro-4-methyl-3,4-dihydro-2H-benzo[1,4]oxazine |
| 9 | 2-(R)-methoxymethyl-6-methoxy-4-methyl-3,4-dihydro-2H-benzo[1,4]oxazine |
| 10 | 2-(R)-methoxymethyl-5-fluoro-4-methyl-3,4-dihydro-2H-benzo[1,4]oxazine |
| 11 | 2-(R)-methoxymethyl-5-methoxy-4-methyl-3,4-dihydro-2H-benzo[1,4]oxazine |
| 12 | 2-(R)-methoxymethyl-2,3-dihydro-benzo[1,4]dioxine |
| 13 | 2-(R)-methoxymethyl-5-fluoro-2,3-dihydro-benzo[1,4]dioxine |

TABLE 48-continued
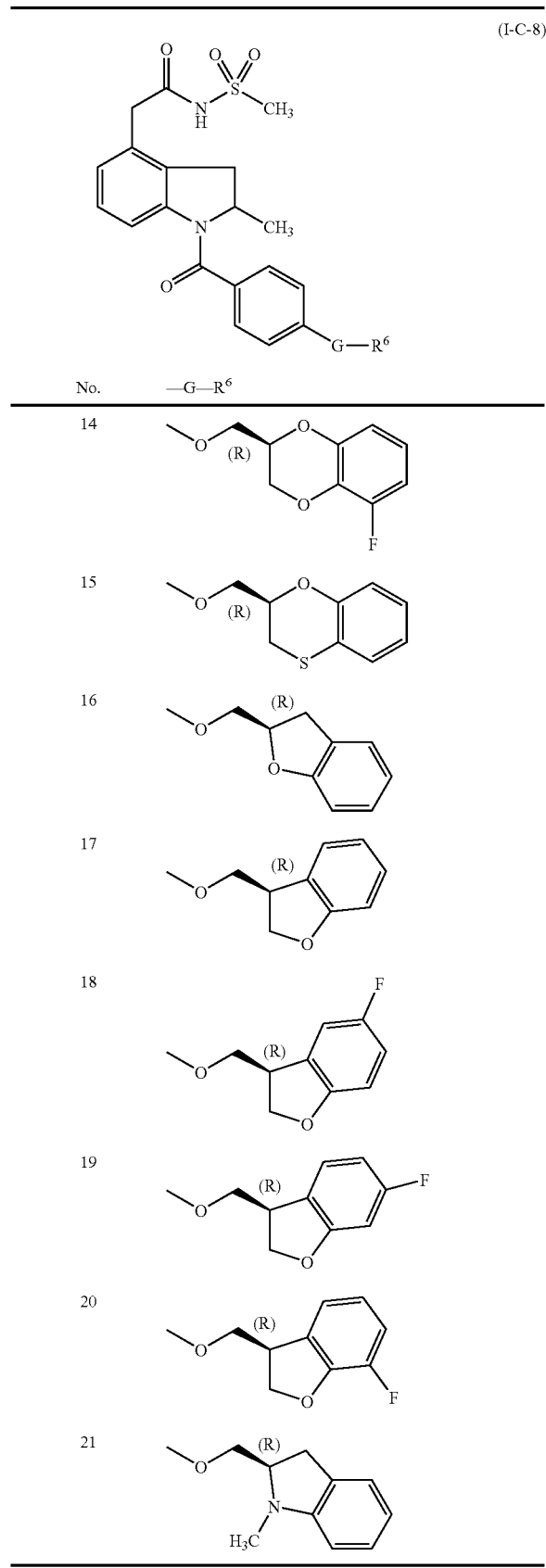
TABLE 49
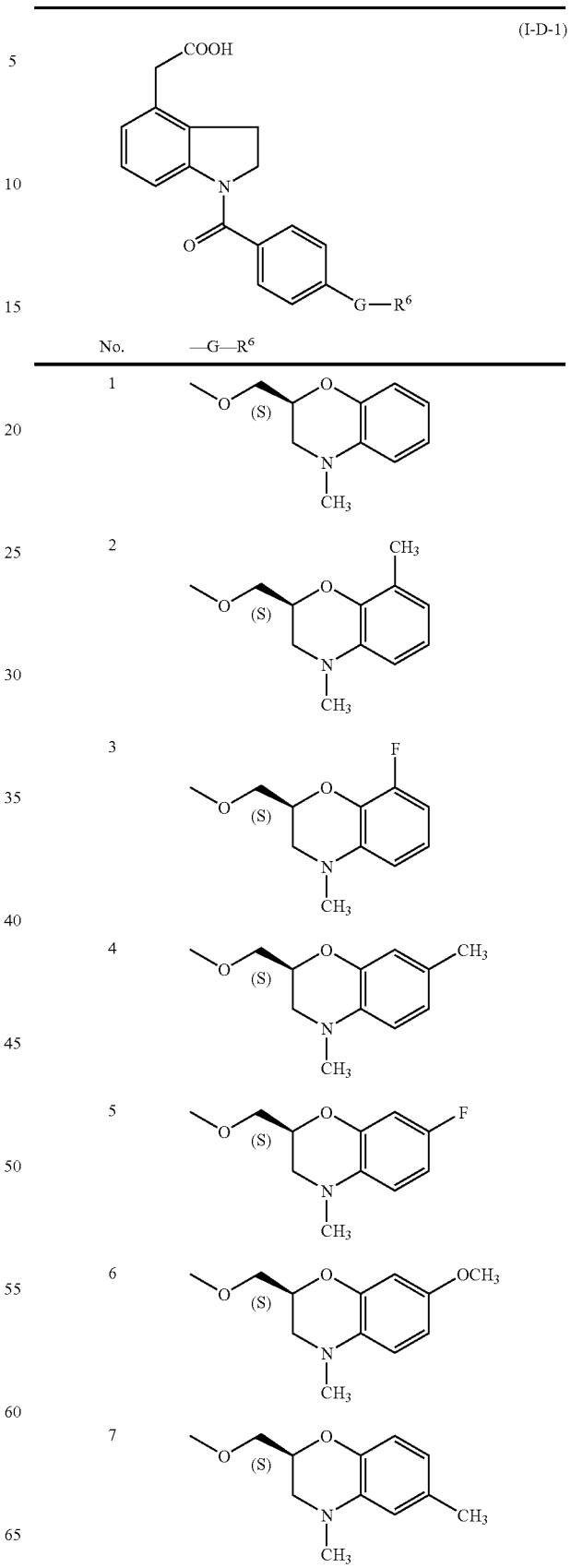

TABLE 49-continued (I-D-1)

| No. | —G—R⁶ |
|---|---|
| 8 | 6-fluoro-4-methyl-2(S)-(methoxymethyl)-3,4-dihydro-2H-1,4-benzoxazine |
| 9 | 6-methoxy-4-methyl-2(S)-(methoxymethyl)-3,4-dihydro-2H-1,4-benzoxazine |
| 10 | 5-fluoro-4-methyl-2(S)-(methoxymethyl)-3,4-dihydro-2H-1,4-benzoxazine |
| 11 | 5-methoxy-4-methyl-2(S)-(methoxymethyl)-3,4-dihydro-2H-1,4-benzoxazine |
| 12 | 2(S)-(methoxymethyl)-2,3-dihydro-1,4-benzodioxine |
| 13 | 5-fluoro-2(S)-(methoxymethyl)-2,3-dihydro-1,4-benzodioxine |
| 14 | 8-fluoro-2(S)-(methoxymethyl)-2,3-dihydro-1,4-benzodioxine |
| 15 | 2(S)-(methoxymethyl)-2,3-dihydro-1,4-benzoxathiine |
| 16 | 2(S)-(methoxymethyl)-2,3-dihydrobenzofuran |
| 17 | 3(S)-(methoxymethyl)-2,3-dihydrobenzofuran |
| 18 | 5-fluoro-3(S)-(methoxymethyl)-2,3-dihydrobenzofuran |
| 19 | 6-fluoro-3(S)-(methoxymethyl)-2,3-dihydrobenzofuran |
| 20 | 7-fluoro-3(S)-(methoxymethyl)-2,3-dihydrobenzofuran |
| 21 | 1-methyl-2(S)-(methoxymethyl)indoline |

TABLE 50

(I-D-1)

| No. | —G—R⁶ |
|---|---|
| 1 | (R)-2-(methoxymethyl)-4-methyl-3,4-dihydro-2H-benzo[b][1,4]oxazine |
| 2 | (R)-2-(methoxymethyl)-4,8-dimethyl-3,4-dihydro-2H-benzo[b][1,4]oxazine |
| 3 | (R)-8-fluoro-2-(methoxymethyl)-4-methyl-3,4-dihydro-2H-benzo[b][1,4]oxazine |
| 4 | (R)-2-(methoxymethyl)-4,7-dimethyl-3,4-dihydro-2H-benzo[b][1,4]oxazine |
| 5 | (R)-7-fluoro-2-(methoxymethyl)-4-methyl-3,4-dihydro-2H-benzo[b][1,4]oxazine |
| 6 | (R)-2-(methoxymethyl)-7-methoxy-4-methyl-3,4-dihydro-2H-benzo[b][1,4]oxazine |
| 7 | (R)-2-(methoxymethyl)-4,6-dimethyl-3,4-dihydro-2H-benzo[b][1,4]oxazine |
| 8 | (R)-6-fluoro-2-(methoxymethyl)-4-methyl-3,4-dihydro-2H-benzo[b][1,4]oxazine |
| 9 | (R)-2-(methoxymethyl)-6-methoxy-4-methyl-3,4-dihydro-2H-benzo[b][1,4]oxazine |
| 10 | (R)-5-fluoro-2-(methoxymethyl)-4-methyl-3,4-dihydro-2H-benzo[b][1,4]oxazine |
| 11 | (R)-2-(methoxymethyl)-5-methoxy-4-methyl-3,4-dihydro-2H-benzo[b][1,4]oxazine |
| 12 | (R)-2-(methoxymethyl)-2,3-dihydro-1,4-benzodioxine |
| 13 | (R)-5-fluoro-2-(methoxymethyl)-2,3-dihydro-1,4-benzodioxine |

TABLE 50-continued (I-D-1)

| No. | —G—R⁶ |
|---|---|
| 14 | (R), benzodioxane-OCH₃, F |
| 15 | (R), benzoxathiane-OCH₃ |
| 16 | (R), benzofuran-2-yl-CH₂OCH₃ |
| 17 | (R), benzofuran-3-yl-CH₂OCH₃ |
| 18 | (R), 5-fluorobenzofuran-3-yl-CH₂OCH₃ |
| 19 | (R), 6-fluorobenzofuran-3-yl-CH₂OCH₃ |
| 20 | (R), 7-fluorobenzofuran-3-yl-CH₂OCH₃ |
| 21 | (R), 1-methylindoline-2-yl-CH₂OCH₃ |

TABLE 51

(I-D-2)

| No. | —G—R⁶ |
|---|---|
| 1 | (S), 4-methyl-benzoxazine-OCH₃ |
| 2 | (S), 4,8-dimethyl-benzoxazine-OCH₃ |
| 3 | (S), 8-fluoro-4-methyl-benzoxazine-OCH₃ |
| 4 | (S), 4,7-dimethyl-benzoxazine-OCH₃ |
| 5 | (S), 7-fluoro-4-methyl-benzoxazine-OCH₃ |
| 6 | (S), 7-methoxy-4-methyl-benzoxazine-OCH₃ |

TABLE 51-continued
(I-D-2)
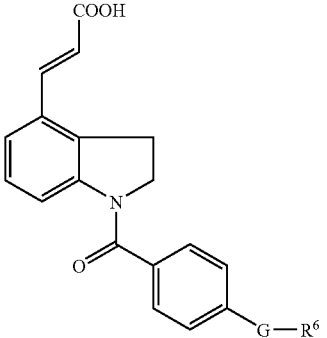
| No. | —G—R⁶ |
|---|---|
| 7 | 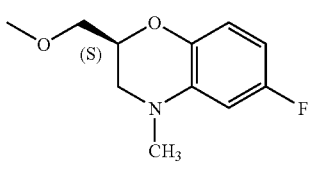 |
| 8 | 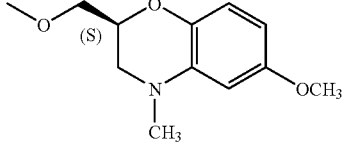 |
| 9 | 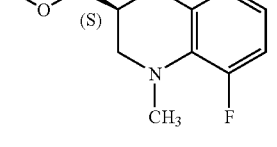 |
| 10 | 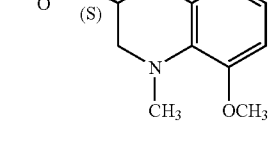 |
| 11 | 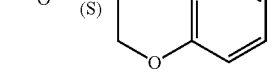 |
| 12 | 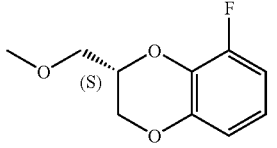 |
| 13 | 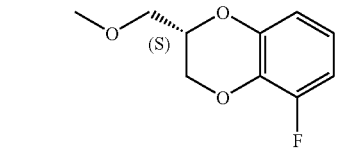 |
TABLE 51-continued
(I-D-2)
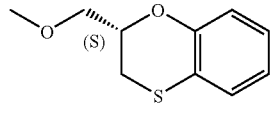
| No. | —G—R⁶ |
|---|---|
| 14 | 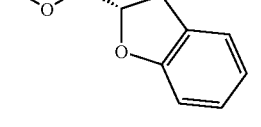 |
| 15 | 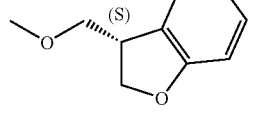 |
| 16 | 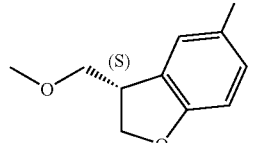 |
| 17 | 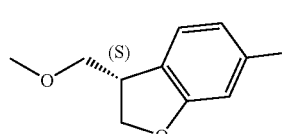 |
| 18 | 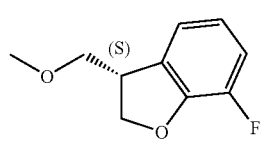 |
| 19 | |
| 20 | |

TABLE 51-continued (I-D-2)

| No. | —G—R⁶ |
|---|---|
| 21 | (S)-1-methyl-2-(methoxymethyl)indoline |

TABLE 52

(I-D-2)

| No. | —G—R⁶ |
|---|---|
| 1 | (R)-4-methyl-2-(methoxymethyl)-3,4-dihydro-2H-benzo[1,4]oxazine |
| 2 | (R)-4,8-dimethyl-2-(methoxymethyl)-3,4-dihydro-2H-benzo[1,4]oxazine |
| 3 | (R)-8-fluoro-4-methyl-2-(methoxymethyl)-3,4-dihydro-2H-benzo[1,4]oxazine |
| 4 | (R)-4,7-dimethyl-2-(methoxymethyl)-3,4-dihydro-2H-benzo[1,4]oxazine |
| 5 | (R)-7-fluoro-4-methyl-2-(methoxymethyl)-3,4-dihydro-2H-benzo[1,4]oxazine |
| 6 | (R)-7-methoxy-4-methyl-2-(methoxymethyl)-3,4-dihydro-2H-benzo[1,4]oxazine |
| 7 | (R)-4,6-dimethyl-2-(methoxymethyl)-3,4-dihydro-2H-benzo[1,4]oxazine |
| 8 | (R)-6-fluoro-4-methyl-2-(methoxymethyl)-3,4-dihydro-2H-benzo[1,4]oxazine |

TABLE 52-continued
(I-D-2)
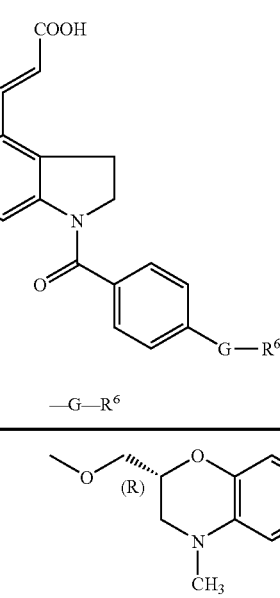
| No. | —G—R⁶ |
|---|---|
| 9 | 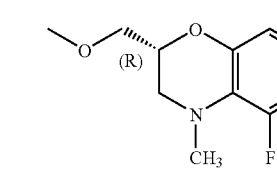 |
| 10 | 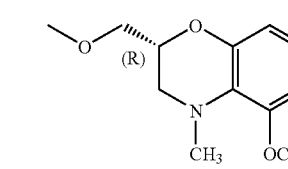 |
| 11 | 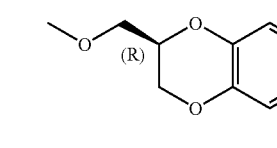 |
| 12 | 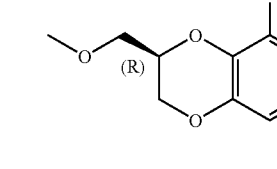 |
| 13 | 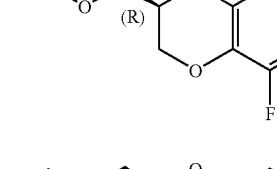 |
| 14 | 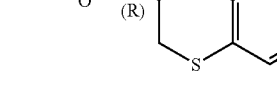 |
| 15 | 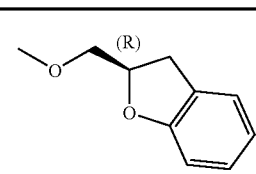 |
TABLE 52-continued
(I-D-2)
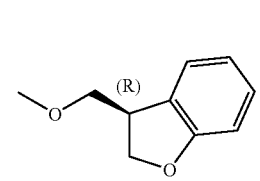
| No. | —G—R⁶ |
|---|---|
| 16 | 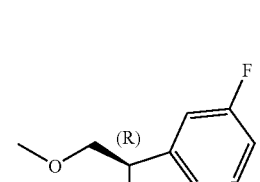 |
| 17 | 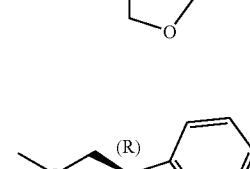 |
| 18 | 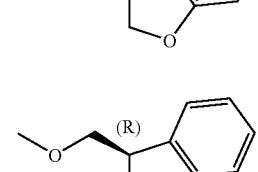 |
| 19 | 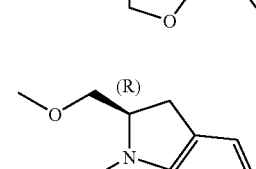 |
| 20 | |
| 21 | |

TABLE 53
(I-D-3)
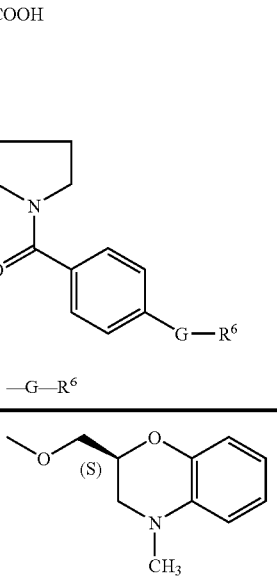
| No. | —G—R6 |
|---|---|
| 1 | 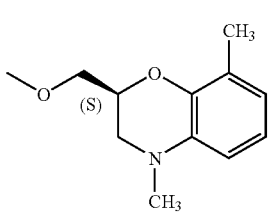 |
| 2 | 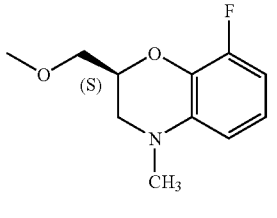 |
| 3 | 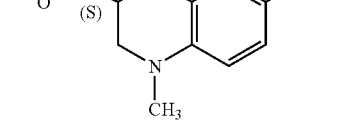 |
| 4 | 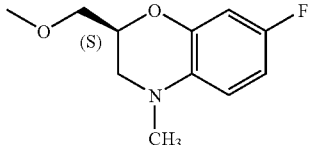 |
| 5 | 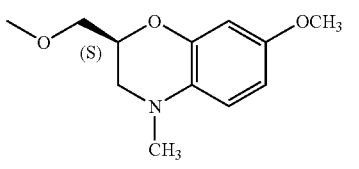 |
| 6 | 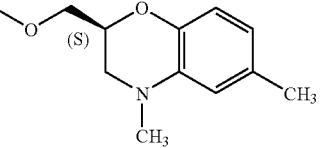 |
TABLE 53-continued
(I-D-3)
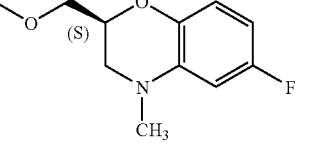
| No. | —G—R6 |
|---|---|
| 7 | 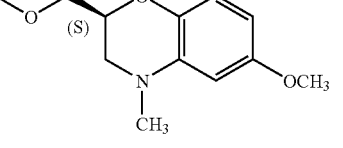 |
| 8 | 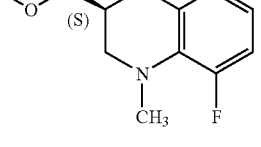 |
| 9 | 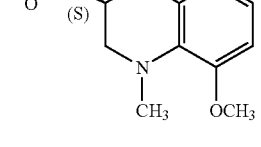 |
| 10 | 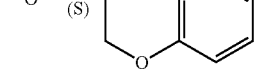 |
| 11 | 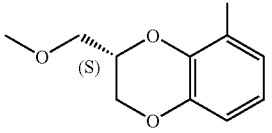 |
| 12 |  |
| 13 |  |

TABLE 53-continued (I-D-3)

| No. | —G—R⁶ |
|---|---|
| 14 | [2-(methoxymethyl)-(S)-5-fluoro-1,4-benzodioxine] |
| 15 | [2-(methoxymethyl)-(S)-1,4-benzoxathiine] |
| 16 | [2-(methoxymethyl)-(S)-2,3-dihydrobenzofuran] |
| 17 | [3-(methoxymethyl)-(S)-2,3-dihydrobenzofuran] |
| 18 | [3-(methoxymethyl)-(S)-5-fluoro-2,3-dihydrobenzofuran] |
| 19 | [3-(methoxymethyl)-(S)-6-fluoro-2,3-dihydrobenzofuran] |
| 20 | [3-(methoxymethyl)-(S)-7-fluoro-2,3-dihydrobenzofuran] |

TABLE 53-continued (I-D-3)

| No. | —G—R⁶ |
|---|---|
| 21 | [2-(methoxymethyl)-(S)-1-methyl-2,3-dihydroindole] |

TABLE 54

(I-D-3)

| No. | —G—R⁶ |
|---|---|
| 1 | [2-(methoxymethyl)-(R)-4-methyl-3,4-dihydro-2H-1,4-benzoxazine] |
| 2 | [2-(methoxymethyl)-(R)-4,8-dimethyl-3,4-dihydro-2H-1,4-benzoxazine] |

TABLE 54-continued
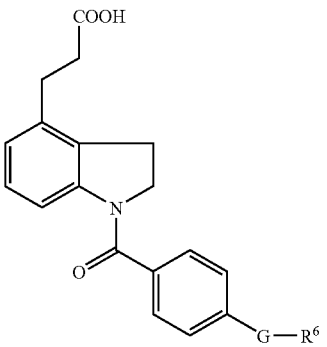
(I-D-3)
| No. | —G—R⁶ |
|---|---|
| 3 | 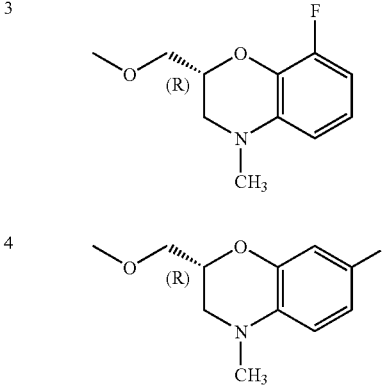 |
| 4 | 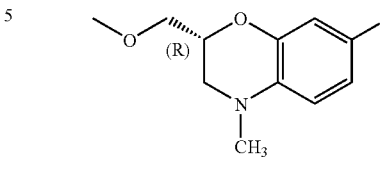 |
| 5 | 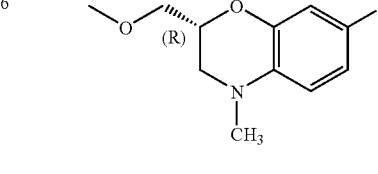 |
| 6 | 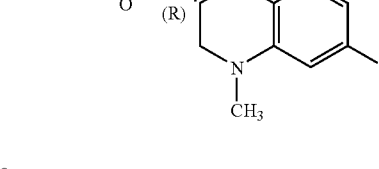 |
| 7 | 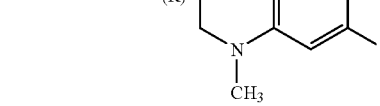 |
| 8 | 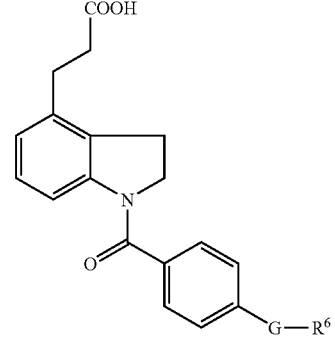 |
TABLE 54-continued
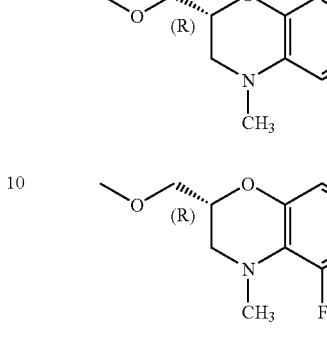
(I-D-3)
| No. | —G—R⁶ |
|---|---|
| 9 | 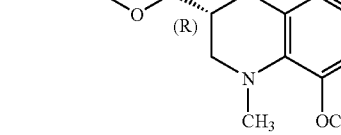 |
| 10 | 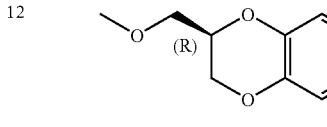 |
| 11 | 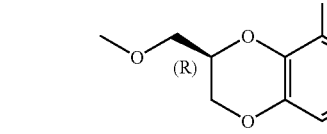 |
| 12 | 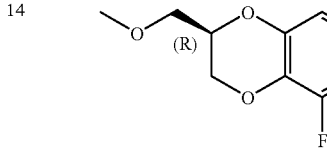 |
| 13 | 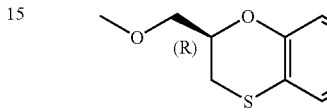 |
| 14 |  |
| 15 |  |

TABLE 54-continued (I-D-3)

| No. | —G—R⁶ |
|---|---|
| 16 | (R) 2-(methoxymethyl)-2,3-dihydrobenzofuran |
| 17 | (R) 3-(methoxymethyl)-2,3-dihydrobenzofuran |
| 18 | (R) 5-fluoro-3-(methoxymethyl)-2,3-dihydrobenzofuran |
| 19 | (R) 6-fluoro-3-(methoxymethyl)-2,3-dihydrobenzofuran |
| 20 | (R) 7-fluoro-3-(methoxymethyl)-2,3-dihydrobenzofuran |
| 21 | (R) 2-(methoxymethyl)-1-methylindoline |

TABLE 55

(I-D-4)

| No. | —G—R⁶ |
|---|---|
| 1 | (S) 2-(methoxymethyl)-4-methyl-3,4-dihydro-2H-benzo[b][1,4]oxazine |
| 2 | (S) 2-(methoxymethyl)-4,8-dimethyl-3,4-dihydro-2H-benzo[b][1,4]oxazine |
| 3 | (S) 8-fluoro-2-(methoxymethyl)-4-methyl-3,4-dihydro-2H-benzo[b][1,4]oxazine |
| 4 | (S) 2-(methoxymethyl)-4,7-dimethyl-3,4-dihydro-2H-benzo[b][1,4]oxazine |
| 5 | (S) 7-fluoro-2-(methoxymethyl)-4-methyl-3,4-dihydro-2H-benzo[b][1,4]oxazine |
| 6 | (S) 7-methoxy-2-(methoxymethyl)-4-methyl-3,4-dihydro-2H-benzo[b][1,4]oxazine |

TABLE 55-continued (I-D-4)

| No. | —G—R⁶ |
|---|---|
| 7 | 6-methyl-4-methyl-(S)-2-(methoxymethyl)-3,4-dihydro-2H-1,4-benzoxazine |
| 8 | 6-fluoro-4-methyl-(S)-2-(methoxymethyl)-3,4-dihydro-2H-1,4-benzoxazine |
| 9 | 6-methoxy-4-methyl-(S)-2-(methoxymethyl)-3,4-dihydro-2H-1,4-benzoxazine |
| 10 | 5-fluoro-4-methyl-(S)-2-(methoxymethyl)-3,4-dihydro-2H-1,4-benzoxazine |
| 11 | 5-methoxy-4-methyl-(S)-2-(methoxymethyl)-3,4-dihydro-2H-1,4-benzoxazine |
| 12 | (S)-2-(methoxymethyl)-2,3-dihydro-1,4-benzodioxine |
| 13 | 5-fluoro-(S)-2-(methoxymethyl)-2,3-dihydro-1,4-benzodioxine |
| 14 | 8-fluoro-(S)-2-(methoxymethyl)-2,3-dihydro-1,4-benzodioxine |
| 15 | (S)-2-(methoxymethyl)-2,3-dihydro-1,4-benzoxathiine |
| 16 | (S)-2-(methoxymethyl)-2,3-dihydrobenzofuran |
| 17 | (S)-3-(methoxymethyl)-2,3-dihydrobenzofuran |
| 18 | 5-fluoro-(S)-3-(methoxymethyl)-2,3-dihydrobenzofuran |
| 19 | 6-fluoro-(S)-3-(methoxymethyl)-2,3-dihydrobenzofuran |
| 20 | 7-fluoro-(S)-3-(methoxymethyl)-2,3-dihydrobenzofuran |
| 21 | 1-methyl-(S)-3-(methoxymethyl)indoline |

TABLE 56

(I-D-4)

Structure: 1-(4-(G-R⁶)benzoyl)-2,3-dihydro-1H-indole-4-carboxylic acid

| No. | —G—R⁶ |
|---|---|
| 1 | (R)-4-methyl-2-(methoxymethyl)-3,4-dihydro-2H-benzo[1,4]oxazine |
| 2 | (R)-4,8-dimethyl-2-(methoxymethyl)-3,4-dihydro-2H-benzo[1,4]oxazine |
| 3 | (R)-8-fluoro-4-methyl-2-(methoxymethyl)-3,4-dihydro-2H-benzo[1,4]oxazine |
| 4 | (R)-4,7-dimethyl-2-(methoxymethyl)-3,4-dihydro-2H-benzo[1,4]oxazine |
| 5 | (R)-7-fluoro-4-methyl-2-(methoxymethyl)-3,4-dihydro-2H-benzo[1,4]oxazine |
| 6 | (R)-7-methoxy-4-methyl-2-(methoxymethyl)-3,4-dihydro-2H-benzo[1,4]oxazine |
| 7 | (R)-4,6-dimethyl-2-(methoxymethyl)-3,4-dihydro-2H-benzo[1,4]oxazine |

TABLE 56-continued (I-D-4)

| No. | —G—R⁶ |
|---|---|
| 8 | (R)-6-fluoro-4-methyl-2-(methoxymethyl)-3,4-dihydro-2H-benzo[1,4]oxazine |
| 9 | (R)-6-methoxy-4-methyl-2-(methoxymethyl)-3,4-dihydro-2H-benzo[1,4]oxazine |
| 10 | (R)-5-fluoro-4-methyl-2-(methoxymethyl)-3,4-dihydro-2H-benzo[1,4]oxazine |
| 11 | (R)-5-methoxy-4-methyl-2-(methoxymethyl)-3,4-dihydro-2H-benzo[1,4]oxazine |
| 12 | (R)-2-(methoxymethyl)-2,3-dihydro-1,4-benzodioxine |
| 13 | (R)-5-fluoro-2-(methoxymethyl)-2,3-dihydro-1,4-benzodioxine |
| 14 | (R)-8-fluoro-2-(methoxymethyl)-2,3-dihydro-1,4-benzodioxine |
| 15 | (R)-3-(methoxymethyl)-2,3-dihydro-1,4-benzoxathiine |

TABLE 56-continued
(I-D-4)
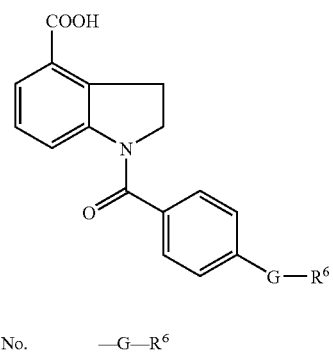
| No. | —G—R⁶ |
|---|---|
| 16 | 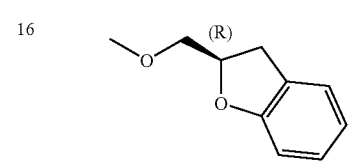 |
| 17 | 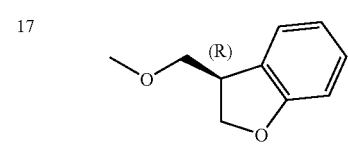 |
| 18 | 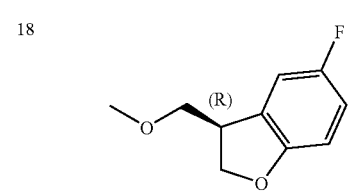 |
| 19 | 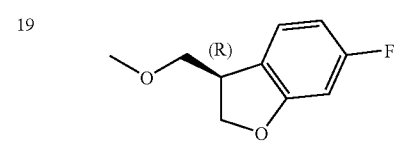 |
| 20 | 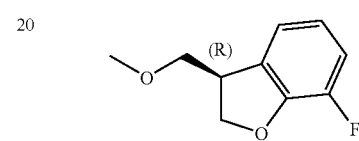 |
| 21 | 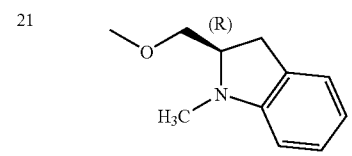 |
TABLE 57
(I-D-5)
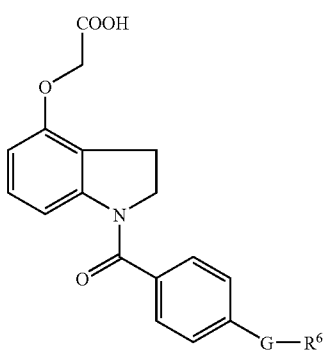
| No. | —G—R⁶ |
|---|---|
| 1 | 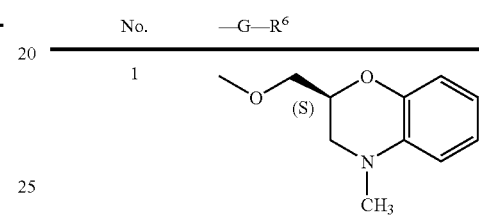 |
| 2 | 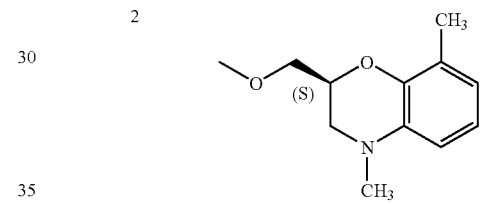 |
| 3 | 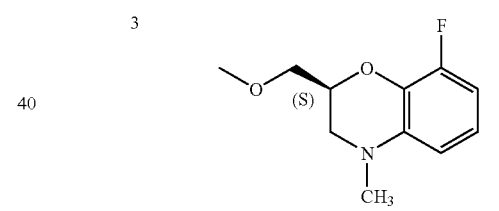 |
| 4 | 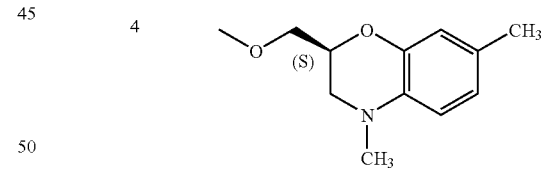 |
| 5 | 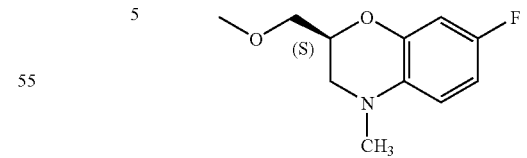 |
| 6 | 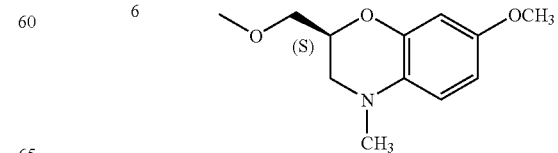 |

TABLE 57-continued (I-D-5)

| No. | —G—R⁶ |
|---|---|
| 7 | (S)-2-(methoxymethyl)-4-methyl-6-methyl-3,4-dihydro-2H-benzo[b][1,4]oxazine |
| 8 | (S)-2-(methoxymethyl)-4-methyl-6-fluoro-3,4-dihydro-2H-benzo[b][1,4]oxazine |
| 9 | (S)-2-(methoxymethyl)-4-methyl-6-methoxy-3,4-dihydro-2H-benzo[b][1,4]oxazine |
| 10 | (S)-2-(methoxymethyl)-4-methyl-5-fluoro-3,4-dihydro-2H-benzo[b][1,4]oxazine |
| 11 | (S)-2-(methoxymethyl)-4-methyl-5-methoxy-3,4-dihydro-2H-benzo[b][1,4]oxazine |
| 12 | (S)-2-(methoxymethyl)-2,3-dihydro-1,4-benzodioxine |
| 13 | (S)-2-(methoxymethyl)-5-fluoro-2,3-dihydro-1,4-benzodioxine |

TABLE 57-continued (I-D-5)

| No. | —G—R⁶ |
|---|---|
| 14 | (S)-2-(methoxymethyl)-8-fluoro-2,3-dihydro-1,4-benzodioxine |
| 15 | (S)-2-(methoxymethyl)-2,3-dihydro-1,4-benzoxathiine |
| 16 | (S)-2-(methoxymethyl)-2,3-dihydrobenzofuran |
| 17 | (S)-3-(methoxymethyl)-2,3-dihydrobenzofuran |
| 18 | (S)-3-(methoxymethyl)-5-fluoro-2,3-dihydrobenzofuran |
| 19 | (S)-3-(methoxymethyl)-6-fluoro-2,3-dihydrobenzofuran |
| 20 | (S)-3-(methoxymethyl)-7-fluoro-2,3-dihydrobenzofuran |

TABLE 57-continued (I-D-5)

| No. | —G—R⁶ |
|---|---|
| 21 | (S)-2-(methoxymethyl)-1-methylindoline |

TABLE 58

(I-D-5)

| No. | —G—R⁶ |
|---|---|
| 1 | (R)-2-(methoxymethyl)-4-methyl-3,4-dihydro-2H-benzo[b][1,4]oxazine |
| 2 | (R)-2-(methoxymethyl)-4,8-dimethyl-3,4-dihydro-2H-benzo[b][1,4]oxazine |
| 3 | (R)-8-fluoro-2-(methoxymethyl)-4-methyl-3,4-dihydro-2H-benzo[b][1,4]oxazine |
| 4 | (R)-2-(methoxymethyl)-4,7-dimethyl-3,4-dihydro-2H-benzo[b][1,4]oxazine |
| 5 | (R)-7-fluoro-2-(methoxymethyl)-4-methyl-3,4-dihydro-2H-benzo[b][1,4]oxazine |
| 6 | (R)-2-(methoxymethyl)-7-methoxy-4-methyl-3,4-dihydro-2H-benzo[b][1,4]oxazine |
| 7 | (R)-2-(methoxymethyl)-4,6-dimethyl-3,4-dihydro-2H-benzo[b][1,4]oxazine |
| 8 | (R)-6-fluoro-2-(methoxymethyl)-4-methyl-3,4-dihydro-2H-benzo[b][1,4]oxazine |

TABLE 58-continued (I-D-5)

| No. | —G—R⁶ |
|---|---|
| 9 | 2-(methoxymethyl)-4-methyl-6-methoxy-3,4-dihydro-2H-1,4-benzoxazine (R) |
| 10 | 2-(methoxymethyl)-4-methyl-5-fluoro-3,4-dihydro-2H-1,4-benzoxazine (R) |
| 11 | 2-(methoxymethyl)-4-methyl-5-methoxy-3,4-dihydro-2H-1,4-benzoxazine (R) |
| 12 | 2-(methoxymethyl)-2,3-dihydro-1,4-benzodioxine (R) |
| 13 | 2-(methoxymethyl)-5-fluoro-2,3-dihydro-1,4-benzodioxine (R) |
| 14 | 2-(methoxymethyl)-8-fluoro-2,3-dihydro-1,4-benzodioxine (R) |
| 15 | 2-(methoxymethyl)-2,3-dihydro-1,4-benzoxathiine (R) |

TABLE 58-continued (I-D-5)

| No. | —G—R⁶ |
|---|---|
| 16 | 2-(methoxymethyl)-2,3-dihydrobenzofuran (R) |
| 17 | 3-(methoxymethyl)-2,3-dihydrobenzofuran (R) |
| 18 | 3-(methoxymethyl)-5-fluoro-2,3-dihydrobenzofuran (R) |
| 19 | 3-(methoxymethyl)-6-fluoro-2,3-dihydrobenzofuran (R) |
| 20 | 3-(methoxymethyl)-7-fluoro-2,3-dihydrobenzofuran (R) |
| 21 | 2-(methoxymethyl)-1-methyl-2,3-dihydro-1H-indole (R) |

TABLE 59
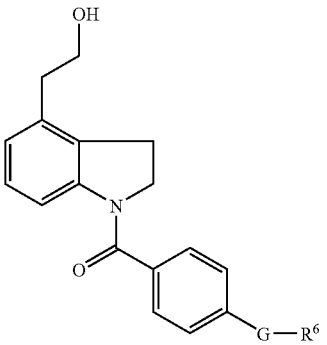
(I-D-6)
| No. | —G—R⁶ |
|---|---|
| 1 | 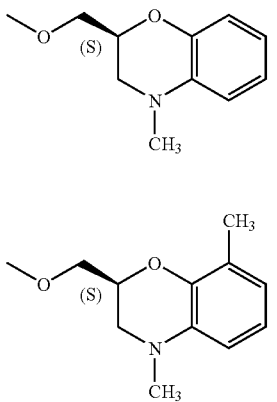 |
| 2 | 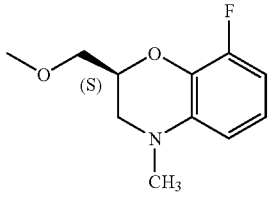 |
| 3 | 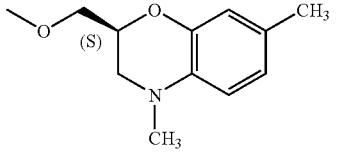 |
| 4 | 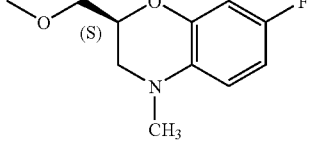 |
| 5 |  |
| 6 | 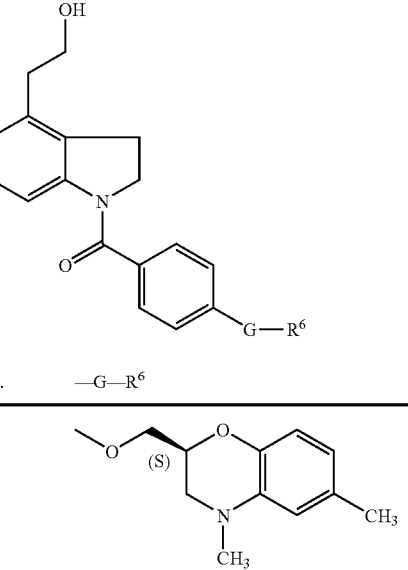 |
TABLE 59-continued
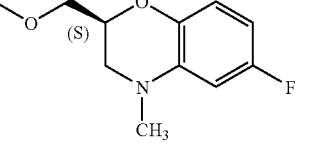
(I-D-6)
| No. | —G—R⁶ |
|---|---|
| 7 | 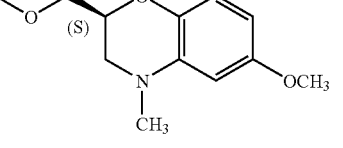 |
| 8 | 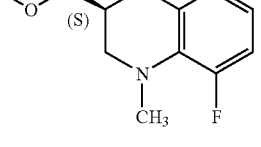 |
| 9 | 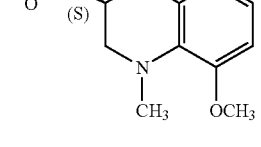 |
| 10 | 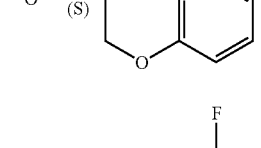 |
| 11 | 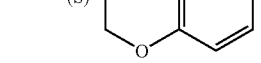 |
| 12 | |
| 13 | |

TABLE 59-continued (I-D-6)

| No. | —G—R⁶ |
|---|---|
| 14 | (S)-methoxymethyl-8-fluoro-2,3-dihydro-1,4-benzodioxine |
| 15 | (S)-methoxymethyl-2,3-dihydro-1,4-benzoxathiine |
| 16 | (S)-methoxymethyl-2,3-dihydrobenzofuran |
| 17 | (S)-methoxymethyl-2,3-dihydrobenzofuran |
| 18 | (S)-methoxymethyl-5-fluoro-2,3-dihydrobenzofuran |
| 19 | (S)-methoxymethyl-6-fluoro-2,3-dihydrobenzofuran |
| 20 | (S)-methoxymethyl-7-fluoro-2,3-dihydrobenzofuran |

TABLE 59-continued (I-D-6)

| No. | —G—R⁶ |
|---|---|
| 21 | (S)-methoxymethyl-1-methyl-2,3-dihydroindole |

TABLE 60

(I-D-6)

| No. | —G—R⁶ |
|---|---|
| 1 | (R)-methoxymethyl-4-methyl-3,4-dihydro-2H-1,4-benzoxazine |
| 2 | (R)-methoxymethyl-4,8-dimethyl-3,4-dihydro-2H-1,4-benzoxazine |

TABLE 60-continued (I-D-6)

| No. | —G—R⁶ |
|---|---|
| 3 | 8-fluoro-4-methyl-2(R)-(methoxymethyl)-3,4-dihydro-2H-1,4-benzoxazine |
| 4 | 7-methyl-4-methyl-2(R)-(methoxymethyl)-3,4-dihydro-2H-1,4-benzoxazine |
| 5 | 7-fluoro-4-methyl-2(R)-(methoxymethyl)-3,4-dihydro-2H-1,4-benzoxazine |
| 6 | 7-methoxy-4-methyl-2(R)-(methoxymethyl)-3,4-dihydro-2H-1,4-benzoxazine |
| 7 | 6-methyl-4-methyl-2(R)-(methoxymethyl)-3,4-dihydro-2H-1,4-benzoxazine |
| 8 | 6-fluoro-4-methyl-2(R)-(methoxymethyl)-3,4-dihydro-2H-1,4-benzoxazine |
| 9 | 6-methoxy-4-methyl-2(R)-(methoxymethyl)-3,4-dihydro-2H-1,4-benzoxazine |
| 10 | 5-fluoro-4-methyl-2(R)-(methoxymethyl)-3,4-dihydro-2H-1,4-benzoxazine |
| 11 | 5-methoxy-4-methyl-2(R)-(methoxymethyl)-3,4-dihydro-2H-1,4-benzoxazine |
| 12 | 2(R)-(methoxymethyl)-2,3-dihydro-1,4-benzodioxine |
| 13 | 5-fluoro-2(R)-(methoxymethyl)-2,3-dihydro-1,4-benzodioxine |
| 14 | 8-fluoro-2(R)-(methoxymethyl)-2,3-dihydro-1,4-benzodioxine |
| 15 | 2(R)-(methoxymethyl)-2,3-dihydro-1,4-benzoxathiine |

(Note: the structural drawings in the table show the parent scaffold 1-[4-(substituent)benzoyl]-4-(2-hydroxyethyl)-2,3-dihydro-1H-indole, with —G—R⁶ groups shown for each No.)

TABLE 60-continued (I-D-6)

| No. | —G—R⁶ |
|---|---|
| 16 | (R)-methoxymethyl-2,3-dihydrobenzofuran |
| 17 | (R)-methoxymethyl-2,3-dihydrobenzofuran (3-position) |
| 18 | (R)-3-methoxymethyl-5-fluoro-2,3-dihydrobenzofuran |
| 19 | (R)-3-methoxymethyl-6-fluoro-2,3-dihydrobenzofuran |
| 20 | (R)-3-methoxymethyl-7-fluoro-2,3-dihydrobenzofuran |
| 21 | (R)-2-methoxymethyl-1-methyl-2,3-dihydroindole |

TABLE 61

(I-D-7)

| No. | —G—R⁶ |
|---|---|
| 1 | (S)-2-methoxymethyl-4-methyl-3,4-dihydro-2H-benzo[1,4]oxazine |
| 2 | (S)-2-methoxymethyl-4,8-dimethyl-3,4-dihydro-2H-benzo[1,4]oxazine |
| 3 | (S)-2-methoxymethyl-8-fluoro-4-methyl-3,4-dihydro-2H-benzo[1,4]oxazine |
| 4 | (S)-2-methoxymethyl-4,7-dimethyl-3,4-dihydro-2H-benzo[1,4]oxazine |
| 5 | (S)-2-methoxymethyl-7-fluoro-4-methyl-3,4-dihydro-2H-benzo[1,4]oxazine |
| 6 | (S)-2-methoxymethyl-7-methoxy-4-methyl-3,4-dihydro-2H-benzo[1,4]oxazine |

TABLE 61-continued (I-D-7)

| No. | —G—R⁶ |
|---|---|
| 7 | 2-(methoxymethyl)-(S)-4-methyl-6-methyl-3,4-dihydro-2H-1,4-benzoxazine |
| 8 | 2-(methoxymethyl)-(S)-4-methyl-6-fluoro-3,4-dihydro-2H-1,4-benzoxazine |
| 9 | 2-(methoxymethyl)-(S)-4-methyl-6-methoxy-3,4-dihydro-2H-1,4-benzoxazine |
| 10 | 2-(methoxymethyl)-(S)-4-methyl-5-fluoro-3,4-dihydro-2H-1,4-benzoxazine |
| 11 | 2-(methoxymethyl)-(S)-4-methyl-5-methoxy-3,4-dihydro-2H-1,4-benzoxazine |
| 12 | 2-(methoxymethyl)-(S)-2,3-dihydro-1,4-benzodioxine |
| 13 | 2-(methoxymethyl)-(S)-5-fluoro-2,3-dihydro-1,4-benzodioxine |
| 14 | 2-(methoxymethyl)-(S)-8-fluoro-2,3-dihydro-1,4-benzodioxine |
| 15 | 2-(methoxymethyl)-(S)-2,3-dihydro-1,4-benzoxathiine |
| 16 | 2-(methoxymethyl)-(S)-2,3-dihydrobenzofuran |
| 17 | 3-(methoxymethyl)-(S)-2,3-dihydrobenzofuran |
| 18 | 3-(methoxymethyl)-(S)-5-fluoro-2,3-dihydrobenzofuran |
| 19 | 3-(methoxymethyl)-(S)-6-fluoro-2,3-dihydrobenzofuran |
| 20 | 3-(methoxymethyl)-(S)-7-fluoro-2,3-dihydrobenzofuran |

TABLE 61-continued (I-D-7)

| No. | —G—R⁶ |
|---|---|
| 21 | 2-(methoxymethyl)-1-methylindoline, (S) |

TABLE 62

(I-D-7)

| No. | —G—R⁶ |
|---|---|
| 1 | (R)-2-(methoxymethyl)-4-methyl-3,4-dihydro-2H-benzo[b][1,4]oxazine |
| 2 | (R)-2-(methoxymethyl)-4,8-dimethyl-3,4-dihydro-2H-benzo[b][1,4]oxazine |

TABLE 62-continued (I-D-7)

| No. | —G—R⁶ |
|---|---|
| 3 | (R)-8-fluoro-2-(methoxymethyl)-4-methyl-3,4-dihydro-2H-benzo[b][1,4]oxazine |
| 4 | (R)-2-(methoxymethyl)-4,7-dimethyl-3,4-dihydro-2H-benzo[b][1,4]oxazine |
| 5 | (R)-7-fluoro-2-(methoxymethyl)-4-methyl-3,4-dihydro-2H-benzo[b][1,4]oxazine |
| 6 | (R)-2-(methoxymethyl)-7-methoxy-4-methyl-3,4-dihydro-2H-benzo[b][1,4]oxazine |
| 7 | (R)-2-(methoxymethyl)-4,6-dimethyl-3,4-dihydro-2H-benzo[b][1,4]oxazine |
| 8 | (R)-6-fluoro-2-(methoxymethyl)-4-methyl-3,4-dihydro-2H-benzo[b][1,4]oxazine |

TABLE 62-continued (I-D-7)

| No. | —G—R⁶ |
|---|---|
| 9 | (R)-2-(methoxymethyl)-4-methyl-7-methoxy-3,4-dihydro-2H-1,4-benzoxazine |
| 10 | (R)-2-(methoxymethyl)-4-methyl-5-fluoro-3,4-dihydro-2H-1,4-benzoxazine |
| 11 | (R)-2-(methoxymethyl)-4-methyl-5-methoxy-3,4-dihydro-2H-1,4-benzoxazine |
| 12 | (R)-2-(methoxymethyl)-2,3-dihydro-1,4-benzodioxine |
| 13 | (R)-2-(methoxymethyl)-5-fluoro-2,3-dihydro-1,4-benzodioxine |
| 14 | (R)-2-(methoxymethyl)-8-fluoro-2,3-dihydro-1,4-benzodioxine |
| 15 | (R)-3-(methoxymethyl)-2,3-dihydro-1,4-benzoxathiine |
| 16 | (R)-2-(methoxymethyl)-2,3-dihydrobenzofuran |
| 17 | (R)-3-(methoxymethyl)-2,3-dihydrobenzofuran |
| 18 | (R)-3-(methoxymethyl)-5-fluoro-2,3-dihydrobenzofuran |
| 19 | (R)-3-(methoxymethyl)-6-fluoro-2,3-dihydrobenzofuran |
| 20 | (R)-3-(methoxymethyl)-7-fluoro-2,3-dihydrobenzofuran |
| 21 | (R)-2-(methoxymethyl)-1-methylindoline |

TABLE 63
(I-D-8)
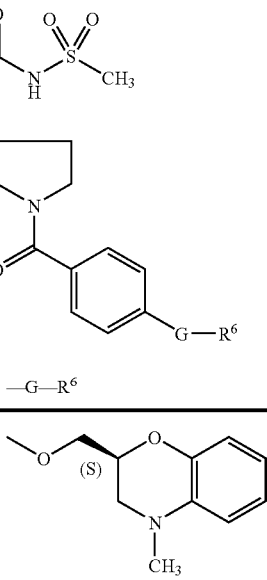
| No. | —G—R6 |
|---|---|
| 1 | 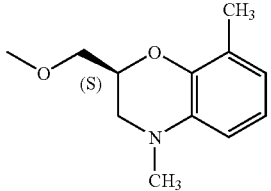 |
| 2 | 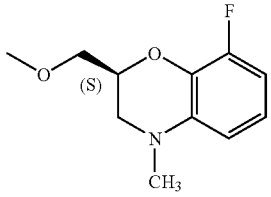 |
| 3 | 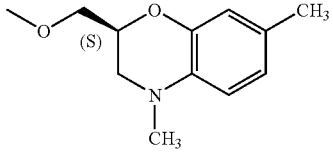 |
| 4 | 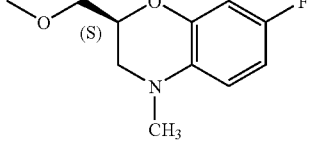 |
| 5 | 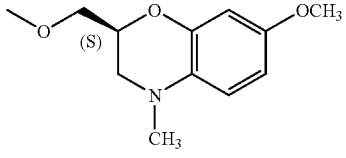 |
| 6 | 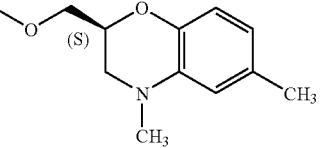 |
TABLE 63-continued
(I-D-8)
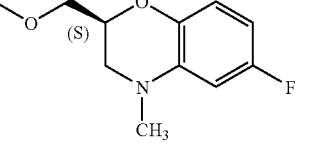
| No. | —G—R6 |
|---|---|
| 7 | 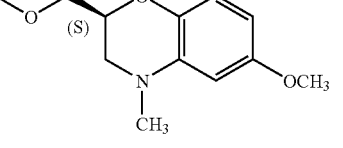 |
| 8 | 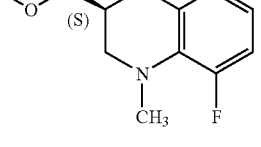 |
| 9 | 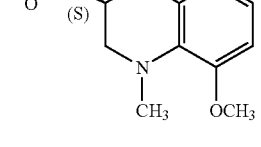 |
| 10 | 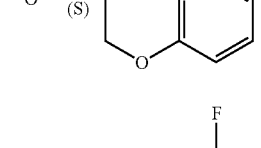 |
| 11 | 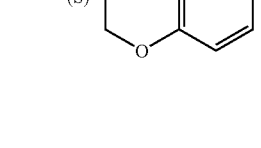 |
| 12 | |
| 13 | |

TABLE 63-continued (I-D-8)

| No. | —G—R⁶ |
|---|---|
| 14 | methoxymethyl-(S)-2,3-dihydro-1,4-benzodioxin with 5-F |
| 15 | methoxymethyl-(S)-2,3-dihydro-1,4-benzoxathiin |
| 16 | methoxymethyl-(S)-2,3-dihydrobenzofuran (2-position) |
| 17 | methoxymethyl-(S)-2,3-dihydrobenzofuran (3-position) |
| 18 | methoxymethyl-(S)-2,3-dihydrobenzofuran (3-position) with 5-F |
| 19 | methoxymethyl-(S)-2,3-dihydrobenzofuran (3-position) with 6-F |
| 20 | methoxymethyl-(S)-2,3-dihydrobenzofuran (3-position) with 7-F |

TABLE 63-continued (I-D-8)

| No. | —G—R⁶ |
|---|---|
| 21 | methoxymethyl-(S)-1-methyl-2,3-dihydroindole |

TABLE 64

(I-D-8)

| No. | —G—R⁶ |
|---|---|
| 1 | methoxymethyl-(R)-4-methyl-3,4-dihydro-2H-1,4-benzoxazine |
| 2 | methoxymethyl-(R)-4,8-dimethyl-3,4-dihydro-2H-1,4-benzoxazine |

TABLE 64-continued (I-D-8)

| No. | —G—R6 |
|---|---|
| 3 | 8-fluoro-4-methyl-(2R)-methoxymethyl-3,4-dihydro-2H-1,4-benzoxazine |
| 4 | 7-methyl-4-methyl-(2R)-methoxymethyl-3,4-dihydro-2H-1,4-benzoxazine |
| 5 | 7-fluoro-4-methyl-(2R)-methoxymethyl-3,4-dihydro-2H-1,4-benzoxazine |
| 6 | 7-methoxy-4-methyl-(2R)-methoxymethyl-3,4-dihydro-2H-1,4-benzoxazine |
| 7 | 6-methyl-4-methyl-(2R)-methoxymethyl-3,4-dihydro-2H-1,4-benzoxazine |
| 8 | 6-fluoro-4-methyl-(2R)-methoxymethyl-3,4-dihydro-2H-1,4-benzoxazine |

TABLE 64-continued (I-D-8)

| No. | —G—R6 |
|---|---|
| 9 | 6-methoxy-4-methyl-(2R)-methoxymethyl-3,4-dihydro-2H-1,4-benzoxazine |
| 10 | 5-fluoro-4-methyl-(2R)-methoxymethyl-3,4-dihydro-2H-1,4-benzoxazine |
| 11 | 5-methoxy-4-methyl-(2R)-methoxymethyl-3,4-dihydro-2H-1,4-benzoxazine |
| 12 | (2R)-methoxymethyl-2,3-dihydro-1,4-benzodioxine |
| 13 | 5-fluoro-(2R)-methoxymethyl-2,3-dihydro-1,4-benzodioxine |
| 14 | 8-fluoro-(2R)-methoxymethyl-2,3-dihydro-1,4-benzodioxine |
| 15 | (2R)-methoxymethyl-2,3-dihydro-1,4-benzoxathiine |

TABLE 64-continued (I-D-8)

| No. | —G—R[6] |
|---|---|
| 16 | (R) benzofuran-2-ylmethoxy |
| 17 | (R) 2,3-dihydrobenzofuran-3-ylmethoxy |
| 18 | (R) 4-fluoro-2,3-dihydrobenzofuran-3-ylmethoxy |
| 19 | (R) 6-fluoro-2,3-dihydrobenzofuran-3-ylmethoxy |
| 20 | (R) 7-fluoro-2,3-dihydrobenzofuran-3-ylmethoxy |
| 21 | (R) 1-methyl-2,3-dihydroindol-2-ylmethoxy |

PGD$_2$ receptor in this specification represents receptors that PGD$_2$ binds, not only the one found by present, but also the one that will be found in the future is included in the receptor. The desirable one is DP receptor or CRTH2 receptor, and more desirably DP receptor.

[Salts]

All non-toxic salts are included in the present invention.

The compounds represented by formula (I) in the present invention may be converted into the non-toxic salts by a well-known method. The non-toxic salts are suitable to be allowed in pharmacology, and water-soluble.

The non-toxic salts of the compounds represented by formula (I) in the present invention include, for example, alkali metal salts (potassium, sodium, lithium, etc.), alkaline earth metal salts (calcium, magnesium, etc.), ammonium salts (tetramethylammonium, tetrabutylammmonium, etc.), organic amine salts (triethylamine, methylamine, dimethylamine, cyclopentylamine, benzylamine, phenethylamine, piperidine, monoethanolamine, diethanolamine, tris(hydroxymethyl)methylamine, lysine, arginine, N-methyl-D-glucamine, etc.), acid-addition salts (inorganic acid salts (hydrochloride, hydrobromate, hydroiodate, sulfate, phosphate, and nitrate, etc.), organic acid salts (acetate, trifluoroacetate, lactate, tartrate, oxalate, fumarate, maleate, benzoate, citrate, methane sulfonate, ethane sulfonate, benzene sulfonate, toluene sulfonate, isethionate, glucuronate, gluconate, etc.), etc.

In the non-toxic salts of the compounds represented by formula (I) in the present invention, solvates thereof, or solvates of alkali (earth) metal salts, ammonium salts, organic amine salts, and acid-addition salts of the above compound in the present invention, are included.

The solvates are preferably non-toxic and water-soluble. Appropriate solvates, for example, solvates such as water, alcohol solvents (ethanol, etc.), etc. are included.

All compounds represented by formula (I) or all non-toxic salts thereof are suitable. Concretely, the compounds described to example or non-toxic salts thereof are included.

[Processes for the Preparation of the Compound of the Present Invention]

The compounds of the present invention represented by formula (I) may be prepared by the following processes and the processes represented in examples.

(a) Among the compounds represented by formula (I), a compound wherein R represents —COR$^1$ and R$^1$ is hydroxy, that is, a compound represented by formula (Ia):

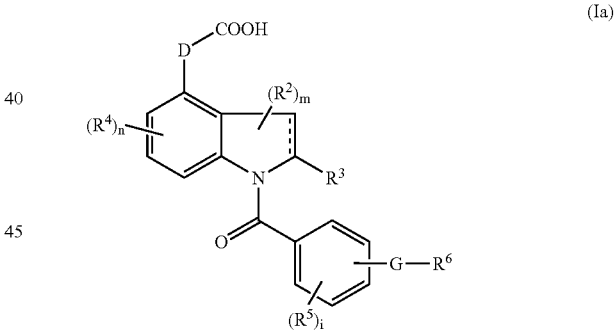

(Ia)

wherein all symbols represent the same meanings as the described above may be prepared by subjecting a compound represented by formula (IV);

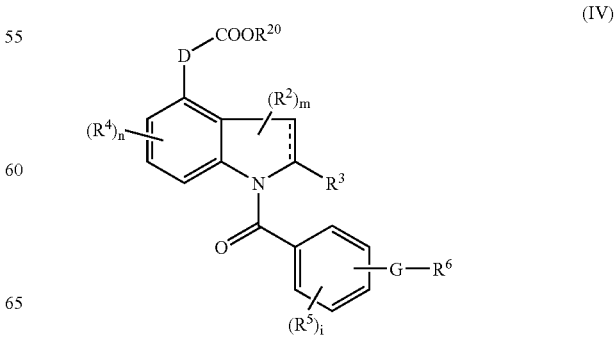

(IV)

wherein $R^{20}$ is an allyl or benzyl group and other symbols have the same meanings as the described above to deprotection reaction of allyl ester or benzyl ester.

A deprotection reaction of allylic ester, which is well known, may be reacted at 0–50° C., for example, in an organic solvent (dichloromethane, dimetbyl formamide, tetrahydrofuran, dioxane, ethyl acetate, and ethanol, etc.), under the absence or presence of a trap reagent (tributyltin hydroxide, dimedon, morpholine, pyrrolidine, and 2-ethylhexanoic acid, etc.) and/or an organic acid (acetate, etc.), using a metal complex (tetrakis(triphenylphosphine) palladium(0), bis(triphenylphosphine) palladium(II) dichloride, palladium acetate(II), and tris(triphenylphosphine)rhodium (I) chloride, etc.).

A deprotection reaction of benzyl ester, which is well known, may be carried out at 0–200° C., for example, in a solvent (ether (tetrahydrofuran, dioxane, dimethoxyethane, and diethyl ether, etc.), alcohols (methanol and ethanol, etc.), benzenes (benzene and toluene, etc.), ketones (acetone and methylethylketone, etc.), nitriles (acetonitrile etc.), amides (dimethylformamide etc.), water, ethyl acetate, acetate, or two or more mixed solvent(s) thereof, etc.), under the presence of a catalyst (palladium-carbon, palladium black, hydroxide palladium, platinum oxide, and raney nickel, etc.), atmospheric or pressurized hydrogen atmosphere, or formate ammonium.

(b) Among the compounds represented by formula (I), a compound wherein R represents —$COR^1$ and $R^1$ is C1–6 alkoxy, that is, a compound represented by formula (Ib):

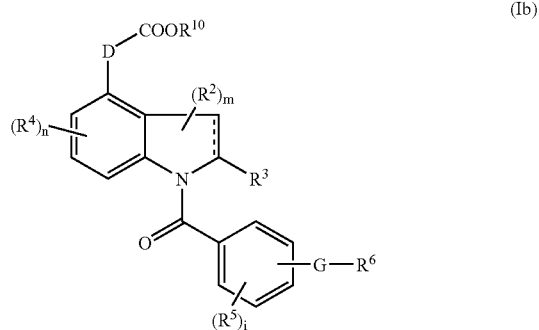

(Ib)

wherein $R^{10}$ represents C1–6 alkyl and other all symbols have the same meanings as the described above can be prepared by subjecting a compound represented by formula (Ia) with a compound represented by formula (III):

(III)

wherein all symbols have the same meanings as the described above to esterification reaction, followed by optionally a deprotection reaction.

As esterification reactions that are well-known, for example,
(1) a method using acyl halide,
(2) a method using mixed acid anhydride, and
(3) a method using a condensing agent are included.

These methods are concretely explained as follows,
(1) The method using acyl halide may be carried out, for example, by reacting carboxylic acid with acyl halide (oxalyl chloride or thionyl chloride, etc.) in an organic solvent (chloroform, methylene chloride, diethyl ether or tetrahydrofuran, etc.) or without a solvent at −20° C. to reflux temperature and then reacting the obtained acyl halide with alcohol in an inactive organic solvent (chloroform, methylene chloride, diethyl ether or tetrahydrofuran, etc.), under the presence of a tertiary amine (pyridine, triethyl amine, dimethyl aniline, dimethylaminopyridine or diisopropylethylamine, etc.) at 0–40° C. The method may be carried out by reacting with acyl halide in an organic solvent (dioxane, tetrahydrofuran) using an alkaline solution (sodium bicarbonate, sodium hydroxide, etc.) at 0–40° C.

(2) The method using mixed acid anhydride may be carried out, for example, by reacting carboxylic acid with acyl halide (epivaloyl chloride, tosyl chloride, mesyl chloride, etc.), or an acid derivative (ethyl chloroformate or isobutyl chloroformate, etc.) in an organic solvent (chloroform, methylene chloride, diethyl ether, tetrahydrofuran, etc.) or without a solvent, under the presence of a tertiary amine (pyridine, triethylamine, dimethylaniline, dimethylaminopyridine or diisopropylethylamine, etc.) at 0–40° C., and then reacting the obtained mixed acid anhydride with alcohol in an organic solvent (chloroform, methylene chloride, diethyl ether or tetrahydrofuran, etc.) at 0–40° C.

(3) The method using a condensing agent may be carried out, for example, by reacting carboxylic acid with alcohol in an organic solvent (chloroform, methylene chloride, dimethylformamide, diethyl ether or tetrahydrofuran, etc.), these mixed solvents, or without a solvent, under the presence or absence of a tertiary amine (pyridine, triethylamine, dimethylaniline or dimethylaminopyridine, etc.), using a condensing agent(1,3-dicyclohexyl carbodiimide (DCC), 1-ethyl-3-[3-(dimethylamino)propyl] carbodiimide (EDC), 1,1'-carbodiimidazole (CDI), 2-chloro-1-methylpyridinium iodide, methanesulphonyloxybenzotriazole, 3-methyl-2-fluoropyridinium tosilate methyl or 1-propanephosphonic acid cyclic anhydride;PPA, etc.), with or without 1-hydroxybenzotiazole (HOBt), at 0–40° C.

It is suitable that the reaction described in (1), (2) and (3) may be carried out under an inert gas (argon and nitrogen, etc.) and water free condition.

(c) Among the compounds represented by formula (I), a compound wherein R represents —COR1 and $R^1$ represents —$NR^8R^9$, that is, the compound represented by formula (IC)

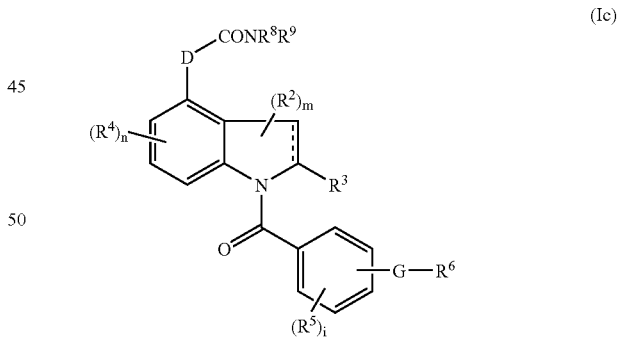

(Ic)

wherein all symbols represent the same meaning as the described above may be prepared by subjecting the compound represented by formula (Ia) and a compound represented by formula (II)

(II)

wherein all symbols represent the same meaning as the described above to amidation reaction, and further, to the deprotection of the protecting group optionally.

As the amidation reactions that are well-known, for example, (1) a method using acyl halide,
(2) a method using mixed acid anhydride, and
(3) a method using a condensing agent are included.

These methods are concretely explained as follows.

(1) The method using an acyl halide may be carried out, for example, by reacting carboxylic acid with acyl halide (oxalyl chloride or thionyl chloride, etc.) in an organic solvent(chloroform, methylene chloride, diethyl ether or tetrahydrofuran, etc.) or without a solvent at −20° C. to reflux temperature and then reacting the obtained acyl halide with amine in an inactive organic solvent(chloroform, methylene chloride, diethyl ether, tetrahydrofuran, ethyl acetate, or acetonitrile, etc.), under the presence of tertiary amine (pyridine, triethyl amine, dimethyl aniline, dimethylaminopyridine or diisopropylethylamine, etc.) at 0–40° C. The method may be carried out by reacting with the acyl halide in an organic solvent (dioxane, tetrahydrofuran, toluene, or dimethoxyethane, etc.) using an alkaline solution (sodium bicarbonate, sodium hydroxide, etc.) at 0–40° C.

(2) The method using a mixed acid anhydride may be carried out, for example, by reacting carboxylic acid with acyl halide (epivaloyl chloride, tosyl chloride, mesyl chloride, etc.), or an acid derivative (ethyl chloroformate or isobutyl chloroformate, etc.) in an organic solvent (chloroform, methylene chloride, diethyl ether, tetrahydrofuran, etc.) or without a solvent, under the presence of a tertiary amine (pyridine, triethylamine, dimethylaniline, dimethylaminopyridine or diisopropylethylamine, etc.) at 0–40° C., and then reacting the obtained mixed acid anhydride with amine in an organic solvent (chloroform, methylene chloride, diethyl ether or tetrahydrofuran, etc.) at 0–40° C.

(3) The method using a condensing agent may be carried out, for example, by reacting carboxylic acid with amine in an organic solvent (chloroform, methylene chloride, dimethylformamide, diethyl ether or tetrahydrofuran, etc.) or without a solvent, under the presence or absence of a tertiary amine (pyridine, triethylamine, dimethylaniline or dimethylaminopyridine, etc.), using a condensing agent(1,3-dicyclohexyl carbodiimide (DCC), 1-ethyl-3-[3-(dimethylamino) propyl]carbodiimide (EDC), 1, 1'-carbodiimidazole (CDI), 2-chloro-1-methylpyridinium iodide, methanesulphonyloxybenzotriazole, or 1-propanephosphonic acid cyclic anhydride; PPA, etc.), with or without 1-hydroxybenzotiazole (HOBt), at 0–40° C.

It is suitable that the reaction described in (1), (2) and (3) may be carried out under an inert gas (argon and nitrogen, etc.) and water free condition.

(d) Among the compounds represented by formula (I), a compound wherein R represents —CH$_2$OR$^0$ and R$^0$ is a hydrogen atom, that is, a compound represented by formula (Id)

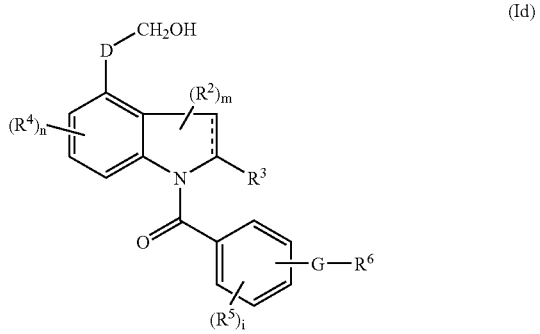

(Id)

wherein all symbols represent the same meaning as the described above may be prepared by subjecting the compound represented by formula (Ia) to the reductive reaction, and then, the deprotection of the protecting group optionally.

The reductive reaction, which is well-known, may be carried out at 0–80° C., for example, in an organic solvent (tetrahydrofuran etc.) using an borane complex (borane-tetrahydrofuran complex, and borane-dimethylsulfide complex, etc.) or by reacting carboxylic acid with the acid derivative chloro ethyl formate and chloro formate isobutyl, etc.) at 0–40° C. in an inert organic solvent (chloroform, methylene chloride, diethyl ether, and tetrahydrofuran, etc.) or without a solvent under the presence of tertiary amine (pyridine, triethylamine, dimethyl aniline, and dimethylaminopyridine, etc.), and further, reacting the obtained mixed acid anhydride at 0–40° C. in an inert organic solvent (chloroform, methylene chloride, diethyl ether, and tetrahydrofuran, etc.) using a reducing agent (sodium borohydride etc.).

(e) Among the compounds represented by formula (I), a compound wherein R represents —CH$_2$OR$^0$ and R$^0$ represents C2–6 acyl group, that is, a compound represented by formula (Ie)

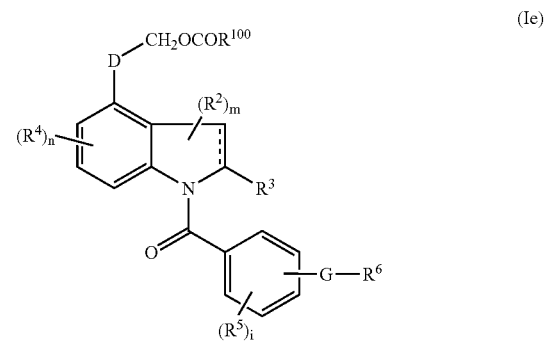

(Ie)

wherein R$^{100}$ represents C1–5 alkyl group, other symbols represent the same meaning as the described above may be prepared by subjecting the compound represented by formula (Id) and a compound represented by formula (IX)

(IX)

wherein all symbols represent the same meaning as the described above to the esterification reaction.

As esterification reactions that are well-known, for example, (1) a method using acyl halide,
(2) a method using mixed acid anhydride,
(3) a method using a condensing agent, and
(4) a method using acid anhydride are included.

The methods described in (1) to (3) are carried out by the method of the above esterification reaction.

The method described in (4) using acid anhydride is carried out by subjecting acid anhydride to react with alcohol at 0–40° C., for example, in organic solvent (chloroform, dichloromethane, diethyl ether, and tetrahydrofuran, etc.) or without solvents, under the presence of tertiary amine (pyridine, triethylamine, dimethylaniline, and dimethylaminopyridine, etc.).

It is suitable that the reaction described in (1), (2), (3), and (4) may be carried out under an inert gas (argon and nitrogen, etc.) and water free condition.

A compound represented by formula (IV) may be prepared by subjecting a compound represented by formula (V);

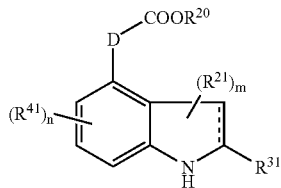

(V)

wherein $R^{21}$, $R^{31}$, and $R^{41}$ represent the same meaning as $R^2$, $R^3$, and $R^4$, respectively; however, they are protected by the protecting group when they represent amino or hydroxyl group, and other symbols represent the same meaning as the described above and a compound represented by formula (VI);

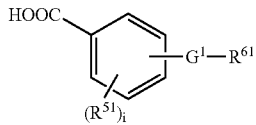

(VI)

wherein $R^{51}$ represents the same meaning as $R^5$; however, they are protected by the protecting group when they represent amino or hydroxyl group, and $G^1$ and $R^{61}$ represent the same meaning as G and $R^6$, respectively; however, they are protected by the protecting group when they contain amino or hydroxyl group to the amidification reaction, and further, the deprotection reaction optionally. The amidification reaction is carried out by the above method.

Deprotection reaction of the protecting group may be carried out by the following methods.

The deprotection reactions of the protecting groups of hydroxyl or amino group are known well, for example,
(1) alkaline hydrolysis,
(2) a deprotection reaction under acid condition,
(3) a deprotection reaction by hydrolysis, and
(4) a deprotection reaction of silyl group, etc. are included.

These methods are concretely explained as follows, (1) The deprotection reaction by alkaline hydrolysis may be carried out at 0–40° C., for example, in an organic solvent (methanol, tetrahydrofuran, dioxane or these mixed solvents, etc.), using an alkali metal (sodium hydroxide, potassium hydroxide, and lithium hydroxide, etc.), an alkaline earth metal (barium hydroxide and calcium hydroxide, etc.), a carbonate (sodium carbonate and potassium carbonate, etc.), the solution, or these compounds.

(2) The deprotection reaction under acid condition may be carried out at 0–100° C., for example, under the presence or absence of an organic solvent (methylene chloride, chloroform, dioxane, ethyl acetate, anisole, methanol, ethanol, and isopropyl alcohol, etc.), or in the solution, an organic acid (acetate, trifluoroacetic acid, and methanesulfonic acid, etc.), an inorganic acid (hydrochloric acid and sulfate, etc.), or these compounds (hydrogen bromide/acetate etc.).

(3) The deprotection reaction by hydrolysis may be carried out at 0–200° C., for example, in a solvent (ethers (tetrahydrofuran, dioxane, dimethoxyethane, and diethyl ether, etc.), alcohol (methanol and ethanol, etc.), benzenes (benzene and toluene, etc.), ketone (acetone and methyl ethyl ketone, etc.), nitriles (acetonitrile etc.), amide (dimethyl formamide etc.), water, ethyl acetate, acetate, or two or more mixed solvent(s) thereof, etc. ), under the presence of a catalyst (palladium-carbon, palladium black, hydroxide palladium, platinum oxide, and raney nickel, etc.), atmospheric or pressurized hydrogen atmosphere, or formate ammonium.

(4) The deprotection reaction of silyl group may be carried out at 0–40° C., for example, in water and an organic solvent (tetrahydrofuran and acetonitrile, etc.) that can be mixed, using tetrabutylammoniumfluoride.

As protecting groups of hydroxyl group, for example, methoxymethyl, 2-tetrahydropyranyl, tert-butyl dimethylsilyl, tert-butyl diphenyl silyl, acetyl, benzyl, and 4-methoxybenzyl group, etc. are included.

As protecting groups of amino group, for example, benzyloxycarbonyl, t-butoxycarbonyl, trifluoroacetyl, and 9-fluorenylmethoxycarbonyl group, etc. are included.

They only have to be a group that can be left easily and selectively except the above as protecting groups of hydroxyl or amino group, and are not especially limited. For example, the group described in T. W. Greene, Protective Groups in Organic Synthesis 3rd edition, Wiley, N.Y., (1999) may be used.

Though the persons skilled in the art can understand easily, the aimed compound of the present invention can be easily prepared by using these deprotection reactions properly.

Among the compounds represented by formula (IV), a compound wherein G represents —O—$CH_2$—, that is, the compound represented by formula (IV-1)

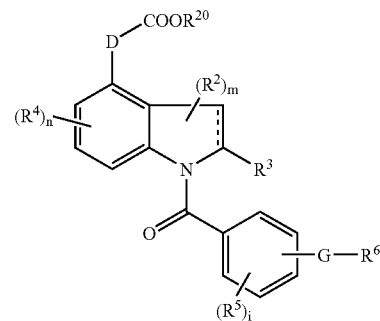

(IV-1)

wherein $G^2$ represents —$OCH_2$—, and other symbols represent the same meaning as the described above may be prepared by subjecting a compound represented by formula (VII)

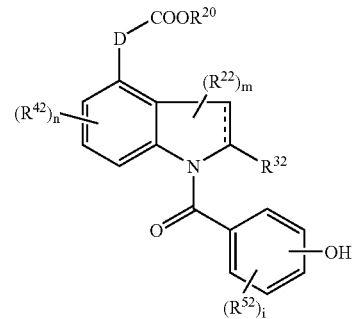

(VII)

wherein $R^{22}$, $R^{32}$, $R^{42}$, and $R^{52}$ represent the same meaning as $R^2$, $R^3$, $R^4$, and $R^5$, respectively, if they represent amino or hydroxyl group, they are necessary to be protected by the protecting group, and other symbols represent the same meaning as the described above and a compound represented by formula (VIII)

HO-J-$R^{62}$ (VIII)

wherein $R^{62}$ represents the same meaning as $R^6$, if amino or hydroxyl group is included in them, they are necessary to be protected by the protecting group and J represents —CH$_2$— to the etherification, and then, the deprotection optionally.

The etherification, which is well known, is carried out by subjecting to react with a corresponding alcoholic compound at 0–60° C., for example, in an organic solvent (dichloromethane, diethyl ether, tetrahydrofuran, acetonitrile, benzene, and toluene, etc.), under the existence of azo compounds (diethyl azodicarboxylate, diisopropyl azodicarboxylate, 1,1'-(azodicarbonyl)dipiperidine, 1,1'-azobis(N,N-dimethylformamide), etc.) and phosphine compounds (triphenylphosphine, tributylphosphine, and trimethylphosphine, etc.).

The deprotection reaction of the protecting group may be carried out by the method similar to the above.

The compounds represented by formula (II), (III), (V), (VI), (VII), (VIII), and (IX) are well-known or may be easily prepared by a well-known method.

For example, in the compound represented by formula (VIII), a compound wherein R62 represents -3,4-dihydro-2H-1,4-benzoxazine may be prepared by the method shown by the following reaction process 1.

In the reaction process 1, $R^{200}$ represents the group selected from C1–6 alkyl, C1–10 alkoxy, C2–6 alkoxyalkyl group, a halogen atom, hydroxyl, trihalomethyl, nitro, amino, phenyl, phenoxy, C2–6 acyl, C1–6 alkanesulfonyl, and cyano group and j represents the integer from 0 or 1 to 4, X represents a leaving group (for example, a halogen atom, methanesulfonyloxy, p-toluenesulfonyloxy, 3-nitrobenzenesulfonyloxy group, etc.), and other symbols represents the same meaning as the described above.

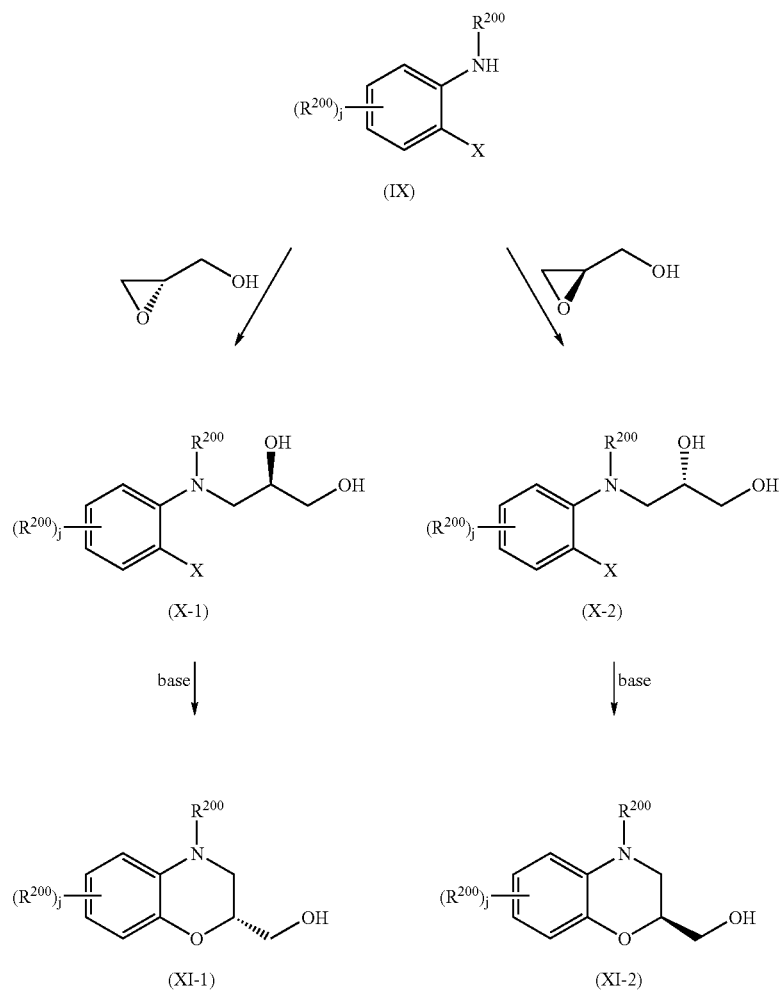

Reaction process 1

For example, among compounds represented by formula (VIII) a compound wherein $R^{62}$ represents -2,3-dihydrobenzofuran may be manufactured according to the method represented by the following reaction process 2.

In the reaction process 2, halo represents a halogen atom and other symbols represent the same meaning as the described above.

Reaction process 2

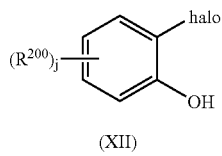

(XII)

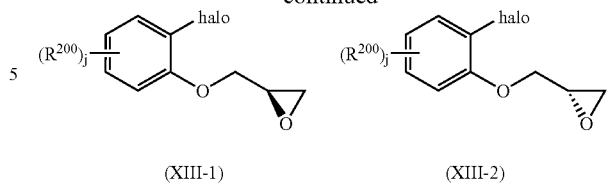

(XIII-1)   (XIII-2)

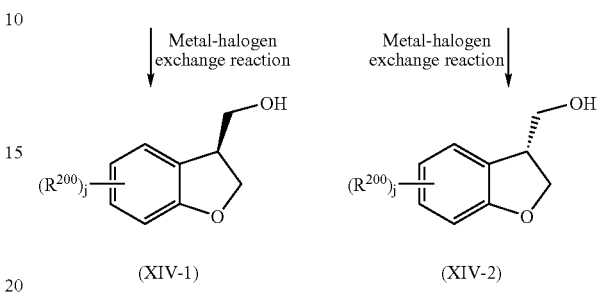

(XIV-1)   (XIV-2)

For example, among compounds shown by formula (VIII), the compound wherein $R^{62}$ represents -1,4-benzoxathiane may be manufactured according to the method represented by the following reaction process 3.

All symbols represent the same meaning as the described above in the reaction process 3.

Reaction process 3

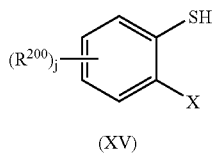

(XV)

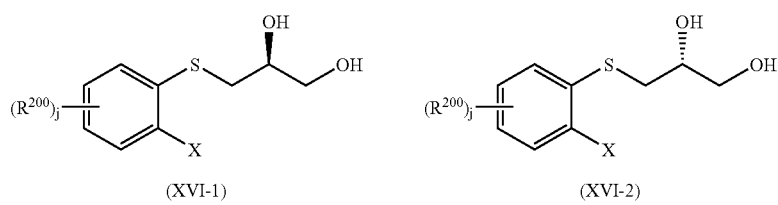

(XVI-1)   (XVI-2)

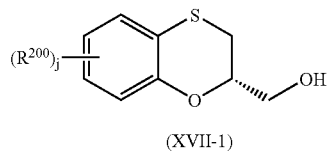

(XVII-1)   (XVII-2)

For example, among compounds shown by formula (VIII), the compound wherein $R^{62}$ represents indoline may be manufactured according to the method represented by the following reaction process 4.

All symbols represent the same meaning as the described above in the reaction process 4.

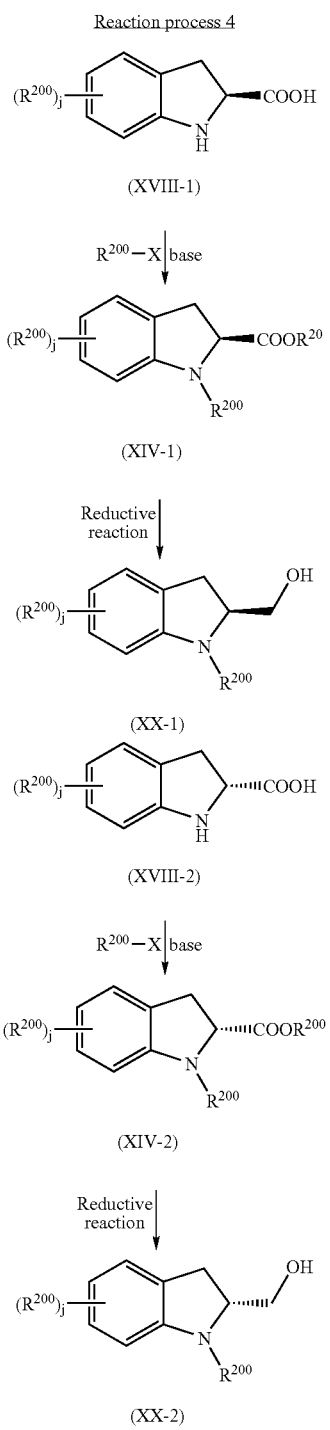

For example, among compounds shown by formula (VI), the compound (VI-1) wherein $G^1$ represents —$OCH_2$— may be manufactured according to the method represented by the following reaction process 5.

All symbols represent the same meaning as the described above in the reaction process 5.

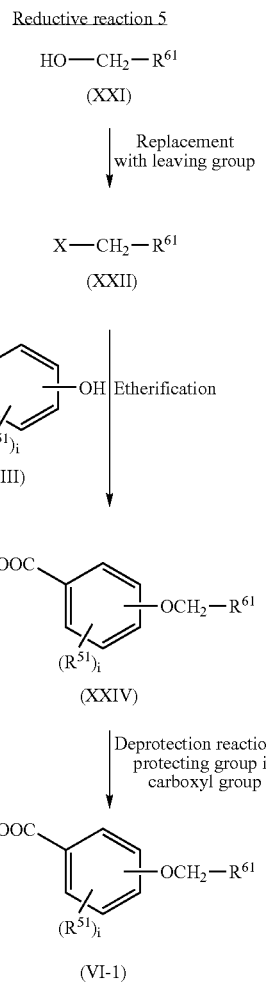

In the reaction process 1 to 5, the compounds represented by formula (IX), (XII), (XV), (XVIII-1), (XVIII-2), (XXI), and (XXIII), which are used as starting materials, are well-known or may be easily prepared by a well-known method.

The reaction product may be purified by usual purification methods, for example, distillation and silicagel under normal or reduced pressure, high performance liquid chromatography, thin layer chromatography or column chromatography that used magnesium trisilicate, or wash and recrystallization, etc. The purification may be carried out at each reaction or after some reactions.

In the present invention, other starting materials and each reagent are well-known or may be easily prepared by a well-known method.

Pharmacological Activities:

The compound of the present invention represented by formula (I) potently binds to a DP receptor and shows an antagonistic activity. This effect was confirmed by the following receptor binding test using prostanoid receptor-expressing cells.

(i) Receptor Binding Test Using Prostanoid DP Receptor-Expressing Cells

CHO cells expressing mouse DP receptors were prepared according to the method of Hirata et al. (*Proc. Natl. Acad. Sci.*, 91, 11192–11196 (1994)) and used as a membrane standard.

A reaction solution (200 μL) containing the prepared membrane standard (30–166 μg) and $^3$H-PGD$_2$ was incubated at room temperature for 20 minutes. The reaction was stopped with an ice-cold buffer (1 mL) and the binding $_3$H-PGD$_2$ was trapped in on a glass filter by immediate aspiration-filtration under a reduced pressure, and its binding radioactivity was measured using a liquid scintillation counter.

Kd value and Bmax value were obtained from Scatchard plots (*Ann. N. Y. Acad. Sci.*, 51, 660 (1949)]. Non-specific binding was obtained as the binding radioactivity in the presence of unlabeled PGD$_2$ at an excess amount (10 μmol/L). 3H-PGD$_2$ binding inhibition by the compound of the present invention was measured by adding $^3$H-PGD$_2$ (2.5 nmol/L) and the compound of the present invention as various concentrations. Also, the following buffers were used for the reactions.

Incubation Buffer:
  HEPES-NaOH (25 mmol/L, pH 7.4)
  EDTA (1 mmol/L)
  MgCl$_2$ (5 mmol/L)
  MnCl$_2$ (10 mmol/L)

Buffer for Washing:
  Tris-HCl (10 mmol/L, pH 7.5)
  NaCl (0.1 mol/L)
  Bovine serum albumin (0.01%)

The dissociation constant (Ki) (μmol/L) of each compound was obtained by the following equation.

$$Ki = IC_{50}/(1+([L^*]/Kd))$$

[L*]: Concentration of radioligand
The result is shown in table 55.

TABLE 65

| Example Num | DP Ki (μM) |
|---|---|
| 2(16) | 0.031 |

As shown in the above results, it is apparent that the compound of the present invention potently binds to DP receptor.

(ii) DP antagonistic activity assay using prostanoid DP receptor-expressing cells may be examined by the following method.

CHO cells expressing mouse DP receptor were prepared, inoculated onto a 24-well microplate at 10$^5$ cells/well, followed by culturing for 2 days, and used for the assay. Each well was washed with 500 μL of MEM (minimum essential medium), and 450 μL of assay medium (MEM containing 1 mmol/L IBMX, 2 μmol/L diclofenac and 0.1 or 1% BSA), followed by incubation at 37° C. for 10 minutes. Then, an assay medium (50 μL) containing PGD$_2$ alone or PGD$_2$ with a compound of the present invention was added thereto to start the reaction, and after the reaction at 37° C. for 10 minutes, 500 μL of ice-cold trichloroacetic acid (TCA) (10% w/v) was added thereto to stop the reaction. The reaction solution was frozen once (−80° C.) and thawed, and cells were peeled using a scraper, followed by centrifugation at 13,000 rpm for 3 minutes. The cAMP concentration was measured with a cAMP assay kit using the resulting supernatant. That is, [$^{125}$I]-cAMP assay kit buffer was added to 125 μL of the supernatant to give a total amount of 500 μL, and the resulting mixture was mixed with 1 mL of a chloroform solution of 0.5 mol/L tri-n-octylamine. Trichloroacetic acid (TCA) was extracted to the chloroform layer and removed, the cAMP amount in a sample was determined using the aqueous layer as the sample according to the method described in the [$^{125}$I]cAMP assay kit.

Also, with regard to the antagonistic activity (IC$_{50}$) of the test compound, the IC$_{50}$ value was calculated as an inhibition rate based on the reaction at 100 nM which was a concentration showing submaximal cAMP production by PGD$_2$ alone.

Toxicity:

The toxicity of the compound represented by formula (I) of the present invention is very low so that it is confirmed that the compound is sufficiently safe for using as a pharmaceutical.

INDUSTRIAL APPLICABILITY

Application to Pharmaceuticals:

Since the compound represented by formula (I) in the present invention binds and is antagonistic to PGD$_2$ receptor, especially DP receptor, it is considered to be useful for the prevention and/or treatment of diseases, for example, allergic diseases (allergic rhinitis, allergic conjunctivitis, atopic dermatitis, bronchial asthma, food allergy, etc.), systemic mastocytosis, disorders due to systemic mastocyte activation, anaphylactic shock, bronchoconstriction, urticaria, eczema, psoriasis, allergic bronchopulmonary aspergillosis, paranasal sinusitis, migraine, nasal polyp, hypersensitive angitis, eosinophilia, contact dermatitis, diseases accompanied with itching (such as atopic dermatitis, urticaria, allergic conjunctivitis, allergic rhinitis, contact dermatitis, etc.), secondary diseases (such as cataracta, retinodialysis, inflammation, infection, dysgryphia, etc.) generated by behaviors caused by itching (scratching behaviors, beating, etc.), inflammation, chronic obstructive pulmonary disease, ischemic reperfusion disorder, cerebrovascular disorder, brain damage, hepatopathy, graft rejection, autoimmune disease, rheumatoid arthritis, pleuritis complicated by rheumatoid arthritis, osteoarthritis, crohn's disease, ulcerative colitis, pain and the like. Moreover, it is considered to relate to sleeping and platelet aggregation and to be useful for these diseases.

Since a compound that weakly binds with receptors other than DP receptor doesn't appear other actions, it is a possibility to become a medicine having a little side reaction.

Since the compound represented by formura (I) in the present invention binds to CRTH2 receptor and it expected to be antagonistic to the biological activity, it is considered to be useful for the prevention and/or treatment of diseases, allergic diseases (allergic rhinitis, allergic conjunctivitis, atopic dermatitis, bronchial asthma, food allergy, etc.), systemic mastocytosis, disorders due to systemic mastocyte activation, anaphylactic shock, bronchoconstriction, urticaria, eczema, psoriasis, allergic bronchopulmonary aspergillosis, paranasal sinusitis, migraine, nasal polyp, hypersensitive angitis, eosinophilia, contact dermatitis, diseases accompanied with itching (such as atopic dermatitis, urticaria, allergic conjunctivitis, allergic rhinitis, contact dermatitis, etc.), secondary diseases (such as cataracta, retinodialysis, inflammation, infection, dysgryphia, etc.) generated by behaviors caused by itching (scratching behaviors, beating, etc.), inflammation, chronic obstructive pulmonary disease, ischemic reperfusion disorder, cerebrovascular disorder, brain damage, hepatopathy, graft rejection, autoimmune disease, rheumatoid arthritis, pleuritis complicated by rheumatoid arthritis, osteoarthritis, crohn's disease, ulcerative colitis, pain and the like.

The compound represented by formula (I) may be administered as other concomitant drug combining with other medicines, in order to
1) supplement and/or reinforce the prophylactic and/or therapeutic effect of the compounds,
2) improve the movement and absorption of the compounds, and to decrease the dosage, and/or
3) reduce the side effects of the compounds.

A combind drug with the compound represented by formula (I) and other medicine may be administered in the compounding agent that mixes both elements in a formulation or in the form administered as separate formulation. In the form administered as separate formulation, the different and simultaneous administration are included. In the different administration, the compound represented by formula (I) may be previously administered, followed by other medicines, or other medicines may be previously administered, followed by the compound represented by formula (I). Each medication method may be different or same.

Illnesses that the prophylactic and/or therapeutic effects of the above combind drugs can be expected, which only has to be one that the prophylactic and/or therapeutic effects of the compound represented by formula (I) is/are supplemented and/or reinforced, are not limited especially.

As other medicines to supplement and/or reinforce the prophylactic and/or therapeutic effects of the compounds represented by formula (I) on allergic rhinitis, for example, antihistamine agents, mediator release inhibitors, thromboxane synthesis enzyme inhibitors, thromboxane A2 receptor antagonists, leukotriene receptor antagonists, steroid drugs, alpha-adrenergic receptor agonists, xanthine derivatives, cholinergic-blocking agents, and nitric oxide synthase inhibitors, etc. are included.

As other medicines to supplement and/or reinforce the prophylactic and/or therapeutic effects of the compounds represented by formula (I) on allergic conjunctivitis, for example, leukotriene receptor antagonists, antihistamine agents, mediator release inhibitors, nonsteroidal anti-inflammatory drugs, prostaglandins, steroid drugs, and nitric oxide synthase inhibitors, etc. are included.

As antihistamine agents, for example, ketotifen fumarate, mequitazine, azelastine hydrochloride, oxatomide, terfenadine, emedastine fumarate, epinastine hydrochloride, astemizole, ebastine, cetirizine hydrochloride, bepotastine, fexofenadine, lolatadine, desloratadine, olopatadine hydrochloride, TAK-427, ZCR-2060, NIP-530, mometasone furoate, mizolastine, BP-294, andolast, auranofine, and acribastin, etc. are included.

As mediator release inhibitors, for example, tranilast, sodium cromoglycate, amlexanox, repirinast, ibudilast, tazanolast, and pemirolast potassium, etc. are included.

As thromboxane synthesis enzyme inhibitors, for example, ozagrel hydrochloride and imitrodast sodium, etc. are included.

As thromboxane A2 receptor antagonists, for example, seratrodast, ramatroban, domitroban calcium hydrate, and KT-2-962, etc. are included.

As leukotriene receptor antagonist, for example, pranlukast hydrate, montelukast, zafirlukast, MCC-847, KCA-757, CS-615, YM-158, L-740515, CP-195494, LM-1484, RS-635, A-93178, S-36496, BIIL-284, and ONO-4057, etc. are included.

In steroid drugs, for example, as drugs for external use, clobetasol propionate, diflorazone diacetate, fluocinonide, mometasone furancarboxylate, betamethasone dipropionate, betamethasone butyrate propionate, betamethasone valerate, difluprednate, budesonid, diflucortolone valerate, amcinonide, halcinonide, dexamethasone, dexamethasone propionate, dexamethason valerate, dexamethasone acetate, hydrocortisone acetate, hydrocortisone butyrate, hydrocortisone butyrate propionate, deprodone propionate, prednisolone valerate-acetate, fluocinolone acetonide, beclometasone dipropionate, triamcinolone acetonide, flumetasone pivalate, alclometasone propionate, clobetasone butyrate, prednisolone, beclomethasone propionate, and fludroxycortide, etc. are included.

As internal medicines and injections, cortisone acetate, hydrocortisone, hydrocortisone sodium phosphate, hydrocortisone sodium succinate, fludrocortisone acetate, prednisolone, prednisolone acetate, prednisolone sodium succinate, prednisolone butylacetate, prednisolone sodium phosphate, halopredone acetate, methylprednisolone, methylprednisolone acetate, sodium methylprednisolone succinate, triamcinolone, triamcinolone diacetate, triamcinolone acetonide, dexamethasone, dexamethasone acetate, dexamethasone sodium phosphate, dexamethasone palmitate, paramethasone acetate, and betamethasone, etc. are included.

As inhalants, beclometasone dipropionate, fluticasone propionate, budesonide, flunisolide, triamcinolone, ST-126P, ciclesonide, dexamethasone palmitate, mometasone furancarboxylate, prasterone sulfonate, deflazacort, methylprednisolone suleptanate, and methylprednisolone sodium succinate, etc. are included.

As xanthine derivatives, for example, aminophylline, theophylline, doxophylline, cipamfylline, and diprophylline, etc. are included.

As cholilytic drugs, for example, ipratropium bromide, oxitropium bromide, flutropium bromde, cimetropium bromide, temiverine, tiotropium bromide, and revatropate(UK-112166), etc. are included.

As non-steroidal anti-inflammatory drugs, for example, sasapyrine, sodiumsalicylate, aspirin, aspirin dialuminates combination, diflunisal, indomethacin, suprofen, ufenamate, dimethylisopropylazulene, bufexamac, felbinac, diclofenac, tolmetin sodium, clinoril, fenbufen, nabumetone, puroglumetacine, indomethacin farnesyl, acemetacin, proglumetacin maleate, amfenac sodium, mofezolac, etodolac, ibuprofen, ibuprofen piconol, naproxen, flurbiprofen, flurbiprofen axetil, ketoprofen, fenoprofen calcium, tiaprofen, oxaprozin, pranoprofen, loxoprofen sodium, aluminoprophen, zaltoprofen, mefenamic acid, mefenamic acid aluminum, tolfenamic acid, floctafenine, ketophenylbutazone, oxyphenbutazone, piroxicam, tenoxicam, ampiroxicam, napageln ointment, epirizole, tiaramide hydrochloride, tinoridine hydrochloride, emorfazone sulpyrine, migrenin, saridon, sedes G, amipylo-N, sorbon, pyrine drug for common cold, acetaminophen, phenacetin, dimetotiazine mesilate, simetride combination drug, and non-pyrine drug for common cold, etc. are included.

As prostaglandins (hereafter, abbreviated with PG), PG receptor agonists and PG receptor antagonist, etc. are included.

As PG receptor, PGE receptor (EP1, EP2, EP3, EP4), PGD receptor (DP, CRTH2), PGF receptor (FP), PGI receptor (IP), and TX receptor (TP), etc. are included.

Mass ratio of the compound represented by formula (I) to other medicine is not especially limited.

Other medicines may be administered combining with two arbitrary kinds or more.

In other medicines that supplement and/or reinforce prophylactic and/or therapeutic effects of the compounds represented by formula (I), not only one that has been found by present according on the above mechanism but also one that will be found in the future are included.

To use the compound represented by formula (I) or non-toxic salt thereof, or a combind drug containing the compound represented by formula (I) and other medicines by the above purpose, it is usually administered systemically or locally, and orally or parenterally.

The dosage is determined depending on age, body weight, symptom, therapeutic effect, administration route, duration of the treatment and the like. Generally, 1 mg to 1000 mg per adult is orally administered once to several times per day, or 1 mg to 100 mg per adult is parenterally administered (preferably, nose drop, ophthalmic solution, ointment) once to several times per day, or intravenously administered for 1 to 24 hours per day, continuously.

Since the dose changes depending on various conditions as described above, there are cases in which doses lower than or greater than the above ranges may be used.

When the compound represented by the formula (I) or the combind drug containing it and other medicines are administered, they are used as solid medicines, liquid medicines, and other compositions for internal use, and injections, external preparations, and suppositoriums, etc. for parenteral administration.

The solid compositions for oral administration include compressed tablets, pills, capsules, dispersing powders, granules, etc.

The capsules include hard capsules and soft capsules.

In such solid compositions, one or more active compound(s) is/are mixed with at least one inert diluent such as lactose, mannitol, glucose, hydroxypropyl cellulose, microcrystalline cellulose, starch, polyvinyl pyrrolidone or magnesium metasilicate aluminate. The compositions may also contain additional substances other than inert diluents, for example, lubricating agents such as magnesium stearate, disintegrating agents such as cellulose calcium glycolate, stabilizers such as lactose and solubilizers such as glutamic acid or asparatic acid according to usual methods. The tablets or pills may, if desired, be coated with film of gastric or enteric coating agents such as sugar, gelatin, hydroxypropyl cellulose or hydroxypropyl cellulose phthalate, or be coated with two or more films. Furthermore, capsules of absorbable materials such as gelatin are included.

The liquid compositions for oral administration include pharmaceutically acceptable emulsions, solutions, syrups and elixirs. In such liquid compositions, one or more active compound(s) is/are contained in inert diluents commonly used (purified water and ethanol, etc.). Furthermore, these compositions may also contain wetting agents, adjuvants such as suspending agents, sweetening agents, flavoring agents, perfuming agents, and preserving agents besides inert diluents.

Other compositions for oral administration include sprays that are prepared by known methods, and one or more active compound(s). These compositions may contain stabilizing agents such as sodium hydrogen sulfate, buffers to give isotonicity, and isotonic solutions such as sodium chloride, sodium citrate or citric acid besides inert diluents. Processes for preparing the sprays have been described in U.S. Pat. Nos. 2,868,691 and 3,095,355.

The injections for parenteral administration include sterile aqueous and/or non-aqueous solutions, suspensions and emulsions. The aqueous solutions or suspensions include, for example, distilled water for injection and a physiological salt solution. The non-aqueous solutions or suspensions include propylene glycol, polyethylene glycol, plant oil such as olive oil, alcohol such as ethanol, POLYSORBATE 80 (registered trade mark), and the like. They may be used mixing sterile aqueous or non-aqueous solutions, suspensions and emulsions. These compositions may contain preserving agents, wetting agents, emulsifying agents, dispersing agents, stabilizing agents (for example, lactose), and adjuvants such as solubilizer (glutamic acid and aspartic acid, etc.). These may be sterilized by filtrating through a bacteria-retaining filter, mixing with antimicrobial agents, or irradiation. These may also be manufactured, for example, by making to be aseptic or dissolving to aseptic distilled water for injection or other solvents before use of sterile solid compositions.

As dosage forms of the ophthalmic solution for parenteral administration, ophthalmic solutions, ophthalmic suspensions, ophthalmic emulsions, ophthalmic solutions dissolved time of use, and ophthalmic ointment are included.

These ophthalmic solutions are manufactured based on a well-known method. For example, the ophthalmic solutions are made with tonicity agents (sodium chloride and concentrated glycerin, etc.), buffers (sodium phosphate and sodium acetate, etc.), surfactants (polysorbate 80 (trade name), polyoxyl 40 stearate, and polyoxyethylene hydrogenated castor oil, etc.), stabilizers (sodium citrate and disodium edetate, etc.), and preservatives (benzalkonium chloride and paraben, etc.), etc., which are properly selected optionally. These are sterilized in the final process or manufactured by the aseptic manipulation.

Inhalants for parenteral administration may include aerosol agents, inhalant powders or inhalant liquids, which may be used by being dissolved or suspended in water or other suitable media before using.

The inhalants are manufactured according to a well-known method.

For example, inhalant liquids are prepared properly selecting, if necessary, preservatives (benzalkonium chloride and paraben, etc.), coloring agents, buffers (sodium phosphate and sodium acetate, etc.), tonicity agents(sodium chloride and concentrated glycerin, etc.), thickeners (carboxyvinyl polymer, etc.), and absorption enhancers, etc.

Inhalant powders are prepared properly selecting, if necessary, lubricants (stearic acid and the salt, etc.), binders (starch and dextrin, etc.), fillers (lactose and cellulose, etc.), coloring agents, preservatives (benzalkonium chloride and paraben, etc.), and absorption enhancers, etc.

When the inhalant liquid is administered, sprayers (atomizer and nebulizer) are usually used, and when the inhalant powder is administered, an inhalation administering machine for powder is usually used.

As other compositions for parenteral administration, liquids for external use, ointments, liniments, suppositories for intrarectal administration, and pessaries for administering in vagina, which contain one or more activators and are prescribed with common procedure, are included.

BEST MODE FOR CARRYING OUT THE INVENTION

The following reference examples and examples illustrate the present invention, but do not limit the present invention.

In the following chemical formula, Tf represents trifluoromethanesulfonyl group, Boc represents tert-butoxycarbonyl group, and TMS represents trimethylsilyl group.

The solvents in the parentheses in chromatographic separations or TLC show the developing or eluting solvents and the ratio shows volume ratio.

The solvents in the parentheses in NMR show the solvents for measurement.

REFERENCE EXAMPLE 1

2-methyl-4-trifluoromethanesulfoxy-1H-indole

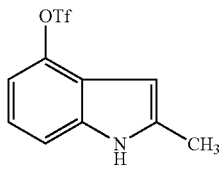

Dichloromethane (100 ml) solution containing 2-methyl-4-hydroxy-2H-indole (10 g) was stirred at 0° C., and lutidine (10.28 ml) and anhydrous trifluoromethane sulfonic acid (13.72 ml) were added to the solution, which was stirred at the same temperature for 1 hour. Further, water was added to the mixture, which was extracted by ethyl acetate. The water layer was extracted by ethyl acetate and the mixed organic layer was sequentially washed with water and saturated brine and dried by anhydrous sodium sulfate, and then concentrated by vacuum concentration to give a title compound having the following physical properties. The obtained title compound was used for the following reaction without further purification.

TLC:Rf 0.57 (hexane:ethyl acetate=7:3)

REFERENCE EXAMPLE 2

1-tert-butoxycarbonyl-2-methyl-4-trifluoromethanesulfoxy-1H-indole

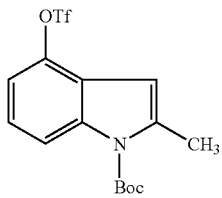

N,N-dimethylaminopyridine (catalyst quantity) were added to acetonitrile (12 ml) solution containing the compound (1 g) prepared according to reference example 1 and di-tert-butyldicarbonate (1 ml), which was stirred at room temperature over night. Further, water and ethyl acetate were added to the reaction solution, which was separated. The organic layer was sequentially washed with water and saturated brine and dried by anhydrous sodium sulfate, and concentrated by vacuum concentration to give a title compound (1.38 g) having the following physical properties.

TLC:Rf 0.50 (hexane:ethyl acetate=1:1)

REFERENCE EXAMPLE 3

1-tert-butoxycarbonyl-2-methyl-4(2-trimethylsilylethynyl)-1H-indole

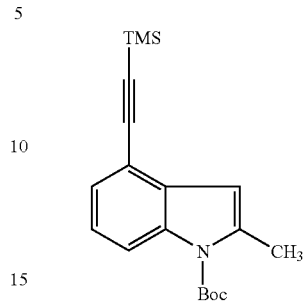

Trimethylsilylacetylene (11 ml) was added to N,N-dimethylformamide (180 ml) solution containing the compound (17.9 g) prepared according to reference example 2, dichloridebis (triphenylphosphine) palladium (II) (1.6 g), copper iodide (0.88 g), and tetrabutylammonium (3.4 g), and the mixture was stirred at 65° C. for 2 hours. Further, 0.5N hydrochloric acid-ethyl acetate was added to the reactive mixture, and the insoluble matter was filtered through celite (registered trademark) and removed. The organic layer was sequentially washed with water (twice) and saturated brine and dried, and then concentrated by vacuum concentration. The residue was purified by silica gel column chromatography (hexane:ethyl acetate=10:1) to give a title compound (15.0 g) having the following physical properties.

NMR (CDCl$_3$): δ 8.09–8.05 (d, J=8.5 Hz, 1H), 7.32–7.29 (m, 1H), 7.17–7.08 (m, 1H), 6.49 (s, 1H), 2.61 (s, 3H), 0.29 (s, 9H).

REFERENCE EXAMPLE 4

1-tert-butoxycarbonyl-2-methyl-1H-indol-4-ylacetic acid

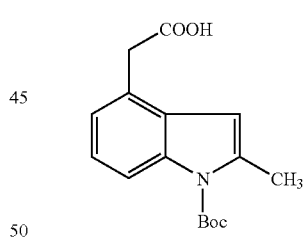

Tetrahydrofuran (160 ml) solution containing cyclohexane (16.1 ml) was cooled to −10° C. and borane tetrahydrofuran complex (1M, 80 ml) was dropped to the mixture, which was stirred at 0° C. for 1 hour. Tetrahydrofuran (60 ml) solution containing the compound (13.1 g) prepared according to reference example 3 was dropped to this solution, which was stirred at room temperature for 1 hour. Further, 3N sodium hydroxide solution (40 ml) and 30% hydrogen peroxide (45 ml) were sequentially dropped to the reaction solution, which was stirred for 12 hours. The reactive mixture was extracted by water-diethyl ether, and the water layer was acidified with hydrochloric acid and extracted by ethyl acetate. The organic layer was sequentially washed with water and saturated brine and dried, and concentrated by vacuum concentration to give a title compound (10.4 g; crude product).

REFERENCE EXAMPLE 5

2-methyl-1H-indol-4-ylacetic acid

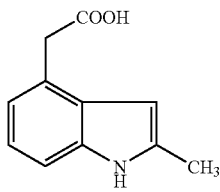

5N sodium hydroxide solution (200 ml) was dropped to methanol(200 ml)-water (100 ml) mixed solution containing the compound (96.3 g) prepared according to reference example 4 at room temperature and the solution was stirred at 50° C. for 3 hours and at room temperature for 12 hours. The reaction solution was extracted by hexane-ether and the water layers was acidified with hydrochloric acid and extracted by ethyl acetate. The extracted solution was sequentially washed with water and saturated brine and dried, and then concentrated by vacuum concentration to give a title compound (53.9 g; crude product).

REFERENCE EXAMPLE 6

2-methyl-1H-indol-4-ylacetic acid benzyl ester

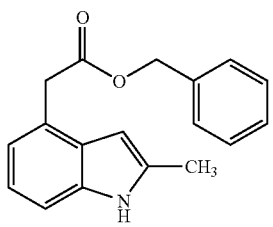

Under argon gas, potassium carbonate (109 g) was added to N,N-dimethyl formamide (500 ml) solution containing the compound (55.0 g) prepared according to reference example 5 over violent stir. Benzyl bromide (34.6 ml) was added to the mixture, which was stirred at room temperature for 2 hours. The solution was poured into water and extracted with toluene. The organic layer was sequentially washed with water and saturated brine and dried by sulfuric anhydride sodium, and filtered. The filtrate was concentrated by vacuum concentration. The residue was purified by silica gel column chromatography (hexane:ethyl acetate=5:1) to give a title compound (70.3 g) having the following physical properties.

TLC:Rf 0.85 (hexane:ethyl acetate=1:1)

REFERENCE EXAMPLE 7

1-(4-acetoxybenzoyl)-2-methyl-1H-indol-4-ylacetic acid benzyl ester

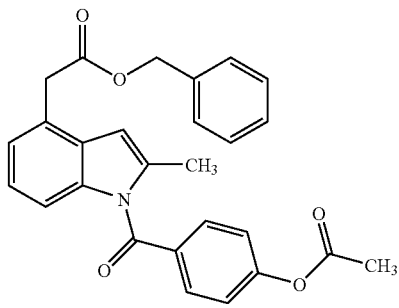

Under argon gas, a mixture of 4-acetoxybenzoic acid (516 mg), oxalylchloride (0.5 ml), and N,N-dimethylformamide (5 μl) was stirred for 3 hours. The mixture was concentrated by vacuum concentration and 4-acetoxybenzoic acid chloride was prepared. Sodium hydroxide (286 mg) and tetrabutylammonium chloride (20 mg) were added to dichloromethane (7 ml) solution containing the compound (400 mg) prepared according to reference example 6 at room temperature over stir. Dichloromethane (3 ml) solution containing 4-acetoxybenzoic acid chloride prepared by the described above was added to the mixture, which was stirred at room temperature for 1 hour. The reaction mixture was filtered and the filtrate was concentrated, and the residue was purified by silica gel column chromatography (hexane:ethyl acetate=7:3) to give a title compound (500 mg) having the following physical properties.

TLC:Rf 0.34 (hexane:ethyl acetate=7:3) NMR (CDCl$_3$): δ 7.76 (d, J=8.7 Hz, 2H), 7.40–7.20 (m, 7H), 7.08–6.92 (m, 3H), 6.47 (s, 1H), 5.15 (s, 2H), 3.88 (s, 2H), 2.40 (s, 3H), 2.35 (s, 3H).

REFERENCE EXAMPLE 8

1-(4-hydroxybenzoyl)-2-methyl-1H-indol-4-ylacetic acid benzyl ester

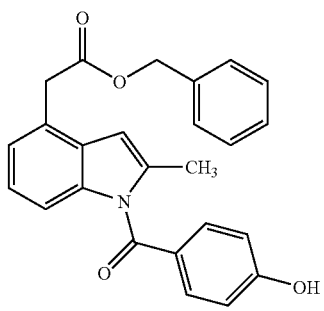

The compound (500 mg) prepared according to reference example 7 was dissolved to dichloromethane (5 ml) solution, and piperidine (0.22 ml) was added, and then the solution stirred for 1 hour. The reaction mixture was concentrated and the residue was purified by silica gel column chromatography (chloroform:methanol=19:1) to give a title compound (450 mg) having the following physical properties.

TLC:Rf 0.61 (chloroform:methanol=9:1) NMR(CDCl₃): δ 7.72 (m, 2H), 7.44–7.26 (m, 5H), 7.08–6.84 (m, 5H), 6.45 (s, 1H), 5.83 (brs, 1H), 5.15 (s, 2H), 3.88 (s, 2H), 2.42 (s, 3H).

REFERENCE EXAMPLE 9

2-fluoro-N-formyl aniline

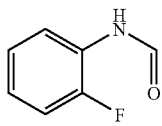

Under argon gas, at 0° C., formic acid (6.1 ml) was dropped to acetic anhydride (15.5 ml), which was stirred at 50° C. for 2 hours. The reaction solution was left up to room temperature, and diluted with tetrahydrofuran (10 ml). At room temperature, tetrahydrofuran (20 ml) solution containing 2-fluoroaniline (5.56 g) added to the above solution, which was stirred at room temperature for 1 hour. The reaction solution was concentrated to give a title compound having the following physical properties. The obtained title compound was used for the following reaction without further purification.

TLC:Rf 0.70 (hexane:ethyl acetate=2:1)

REFERENCE EXAMPLE 10

2-fluoro-N-methylaniline

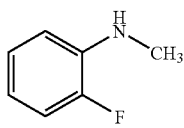

Under argon gas, borane tetrahydrofuran complex (1M tetrahydrofuran solution, 125 ml) was added to anhydrous tetrahydrofuran (25 ml) solution containing the compound (7 g) prepared according to reference example 9 at 0° C., which was stirred at 50° C. for 2 hours. The reaction solution was left up to room temperature and cold methanol (30 ml) was added. 4N hydrogen chloride dioxane solution (10 ml) was added to the reaction solution, which was stirred at 60° C. for 1 hour. The reaction solution was concentrated and poured into 2N sodium hydroxide solution, and extracted by ethyl acetate. The organic layer was washed with saturated brine and dried by sulfuric anhydride sodium. The solution was filtered through celite (registered trademark), and concentrated. The mixture of hexane and ethyl acetate (10:1) was added to the residue and filtered by silicagel. The solution was concentrated to give a title compound (6.45 g) having the following physical properties.

TLC:Rf 0.85 (hexane:ethyl acetate=5:1) NMR(CDCl₃):δ 7.00–6.91 (m, 2H), 6.80–6.55 (m, 2H), 3.90 (br.s, 1H), 2.82 (s, 3H).

REFERENCE EXAMPLE 11

(2S)-3-(N-(2-fluorophenyl)-N-methylamino)-1,2-propanediol

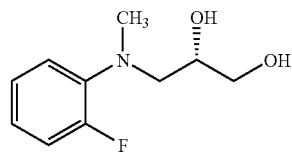

Under argon gas, the mixture of the compound (1.24 g) prepared according to reference example 10, (R)-(+)-glycidol (1.11 g, made by Aldrich Corporation, 98% ee), and ethanols(1 ml) was stirred at 50° C. for 12 hours. The reaction solution was consentrated to give a title compound having the following physical properties. The obtained title compound was used for the following reaction without further purification.

TLC:Rf 0.40 (hexane:ethyl acetate=1:1)

REFERENCE EXAMPLE 12

(2S)-2-hydroxymethyl-4-methyl-3,4-dihydro-2H-1,4-benzoxazine

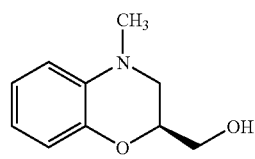

On ice, potassium tert-butoxide (1.68 g) was added to anhydrous N,N-dimethyl formamide (10 ml) solution containing the compound prepared according to reference example 11 over stir. The reaction solution was stirred at 80° C. for 3 hours and poured into water, and extracted by ethyl acetate. The organic layer was washed with saturated brine and dried by the sulfuric anhydride sodium. The solution was filtered through celite (registered trademark) and concentrated. The residue was purified by silica gel column chromatography (hexane:ethyl acetate=3:1) to give a title compound(1.55 g 97.6% ee) having the following physical properties.

TLC:Rf 0.35 (hexane:ethyl acetate=2:1) NMR(CDCl₃):δ 7.90–6.79 (m, 2H), 6.70–6.60 (m, 2H), 4.33 (m, 1H), 3.82 (dd, J=13.0, 4.2 Hz, 1H), 3.79 (dd, J=13.0, 4.2 Hz, 1H), 3.19 (dd, J=10.2, 2.1 Hz, 1H), 3.17 (dd, J=11.4, 5.4 Hz, 1H), 2.86 (s, 3H).

The optical purity of this title compound was decided by using high performance liquid chromatography (HPLC).

Column: CHIRALCEL OD (Daicel Chemical Industries Ltd.)

0.46 cmφ×25 cm

Flow rate: 1 ml/minute

Solvent: hexane:2-propanol=93:7

Detected wave-length: 254 nm

Retention time: 30.70 minutes

Temperature: 24° C.

EXAMPLE 1

1-(4-((2S)-4-methyl-3,4-dihydro-2H-1,4-benzox-azin-2-ylmethoxy)benzoyl)-2-methyl-1H-indol-4-ylacetic acid benzyl ester

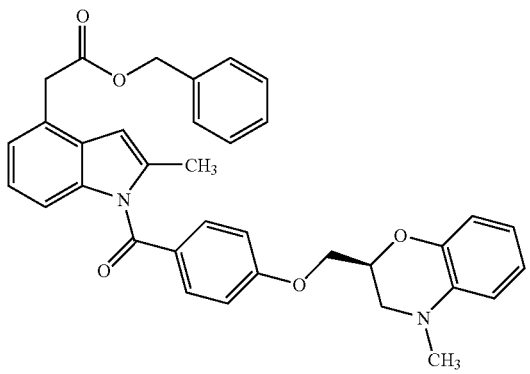

Under argon gas, the compound(33.0 g) prepared according to reference example 12 and triphenylphosphine(44.8 g) were added to tetrahydrofuran(300 ml) solution containing the compound(65.0 g) prepared according to reference example 8, and then diethyl azodicarbonate (40% toluene solution; 74.6 ml) was added to the solution, which was stirred at room temperature for 1 hour. The reaction solution was consentrated and the residue was purified by silica gel column chromatography (ethyl acetate:hexane=1:4 to 1:3) to give a title compound (168 g) having the following physical properties.

TLC:Rf 0.25 (ethyl acetate:hexane=1:3) NMR(CDCl$_3$):δ 7.71 (d, J=8.8 Hz, 2H), 7.43–7.18 (m, 4H), 7.08–6.80 (m, 8H), 6.80–6.65 (m, 2H), 6.46 (s, 1H), 5.15 (s, 2H), 4.68 (m, 1H), 4.31 (dd, J=9.8, 5.0 Hz, 1H), 4.21 (dd, J=9.8, 6.2 Hz, 1H), 3.88 (s, 2H), 3.41 (dd, J=11.4, 3.0 Hz, 1H), 3.28 (dd, J=11.4, 6.4 Hz, 1H), 2.92 (s, 3H), 2.42 (s, 3H).

EXAMPLE 1(1)

1-(4-((2S)-4-methyl-3,4-dihydro-2H-1,4-benzox-azin-2-ylmethoxy)benzoyl)-2-methyl-1H-indol-4-ylacetic acid benzyl ester

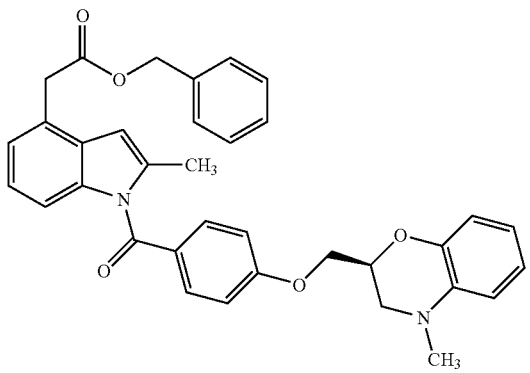

The compound (910 mg) prepared according to reference example 18 was suspended to tetrahydrofuran(2 ml), and oxalylchloride(0.29 ml) was added to the mixture, which was stirred for 1.5 hours at 40° C. The reaction solution was cooled up to room temperature. The compound (559 mg) prepared according to reference example 6 was dissolved to a mixture of acetonitrile (1 ml) and ethyl acetate (1 ml), and then triethylamine (1.7 ml) and N,N-dimethylaminopyridine (73 mg) were added to the mixture, which was cooled. The tetrahydrofuran solution containing the above acid chloride was dropped to the solution, which was stirred for 8 hours at 40° C. and cooled up to room temperature. Saturated sodium bicarbonate solution (10 ml) was added to the reaction solution, which was extracted by ethyl acetate, and then the water layer was extracted by ethyl acetate. Further, it was mixed with the organic layer and sequentially washed with water and saturated brine and dried by sulfuric anhydride sodium. The residue obtained by removal of the solvent was purified by silica gel column chromatography (hexane:ethyl acetate=4:1 to 2:1) to give the compound (991 g) of the present compound having the same physical properties as example 1.

EXAMPLE 2

1-(4-((2S)-4-methyl-3,4-dihydro-2H-1,4-benzox-azin-2-ylmethoxy)benzoyl)-2-methyl-1H-indol-4-ylacetic acid

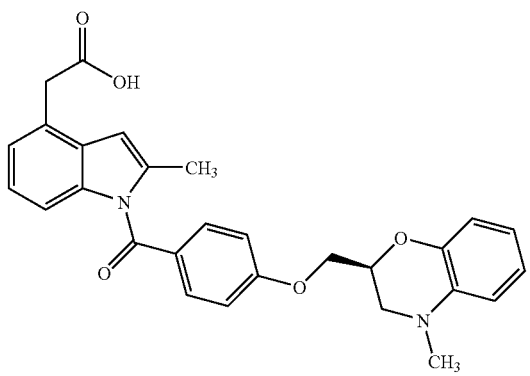

Under hydrogen gas, 20% hydroxide palladium carbon (50% hydrate, 17 g) was added to ethyl acetate (830 ml) solution containing the compound (168 g) prepared according to example 1 or example 1(1), and stirred for 4 hours at room temperature. The reaction solution was filtered through celite (registered trademark) and the filtrate was concentrated. The mixture of ethanol water-ethyl acetate was added to the obtained residue, and solidified. The solid was obtained by filtration and dried after washing with diethyl ether to give the present compound (85.8 g, 99.6% ee) having the following physical properties. Further, it was optionally converted into the corresponding salt by a well-known method to give the following compound of the present invention.

Free boby;
TLC:Rf 0.26 (methanol:chloroform=1:10); NMR (CDCl$_3$):δ 7.71 (d, J=9.0 Hz, 2H), 7.20–6.78 (m, 7H), 6.78–6.64 (m, 2H), 6.49 (s, 1H), 4.68 (m, 1H), 4.30 (dd, J=9.9. 5.4 Hz, 1H), 4.21 (dd, J=9.9, 6.0 Hz, 1H), 3.86 (s, 2H), 3.40 (dd, J=11.4, 2.7 Hz, 1H), 3.27 (dd, J=11.4, 6.6 Hz, 1H), 2.92 (s, 3H), 2.44 (s, 3H).

The optical purity of this title compound was decided by using high performance liquid chromatography (HPLC).
Column: CHIRALCEL OD (Daicel Chemical Industries Ltd.)
0.46 cmφ×25 cm
Flow rate: 0.5 ml/minute
Solvent: acetonitrile:1.0N sodium perchlorate solution=85:15
Detected wave-length: 262 nm
Retention time: 14.38 minutes
Temperature: 25° C.

Sodium trihydrate:
TLC:Rf 0.37 (chloroform:methanol=10:1); NMR (CDCl$_3$+CD$_3$OD):δ 7.68 (d, J=8.8 Hz, 2H), 7.35–6.77 (m, 7H), 6.77–6.60 (m, 2H), 6.54 (s, 1H), 4.72–4.60 (m, 1H), 4.29 (dd, J=9.6, 5.0 Hz, 1H), 4.25–4.20 (dd, 9.6, 5.8 Hz, 1H), 3.71 (s, 2H), 3.40 (dd, J=11.6, 2.8 Hz, 1H), 3.28 (dd, J=11.6, 6.4 Hz, 1H), 2.91 (s, 3H), 2.39 (s, 3H).

EXAMPLE 2(1) TO EXAMPLE 2(27)

Instead of the compound prepared according to reference example 8 and the compound prepared according to reference example 12, using the compounds prepared according to reference example 23(1)–(11) described later, reference example 25, reference example 25(1)–(6), reference example 26, reference example 28, reference examples 28(1), or the corresponding alcoholic derivatives, the following compounds in the present invention, which were converted into the corresponding salts, were obtained by an operation similar to the method represented from example 1 to example 2, and then a well-known method optionally.

EXAMPLE 2(1)

1-(4-((2R)-1,4-benzodioxan-2-ylmethoxy)benzoyl)-2-methyl-1H-indol-4-ylacetic acid

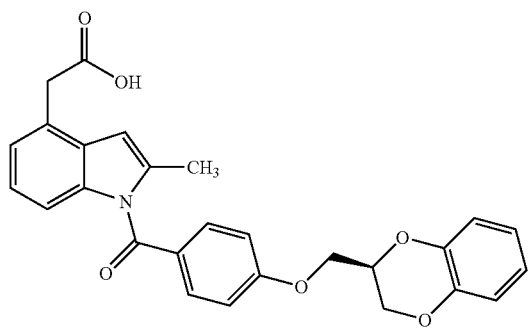

TLC:Rf 0.30 (chloroform:methanol=10:1); NMR (CDCl$_3$):δ 7.75–7.70 (m, 2H), 7.07–6.86 (m, 9H), 6.49 (m, 1H), 4.61 (m, 1H), 4.42 (dd, J=11.4, 2.1Hz, 1H), 4.33 (dd, J=10.2, 5.1Hz, 1H), 4.26 (dd, J=11.4, 6.3 Hz, 1H), 4.25 (dd, J=10.2, 6.0 Hz, 1H), 3.87 (s, 2H), 2.44 (d, J=1.2 Hz, 3H).

EXAMPLE 2(2)

1-(4-((2S)-1,4-benzodioxan-2-ylmethoxy)benzoyl)-2-methyl-1H-indole-4-ylacetic acid

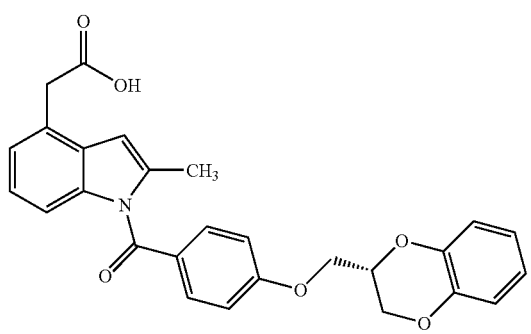

TLC:Rf 0.30 (chloroform:methanol=10:1); NMR (CDCl$_3$): δ 7.75–7.70 (m, 2H), 7.07–6.86 (m, 9H), 6.50 (m, 1H), 4.61 (m, 1H), 4.42 (dd, J=11.4, 2.4 Hz, 1H), 4.33 (dd, J=9.9, 5.1 Hz, 1H), 4.26 (dd, J=11.4, 6.6 Hz, 1H), 4.25 (dd, J=9.9, 6.0 Hz, 1H), 3.87 (s, 2H), 2.44 (d, J=1.2 Hz, 3H).

EXAMPLE 2(3)

1-(4-((2S)-1-methylindolin-2-ylmethoxy)benzoyl)-2-methyl-1H-indol-4-ylacetic acid

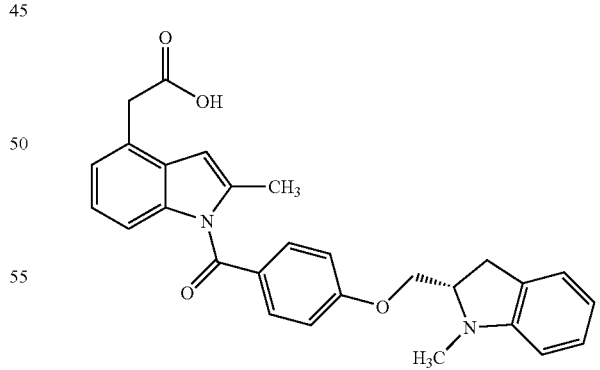

TLC:Rf 0.49 (chloroform:methanol=9:1); NMR (CDCl$_3$):δ 7.76–7.66 (m, 2H), 7.20–6.46 (m, 10H), 5.00–2.80 (m, 5H), 3.87 (s, 2H), 2.94 and 2.91 (each s, total 3H), 2.45 (s, 3H).

EXAMPLE 2(4)

1-(4-((2R)-4-methyl-3,4-dihydro-2H-1,4-benzoxazin-2-ylmethoxy)benzoyl)-2-methyl-1H-indol-4-ylacetic acid

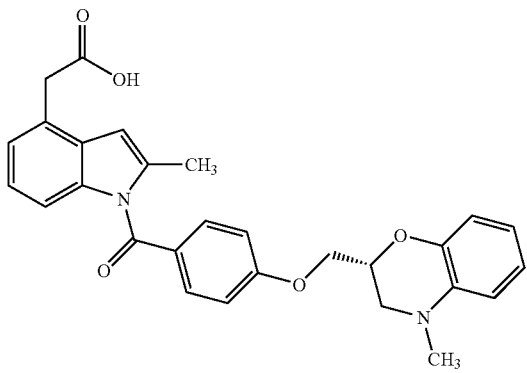

TLC:Rf 0.26 (methanol:chloroform:=1:10); NMR (CDCl$_3$):δ 7.72 (d, J=8.8 Hz, 2H), 7.12–6.79 (m, 7H), 6.72 (d, J=7.4 Hz, 2H), 6.49 (s, 1H), 4.68 (m, 1H), 4.31 (dd, J=9.6, 5.2 Hz, 1H), 4.20 (dd, J=9.6, 6.2 Hz, 1H), 3.87 (s, 2H), 3.40 (dd, J=11.6, 2.8 Hz, 1H), 3.28 (dd, J=11.6, 6.2 Hz, 1H), 2.92 (s, 3H), 2.45 (s, 3H).

The optical purity of this title compound was decided by using high performance liquid chromatography (HPLC).
Column: CHIRALCEL OD (Daicel Chemical Industries Ltd.)
0.46 cmφ×25 cm
Flow rate: 0.5 ml/minute
Solvent: acetonitrile:1.0N sodium perchlorate solution=85:15
Detected wave-length: 262 nm
Retention time: 16.88 minutes
Temperature: 25° C.

EXAMPLE 2(5)

1-(4-((2S)-4,6-dimethyl-3,4-dihydro-2H-1,4-benzoxazin-2-ylmethoxy)benzoyl)-2-methyl-1H-indol-4-ylacetic acid

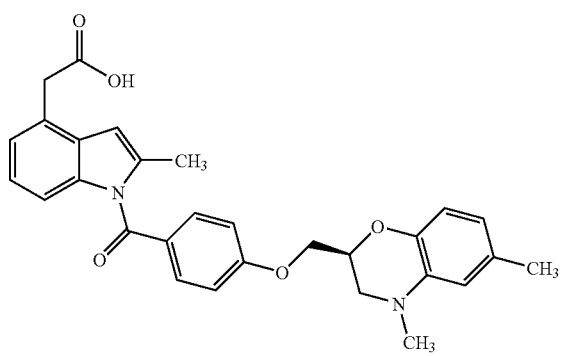

Free body:
TLC:Rf 0.37 (chloroform:methanol=10:1); NMR (CDCl$_3$):δ 7.74–7.69 (m, 2H), 7.06–6.82 (m, 5H), 6.73 (d, J=8.1 Hz, 1H), 6.54–6.47 (m, 3H), 4.64 (m, 1H), 4.30 (dd, J=9.9, 5.1 Hz, 1H), 4.20 (dd, J=9.9, 6.3 Hz, 1H), 3.87 (s, 2H), 3.39 (dd, J=11.4, 2.7 Hz, 1H), 3.26 (dd, J=11.4, 6.6 Hz, 1H), 2.90 (s, 3H), 2.45 (d, J=0.9 Hz, 3H), 2.28 (s, 3H).

Hydrochloride:
TLC:Rf 0.45 (chloroform:methanol=9:1); NMR (CDCl$_3$):δ 7.72 (d, J=8.4 Hz, 1H), 7.10–6.87 (m, 8H), 6.50 (s, 1H), 4.85 (m, 1H), 4.35 (m, 2H), 3.86 (s, 2H), 3.75 (m, 1H), 3.55 (m, 1H), 3.18 (s, 3H), 2.44 (s, 3H), 2.32 (s, 3H).

EXAMPLE 2(6)

1-(4-((2S)-6-fluoro-4-methyl-3,4-dihydro-2H-1,4-benzoxazin-2-ylmethoxy)benzoyl)-2-methyl-1H-indol-4-ylacetic acid

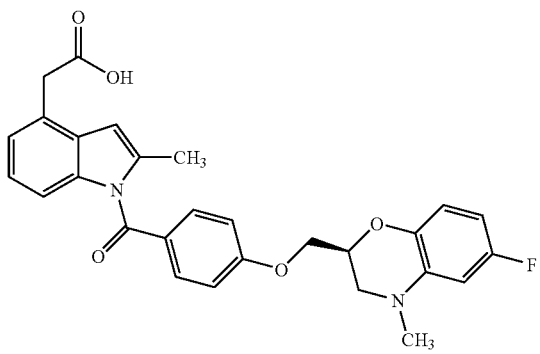

TLC:Rf 0.33 (chloroform:methanol=10:1); NMR (CDCl$_3$):δ 7.72 (d, J=8.7 Hz, 2H), 7.07–6.90 (m, 5H), 6.74 (dd, J=9.0, 5.7 Hz, 1H), 6.49 (s, 1H), 6.45–6.30 (m, 2H), 4.66–4.53 (m, 1H), 4.29 (dd, J=9.6, 4.8 Hz, 1H), 4.18 (dd, J=9.6, 6.3 Hz, 1H), 3.87 (s, 2H), 3.40 (dd, J=12.0, 3.0 Hz, 1H), 3.30 (dd, J=12.0, 6.9 Hz, 1H), 2.91 (s, 3H), 2.45 (s, 3H).

EXAMPLE 2(7)

1-(4-((2S)-6-methoxy-4-methyl-3,4-dihydro-2H-1,4-benzoxazin-2-ylmethoxy)benzoyl)-2-methyl-1H-indol-4-ylacetic acid

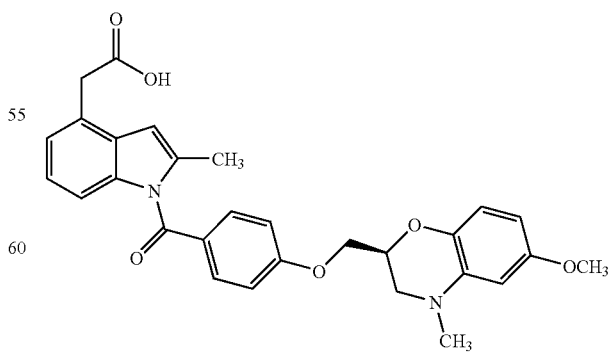

TLC:Rf 0.36 (chloroform:methanol=10:1); NMR (CDCl$_3$):δ 7.74–7.69 (m, 2H), 7.06–6.92 (m, 5H), 6.74 (d, J=8.4 Hz, 1H), 6.49 (m, 1H), 6.29 (d, J=3.0 Hz, 1H), 6.23 (dd, J=8.4, 3.0 Hz, 1H), 4.68 (m, 1H), 4.29 (dd, J=9.9, 4.8 Hz, 1H), 4.18 (dd, J=9.9, 6.3 Hz, 1H), 3.85 (s, 2H), 3.76 (s, 3H), 3.39 (dd, J=11.4, 2.7 Hz, 1H), 3.28 (dd, J=11.4, 6.6 Hz, 1H), 2.90 (s, 3H), 2.44 (d, J=0.9 Hz, 3H).

EXAMPLE 2(8)

1-(4-((2S)-7-methoxy-4-methyl-3,4-dihydro-2H-1,4-benzoxazin-2-ylmethoxy)benzoyl)-2-methyl-1H-indol-4-ylacetic acid

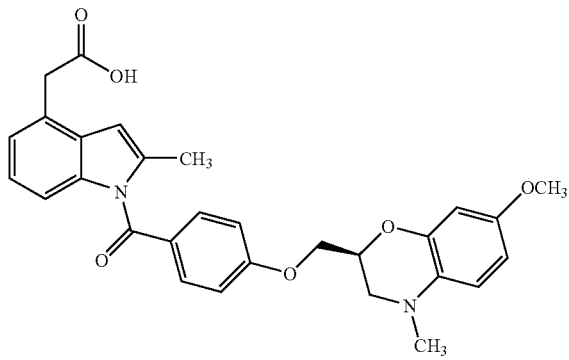

TLC:Rf 0.41 (chloroform:methanol=9:1); NMR (CDCl₃):δ 7.72 (d, J=9.0 Hz, 2H), 7.08–6.90 (m, 5H), 6.69–6.62 (m, 1H), 6.52–6.43 (m, 3H), 4.75–4.64 (m, 1H), 4.31 (dd, J=9.9, 5.1 HZ, 1H), 4.22 (dd, J=9.9, 6.0 Hz, 1H), 3.87 (s, 2H), 3.74 (s, 3H), 3.33 (dd, J=11.7, 2.7 Hz, 1H), 3.18 (dd, J=11.7, 6.9 Hz, 1H), 2.86 (s, 3H), 2.45 (s, 3H).

EXAMPLE 2(9)

1-(4-((2S)-4,7-dimethyl-3,4-dihydro-2H-1,4-benzoxazin-2-ylmethoxy)benzoyl)-2-methyl-1H-indol-4-ylacetic acid

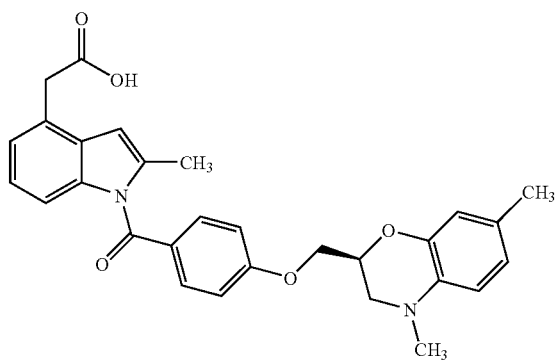

TLC:Rf 0.41 (chloroform:methanol=9:1); NMR (CDCl₃):δ 7.71 (d, J=9.0 Hz, 2H), 7.08–6.85 (m, 5H), 6.73–6.59 (m, 3H), 6.50 (s, 1H), 4.73–4.62 (m, 1H), 4.30 (dd, J=9.9, 5.1 HZ, 1H), 4.21 (dd, J=9.9, 6.3 Hz, 1H), 3.87 (s, 2H), 3.36 (dd, J=11.7, 3.0 Hz, 1H), 3.22 (dd, J=11.7, 6.3 Hz, 1H), 2.88 (s, 3H), 2.45 (s, 3H), 2.23 (s, 3H).

EXAMPLE 2(10)

1-(4-((2S)-7-fluoro-4-methyl-3,4-dihydro-2H-1,4-benzoxazin-2-ylmethoxy)benzoyl)-2-methyl-1H-indol-4-ylacetic acid

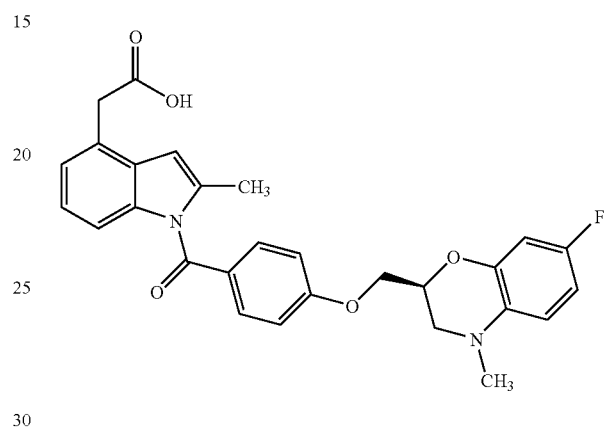

TLC:Rf 0.34 (chloroform:methanol=9:1); NMR (CDCl₃):δ 7.72 (d, J=9.0 Hz, 2H), 7.09–6.92 (m, 5H), 6.60 (d, J=8.1 Hz, 3H), 6.50 (s, 1H), 4.75–4.65 (m, 1H), 4.36–4.17 (m, 2H), 3.87 (s, 2H), 3.39–3.18 (m, 2H), 2.88 (s, 3H), 2.45 (s, 3H).

EXAMPLE 2(11)

1-(4-((2S)-1-ethylindolin-2-ylmethoxy)benzoyl)-2-methyl-1H-indol-4-ylacetic acid

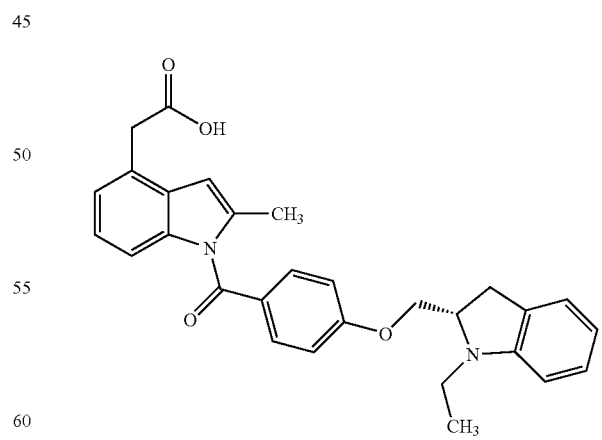

TLC:Rf 0.45 (chloroform:methanol=9:1); NMR (CDCl₃):δ 7.72 (dd, J=9.0, 1.2 Hz, 2H), 7.17–6.82 (m, 7H), 6.70–6.60 (m) and 6.53–6.43 (m) total 3H, 4.97–4.84 (m) and 4.33–4.03 (m) total 2H, 3.86 (s, 2H), 3.58–3.15 (m) and 3.07–2.83 (m) total 5H, 2.44 (s, 3H), 1.21–1.10 (m, 3H).

EXAMPLE 2(12)

1-(4-((2S)-4,8-dimethyl-3,4-dihydro-2H-1,4-benzoxazin-2-ylmethoxy)benzoyl)-2-methyl-1H-indol-4-ylacetic acid

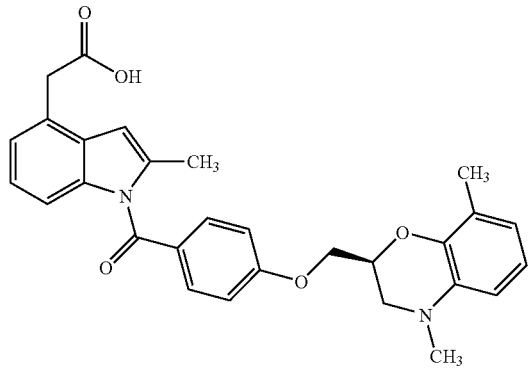

TLC:Rf 0.39 (chloroform:methanol=9:1); NMR (CDCl$_3$):δ 7.74–7.69 (m, 2H), 7.08–6.93 (m, 5H), 6.78 (dd, J=8.1, 7.5 Hz, 1H), 6.58 (d, J=8.1 Hz, 1H), 6.58 (d, J=7.5 Hz, 1H), 6.49 (m, 1H), 4.68 (m, 1H), 4.32 (dd, J=9.9, 4.8 Hz, 1H), 4.23 (dd, J=9.9, 6.6 Hz, 1H), 3.86 (s, 2H), 3.40 (dd, J=11.4, 2.7 Hz, 1H), 3.25 (dd, J=11.4, 6.6 Hz, 1H), 2.90 (s, 3H), 2.44 (d, J=1.2 Hz, 3H), 2.18 (s, 3H).

EXAMPLE 2(13)

1-(4-((2S)-5-methoxy-4-methyl-3,4-dihydro-2H-1,4-benzoxazin-2-ylmethoxy)benzoyl)-2-methyl-1H-indol-4-ylacetic acid

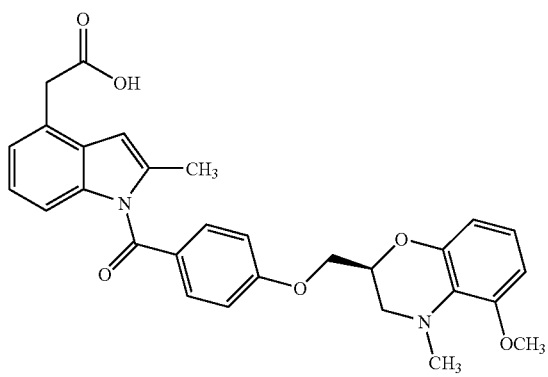

TLC:Rf 0.38 (chloroform:methanol=9:1); NMR (CDCl$_3$):δ 7.72 (d, J=8.4 Hz, 2H), 7.10–6.86 (m, 6H), 6.60 (dd, J=8.4, 1.5 Hz, 1H), 6.55–6.45 (m, 2H), 4.46–4.31 (m, 2H), 4.27–4.17 (m, 1H), 3.90 (s, 3H), 3.85 (s, 2H), 3.28 (dd, J=13.5, 2.1 Hz, 1H), 3.13 (dd, J=13.5, 9.3 Hz, 1H), 2.90 (s, 3H), 2.44 (s, 3H).

EXAMPLE 2(14)

1-(4-((2S)-5-fluoro-4-methyl-3,4-dihydro-2H-1,4-benzoxazin-2-ylmethoxy)benzoyl)-2-methyl-1H-indol-4-ylacetic acid

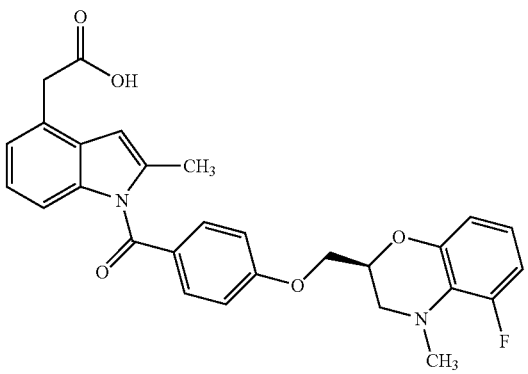

TLC:Rf 0.36 (chloroform:methanol=9:1); NMR (CDCl$_3$):δ 7.73 (d, J=9.0 Hz, 2H), 7.09–6.92 (m, 5H), 6.81–6.62 (m, 3H), 6.49 (s, 1H), 4.49–4.40 (m, 1H), 4.38–4.18 (m, 2H), 3.87 (s, 2H), 3.38–3.15 (m, 2H), 3.00 (d, J=1.8 Hz, 3H), 2.45 (s, 3H).

EXAMPLE 2(15)

1-(4-((2S)-2,3-dihydrobenzofuran-2-ylmethoxy)benzoyl)-2-methyl-1H-indol-4-ylacetic acid

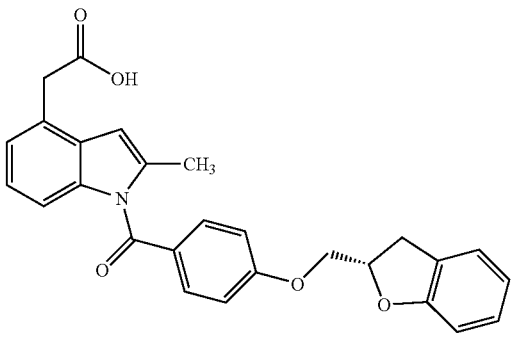

TLC:Rf 0.51 (chloroform:methanol=9:1); NMR (CDCl$_3$):δ 7.71 (d, J=8.7 Hz, 2H), 7.21 (d, J=7.2 Hz, 1H), 7.15 (t, J=7.2 Hz, 1H), 7.08–6.81 (m, 7H), 6.49 (s, 1H), 5.25–5.14 (m, 1H), 4.29 (dd, J=10.2, 6.3 Hz, 1H), 4.21 (dd, J=10.2, 4.2 Hz, 1H), 3.87 (s, 2H), 3.43 (dd, J=15.9, 9.6 Hz, 1H), 3.17 (dd, J=15.9, 7.2 Hz, 1H), 2.45 (s, 3H).

EXAMPLE 2(16)

1-(4-((2R)-2,3-dihydrobenzofuran-2-ylmethoxy)benzoyl)-2-methyl-1H-indol-4-ylacetic acid

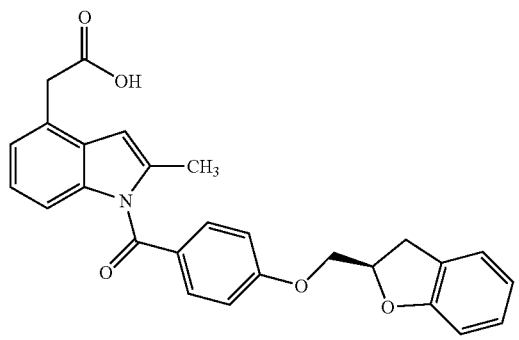

TLC:Rf 0.51 (chloroform:methanol=9:1); NMR (CDCl$_3$):δ 7.71 (d, J=8.7 Hz, 2H), 7.21 (d, J=7.2 Hz, 1H), 7.15 (t, J=7.2 Hz, 1H), 7.08–6.81 (m, 7H), 6.49 (s, 1H), 5.25–5.14 (m, 1H), 4.29 (dd, J=10.2, 6.3 Hz, 1H), 4.21 (dd, J=10.2, 4.2 Hz, 1H), 3.87 (s, 2H), 3.43 (dd, J=15.9, 9.6 Hz, 1H), 3.17 (dd, J=15.9, 7.2 Hz, 1H), 2.45 (s, 3H).

EXAMPLE 2(17)

1-(4-((2S)-8-fluoro-4-methyl-3,4-dihydro-2H-1,4-benzoxazin-2-ylmethoxy)benzoyl)-2-methyl-1H-indol-4-ylacetic acid

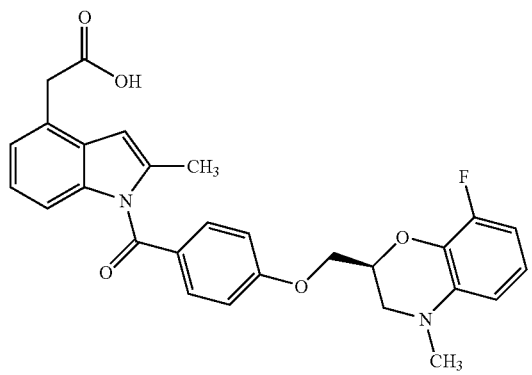

TLC:Rf 0.52 (chloroform:methanol=9:1); NMR (CDCl$_3$):δ 7.72 (d, J=8.7 Hz, 2H), 7.09–6.90 (m, 5H), 6.83–6.72 (m, 1H), 6.59–6.40 (m, 3H), 4.78–4.65 (m, 1H), 4.40–4.20 (m, 2H), 3.87 (s, 2H), 3.50–3.30 (m, 2H), 2.94 (s, 3H), 2.44 (s, 3H).

EXAMPLE 2(18)

1-(4-((2R)-1,4-benzoxathian-2-ylmethoxy)benzoyl)-2-methyl-1H-indol-4-ylacetic acid

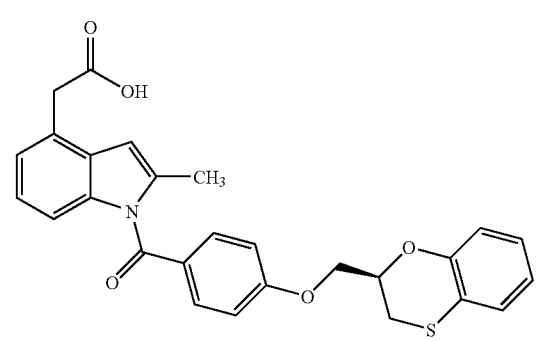

TLC:Rf 0.40 (chloroform:methanol=10:1); NMR (CDCl$_3$):δ 7.75–7.69 (m, 2H), 7.10–6.86 (m, 9H), 6.50 (s, 1H), 4.72–7.65 (m, 1H), 4.40–4.22 (m, 2H), 3.87 (s, 2H), 3–2,3–3.21 (m, 2H), 2.45 (s, 3H).

EXAMPLE 2(19)

1-(4-((3S)-2,3-dihydrobenzofuran-3-ylmethoxy)benzoyl)-2-methyl-1H-indol-4-ylacetic acid

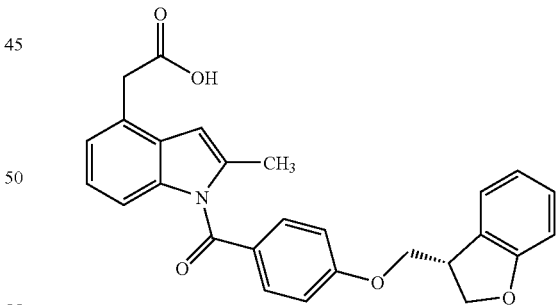

TLC:Rf 0.40 (chloroform:methanol=10:1); NMR (CDCl$_3$):δ 7.71 (d, J=8.7 Hz, 2H), 7.31 (d, J=7.5 Hz, 1H), 7–2,3–7.17 (m, 1H), 7.07–6.84 (m, 7H), 6.49 (s, 1H), 4.73 (t, J=9.0 Hz, 1H), 4.55 (dd, J=9.0, 4.8 Hz, 1H), 4.23 (dd, J=8.7, 5.4 Hz, 1H), 4.10 (t, J=8.7 Hz, 1H), 4.02–3.93 (m, 1H), 3.86 (s, 2H), 2.44 (s, 3H).

EXAMPLE 2(20)

1-(4-((3R)-2,3-dihydrobenzofuran-3-ylmethoxy) benzoyl)-2-methyl-1H-indol-4-ylacetic acid

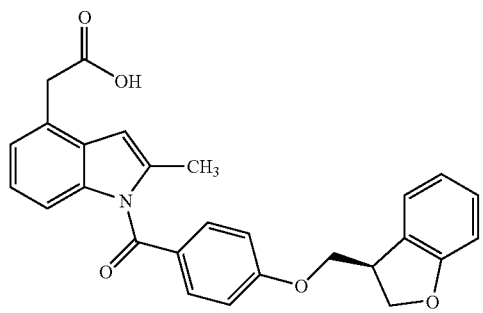

TLC:Rf 0.40 (chloroform:methanol=10:1); NMR (CDCl$_3$):δ 7.71 (d, J=8.7 Hz, 2H), 7.31 (d, J=7.5 Hz, 1H), 7–2,3–7.17 (m, 1H), 7.07–6.84 (m, 7H), 6.49 (s, 1H), 4.73 (t, J=9.0 Hz, 1H), 4.55 (dd, J=9.0, 4.8 Hz, 1H), 4.23 (dd, J=8.7, 5.4 Hz, 1H), 4.10 (t, J=8.7 Hz, 1H), 4.02–3.93 (m, 1H), 3.86 (s, 2H), 2.44 (s, 3H).

EXAMPLE 2(21)

1-(4-((3R)-5-fluoro-2,3-dihydrobenzofuran-3-yl-methoxy)benzoyl)-2-methyl-1H-indol-4-ylacetic acid

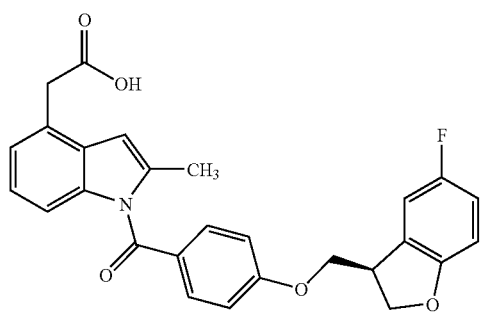

TLC:Rf 0.37 (methanol:chloroform=1:8); NMR (CDCl$_3$):δ 7.71 (d, J=9.0 Hz, 2H), 7.22–7.10 (m, 1H), 7.10–6.85 (m, 5H), 6.75–6.55 (m, 2H), 6.48 (s, 1H), 4.82–4.60 (m, 2H), 4.50–4.33 (m, 1H), 4.20–4.00 (m, 2H), 3.85 (s, 2H), 2.44 (s, 3H).

EXAMPLE 2(22)

1-(4-((3R)-5-methyl-2,3-dihydrobenzofuran-3-yl-methoxy)benzoyl)-2-methyl-1H-indol-4-ylacetic acid

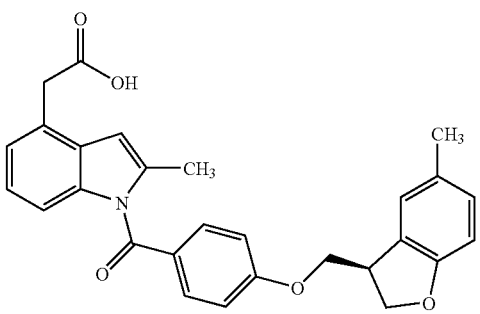

TLC:Rf 0.25 (methanol:chloroform=1:8); NMR (CDCl$_3$):δ 7.71 (d, J=9.0 Hz, 2H), 7.10 (s, 1H), 7.07–6.87 (m, 4H), 6.73 (d, J=8.4 Hz, 2H), 6.49 (s, 1H), 4.70 (t, J=9.0 Hz, 1H), 4.70 (t, J=9.0 Hz, 1H), 4.53 (dd, J=9.0, 4.8 Hz, 1H), 4.22 (dd, J=8.7, 5.4 Hz, 1H), 4.08 (t, J=8.7 Hz, 1H), 3.92 (m, 1H), 3.86 (s, 2H), 2.44 (s, 3H), 2.30 (s, 3H).

EXAMPLE 2(23)

1-(4-((3R)-6-fluoro-2,3-dihydrobenzofuran-3-yl-methoxy)benzoyl)-2-methyl-1H-indol-4-ylacetic acid TLC:Rf 0.55 (chloroform:methanol=10:1); NMR (CDCl$_3$):δ 7.70 (dd, J=6.9, 1.8 Hz, 2H), 7.20–7.10 (m, 1H), 7.05–6.90 (m, 5H), 6.70–6.55 (m, 2H), 6.48 (s, 1H), 4.75 (dd, J=9.3, 8.1 Hz, 1H), 4.65 (dd, J=9.3, 4.5 Hz, 1H), 4.41 (m, 1H), 4.18–4.08 (m, 2H), 3.84 (s, 2H), 2.43 (s, 3H).

EXAMPLE 2(24)

1-(4-((3R)-7-methyl-2,3-dihydrobenzofuran-3-yl-methoxy)benzoyl)-2-methyl-1H-indol-4-ylacetic acid

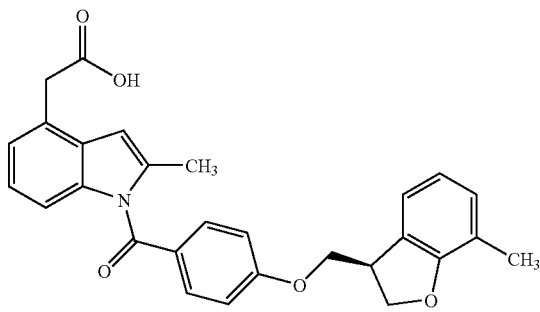

TLC:Rf 0.45 (chloroform:methanol=10:1); NMR (CDCl$_3$):δ 7.70 (d, J=8.7 Hz, 2H), 7.12 (d, J=6.9 Hz, 1H), 7.03–6.93 (m, 6H), 6.81 (t, J=7.2 Hz, 1H), 6.47 (s, 1H), 4.71 (dd, J=9.6, 8.7 Hz, 1H), 4.54 (dd, J=9.6, 5.1 Hz, 1H), 4.21 (dd, J=9.3, 5.7 Hz, 1H), 4.08 (dd, J=9.3, 9.1 Hz, 1H), 3.97 (m, 1 H), 3.84 (s, 2H), 2.43 (s, 3H), 2.23 (s, 3H).

EXAMPLE 2(25)

1-(4-((2R)-5-fluoro-1,4-benzodioxan-2-ylmethoxy)benzoyl)-2-methyl-1H-indol-4-ylacetic acid

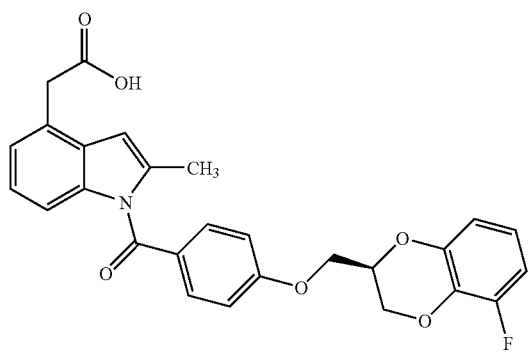

TLC:Rf 0.31 (chloroform:methanol=10:1); NMR (CDCl$_3$):δ 7.72 (d, J=8.7 Hz, 2H), 7.13–6.88 (m, 5H), 6.85–6.65 (m, 3H), 6.49 (s, 1H), 4.68–4.59 (m, 1H), 4.48 (dd, J=11.4, 2.4 Hz, 1H), 4.42–4.22 (m, 3H), 3.85 (s, 2H), 2.44 (s, 3H).

EXAMPLE 2(26)

1-(4-((2S)-8-fluoro-1,4-benzodioxan-2-ylmethoxy)benzoyl)-2-methyl-1H-indol-4-ylacetic acid

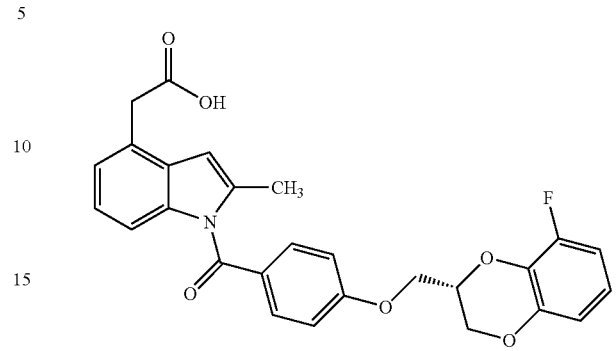

TLC:Rf 0.31 (chloroform:methanol=10:1); NMR (CDCl$_3$):δ 7.71 (d, J=8.4 Hz, 2H), 7.13–6.87 (m, 5H), 6.87–6.60 (m, 3H), 6.49 (s, 1H), 4.71–4.59 (m, 1H), 4.53–4.22 (m, 4H), 3.85 (s, 2H), 2.44 (s, 3H).

EXAMPLE 2(27)

1-(4-((3R)-7-fluoro-2,3-dihydrobenzofuran-3-yl-methoxy)benzoyl)-2-methyl-1H-indol-4-ylacetic acid

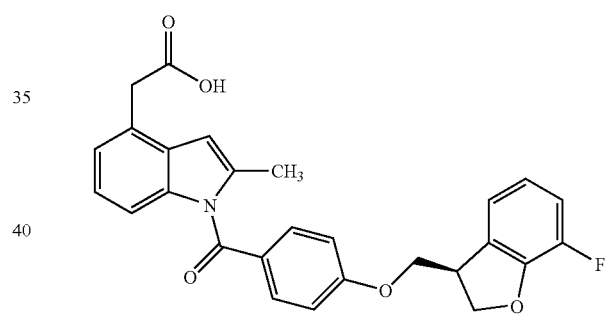

TLC:Rf 0.55 (chloroform:methanol=10:1); NMR (CDCl$_3$):δ 7.70 (dd, J=6.9, 2.1 Hz, 2H), 7.09–6.93 (m, 7H), 6.84 (m, 1H), 6.48 (s, 1H), 4.82 (t, J=9.3 Hz, 1H), 4.64 (dd, J=9.3, 5.4 Hz, 1H), 4.23 (dd, J=8.7, 5.7 Hz, 1H), 4.15–4.08 (m, 1H), 4.01 (m, 1H), 3.84 (s, 2H), 2.43 (s, 3H).

REFERENCE EXAMPLE 13

3-(2-methyl-1H-indol-4-yl)acrylic acid methyl ester

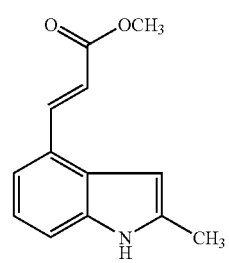

Acrylic methylester (2.24 ml), diisopropyl ethylamine (5.9 ml), and bis(triphenylphosphine) palladium (II) dichloride (238 mg) were added to N,N-dimethylformamide (50 ml) solution containing the compound (3.2 g) prepared according to reference example 1, which was stirred for 2 days at 95° C. Water and ethyl acetate were added to the reaction solution, and separated. The water layer is extracted by ethyl acetate, the mixed organic layer was sequentially washed with water and saturated brine and dried, and then concentrated by vacuum concentration. The residue was purified by silica gel column chromatography (hexane:ethyl acetate=9:1) to give a compound (950 g) having the following physical properties.

TLC:Rf 0.50 (hexane:ethyl acetate=8:2);

REFERENCE EXAMPLE 14

3-(2-methyl-1H-indol-4-yl)acrylic acid

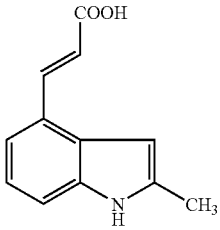

The compound (950 mg) prepared according to reference example 13 was dissolved to the mixture of methanol (10 ml) and tetrahydrofuran (10 ml), and 5N sodium hydroxide solution (5 ml) was added to the mixture, which was stirred for 3 days at room temperature. 1N hydrochloric acid was added to the reactive mixture, which was extracted by ethyl acetate. The organic layer was sequentially washed with water and saturated brine and dried. After removal of the solvent, a compound having the following physical properties was obtained. The obtained title compound was used for the following reaction without further purification.

TLC:Rf 0.54 (chloroform:methanol=9:1);

REFERENCE EXAMPLE 15

3-(2-methyl-1H-indol-4-yl)acrylic acid allyl ester

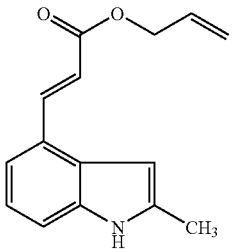

Under argon gas, potassium carbonate (553 mg) and allyl chloride (0.24 ml) were added to N,N-dimethylformamide (5 ml) solution containing the compound (500 mg) prepared according to reference example 14, which was stirred for 3.5 hours at 80° C. The reaction mixture was radiationally cooled and water was added to it, which was extracted by ethyl acetate. The organic layer was sequentially washed with water and saturated brine and dried. After removal of the solvent, the compound having the following physical properties was obtained. The residue was purified by silica gel column chromatography (hexane:ethyl acetate=4:1) to give the title compound having the following physical properties.

TLC:Rf 0.29 (hexane:ethyl acetate=4:1); NMR(CDCl$_3$):δ 8.13–8.00 (m, 2H), 7.37–7.29 (m, 2H), 7.12 (t, J=8.1 Hz, 1H), 6.61 (d, J=15.9 Hz, 1H), 6.53 (brs, 1H), 6.10–5.95 (m, 1H), 5.45–5.35 (m, 1H), 5.33–5.25 (m, 1H), 4.74 (d, J=5.7 Hz, 2H), 2.50 (s, 3H).

REFERENCE EXAMPLE 16

(2S)-4-Methyl-3,4-dihydro-2H-1,4-benzoxazin-2-ylmethyl-4-methylbenzensulfonate

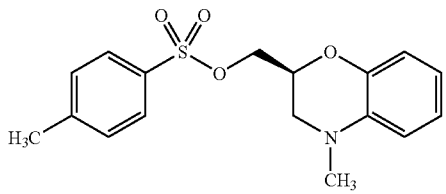

Under argon gas, the compound (3.06 g) prepared according to reference example 12 was dissolved to tetrahydrofuran (9 ml), and triethylamine (5 ml) was added. Tetrahydrofuran (9 ml) solution containing p-toluenesulfonic acid chloride (3.42 g), and N,N-dimethylaminopyridine (209 mg) were added to the reaction solution, which was stirred for 4 hours at room temperature. After adding water, to the reaction solution was extracted by the tert-butyl methyl ether. The organic layer was concentrated and the obtained residue was solidified by adding isopropyl alcohol. The solid filtrated by the filtration was dried and washed by isopropyl alcohol to give a title compound (5.12 g) having the following physical properties values.

TLC:Rf 0.81 (hexane:ethyl acetate=1:1); NMR(CDCl$_3$):δ 7.80 (d, J=8.2 Hz, 2H), 7.34 (d, J=8.2 Hz, 2H), 7.25–7.15 (m, 1H), 6.83 (m, 1H), 6.67–6.61 (m, 2H), 4.45 (m, 1H), 4.19–4.15 (m, 2H), 3.24 (dd, J=11.6, 2.8 Hz, 1H), 3.08 (dd, J=11.6, 6.0 Hz, 1H), 2.82 (s, 3H), 2.45 (s, 3H).

REFERENCE EXAMPLE 17

4-((2S)-4-methyl-3,4-dihydro-2H-1,4-benzoxazin-2-ylmethoxy) benzoic acid methyl ester

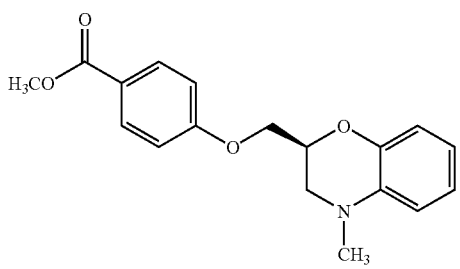

Under argon gas, the compound (3 g) prepared according to reference example 16 and 4-hydroxybenzonate methyl (1.37 g) were dissolved to N,N-dimethylformamide (6 ml), and potassium carbonate (2.74 g) was added to the solution, which was stirred for 14 hours at 80° C. The reaction mixture was radiationally cooled and tert-butylmethylether and water are added to it, which was extracted. The organic layer was concentrated to give a title compound (3.22 g) having the following physical properties values.

TLC:Rf 0.62 (hexane:ethyl acetate=2:1); NMR(CDCl₃):δ 7.99 (d, J=9.0 Hz, 2H), 6.96 (d, J=9.0 Hz, 2H), 6.94–6.79 (m, 2H), 6.70 (d, J=7.5 Hz, 1H), 6.68 (t, J=7.5 Hz, 1H), 4.65 (m, 1H), 4.27 (dd, J=9.9, 4.8 Hz, 1H), 4.17 (dd, J=9.9, 6.6 Hz, 1H), 3.89 (s, 3H), 3.39 (dd, J=11.7, 2.7 Hz, 1H), 3.25 (dd, J=11.7, 6.6 Hz, 1H), 2.90 (s, 3H).

REFERENCE EXAMPLE 18

4-((2S)-4-methyl-3,4-dihydro-2H-1,4-benzoxazin-2-ylmethoxy) benzoic acid

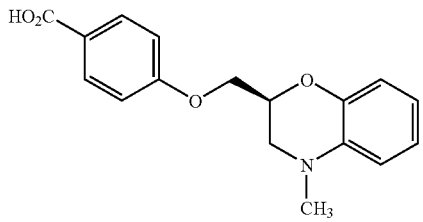

The compound (420 mg) prepared according to reference example 17 was dissolved to the mixture of tetrahydrofuran (1.2 ml) and isopropyl alcohol (1.2 ml), 4N sodium hydroxide solution (0.67 ml) was added to the mixture, which was stirred for 3.5 hours at 80° C. Concentrated hydrochloric acid was added to the reaction solution, and then water was added. Further, the extracted solid was obtained by the filtration and washed by water, and then dried to give a title compound (326 mg) having the following physical properties values.

TLC:Rf 0.13 (ethyl acetate:hexane=1:2); NMR(DMSO-d₆):δ 7.89 (d, J=8.7 Hz, 2H), 7.05 (d, J=8.7 Hz, 2H), 6.78 (t, J=7.2 Hz, 1H), 6.70–6.68 (m, 2H), 6.58 (t, J=7.2 Hz, 1H), 4.57 (m, 1H), 4.23 (d, J=5.4 Hz, 2H), 3.35 (dd, J=11.7, 2.7 Hz, 1H), 3.16 (dd, J=11.7, 7.5 Hz, 1H), 2.82 (s, 3H).

EXAMPLE 3

3-(1-(4-((2S)-4-methyl-3,4-dihydro-2H-1,4-benzoxazin-2-ylmethoxy)benzoyl)-2-methyl-1H-indol-4-yl) acrylic acid allyl ester

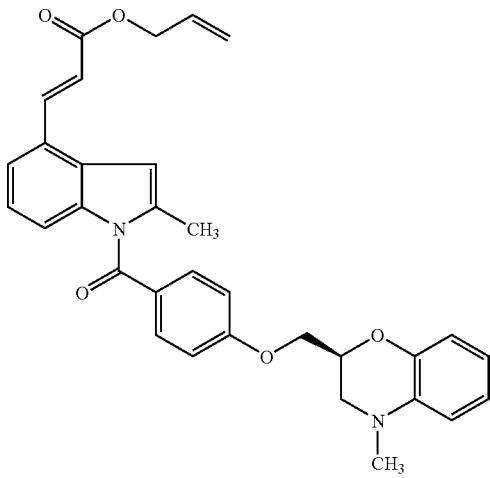

Under argon gas, oxalyl chloride (2.75 ml) was added to 1, 2-dimethoxyethane (21.7 ml) solution containing the compound (5 g) prepared according to reference example 18, which stirred at 40° C. for 1 hour. Acid chloride was obtained by the concentration of the reaction solution. Under argon gas, benzyltriethylammonium chloride (19 mg), the above acid chloride (351 mg), and sodium hydroxide (166 mg) were added to dichloromethane (4 ml) solution containing the compound (200 mg) prepared according to reference example 15, which was stirred at room temperature for 1 hour. Water is added to the reactive mixture, which was extracted by ethyl acetate. The organic layer was sequentially washed with water and saturated brine, and then dried by anhydrous sodium sulfate. The residue obtained by removal of the solvent was purified by silica gel column chromatography (toluene:ethyl acetate=99:1 to 98:2) to give a title compound (375 mg) having the following physical properties.

TLC:Rf 0.55 (toluene:ethyl acetate=9:1); NMR(CDCl₃):δ 8.07 (d, J=15.9 Hz, 1H), 7.72 (d, J=9.0 Hz, 2H), 7.45–6.80 (m, 7H), 6.75–6.65 (m, 3H), 6.59 (d, J=15.9 Hz, 1H), 6.10–5.95 (m, 1H), 5.45–5.35 (m, 1H), 5.33–5.25 (m, 1H), 4.75 (d, J=5.7 Hz, 2H), 4.73–4.63(m, 1H), 4.32 (dd, J=9.6, 5.1 Hz, 1H), 4.22 (dd, J=9.6, 6.3 Hz, 1H), 3.41 (dd, J=11.7, 2.7 Hz, 1H), 3.28 (dd, J=11.7, 6.6 Hz, 1H), 2.92 (s, 3H), 2.47 (s, 3H).

EXAMPLE 4

3-(1-(4-((2S) -4-methyl-3,4-dihydro-2H-1,4-benzoxazin-2-ylmethoxy)benzoyl)-2-methyl-1H-indol-4-yl) acrylic acid

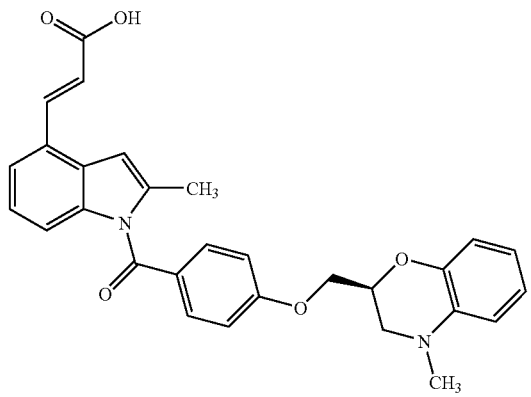

Under argon gas, tetrakis(triphenylphosphine) palladium (0) (79 mg) was added to tetrahydrofuran (5 ml) solution containing the compound (375 mg) prepared according to reference example 20, which was stirred for 10 minutes. Morpholine (0.30 ml) was added to the reaction solution, which was stirred for 1.5 hours at room temperature. 1N hydrochloric acid was added to the reactive mixture, which was extracted by ethyl acetate. The organic layer was sequentially washed with water and saturated brine, and then dried by anhydrous sodium sulfate. The residue obtained by removal of the solvent was purified by silica gel column chromatography (chloroform:methanol=99:1) to give a title compound (375 mg) having the following physical properties.

TLC:Rf 0.37 (chloroform:methanol=9:1); NMR (CDCl₃):δ 8.13 (d, J=15.9 Hz, 1H), 7.72 (d, J=9.0 Hz, 2H), 7.43 (dd, J=6.9, 1.8 Hz, 1H), 7.13–6.98 (m, 4H), 6.94–6.82 (m, 2H), 6.76–6.67 (m, 3H), 6.58 (d, J=15.9 Hz, 1H), 4.74–4.64 (m, 1H), 4.32 (dd, J=9.9, 5.4 Hz, 1H), 4.22 (dd, J=9.9, 6.0 Hz, 1H), 3.41 (dd, J=11.7, 2.7 Hz, 1H), 3.29 (dd, J=11.7, 6.6 Hz, 1H), 2.92 (s, 3H), 2.48 (s, 3H).

EXAMPLE 5

3-(1-(4-((2S)-4-methyl-3,4-dihydro-2H-1,4-benzoxazin-2-ylmethoxy)benzoyl)-2-methyl-1H-indol-4-yl)propanoic acid

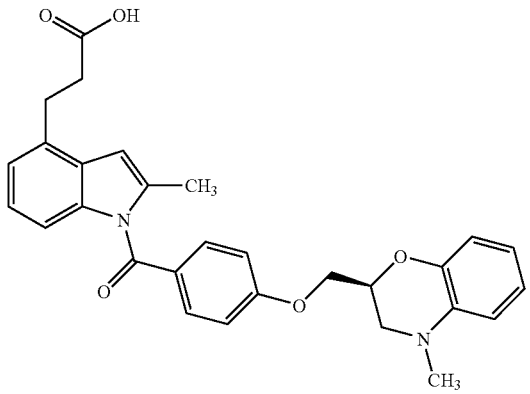

Under argon gas, the compound (230 mg) prepared according to example 4 was dissolved to the mixture of ethyl acetate (7 ml) and methanol (7 ml), and 10% palladium carbon (90 mg) was added to it, which was stirred for 1.5 hours under hydrogen gas. The reaction solution was filtered through celite (registered trademark), and the filtrate was concentrated. The obtained residue was recrystallized by methanol-water to give a title compound (90 mg) having the following physical properties.

TLC:Rf 0.43 (chloroform:methanol=9:1); NMR (CDCl$_3$):δ 7.72 (d, J=8.7 Hz, 2H), 7.05–6.80 (m, 7H), 6.76–6.66 (m, 2H), 6.49 (s, 1H), 4.74–4.64 (m, 1H), 4.31 (dd, J=9.6, 4.8 Hz, 1H), 4.21 (dd, J=9.6, 6.0 Hz, 1H), 3.41 (dd, J=12.0, 3.0 Hz, 1H), 3.28 (dd, J=12.0, 6.6 Hz, 1H), 3.19 (t, J=8.1 Hz, 2H), 2.92 (s, 3H), 2.78 (t, J=8.1 Hz, 2H), 2.45 (s, 3H).

REFERENCE EXAMPLE 19

2-methyl-1H-indol-4-yloxyphenylmethylacetic acid benzyl ester

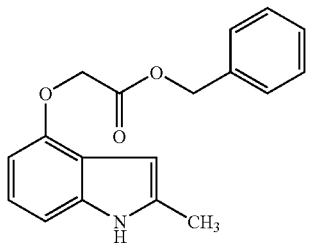

Under argon gas, potassium carbonate (2.14 g) and bromoacetic acid benzyl (1.08 ml) were added to N,N-dimethyl formamide (10 ml) solution containing 4-hydroxy-2-methyl-1H-indole (612 mg), which was stirred at 60° C. for 1 hour. Water was added to the reactive mixture, which was extracted by ethyl acetate. The organic layer was sequentially washed with water and saturated brine, and then dried by anhydrous sodium sulfate. The residue obtained by removal of the solvent was recrystallized by ethylacetate-hexane to give a title compound (1.3 g) having the following physical properties.

TLC:Rf 0.45 (hexane:ethyl acetate=7:3); NMR(CDCl$_3$):δ 7.87 (brs, 1H), 7.40–7.30 (m, 5H), 7.01–6.94 (m, 2H), 6.44–6.36 (m, 2H), 5.25 (s, 2H), 4.80 (s, 2H), 2.43 (s, 3H).

EXAMPLE 6

(1-(4-((2S)-4-methyl-3,4-dihydro-2H-1,4-benzoxazin-2-ylmethoxy)benzoyl)-2-methyl-1H-indol-4-yl)oxyacetic acid benzyl ester

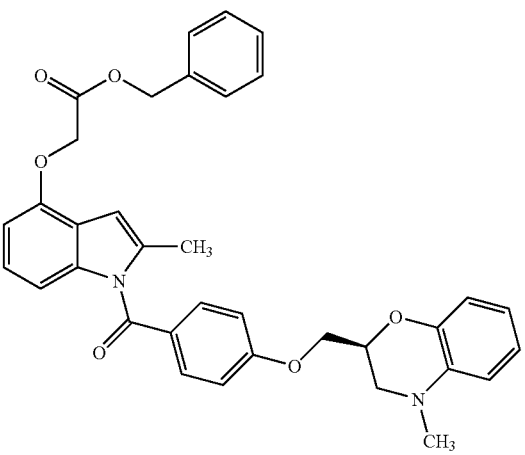

Instead of the compound prepared according to reference example 15, using the compound prepared according to reference example 19, a compound of the present invention having the following physical properties values was obtained by an operation similar to the method represented by example 3.

TLC:Rf 0.60 (toluene:ethyl acetate=9:1); NMR(CDCl$_3$): δ 7.71 (d, J=9.0 Hz, 2H), 7.40–7.30 (m, 5H), 7.30–6.60 (m, 10H), 5.25 (s, 2H), 4.79 (s, 2H), 4.75–4.65 (m, 1H), 4.31 (dd, J=9.9, 5.4 Hz, 1H), 4.21 (dd, J=9.6, 6.3 Hz, 1H), 3.41 (dd, J=11.4, 2.7 Hz, 1H), 3.28 (dd, J=11.4, 6.6 Hz, 1H), 2.92 (s, 3H), 2.42 (s, 3H).

EXAMPLE 7

(1-(4-((2S)-4-methyl-3,4-dihydro-2H-1,4-benzoxazin-2-ylmethoxy)benzoyl)-2-methyl-1H-indol-4-yl)oxyacetic acid

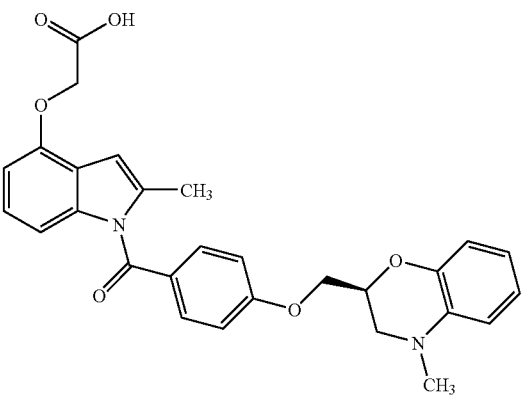

Under argon gas, 20% hydroxide palladium (40 mg) was added to ethyl acetate (10 ml) solution containing the compound (130 mg) prepared according to example 6, which was stirred for 80 minutes at room temperature under hydrate gas. The reaction solution was filtered through celite (registered trademark), and the filtrate was concentrated. The obtained residue was purified by silica gel column chromatography (chloroform:methanol=99:1) to give a title compound (75 mg) having the following physical properties.

TLC:Rf 0.23 (chloroform:methanol=9:1); NMR (CDCl₃):δ 7.71 (d, J=8.7 Hz, 2H), 7.06–6.81 (m, 5H), 6.76–6.66 (m, 3H), 6.59 (s, 1H), 6.52 (d, J=8.1 Hz, 1H), 4.80 (s, 2H), 4.73–4.62 (m, 1H), 4.31 (dd, J=9.9, 5.1 Hz, 1H), 4.21 (dd, J=9.9, 6.3 Hz, 1H), 3.41 (dd, J=11.4, 2.7 Hz, 1H), 3.28 (dd, J=11.4, 6.3 Hz, 1H), 2.92 (s, 3H), 2.43 (s, 3H).

REFERENCE EXAMPLE 20

2-methyl-1H-indole-4-carboxylic acid methyl ester

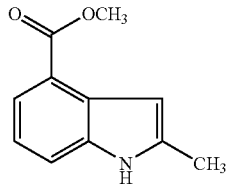

Triethylamine (6.3 ml) and tetrakis(triphenylphosphine) palladium (0) (2.6 g) were added to methanol (33.43 ml)-N,N-dimethyl formamide (200 ml) solution containing the compound (6.32 g) prepared according to reference example 1. The reactor was filled with carbon monoxide, and the reaction solution was stirred at 60° C. over night. Water and ethyl acetate was added to the reaction solution, which was extracted. The water layer was extracted by ethyl acetate and the mixed organic layer was sequentially washed with water and saturated brine and dried, and then concentrated by vacuum concentration. The residue was purified by silica gel column chromatography (hexane:ethyl acetate=85:1) to give a title compound (4.29 mg) having the following physical properties.

TLC:Rf 0.18 (toluene);

REFERENCE EXAMPLE 21

2-methyl-1H-indole-4-carboxylic acid

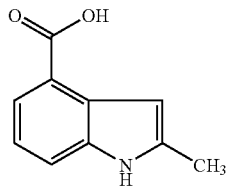

5N sodium hydroxide solution (10 ml) was added to methanol dioxane(10 ml+10 ml) solution containing the compound (4.3 g) prepared according to reference example 20, which was stirred at 60° C. over night. 2N hydrochloric acid was added to the reaction solution, which was extracted by ethyl acetate. The water layer was extracted by ethyl acetate and the mixed organic layer was sequentially washed with water and saturated brine and dried, and then concentrated by vacuum concentration. The residue was purified by silica gel column chromatography (chloroform:methanol=85:1) to give a title compound (1.6 g) having the following physical properties.

TLC:Rf 0.48 (chloroform:methanol=9:1); NMR (CDCl₃):δ 8–1,4–8.04 (br, 1H), 7.94 (dd, J=7.5, 0.9 Hz, 1H), 7.52 (m, 1H), 7.18 (t, J=7.5 Hz, 1H), 6.94 (m, 1H), 2.52 (s, 3H).

REFERENCE EXAMPLE 22

2-methyl-1H-indole-4-carboxylic acid benzyl ester

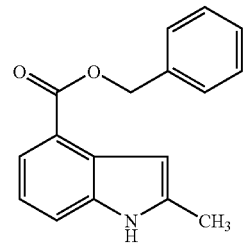

At room temperature, anhydrous potassium carbonate (1.02 g) and benzyl bromide (0.49 ml) were added to N,N-dimethyl formamide (7 ml) solution containing the compound (650 mg) prepared according to reference example 21, which was stirred for 4 hours at room temperature. Water and ethyl acetate are added to the reaction solution, which was extracted. The water layer was extracted by ethyl acetate and the mixed organic layer was sequentially washed with water and saturated brine and dried, and then concentrated by vacuum concentration. The residue was purified by silica gel column chromatography (hexane: ethyl acetate=85:1) to give a title compound (600 mg) having the following physical properties.

TLC:Rf 0.44 (hexane:ethyl acetate=8:2); NMR(CDCl3):δ 8.05 (brs, 1H), 7.91 (d, J=7.5 Hz, 1H), 7.54–7.10 (m, 7H), 6.88 (s, 1H), 5.44 (s, 2H), 2.48 (s, 3H).

EXAMPLE 8

1-(4-((2S)-4-methyl-3,4-dihydro-2H-1,4-benzoxazin-2-ylmethoxy)benzoyl)-2-methyl-1H-indol-4-carboxylic acid benzyl ester

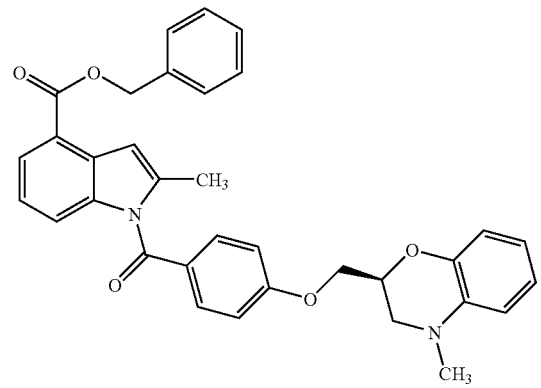

Using the compound prepared according to reference example 22 instead of the compound prepared according to reference example 15, a compound of the present invention having the following physical properties values was obtained by an operation similar to the method represented by example 3.

TLC:Rf 0.58 (hexane:ethyl acetate=7:3); NMR(CDCl₃):δ 7.93 (d, J=8.1 Hz, 1H), 7.69 (d, J=8.7Hz, 2H), 7.54–7.24 (m, 6H), 7.12–6.96 (m, 4H), 6.92–6.80 (m, 2H), 6.74–6.66 (m, 2H), 5.44 (s, 2H), 4.74–4.62 (m, 1H), 4.31 (dd, J=9.9, 5.1 Hz, 1H), 4.21 (dd, J=9.9, 6.0 Hz, 1H), 3.37 (dd, J=11.7, 3.0 Hz, 1H), 3.28 (dd, J=11.7, 6.6 Hz, 1H), 2.92 (s, 3H), 2.43 (s, 3H).

EXAMPLE 9

1-(4-((2S)-4-methyl-3,4-dihydro-2H-1,4-benzoxazin-2-ylmethoxy)benzoyl)-2-methyl-1H-indol-4-carboxylic acid

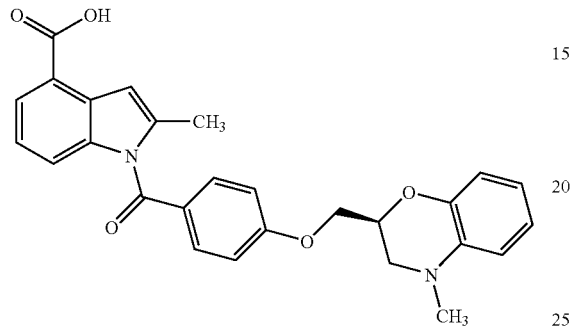

Using the compound prepared according to reference example 8 instead of the compound prepared according to reference example 6, a compound of the present invention having the following physical properties values was obtained by an operation similar to the method represented by example 7.

TLC:Rf 0.55 (chloroform:methanol=9:1); NMR (CDCl$_3$):δ 7.97 (d, J=7.8 Hz, 1H), 7.71 (d, J=8.7 Hz, 2H), 7.34 (d, J=7.8 Hz, 1H), 7.20 (s, 1H), 7.12 (t, J=7.8 Hz, 1H), 7.02 (d, J=8.7 Hz, 2H), 6.95–6.80 (m, 2H), 6.75–6.65 (m, 2H), 4.75–4.65 (m, 1H), 4.32 (dd, J=9.6, 4.8 Hz, 1H), 4.23 (dd, J=9.6, 6.3 Hz, 1H), 3.41 (dd, J=11.7, 3.0 Hz, 1H), 3.29 (dd, J=11.7, 6.6 Hz, 1H), 2.92 (s, 3H), 2.47 (s, 3H).

EXAMPLE 10

1-(4-((2S)-4-methyl-3,4-dihydro-2H-1,4-benzoxazin-2-ylmethoxy)benzoyl)-1H-indol-4-ylacetic acid benzyl ester

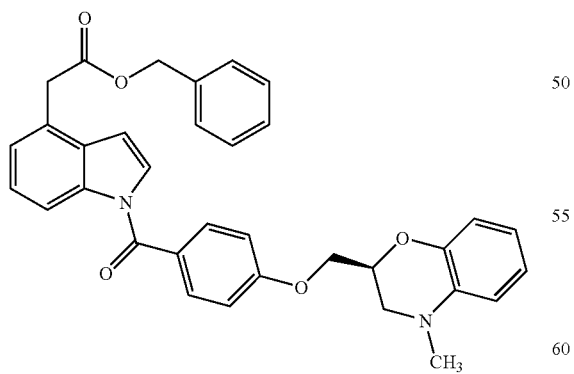

Using 4-hydroxy-1H-indole instead of 2-methyl-4-hydroxy-1H-indole, a compound of the present invention having the following physical properties values was obtained by an operation similar to a method sequentially represented by reference example 1, reference example 2, reference example 3, reference example 4, reference example 5, reference example 6, reference example 7, reference example 8, and example 1.

TLC:Rf 0.22 (hexane:ethyl acetate=3:1); NMR(CDCl$_3$):δ 8.26 (d, J=8.1 Hz, 1H), 7.74 (d, J=9.0 Hz, 2H), 7.40–7.25 (m, 7H), 7.21 (d, J=8.1 Hz, 1H), 7.05 (d, J=9.0 Hz, 2H), 7.25–7.00 (m, 2H), 6.75–6.64 (m, 3H), 5.13 (s, 2H), 4.68 (m, 1H), 4.32 (dd, J=9.9, 4.8 Hz, 1H), 4.21 (dd, J=9.9, 6.3 Hz, 1H), 3.93 (s, 2H), 3.41 (dd, J=11.7, 3.0 Hz, 1H), 3.28 (dd, J=11.7, 6.6 Hz, 1H), 2.92 (s, 3H).

EXAMPLE 11

1-(4-((2S)-4-methyl-3,4-dihydro-2H-1,4-benzoxazin-2-ylmethoxy)benzoyl)-1H-indol-4-ylacetic acid

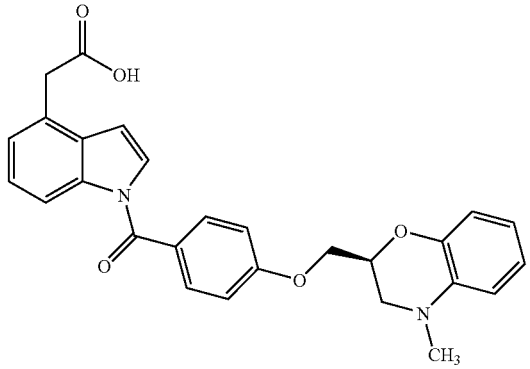

Using the compound prepared according to reference example 10 instead of the compound prepared according to reference example 6, a compound of the present invention having the following physical properties values was obtained by an operation similar to the method represented by example 7.

TLC:Rf 0.33 (ethyl acetate:hexane=2:1); NMR(CDCl$_3$):δ 8.27 (d, J=8.1 Hz, 2H), 7.73 (d, J=8.7 Hz, 2H), 7.37 (d, J=3.9 Hz, 1H), 7.33 (t, J=7.8 Hz, 1H), 7.21 (d, J=6.6 Hz, 1H), 7.05 (d, J=8.7 Hz, 2H), 6.93–6.80 (m, 2H), 6.77–6.63 (m, 3H), 4.73–4.63 (m, 1H), 4.31 (dd, J=9.9, 5.1 Hz, 1H), 4.21 (dd, J=9.9, 6.0 Hz, 1H), 3.90 (s, 2H), 3.40 (dd, J=11.7, 2.7 Hz, 1H), 3.28 (dd, J=11.7, 6.6 Hz, 1H), 2.92 (s, 3H).

EXAMPLE 12

1-(4-((2S)-4-methyl-3,4-dihydro-2H-1,4-benzoxazin-2-ylmethoxy)benzoyl)-2,3-dihydro-1H-indol-4-ylacetic acid

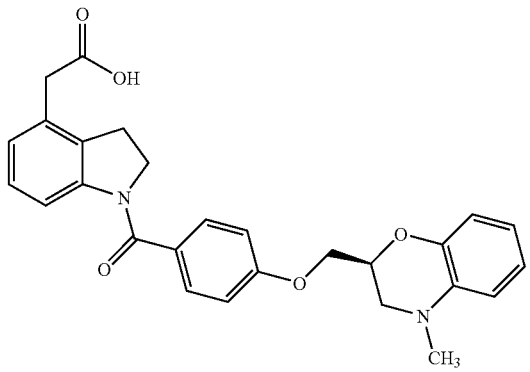

Under argon gas, the compound (0.67 g) prepared according to example 10 was dissolved to ethyl acetate (5 ml) and hydroxide palladium (500 mg) were added to the mixture, which was stirred for 2 days at room temperature under hydrate gas. The reaction solution was filtered through celite (registered trademark), and the filtrate was concentrated. The residue was purified by silica gel column chromatography (ethyl acetate:hexane=3:2) to give a title compound (0.19 g) having the following physical properties.

TLC:Rf 0.10 (ethyl acetate:hexane=2:1); NMR(DMSO-$d_6$):δ 7.88–7.25 (m, 3H), 7.20–6.96 (m, 3H), 6.90 (d, J=7.2 Hz, 1H), 6.84–6.67 (m, 3H), 6.61 (td, J=6.9, 1.8 Hz, 1H), 4.60 (m, 1H), 4.26 (d, J=4.8 Hz, 2H), 4.05 (t, J=8.4 Hz, 2H), 3.54 (s, 2H), 3.50–3.10 (m, 4H), 3.02 (t, J=8.4 Hz, 2H), 2.85 (s, 3H).

EXAMPLE 13

1-(4-((2S)-4-methyl-3,4-dihydro-2H-1,4-benzoxazin-2-ylmethoxy)benzoyl)-2-methyl-2,3-dihydro-1H-indol-4-ylacetic acid

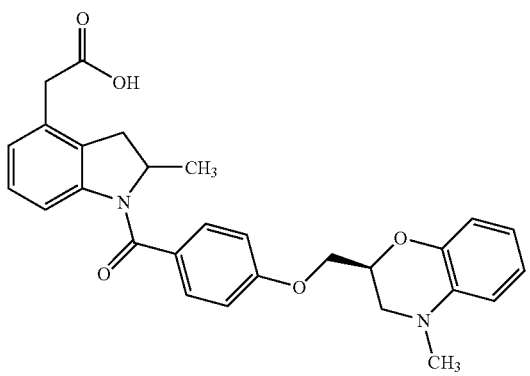

Under argon gas, the compound (200 mg) prepared according to example 2 was dissolved to the mixture of ethyl acetate (10 ml) and methanol (10 ml), and 10% palladium carbon (60 mg) was added. Under hydrate gas, the reactive mixture was violently stirred for 2 days at room temperature. The reaction solution was filtered through celite (registered trademark), and the filtrate was concentrated. The residue was purified by silica gel column chromatography (chloroform:methanol=199:1 to 99:1) to give a title compound (30 mg) having the following physical properties.

TLC:Rf 0.41 (chloroform:methanol=9:1); NMR (CDCl3):δ 7.49 (d, J=8.4 Hz, 2H), 7.08–6.80 (m, 7H), 6.76–6.66 (m, 2H), 4.84–4.70 (m, 1H), 4.70–4.60 (m, 1H), 4.29 (dd, J=9.6, 5.1 Hz, 1H), 4.15 (dd, J=9.6, 6.6 Hz, 1H), 3.61 (s, 2H), 3.44–3.22 (m, 3H), 2.91 (s, 3H), 2.65 (dd, J=15.9, 2.1 Hz, 1H), 1.30–1.20 (m, 3H).

EXAMPLE 14

2-(1-(4-((2S)-4-methyl-3,4-dihydro-2H-1,4-benzoxazin-2-ylmethoxy)benzoyl)-2-methyl-1H-indol-4-yl)ethanol

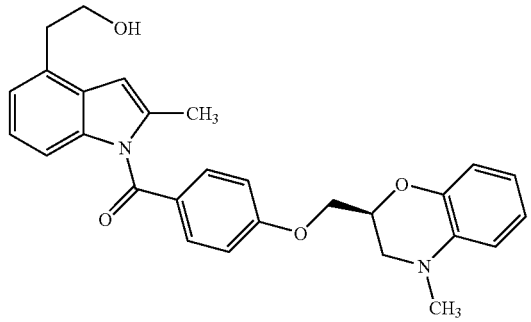

Under argon gas, the compound (420 mg) prepared according to example 2 was dissolved to tetrahydrofuran (20 ml), cold borane-tetrahydrofuran complex (1M, 2.7 ml) was added to the mixture, which was stirred at 10° C. for 2 hours. The reaction solution was poured into ice, and 1N hydrochloric acid added to the solution, which was extracted by ethyl acetate. The organic layer was sequentially washed with water and saturated brine, and then dried by anhydrous sodium sulfate. The residue obtained by removal of the solvent was purified by silica gel column chromatography (ethyl acetate:hexane=2:3 to 1:1) to give a title compound (341 mg) having the following physical properties.

TLC:Rf 0.41 (ethyl acetate:hexane=2:1); NMR(CDCl$_3$):δ 7.72 (d, J=8.7 Hz, 2H), 7.04–6.77 (m, 7H), 6.77–6.60 (m, 2H), 6.50 (s, 1H), 4.72–4.60 (m, 1H), 4.31 (dd, J=9.9, 5.1 Hz, 1H), 4.25–4.10 (m, 1H), 3.95 (t, J=6.3 Hz, 2H), 3.40 (dd, J=11.7, 2.7 Hz, 1H), 3.28 (dd, J=11.7, 6.6 Hz, 1H), 3.10 (t, J=6.3 Hz, 2H), 2.92 (s, 3H), 2.45 (s, 3H).

EXAMPLE 14(1) TO EXAMPLE 14(5)

Using the compound prepared according to example 2(5), example 2(6), example 2(10), example 2(15), and example 2(20) instead of the compound prepared according to reference example 2, the compounds of the present invention having the following physical properties values were obtained by an operation similar to the method represented by example 14.

EXAMPLE 14(1)

2-(1-(4-((2S)-4,6-dimethyl-3,4-dihydro-2H-1,4-benzoxazin-2-ylmethoxy)benzoyl)-2-methyl-1H-indol-4-yl)ethanol

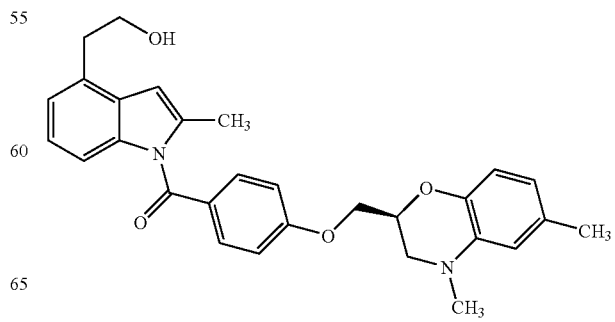

TLC:Rf 0.51 (ethyl acetate:hexane=2:1); NMR(CDCl$_3$):δ 7.72 (d, J=9.0 Hz, 2H), 7.05–6.85 (m, 5H), 6.73 (d, J=7.5 Hz, 1H), 6.56–6.44 (m, 3H), 4.70–4.60 (m, 1H), 4.30 (dd, J=9.9, 5.4 Hz, 1H), 4.20 (dd, J=9.9, 6.3 Hz, 1H), 4.00–3.90 (m, 2H), 3.39 (dd, J=11.4, 2.7 Hz, 1H), 3.26 (dd, J=11.4, 6.6 Hz, 1H), 3.10 (t, J=6.3 Hz, 2H), 2.90 (s, 3H), 2.45 (s, 3H), 2,28 (s, 3H), 1.48–1.38 (m, 1H).

EXAMPLE 14(2)

2-(1-(4-((2S)-6-fluoro-4-methyl-3,4-dihydro-2H-1,4-benzoxazin-2-ylmethoxy)benzoyl)-2-methyl-1H-indol-4-yl)ethanol

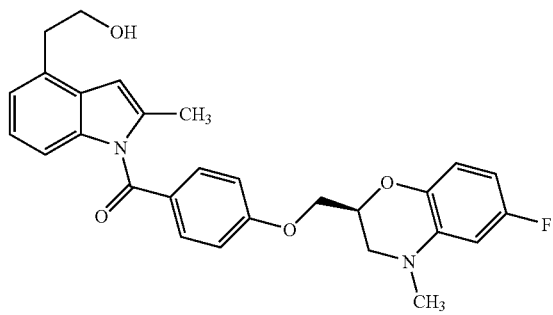

TLC:Rf 0.49 (ethyl acetate:hexane=2:1); NMR(CDCl$_3$):δ 7.72 (d, J=8.1 Hz, 2H), 7.04–6.86 (m, 5H), 6.74 (dd, J=8.4, 5.4 Hz, 1H), 6.50 (s, 1H), 6.45–6.30 (m, 2H), 4.66–4.56 (m, 1H), 4.30 (dd, J=9.9, 5.1 Hz, 1H), 4.19 (dd, J=9.9, 6.3 Hz, 1H), 4.00–3.90 (m, 2H), 3.41 (dd, J=11.4, 2.7 Hz, 1H), 3.30 (dd, J=11.4, 6.9 Hz, 1H), 3.10 (t, J=6.3 Hz, 2H), 2.91 (s, 3H), 2.45 (s, 3H), 1.50–1.4 (m, 1H).

EXAMPLE 14(3)

2-(1-(4-((2S)-7-fluoro-4-methyl-3,4-dihydro-2H-1,4-benzoxazin-2-ylmethoxy)benzoyl)-2-methyl-1H-indol-4-yl)ethanol

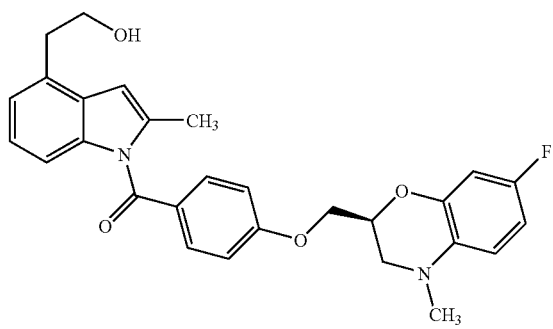

TLC:Rf 0.42 (ethyl acetate:hexane=2:1); NMR(CDCl$_3$):δ 7.73 (d, J=9.0 Hz, 2H), 7.05–6.88 (m, 5H), 6.65–6.58 (m, 3H), 6.50 (s, 1H), 4.75–4.65 (m, 1H), 4.30 (dd, J=9.9, 5.1 Hz, 1H), 4.21 (dd, J=9.9, 6.0 Hz, 1H), 4.00–3.90 (m, 2H), 3.36 (dd, J=11.4, 2.7 Hz, 1H), 3.22 (dd, J=11.4, 6.6 Hz, 1H), 3.10 (t, J=6.3 Hz, 2H), 2.88 (s, 3H), 2.45 (s, 3H), 1.50–1.40 (m, 1H).

EXAMPLE 14(4)

2-(1-(4-((2S)-2,3-dihydrobenzofuran-2-ylmethoxy)benzoyl)-2-methyl-1H-indol-4-yl)ethanol

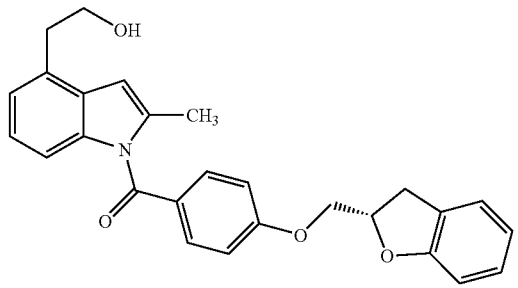

TLC:Rf 0.64 (ethyl acetate:hexane=2:1); NMR(CDCl$_3$):δ 7.71 (d, J=9.3 Hz, 2H), 7.30–7.10 (m, 2H), 7.05–6.80 (m, 7H), 6.49 (s, 1H), 5.25–5.15 (m, 1H), 4.30 (dd, J=10.2, 6.3 Hz, 1H), 4.21 (dd, J=10.2, 4.8 Hz, 1H), 3.95 (brq, J=5.4 Hz, 2H), 3.43 (dd, J=15.6, 9.6 Hz, 1H), 3.17 (dd, J=15.6, 7.2 Hz, 1H), 3.10 (t, J=6.3 Hz, 2H), 2.45 (s, 3H), 1.50–1.40 (m, 1H).

EXAMPLE 14(5)

2-(1-(4-((3R)-2,3-dihydrobenzofuran-3-ylmethoxy)benzoyl)-2-methyl-1H-indol-4-yl)ethanol

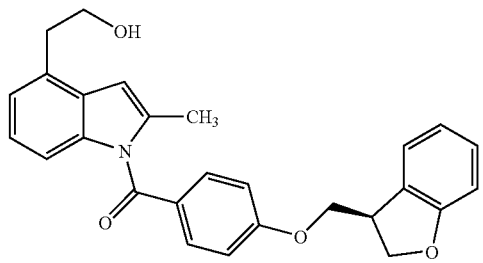

TLC:Rf 0.67 (ethyl acetate:hexane=2:1); NMR(CDCl$_3$):δ 7.72 (d, J=9.0 Hz, 2H), 7.35–7.15 (m, 2H), 7.05–6.85 (m, 7H), 6.50 (s, 1H), 4.73 (t, J=9.0 Hz, 1H), 4.55 (dd, J=9.0, 5.1 Hz, 1H), 4.24 (dd, J=9.0, 5.7 Hz, 1H), 4.11 (t, J=9.0 Hz, 1H), 4.05–3.90 (m, 3H), 3.10 (t, J=6.6 Hz, 2H), 2.45 (s, 3H), 1.50–1.40 (m, 1H).

EXAMPLE 15

N-methylsulfonyl-(1-(4-((2S)-4-methyl-3,4-dihydro-2H-1,4-benzoxazin-2-ylmethoxy)benzoyl)-2-methyl-1H-indol-4-yl)acetamide

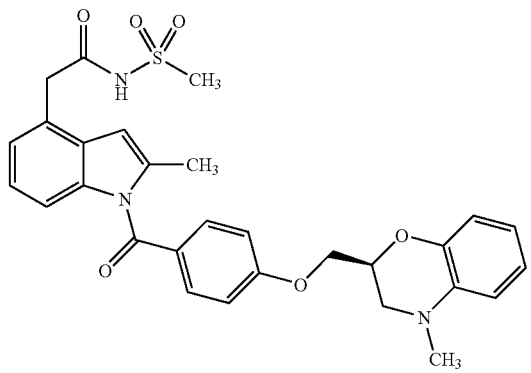

Under argon gas, 1-ethyl-3-[3-(dimethylamino)propyl] carbodiimide (82 mg), N, N-dimethylaminopyridine (39 mg), and methane sulfonamide (51 mg) were added to dichloromethane (5 ml) solution containing the compound (100 mg) prepared according to example 2 at room temperature, which was stirred for 15 hours at room temperature. Saturated ammonium chloride solution was added to the reaction solution, which was extracted by ethyl acetate. The organic layer was sequentially washed with water and saturated brine and dried by anhydrous sodium sulfate. The residue obtained by removal of the solvent was purified by silica gel column chromatography (chloroform:methanol=100:1 to 30:1) to give a title compound (72 mg) having the following physical properties.

TLC:Rf 0.40 (chloroform:methanol=10:1); NMR (CDCl$_3$):δ 7.77–7.73 (m, 2H), 7.07–7.00 (m, 5H), 6.92–6.82 (m, 2H), 6.72 (d, J=7.5 Hz, 2H), 6.43 (s, 1H), 4.69 (m, 1H), 4.33 (dd, J=9.9, 5.4 Hz, 1H), 4.23 (dd, J=9.9, 6.0 Hz, 1H), 3.92 (s, 2H), 3.41 (dd, J=11.4, 2.7 Hz, 1H), 3.29 (dd, J=11.4, 6.6 Hz, 1H), 3.27 (s, 3H), 2.92 (s, 3H), 2.46 (d, J=0.9 Hz, 3H).

EXAMPLE 15(1)

N-phenylsulfonyl-(1-(4-((2S)-4-methyl-3,4-dihydro-2H-1,4-benzoxazin-2-ylmethoxy)benzoyl)-2-methyl-1H-indol-4-yl)acetamide

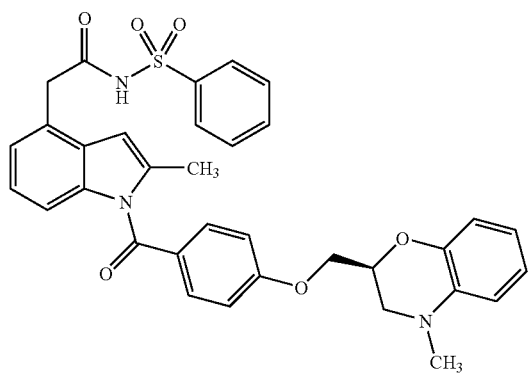

Using benzenesulfonamide instead of methane sulfonamide, a compound of the present invention having the following physical properties values was obtained by an operation similar to example 15.

TLC:Rf 0.58 (chloroform:methanol=9:1); NMR (CDCl$_3$):δ 7.98–7.58 (m, 6H), 7.56–7.46 (m, 2H), 7.08–6.80 (m, 7H), 6.76–6.66 (m, 2H), 6.16 (s, 1H), 4.74–4.64 (m, 1H), 4.33 (dd, J=9.6, 5.1 Hz, 1H), 4.23 (dd, J=9.6, 6.3 Hz, 1H), 3.79 (s, 2H), 3.41 (dd, J=11.4, 2.7 Hz, 1H), 3.29 (dd, J=11.4, 6.6 Hz, 1H), 2.92 (s, 3H), 2.38 (s, 3H).

EXAMPLE 16

2-(1-(4-((2S)-4-methyl-3,4-dihydro-2H-1,4-benzoxazin-2-ylmethoxy)benzoyl)-2-methyl-1H-indol-4-yl) ethyl acetate

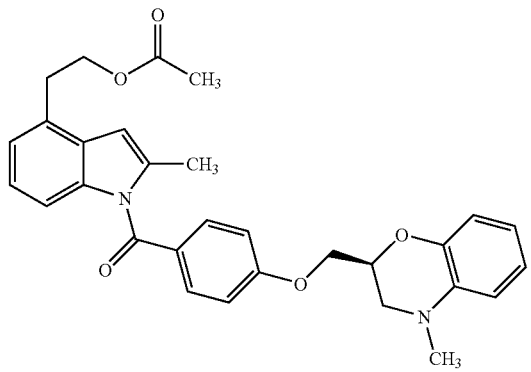

Under argon gas, the compound (49.3 mg) prepared according to example 14 was dissolved to pyridine (3 ml), and cold acetyl chloride (38 μl) was added to the mixture, which was stirred for 1.5 hours at 0° C. Water is added to the reaction solution, which was extracted by ethyl acetate. The organic layer was sequentially washed with saturated sodium bicarbonate solution, 1N hydrochloric acid, water, and saturated brine and dried by anhydrous sodium sulfate. After removal of the solvent, a title compound (54 mg) having the following physical properties was obtained.

TLC:Rf 0.33 (ethyl acetate:hexane=1:2); NMR(CDCl$_3$):δ 7.72 (d, J=8.7 Hz, 2H), 7.04–6.82 (m, 7H), 6.75–6.67 (m, 2H), 6.52 (s, 1H), 4.75–4.65 (m, 1H), 4.36 (t, J=7.2 Hz, 2H), 4.32(dd, J=9.9, 5.1 Hz, 1H), 4.21 (dd, J=9.9, 6.0 Hz, 1H), 3.41 (dd, J=11.4, 3.0 Hz, 1H), 3.28 (dd, J=11.4, 6.6 Hz, 1H), 3.16 (t, J=7.2 Hz, 2H), 2.92 (s, 3H), 2.45 (s, 3H), 2.06 (s, 3H).

REFERENCE EXAMPLE 23(1) TO 23(11)

Using the corresponding aniline derivative instead of the compound prepared according to reference example 10, the compounds of the present invention having the following physical properties values were obtained by an operation similar to a method sequentially represented by reference example 11 and reference example 12.

REFERENCE EXAMPLE 23(1)

(2S)-2-hydroxymethyl-5-methoxy-4-methyl-3,4-dihydro-2H-1,4-benzoxazine

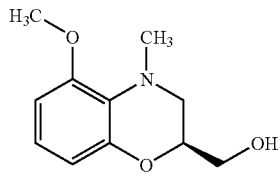

TLC:Rf 0.16 (hexane:ethyl acetate=1:1); NMR(CDCl$_3$):δ 6.89 (t, J=8.4 Hz, 1H), 6.57 (dd, J=8.4, 1.5 Hz, 1H), 6.49 (dd, J=8.4, 1.5 Hz, 1H), 4.16–4.06 (m, 1H), 3.89 (s, 3H), 3.97–3.75 (m, 2H), 3.13–2.98 (m, 2H), 2.85 (s, 3H).

REFERENCE EXAMPLE 23(2)

(2R)-2-hydroxymethyl-4-methyl-3,4-dihydro-2H-1,4-benzoxazine

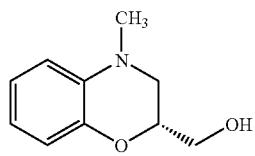

TLC:Rf 0.10 (hexane:ethyl acetate=3:1); NMR(CDCl₃):δ 7.00–6.60 (m, 4H), 4.35 (m, 1H), 4.00–3.70 (m, 2H), 3.33–3.10 (m, 2H), 2.88 (s, 3H), 2.01 (m, 1H).

REFERENCE EXAMPLE 23(3)

(2S)-2-hydroxymethyl-6-fluoro-4-methyl-3,4-dihydro-2H-1,4-benzoxazine

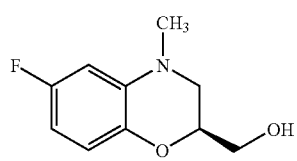

TLC:Rf 0.33 (hexane:ethyl acetate=1:1); NMR(CDCl₃):δ 6.75–6.65 (m, 1H), 6.42–6.26 (m, 2H), 4.30–4.20 (m, 1H), 3.90–3.72 (m, 2H), 3.21 (d, J=5.4 Hz, 2H), 2.87 (s, 3H), 2.05–1.95 (m, 1H).

REFERENCE EXAMPLE 23(4)

(2S)-2-hydroxymethyl-4,6-dimethyl-3,4-dihydro-2H-1,4-benzoxazine

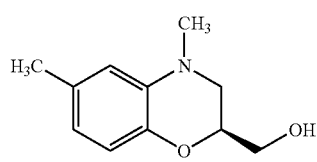

TLC:Rf 0.44 (hexane:ethyl acetate=2:1); NMR(CDCl₃):δ 6.70 (d, J=7.8 Hz, 1H), 6.50–6.46 (m, 2H), 4.30 (m, 1H), 3.90–3.75 (m, 2H), 3–2,3–3.13 (m, 2H), 2.87 (s, 3H), 2.26 (s, 3H), 2.03 (brs, 1H).

REFERENCE EXAMPLE 23(5)

(2S)-2-hydroxymethyl-6-methoxy-4-methyl-3,4-dihydro-2H-1,4-benzoxazine

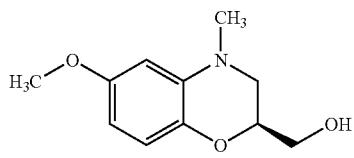

TLC:Rf 0.33 (hexane:ethyl acetate=1:1); NMR(CDCl₃):δ 6.72 (d, J=8.4 Hz, 1H), 6.26 (d, J=2.7 Hz, 1H), 6.20 (dd, J=8.4, 2.7 Hz, 1H), 4.26 (m, 1H), 3.88–3.76 (m, 2H), 3.76 (s, 3H), 3.19 (d, J=5.4 Hz, 2H), 2.87 (s, 3H), 2.00 (t, J=6.3 Hz, 1H).

REFERENCE EXAMPLE 23(6)

(2S)-2-hydroxymethyl-4,8-dimethyl-3,4-dihydro-2H-1,4-benzoxazine

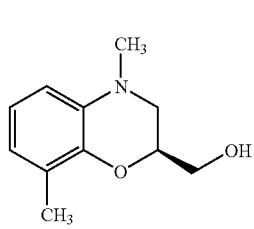

TLC:Rf 0.49 (hexane:ethyl acetate=1:1); NMR(CDCl₃):δ 6.76 (dd, J=7.8, 7.5 Hz, 1H), 6.56 (d, J=7.8 Hz, 1H), 6.56 (d, J=7.5 Hz, 1H), 4.36 (m, 1H), 3.92–3.76 (m, 2H), 3.22 (dd, J=11.1, 3.3 Hz, 1H), 3.16 (dd, J=11.1, 6.9 Hz, 1H), 2.87 (s, 3H), 2.19 (s, 3H), 2.03 (brs, 1H).

REFERENCE EXAMPLE 23(7)

(2S)-2-hydroxymethyl-7-methoxy-4-methyl-3,4-dihydro-2H-1,4-benzoxazine

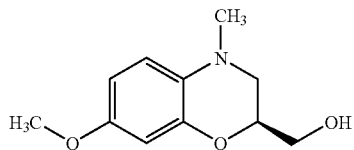

TLC:Rf 0.06 (hexane:ethyl acetate=3:1); NMR(CDCl₃):δ 6.67–6.61 and 6.49–6.43 (m, total 3H), 4.42–4.33 (m, 1H), 3.94–3.75 (m, 2H), 3.73 (s, 3H), 3.16 (dd, J=11.4, 3.0 Hz, 1H), 3.08 (dd, J=11.4, 4.6 Hz, 1H), 2.82 (s, 3H).

REFERENCE EXAMPLE 23(8)

(2S)-2-hydroxymethyl-4,7-dimethyl-3,4-dihydro-2H-1,4-benzoxazine

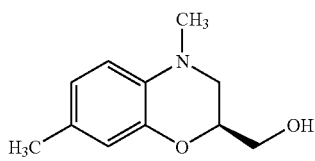

TLC:Rf 0.18 (hexane:ethyl acetate=3:1); NMR(CDCl$_3$):δ 6.70–6.57 (m, 3H), 4.38–4.30 (m, 1H), 3.85 (dd, J=11.7, 4.2 Hz, 1H), 3.79 (dd, J=11.7, 5.7 Hz, 1H), 3.18 (dd, J=11.7, 3.9 Hz, 1H), 3.11 (dd, J=11.7, 7.2 Hz, 1H), 2.84 (s, 3H), 2.22 (s, 3H).

REFERENCE EXAMPLE 23(9)

(2S)-2-hydroxymethyl-7-fluoro-4-methyl-3,4-dihydro-2H-1,4-benzoxazine

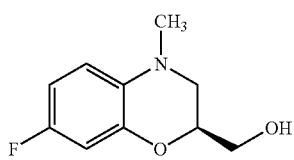

TLC:Rf 0.29 (hexane:ethyl acetate=2:1); NMR(CDCl$_3$):δ 6.59 and 6.57 (each m, total 3H), 4.41–4.31 (m, 1H), 3.86 (dd, J=12.0, 4.2 Hz, 1H), 3.80 (dd, J=12.0, 5.4 Hz, 1H), 3.19 (dd, J=11.4, 3.0 Hz, 1H), 3.12 (dd, J=11.4, 7.2 Hz, 1H), 2.84 (s, 3H).

REFERENCE EXAMPLE 23(10)

(2S)-2-hydroxymethyl-5-fluoro-4-methyl-3,4-dihydro-2H-1,4-benzoxazine

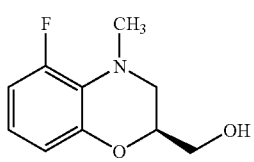

TLC:Rf 0.41 (chloroform:methanol=9:1); NMR (CDCl$_3$):δ 6.80–6.60 (m, 3H), 4.17–4.05 (m, 1H), 3.97–3.77 (m, 2H), 3.18–3.03 (m, 2H), 2.94 (d, J=1.8 Hz, 3H), 2.02–1.92 (m, 1H).

REFERENCE EXAMPLE 23(11)

(2S)-2-hydroxymethyl-8-fluoro-4-methyl-3,4-dihydro-2H-1,4-benzoxazine

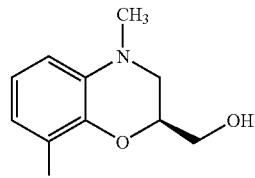

TLC:Rf 0.26 (hexane:ethyl acetate=1:1); NMR(CDCl$_3$): δ6.80–6.62 (m, 1H), 6.55–6.41 (m, 2H), 4.40–4.28 (m, 1H), 3.95–3.79 (m, 2H), 3.25 (d, J=5.1 Hz, 2H), 2.90 (s, 3H).

REFERENCE EXAMPLE 24

(2R)-2-((2-iodinephenoxy)methyl)oxirane

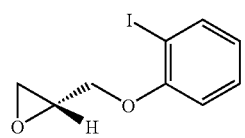

Under argon gas, 2-iodophenol (1.70 g) was dissolved to N,N-dimethyl formamide (15 ml), and (R)-glycidyl nosylate (2.00 g) and cesium carbonate (3.78 g) added, and then the mixture was stirred during 30 minutes at room temperature. Water is added to the reactive mixture, which was extracted by ethyl acetate. The organic layer was sequentially washed with water and saturated brine and dried by anhydrous sodium sulfate. The residue by removal of the solvent was purified by silica gel column chromatography (hexane:ethyl acetate=1:5) to a title compound (2.07 g) having the following physical properties.

TLC:Rf 0.35 (hexane:ethyl acetate=1:5); NMR(CDCl$_3$): δ7.78 (dd, J=7.5, 1.5 Hz, 1H), 7.32–7.27 (m, 1H), 6.85 (dd, J=8.1, 1.2 Hz, 1H), 6.74 (dt, J=1.2, 7.5 Hz, 1H), 4.29 (dd, J=11.1, 3.0 Hz, 1H), 4.07 (dd, J=4.8, 3.0 Hz, 1H), 3.43–3.38 (m, 1H), 2.95–2.89 (m, 2H).

REFERENCE EXAMPLE 25

(3S)-3-hydroxymethyl-2,3-dihydrobenzofuran

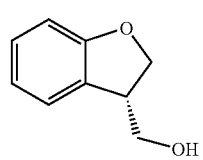

Under argon gas, the compound (1.00 g) prepared according to reference example 24 was dissolved to anhydrous tetrahydrofuran (10 ml), and n-butyllithium (1.59M hexane solution, 2.28 ml) was added at −78° C., and then the mixture was stirred at the same temperature for 1 hour. The reactive mixture was risen up to room temperature, where 1N hydrochloric acid was added. The reactive mixture was extracted by ethyl acetate, and the organic layer was sequentially washed with water and saturated brine and dried by anhydrous sodium sulfate. The residue by removal of the solvent was purified by silica gel column chromatography (hexane:ethyl acetate=3:2) to give a title compound (376 mg) having the following physical properties.

TLC:Rf 0.35 (hexane:ethyl acetate=3:2); NMR(CDCl$_3$):δ 7.26–7.14 (m, 2H), 6.90–6.80 (m, 2H), 4.64 (t, J=9.0 Hz, 1H), 4.48 (dd, J=9.0, 5.4 Hz, 1H), 3.82–3.80 (m, 2H), 3.69–3.60 (m, 1H).

REFERENCE EXAMPLE 25(1) TO (6)

Instead of 2-iodophenol, using the corresponding phenol derivative, a compound of the present invention having the following physical properties values was obtained by an operation similar to a method sequentially represented by reference example 24 and reference example 26.

REFERENCE EXAMPLE 25(1)

(3R)-3-hydroxymethyl-5-methyl-2,3-dihydrobenzofuran

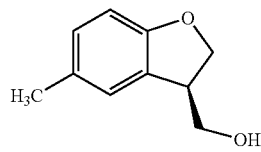

TLC:Rf 0.32 (hexane:ethyl acetate=2:1); NMR(CDCl$_3$):δ 7.03 (s, 1H), 6.96 (m, 1H), 6.70 (d, J=8.4 Hz, 1H), 4.62 (t, J=9.0 Hz, 1H), 4.45 (dd, J=9.0, 5.1 Hz, 1H), 3.86–3.73 (m, 2H), 3.67–3.53 (m, 1H), 2.29 (s, 3H).

REFERENCE EXAMPLE 25(2)

(3R)-3-hydroxymethyl-5-fluoro-2,3-dihydrobenzofuran

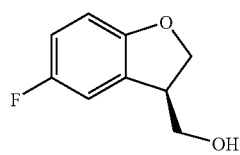

TLC:Rf 0.35 (hexane:ethyl acetate=2:1); NMR(CDCl$_3$):δ 7.10 (dd, J=8.1, 6.0 Hz, 1H), 6.63–6.53 (m, 2H), 4.67 (t, J=9.0 Hz, 1H), 4.59 (dd, J=9.0, 5.1 Hz, 1H), 4.00–3.74 (m, 3H).

REFERENCE EXAMPLE 25(3)

(3R)-3-hydroxymethyl-2,3-dihydrobenzofuran

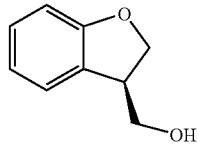

TLC:Rf 0.40 (hexane:ethyl acetate=3:2); NMR(CDCl$_3$):δ 7.26–7.14 (m, 2H), 6.90–6.80 (m, 2H), 4.64 (t, J=9.0 Hz, 1H), 4.48 (dd, J=9.0, 5.4 Hz, 1H), 3.82–3.80 (m, 2H), 3.69–3.60 (m, 1H).

REFERENCE EXAMPLE 25(4)

(3R)-3-hydroxymethyl-6-fluoro-2,3-dihydrobenzofuran

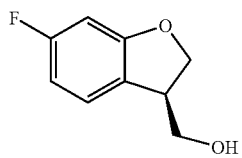

TLC:Rf 0.53 (hexane:ethyl acetate=1:1);

REFERENCE EXAMPLE 25(5)

(3R)-3-hydroxymethyl-7-methyl-2,3-dihydrobenzofuran

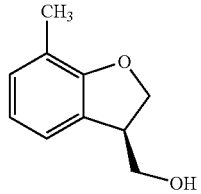

TLC:Rf 0.53 (hexane:ethyl acetate=1:1); NMR(CDCl$_3$): δ7.05 (d, J=7.5 Hz, 1H), 6.98 (d, J=7.5 Hz, 1H),6.78 (t, J=7.5 Hz, 1H), 4.64 (t, J=9.0 Hz, 1H), 4.48 (dd, J=9.0, 5.7 Hz, 1H), 3.85–3.72 (m, 2H), 3.70–3.60 (m, 1H), 2.21 (s, 3H).

REFERENCE EXAMPLE 25(6)

(3R)-3-hydroxymethyl-7-fluoro-2,3-dihydrobenzofuran

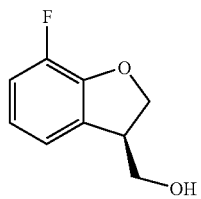

TLC:Rf 0.60 (hexane:ethyl acetate=1:2);

REFERENCE EXAMPLE 26

Instead of the compound prepared from reference example 10, using 2-fluorothiophenol, a title compound having the following physical properties values was obtained by an operation similar to a method sequentially represented by reference example 11 and reference example 12.

(2R)-2-hydroxymethyl-1,4-benzoxathiane

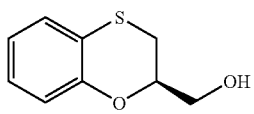

TLC:Rf 0.20 (hexane:ethyl acetate=3:1); NMR(CDCl$_3$):δ 7.10–6.80 (m, 4H), 4.28 (m, 1H), 4.00–3.75 (m, 2H), 3.13 (dd, J=13.2, 8.8 Hz, 1H), 2.95 (dd, J=13.2, 2.2 Hz, 1H).

REFERENCE EXAMPLE 27

(2S)-1-methylindoline-2-carboxylic methyl ester

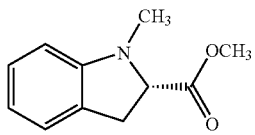

(S)-(−)-indoline-2-carboxylic acid (2.0 g) was dissolved to a mixture of acetone (20 ml) and N,N-dimethylformamide (20 ml), and potassium carbonate (6.78 g) and methyliodide (3.05 ml) were added at room temperature. The reactive mixture was stirred at room temperature over night, and then filtered. The filtrate was concentrated by vacuum concentration and the obtained residue was diluted with ethyl acetate. The solution is poured into water and the water layer has been extracted by ethyl acetate. The organic layer was sequentially washed with water and saturated brine, and then dried by anhydrous sodium sulfate. The residue by removal of the solvent was purified by silica gel column chromatography (hexane:ethyl acetate=4:1) to give a title compound (1.7 g) having the following physical properties.

TLC:Rf 0.70 (hexane:ethyl acetate=7:3); NMR(CDCl$_3$):δ 7.11 (t, J=7.5 Hz, 1H), 7.05 (d, J=7.5 Hz, 1H), 6.70 (t, J=7.5 Hz, 1H), 6.51 (d, J=7.5 Hz, 1H), 4.05 (t, J=9.6 Hz, 1H), 3.80 (s, 3H), 3.34 (dd, J=15.6, 9.6 Hz, 1H), 3.13 (dd, J=15.6, 9.6 Hz, 1H), 2.84 (s, 3H).

REFERENCE EXAMPLE 28

(2S)-2-hydroxymethyl-1-methylindoline

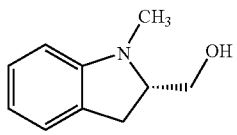

Anhydrous tetrahydrofuran solution (10 ml) of the compound (1.7 g) prepared according to reference example 27 was dropped to anhydrous tetrahydrofuran solution (20 ml) containing lithium aluminohydride (675 mg), which was stirred at room temperature for 1 hour. The reactive mixture was diluted with ether, and saturated brine was dropped, and then the mixture was dried by anhydrous sodium sulfate. The reactive mixture was filtered and the filtrate was concentrated by vacuum concentration to give a title compound (1.4 g) having the following physical properties.

TLC:Rf 0.30 (hexane:ethyl acetate=7:3); NMR(CDCl$_3$):δ 7.16–7.05 (m, 2H), 6.73 (t, J=7.5 Hz, 1H), 6.55 (d, J=7.5 Hz, 1H), 3.95 (dd, J=11.7, 3.6 Hz, 1H), 3.74–3.60 (m, 1H), 3.56–3.44 (m, 1H), 3.16–2.96 (m, 2H), 2.77 (s, 3H), 1.94–1.76 (m, 1H).

REFERENCE EXAMPLE 28(1)

(2S)-2-hydroxymethyl-1-ethylindoline

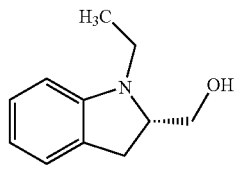

Using ethyliodide instead of methyliodide, a title compound having the following physical properties values was obtained by an operation similar to a method sequentially represented by reference example 27 and reference example 28.

TLC:Rf 0.35 (hexane:ethyl acetate=7:3); NMR(CDCl$_3$):δ 7.08 (t, J=7.5 Hz, 1H), 7.06 (d, J=7.5 Hz, 1H), 6.69 (t, J=7.5 Hz, 1H), 6.51 (d, J=7.5 Hz, 1H), 3.88 (dd, J=11.4, 3.6 Hz, 1H), 3.78 (m, 1H), 3.64 (brd, J=11.4 Hz, 1H), 3.40–3.10 (m, 2H), 3.06 (dd, J=8.7, 2.7 Hz, 2H), 1.98 (brs, 1H), 1.13 (t, J=7.2Hz, 3H).

EXAMPLE 17

1-(4-((2S)-4-methyl-3,4-dihydro-2H-1,4-benzoxazin-2-ylmethoxy)-2-methylbenzoyl)-2-methyl-1H-indol-4-ylacetic acid benzyl ester

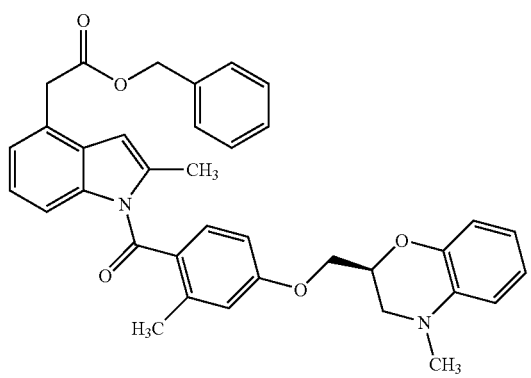

Using 4-hydroxy-2-methylbenzoic acid methyl instead of 4-hydroxybenzonate methyl, a compound of the present invention having the following physical properties values was obtained by an operation similar to a method sequentially represented by reference example 17, reference example 28, and example 1(1).

TLC:Rf 0.44 (hexane:ethyl acetate=7:3); NMR(CDCl$_3$):δ 7.40–7.20 (m, 6H), 7.10–6.76 (m, 7H), 6.75–6.66 (m, 2H), 6.43 (brs, 1H), 5.14 (s, 2H), 4.72–4.62 (m, 1H), 4.29 (dd, J=9.6, 4.8 Hz, 1H), 4.18 (dd, J=9.6, 6.3 Hz, 1H), 3.86 (s, 2H), 3.41 (dd, J=11.7, 2.7 Hz, 1H), 3.28 (dd, J=11.7, 6.6 Hz, 1H), 2.92 (s, 3H), 2.32 (s, 3H), 2.31 (s, 3H).

EXAMPLE 17(1)

1-(4-((2S)-4-methyl-3,4-dihydro-2H-1,4-benzoxazin-2-ylmethoxy)-2-methylbenzoyl)-1H-indol-4-ylacetic acid benzyl ester

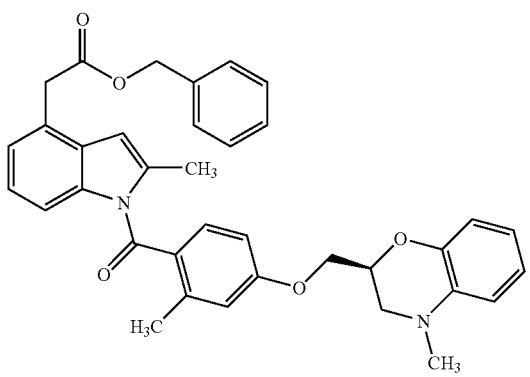

By subjecting a compound obtained by an operation similar to a method sequentially represented by reference example 1, reference example 2, reference example 3, reference example 4, reference example 5, and reference example 6 using 2-methyl-4-hydroxy-1H-indole instead of 4-hydroxy-1H-indole and a compound obtained by an operation similar to a method sequentially represented by reference example 17 and reference example 18 using 4-hydroxy-2-methylbenzoic acid methyl instead of 4-hydroxybenzonate methyl to an operation similar to method represented by example 1(1), the compound of the present invention having the following physical properties values was obtained.

TLC:Rf 0.36 (hexane:ethyl acetate=9:1); NMR(CDCl$_3$):δ 8.26 (d, J=8.7 Hz, 1H), 7.38–7.20 (m, 8H), 7.11 (d, J=3.6 Hz, 1H), 6.93–6.82 (m, 2H), 6.63 (d, J=3.6 Hz, 1H), 5.13 (s, 2H), 4.73–4.63 (m, 1H), 4.29 (dd, J=9.6, 5.1 Hz, 1H), 4.18 (dd, J=9.6, 6.6 Hz, 1H), 3.92 (s, 2H), 3.41 (dd, J=11.7, 3.0 Hz, 1H), 3.28 (dd, J=11.7, 6.6 Hz, 1H), 2.93 (s, 3H), 2.34 (s, 3H), 2.05 (s, 3H).

EXAMPLE 18

1-(4-((2S)-4-methyl-3,4-dihydro-2H-1,4-benzoxazin-2-ylmethoxy)-2-methylbenzoyl)-2-methyl-1H-indol-4-ylacetic acid

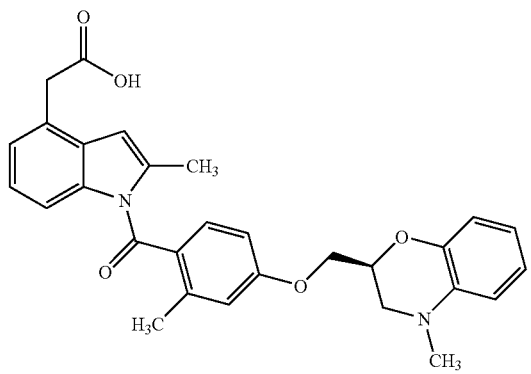

Using the compound prepared according to example 17 instead of the compound prepared according to example 1, a compound of the present invention having the following physical properties values was obtained by an operation similar to example 2.

TLC:Rf 0.53 (chloroform:methanol=9:1); NMR (CDCl$_3$):δ 7.31 (d, J=8.7 Hz, 1H), 7.10–6.98 (m, 3H), 6.92–6.76 (m, 4H), 6.75–6.67 (m, 2H), 6.47 (s, 1H), 4.72–4.62 (m, 1H), 4.28 (dd, J=9.9, 5.4 Hz, 1H), 4.18 (dd, J=9.9, 6.3 Hz, 1H), 3.85 (s, 2H), 3.41 (dd, J=11.4, 2.7 Hz, 1H), 3.27 (dd, J=11.4, 6.6 Hz, 1H), 2.92 (s, 3H), 2.35 (s, 3H), 2.32 (s, 3H).

EXAMPLE 18(1)

1-(4-((2S)-4-methyl-3,4-dihydro-2H-1,4-benzoxazin-2-ylmethoxy)-2-methylbenzoyl)-1H-indol-4-ylacetic acid

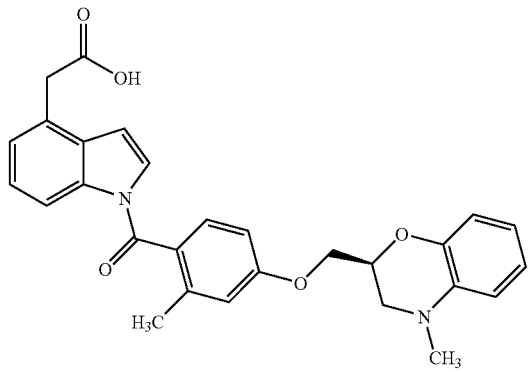

Using the compound prepared according to example 17(1) instead of the compound prepared according to example 1, a compound of the present invention having the following physical properties values was obtained by an operation similar to example 2.

TLC:Rf 0.43 (chloroform:methanol=9:1); NMR (CDCl$_3$):δ 8.27 (d, J=8.1 Hz, 1H), 7.38–7.30 (m, 2H), 7.28–7.18 (m, 1H), 7.14 (d, J=3.9 Hz, 1H), 6.94–6.80 (m, 4H), 6.76–6.67 (m, 2H), 6.64 (d, J=3.9 Hz, 1H), 4.72–4.62 (m, 1H), 4.29 (dd, J=9.9, 4.8 Hz, 1H), 4.18 (dd, J=9.9, 6.6 Hz, 1H), 3.90 (s, 2H), 3.41 (dd, J=11.7, 2.7 Hz, 1H), 3.28 (dd, J=11.7, 6.6 Hz, 1H), 2.92 (s, 3H), 2.34 (s, 3H).

FORMULATION EXAMPLE 1

The following components were admixed in conventional method and punched out to obtain 100 tablets each containing 5 mg of active ingredient.

| | |
|---|---|
| 1-(4-((2R)-2,3-dihudrobenzofuran-2-ylmethoxy)benzoyl)-2-methyl-1H-indol-4-yl acetic acid | 500 mg |
| Carboxymethyl cellulose calcium (disintegrator) | 200 mg |
| Magnesium stearate (lubricant) | 100 mg |
| Microcrystalline cellulose | 9.2 g |

The invention claimed is:

1. An indole compound represented by formula (I):

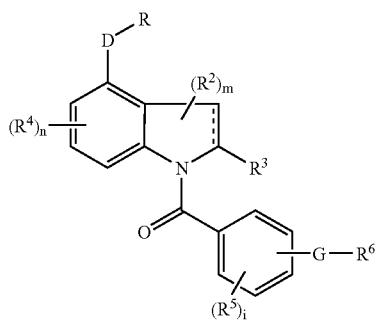

(I)

wherein R represents —$COR^1$, $R^1$ represents a hydroxyl group or C1–6 alkoxy group,
$R^2$ represents a hydrogen atom, C1–6 alkyl, C1–6 alkoxy, C2–6 alkoxyalkyl, a halogen atom, trihalomethyl, cyano, hydroxyl, benzyl, or 4-methoxybenzyl group,
$R^3$ represents a hydrogen atom, C1–6 alkyl, C1–6 alkoxy, a halogen atom, trihalomethyl, cyano, or hydroxyl group,
$R^4$ and $R^5$ each represents a hydrogen atom, C1–6 alkyl, C1–6 alkoxy, C2–6 alkoxyalkyl group, a halogen atom, trihalomethyl, cyano or hydroxyl group,
D represents a single bond, C1–6 alkylene, C2–6 alkenylene, or C1–6 oxyalkylene group,
G represents C1–6 alkylene linking group where one linking carbon atom may be replaced by 1 oxygen atom or C2–6 alkenylene linking group where one linking carbon atom may be replaced by 1 oxygen atom, wherein the alkylene and alkenylene groups may be substituted by hydroxyl or C1–4 alkoxy group,
$R^6$ represents a heterocycle selected from the group consisting of 3,4-dihydro-1,4-benzoxazin-2-yl group, 1,4-benzodioxan-2-yl group, 2,3-dihydrobenzofuran-2-yl group, 2,3-dihydro-benzofuran-3-yl group or an indolin-2-yl group which may be substituted by 1 to 5 group(s) selected from the group consisting of C1–6 alkyl, a halogen atom, hydroxyl, trihalomethyl, phenyl, C2–6 acyl, and cyano group,
n represents 1 to 3,
m represents 1 to 3,
i represents 1 to 4,
----- represents a single bond or a double bond, or non-toxic salts thereof.

2. The indole compound of claim 1, which is represented by formula (I-E):

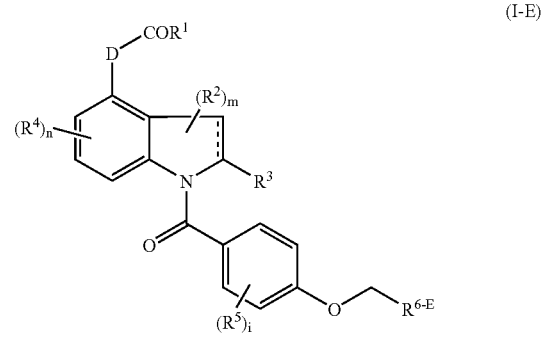

(I-E)

wherein $R^{6-E}$ has the same meaning as $R^6$ in claim 1; and wherein, the carbon atom with which $R^{6-E}$ binds is saturated and the configuration of the carbon atom is S configuration, and the other symbols have the same meaning as those in claim 1, or a non-toxic salt thereof.

3. The indole compound of claim 1, which is represented by formula (I-E):

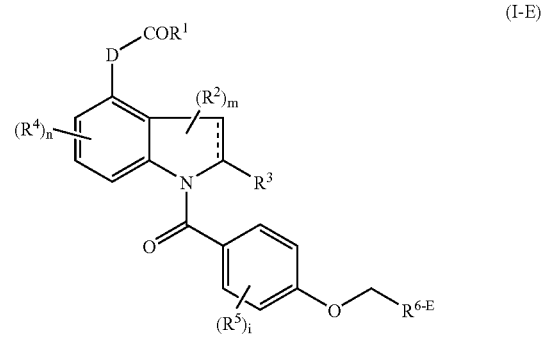

(I-E)

wherein $R^{6-E}$ has the same meaning as $R^6$ in claim 1, and wherein the carbon atom with which $R^{6-E}$ binds is saturated and the configuration of the carbon atom is R configuration, and the other symbols have the same meaning as those in claim 1, or a non-toxic salt thereof.

4. The indole compound of claim 1, which is a compound selected from
(1) 1-(4-((2S)-4-methyl-3,4-dihydro-2H-1,4-benzoxazin-2-ylmethoxy)benzoyl)-2-methyl-1H-indol-4-ylacetic acid,
(2) 1-(4-((2R)-1,4-benzodioxan-2-ylmethoxy)benzoyl)-2-methyl-1H-indol-4-ylacetic acid,
(3) 1-(4-((2S)-1,4-benzodioxan-2-ylmethoxy)benzoyl)-2-methyl-1H-indole-4-ylacetic acid,
(4) 1-(4-((2S)-1-methylindolin-2-ylmethoxy)benzoyl)-2-methyl-1H-indol-4-ylacetic acid,
(5) 1-(4-((2R)-4-methyl-3,4-dihydro-2H-1,4-benzoxazin-2-ylmethoxy)benzoyl)-2-methyl-1H-indol-4-ylacetic acid,
(6) 1-(4-((2S)-4,6-dimethyl-3,4-dihydro-2H-1,4-benzoxazin-2-ylmethoxy)benzoyl)-2-methyl-1H-indol-4-ylacetic acid, (7) 1-(4-((2S)-6-fluoro-4-methyl-3,4-dihydro-2H-1,4-benzoxazin-2-ylmethoxy)benzoyl)-2-methyl-1H-indol-4-ylacetic acid,
(8) 1-(4-((2S)-6-methoxy-4-methyl-3,4-dihydro-2H-1,4-benzoxazin-2-ylmethoxy)benzoyl)-2-methyl-1H-indol-4-ylacetic acid,
(9) 1-(4-((2S)-7-methoxy-4-methyl-3,4-dihydro-2H-1,4-benzoxazin-2-ylmethoxy)benzoyl)-2-methyl-1H-indol-4-ylacetic acid,
(10) 1-(4-((2S)-4,7-dimethyl-3,4-dihydro-2H-1,4-benzoxazin-2-ylmethoxy)benzoyl)-2-methyl-1H-indol-4-ylacetic acid,
(11) 1-(4-((2S)-7-fluoro-4-methyl-3,4-dihydro-2H-1,4-benzoxazin-2-ylmethoxy)benzoyl)-2-methyl-1H-indol-4-ylacetic acid,
(12) 1-(4-((2S)-1-ethylindolin-2-ylmethoxy)benzoyl)-2-methyl-1H-indol-4-ylacetic acid,
(13) 1-(4-((2S)-4,8-dimethyl-3,4-dihydro-2H-1,4-benzoxazin-2-ylmethoxy)benzoyl)-2-methyl-1H-indol-4-ylacetic acid,
(14) 1-(4-((2S)-5-methoxy-4-methyl-3,4-dihydro-2H-1,4-benzoxazin-2-ylmethoxy)benzoyl)-2-methyl-1H-indol-4-ylacetic acid,
(15) 1-(4-((2S)-5-fluoro-4-methyl-3,4-dihydro-2H-1,4-benzoxazin-2-ylmethoxy)benzoyl)-2-methyl-1H-indol-4-ylacetic acid,
(16) 1-(4-((2S)-2,3-dihydrobenzofuran-2-ylmethoxy)benzoyl)-2-methyl-1H-indol-4-ylacetic acid,
(17) 1-(4-((2R)-2,3-dihydrobenzofuran-2-ylmethoxy)benzoyl)-2-methyl-1H-indol-4-ylacetic acid,
(18) 1-(4-((2S)-8-fluoro-4-methyl-3,4-dihydro-2H-1,4-benzoxazin-2-ylmethoxy)benzoyl)-2-methyl-1H-indol-4-ylacetic acid,
(19) 1-(4-((3S)-2,3-dihydrobenzofuran-3-ylmethoxy)benzoyl)-2-methyl-1H-indol-4-ylacetic acid,
(20) 1-(4-((3R)-2,3-dihydrobenzofuran-3-ylmethoxy)benzoyl)-2-methyl-1H-indol-4-ylacetic acid,
(21) 1-(4-((3R)-5-fluoro-2,3-dihydrobenzofuran-3-ylmethoxy)benzoyl)-2-methyl-1H-indol-4-ylacetic acid,
(22) 1-(4-((3R)-5-methyl-2,3-dihydrobenzofuran-3-ylmethoxy)benzoyl)-2-methyl-1H-indol-4-ylacetic acid,
(23) 1-(4-((3R)-6-fluoro-2,3-dihydrobenzofuran-3-ylmethoxy)benzoyl)-2-methyl-1H-indol-4-ylacetic acid,
(24) 1-(4-((3R)-7-methyl-2,3-dihydrobenzofuran-3-ylmethoxy)benzoyl)-2-methyl-1H-indol-4-ylacetic acid,
(25) 1-(4-((2R)-5-fluoro-1,4-benzodioxan-2-ylmethoxy)benzoyl)-2-methyl-1H-indol-4-ylacetic acid,
(26) 1-(4-((2S)-8-fluoro-1,4-benzodioxan-2-ylmethoxy)benzoyl)-2-methyl-1H-indol-4-ylacetic acid,
(27) 1-(4-((3R)-7-fluoro-2,3-dihydrobenzofuran-3-ylmethoxy)benzoyl)-2-methyl-1H-indol-4-ylacetic acid,
(28) 3-(1-(4-((2S)-4-methyl-3,4-dihydro-2H-1,4-benzoxazin-2-ylmethoxy)benzoyl)-2-methyl-1H-indol-4-yl) acrylic acid,
(29) 3-(1-(4-((2S)-4-methyl-3,4-dihydro-2H-1,4-benzoxazin-2-ylmethoxy)benzoyl)-2-methyl-1H-indol-4-yl) propanoic acid,
(30) (1-(4-((2S)-4-methyl-3,4-dihydro-2H-1,4-benzoxazin-2-ylmethoxy)benzoyl)-2-methyl-1H-indol-4-yl) oxyacetic acid,
(31) 1-(4-((2S)-4-methyl-3,4-dihydro-2H-1,4-benzoxazin-2-ylmethoxy)benzoyl)-2-methyl-1H-indol-4-carboxylic acid,
(32) 1-(4-((2S)-4-methyl-3,4-dihydro-2H-1,4-benzoxazin-2-ylmethoxy)benzoyl)-1H-indol-4-ylacetic acid,
(33) 1-(4-((2S)-4-methyl-3,4-dihydro-2H-1,4-benzoxazin-2-ylmethoxy)benzoyl)-2,3-dihydro-1H-indol-4-ylacetic acid,
(34) 1-(4-((2S)-4-methyl-3,4-dihydro-2H-1,4-benzoxazin-2-ylmethoxy)benzoyl)-2-methyl-2,3-dihydro-1H-indol-4-ylacetic acid,
(35) 1-(4-((2S)-4-methyl-3,4-dihydro-2H-1,4-benzoxazin-2-ylmethoxy)-2-methylbenzoyl)-2-methyl-1H-indol-4-yl acetic acid, and
(36) 1-(4-((2S)-4-methyl-3,4-dihydro-2H-1,4-benzoxazin-2-ylmethoxy)-2-methylbenzoyl)-1H-indol-4-yl acetic acid,
or a non-toxic salts thereof.

5. A production method of a compound represented by formula (IV)

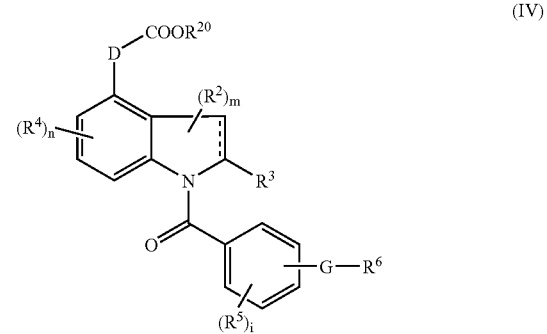

(IV)

wherein $R^{20}$ represents allyl or benzyl group, and other symbols have the same meaning as those in claim 1, which comprises subjecting a compound represented by formula (V)

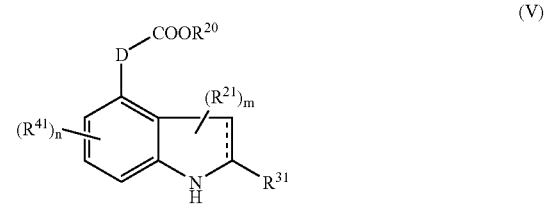

(V)

wherein $R^{20}$ represents allyl or benzyl group and $R^{21}$, $R^{31}$, and $R^{41}$ have the same meaning as $R^2$, $R^3$, and $R^4$ of claim 1 respectively; and wherein they are protected by protecting groups when they represent hydroxyl group, and the other symbols have the same meaning as those in claim 1 and a compound represented by formula (VI)

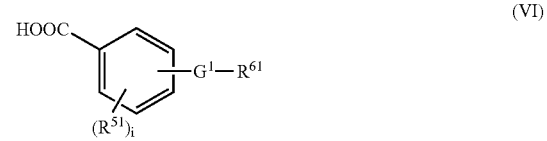

(VI)

wherein $R^{51}$ has the same meaning as $R^5$ of claim 1; and wherein they are protected by protecting groups when $R^{51}$ represents hydroxyl group, and $G^1$ and $R^{61}$ have the same meaning as G and $R^6$ in claim 1, respectively; and wherein they are protected by protecting groups when they contain hydroxyl group to amidation reaction, followed by deprotection reaction optionally.

6. A production method of a compound represented by formula (IV)

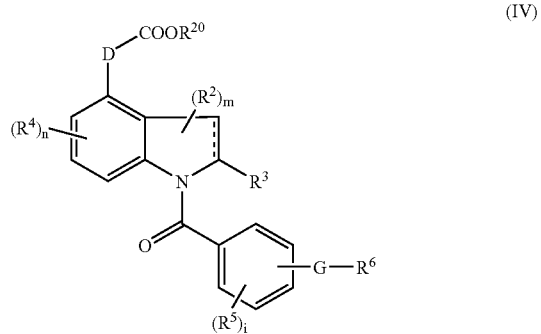

wherein $R^{20}$ represents allyl or benzyl group, and other symbols have the same meaning as those in claim 1, which comprises subjecting a compound represented by formula (VII)

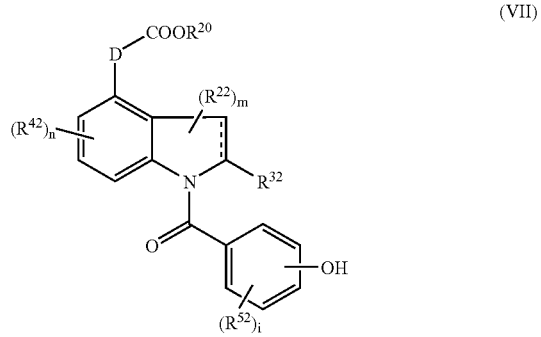

wherein $R^{22}$, $R^{32}$, $R^{42}$ and $R^{52}$ have the same meaning as $R^2$, $R^3$, $R^4$, and $R^5$ of claim 1 respectively; and wherein they are protected by protecting groups when they represent hydroxyl group, and the other symbols have the same meaning as in claim 1, and a compound represented by formula (VIII)

HO-J-$R^{62}$ (VIII)

wherein $R^{62}$ has the same meaning as $R^6$ of claim 1; and wherein they are protected by protecting groups when they contain hydroxyl group, and J represents —$CH_2$— to etherification reaction, followed by deprotection reaction optionally.

7. A medicinal composition comprising the inhole compound represented by formula (I) of claim 1 or a non-toxic salt thereof as an active ingredient.

8. A $PGD_2$ receptor antagonist comprising the indole compound represented by formula (I) of claim 1 or a non-toxic salt thereof as an active ingredient.

9. The antagonist of claim 7, wherein the $PGD_2$ receptor is DP receptor.

10. A treatment medicine for allergic diseases, systemic mastocytosis, disorders due to systemic mastocyte activation, bronchoconstriction, urticaria, contact dermatitis, diseases accompanied with itching, secondary diseases generated by behaviors caused by itching, comprising the indole compound represented by formula (I) of claim 1 or a non-toxic salt thereof as an active ingredient.

11. The medicine according to claim 10, wherein the allergic diseases are selected from the group consisting of allergic rhinitis, allergic conjunctivitis, atopic dermatitis, bronchial asthma and food allergy.

12. The medicine according to claim 10, wherein the diseases accompanied with itching are selected from the group consisting of atopic dermatitis, urticaria, allergic conjunctivitis, allergic rhinitis and contact dermatitis.

13. The medicine according to claim 10, wherein the secondary diseases generated by behaviors caused by itching are selected from the group consisting of cataracta, retinodialysis, inflammation, infection and dysgryphia.

14. The medicine according to claim 10, wherein the behaviors caused by itching are selected from the group consisting of scratching behaviors and beating.

15. A method for the medical treatment of allergic diseases, systemic mastocytosis, disorders due to systemic mastocyte activation, bronchoconstriction, urticaria, contact dermatitis, diseases accompanied with itching, secondary diseases generated by behaviors caused by itching, which comprises administering the indole compound represented by formula (I) of claim 1 or a non-toxic salt thereof.

16. The method according to claim 15, wherein the allergic diseases are selected from the group consisting of allergic rhinitis, allergic conjunctivitis, atopic dermatitis, bronchial asthma and food allergy.

17. The method according to claim 15, wherein the diseases accompanied with itching are selected from the group consisting of atopic dermatitis, urticaria, allergic conjunctivitis, allergic rhinitis and contact dermatitis.

18. The method according to claim 15, wherein the secondary diseases generated by behaviors caused by itching are selected from the group consisting of cataracta, retinodialysis, inflammation, infection and dysgryphia.

19. The method according to claim 15, wherein the behaviors caused by itching are selected from the group consisting of scratching behaviors and beating.

20. A composition comprising the indole compound of claim 1 or non-toxic salts thereof and a pharmaceutically acceptable carrier, diluent, or excipient.

21. A composition comprising the indole compound of claim 2 or a non-toxic salt thereof and a pharmaceutically acceptable carrier, diluent, or excipient.

22. A composition comprising the indole compound of claim 3 or a non-toxic salt thereof and a pharmaceutically acceptable carrier, diluent, or excipient.

23. A composition comprising the indole compound of claim 4 or a non-toxic salt thereof and a pharmaceutically acceptable carrier, diluent, or excipient.

* * * * *